(12) United States Patent
Han et al.

(10) Patent No.: US 10,355,225 B2
(45) Date of Patent: Jul. 16, 2019

(54) HETEROCYCLIC COMPOUND AND ORGANIC LIGHT EMITTING ELEMENT COMPRISING SAME

(71) Applicant: LG CHEM, LTD., Seoul (KR)

(72) Inventors: Miyeon Han, Daejeon (KR); Sung Kil Hong, Daejeon (KR); Dong Hoon Lee, Daejeon (KR); Hyungjin Lee, Daejeon (KR); Boonjae Jang, Daejeon (KR); Minyoung Kang, Daejeon (KR); Dong Uk Heo, Daejeon (KR); Wooyung Jung, Daejeon (KR)

(73) Assignee: LG CHEM, LTD., Seoul (KR)

( * ) Notice: Subject to any disclaimer, the term of this patent is extended or adjusted under 35 U.S.C. 154(b) by 35 days.

(21) Appl. No.: 15/553,405

(22) PCT Filed: Mar. 4, 2016

(86) PCT No.: PCT/KR2016/002209
§ 371 (c)(1),
(2) Date: Aug. 24, 2017

(87) PCT Pub. No.: WO2016/140551
PCT Pub. Date: Sep. 9, 2016

(65) Prior Publication Data
US 2018/0114923 A1 Apr. 26, 2018

(30) Foreign Application Priority Data
Mar. 5, 2015 (KR) .......... 10-2015-0030749

(51) Int. Cl.
*H01L 51/00* (2006.01)
*C07F 9/6561* (2006.01)
*C09K 11/06* (2006.01)
*C07D 471/04* (2006.01)
*C07D 471/12* (2006.01)
*H01L 51/50* (2006.01)

(52) U.S. Cl.
CPC ........ *H01L 51/0072* (2013.01); *C07D 471/04* (2013.01); *C07D 471/12* (2013.01); *C07F 9/6561* (2013.01); *C09K 11/06* (2013.01); *H01L 51/0052* (2013.01); *C09K 2211/1018* (2013.01); *H01L 51/5012* (2013.01); *H01L 51/5056* (2013.01); *H01L 51/5072* (2013.01); *H01L 51/5088* (2013.01); *H01L 51/5092* (2013.01)

(58) Field of Classification Search
CPC .......... H01L 51/0072; H01L 51/0052; H01L 51/5056; H01L 51/5072; H01L 51/5088; H01L 51/5012; H01L 51/5092; C09K 11/06; C09K 2211/1018; C07F 9/6561; C07D 471/04; C07D 471/12
USPC ........................................... 257/40
See application file for complete search history.

(56) References Cited

U.S. PATENT DOCUMENTS

| | | | |
|---|---|---|---|
| 9,000,169 | B2 | 4/2015 | Lee et al. |
| 2012/0261651 | A1 | 10/2012 | Noto et al. |
| 2013/0181196 | A1 | 7/2013 | Lee et al. |

(Continued)

FOREIGN PATENT DOCUMENTS

| | | | |
|---|---|---|---|
| EP | 3312256 A1 | 4/2018 | |
| KR | 1020000051826 A | 8/2000 | |

(Continued)

*Primary Examiner* — Caleen O Sullivan
(74) *Attorney, Agent, or Firm* — Dentons US LLP

(57) ABSTRACT

The present specification provides a hetero-cyclic compound and an organic light emitting device including the same.

12 Claims, 1 Drawing Sheet

| 4 |
|---|
| 8 |
| 7 |
| 6 |
| 5 |
| 2 |
| 1 |

(56) References Cited

U.S. PATENT DOCUMENTS

| | | |
|---|---|---|
| 2014/0048792 A1 | 2/2014 | Chun et al. |
| 2014/0110694 A1 | 4/2014 | Shin et al. |
| 2014/0251816 A1 | 9/2014 | Musselman et al. |
| 2016/0005979 A1 | 1/2016 | Kim et al. |
| 2016/0293852 A1 | 10/2016 | Huh et al. |

FOREIGN PATENT DOCUMENTS

| | | |
|---|---|---|
| KR | 1020120138673 A | 12/2012 |
| KR | 1020130006293 A | 1/2013 |
| KR | 1020130037186 A | 4/2013 |
| KR | 101317495 B1 | 10/2013 |
| KR | 1020140111898 A | 9/2014 |
| KR | 1020160004466 A | 1/2016 |
| WO | 2003012890 A2 | 2/2003 |
| WO | 2007095118 A2 | 8/2007 |
| WO | 201102385 A1 | 2/2011 |
| WO | 2016024728 A1 | 2/2016 |

[Figure 1]
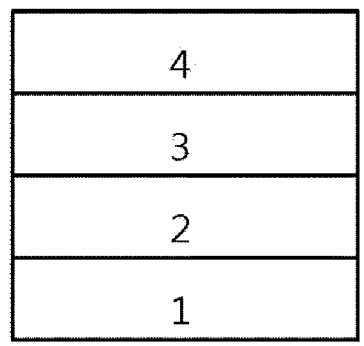
[Figure 2]
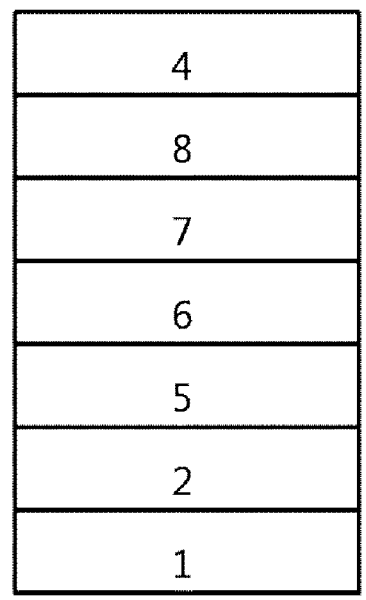

HETEROCYCLIC COMPOUND AND ORGANIC LIGHT EMITTING ELEMENT COMPRISING SAME

TECHNICAL FIELD

The present specification relates to a hetero-cyclic compound and an organic light emitting device comprising the same. This application is a National Stage Entry of International Application No. PCT/KR2016/002209 filed on Mar. 4, 2016, and claims the benefit of Korean Application No. 10-2015-0030749 filed on Mar. 5, 2015, all of which are hereby incorporated by reference in their entirety for all purposes as if fully set forth herein.

BACKGROUND ART

In general, an organic light emitting phenomenon refers to a phenomenon in which electric energy is converted into light energy by using an organic material. An organic light emitting device using the organic light emitting phenomenon usually has a structure including a positive electrode, a negative electrode, and an organic material layer interposed therebetween. Here, the organic material layer may have a multilayered structure composed of different materials in order to improve the efficiency and stability of an organic light emitting device in many cases, and for example, may be composed of a hole injection layer, a hole transporting layer, a light emitting layer, an electron transporting layer, an electron injection layer, and the like. In the structure of the organic light emitting device, if a voltage is applied between two electrodes, holes are injected from a positive electrode into the organic material layer and electrons are injected from a negative electrode into the organic material layer, and when the injected holes and electrons meet each other, an exciton is formed, and light is emitted when the exciton falls down again to a ground state.

There is a continuous need for developing a new material for the aforementioned organic light emitting device.

DETAILED DESCRIPTION OF THE INVENTION

Technical Problem

The present specification describes a hetero-cyclic compound and an organic light emitting device comprising the same.

Technical Solution

An exemplary embodiment of the present specification provides a compound represented by the following Chemical Formula 1:

[Chemical Formula 1]

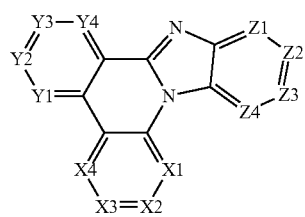

In Chemical Formula 1,

X1 is N or CR1, X2 is N or CR2, X3 is N or CR3, and X4 is N or CR4,

Y1 is N or CR5, Y2 is N or CR6, Y3 is N or CR7, and Y4 is N or CR8,

Z1 is N or CR9, Z2 is N or CR10, Z3 is N or CR11, and Z4 is N or CR12,

X1 to X4, Y1 to Y4, and Z1 to Z4 are not simultaneously N,

R1 to R12 are the same as or different from each other, and are each independently hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylphosphine group; a substituted or unsubstituted phosphine oxide group; a substituted or unsubstituted aryl group; or a substituted or unsubstituted hetero-cyclic group, or may combine with an adjacent group to form a substituted or unsubstituted ring, two or more adjacent groups of R1 to R8 combine with each other to form a substituted or unsubstituted 6-membered ring, at least one of a substituent of the 6-membered ring formed by combining two or more adjacent groups of R1 to R8; a group of R1 to R8, which does not form a ring; and R9 to R12 is

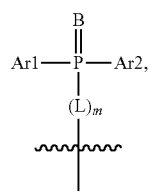

B is O, S, or Se, and

Ar1 and Ar2 are the same as or different from each other, and are each independently a substituted or unsubstituted aryl group; or a substituted or unsubstituted hetero-cyclic group, or combine with each other to form a substituted or unsubstituted ring, L is a substituted or unsubstituted arylene having 10 or more carbon atoms; or a substituted or unsubstituted heteroarylene, m is an integer of 1 to 5, and when m is 2 or more, L's are the same as or different from each other.

Further, an exemplary embodiment of the present specification provides an organic light emitting device including: a first electrode; a second electrode provided to face the first electrode; and one or more organic material layers provided between the first electrode and the second electrode, in which one or more of the organic material layers include the compound of Chemical Formula 1.

Advantageous Effects

The compound described in the present specification may be used as a material for an organic material layer of an organic light emitting device. The compound according to at least one exemplary embodiment may improve the efficiency, achieve low driving voltage and/or improve lifespan characteristics in the organic light emitting device. In particular, the compound described in the present specification may be used as a material for hole injection, hole transport, hole injection and hole transport, light emission, electron transport, or electron injection. In addition, the compound described in the present specification may be preferably used as a material for a light emitting layer, and electron transport or electron injection.

BRIEF DESCRIPTION OF DRAWINGS

FIG. 1 illustrates an example of an organic light emitting device composed of a substrate 1, a positive electrode 2, a light emitting layer 3, and a negative electrode 4.

FIG. 2 illustrates an example of an organic light emitting device composed of a substrate 1, a positive electrode 2, a hole injection layer 5, a hole transporting layer 6, a light emitting layer 7, an electron transporting layer 8, and a negative electrode 4.

BEST MODE

Hereinafter, the present specification will be described in more detail.

An exemplary embodiment of the present specification provides the compound represented by Chemical Formula 1. Examples of the substituents will be described below, but are not limited thereto.

In the present specification, the term "substituted or unsubstituted" means being unsubstituted or substituted with one or more substituents selected from the group consisting of deuterium; a halogen group; a nitrile group; a nitro group; a hydroxy group; a carbonyl group; an ester group; an imide group; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; and a hetero-cyclic group, or being unsubstituted or substituted with a substituent to which two or more substituents are linked among the substituents exemplified above. For example, "the substituent to which two or more substituents are linked" may be a biphenyl group. That is, the biphenyl group may also be an aryl group, and may be interpreted as a substituent to which two phenyl groups are linked.

In the present specification, the "adjacent" group may mean a substituent substituted with an atom directly linked to an atom in which the corresponding substituent is substituted, a substituent disposed sterically closest to the corresponding substituent, or another substituent substituted with an atom in which the corresponding substituent is substituted. For example, two substituents substituted at the ortho position in a benzene ring and two substituents substituted with the same carbon in an aliphatic ring may be interpreted as groups which are "adjacent" to each other.

In the present specification, the number of carbon atoms of a carbonyl group is not particularly limited, but is preferably 1 to 40. Specifically, the imide group may be a compound having the following structures, but is not limited thereto.

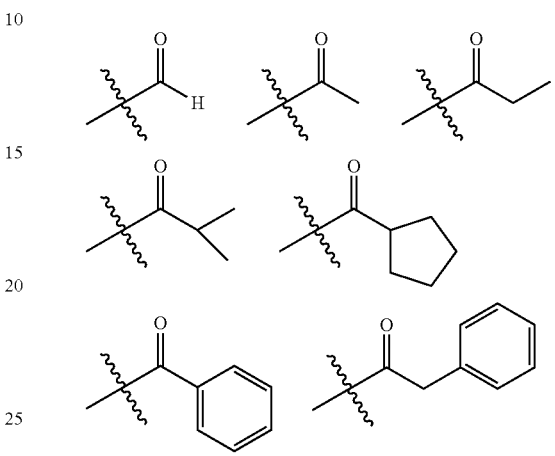

In the present specification, in an ester group, the oxygen of the ester group may be substituted with a straight-chained, branched, or cyclic alkyl group having 1 to 25 carbon atoms, or an aryl group having 6 to 25 carbon atoms. Specifically, the ester group may be a compound having the following structural formulae, but is not limited thereto.

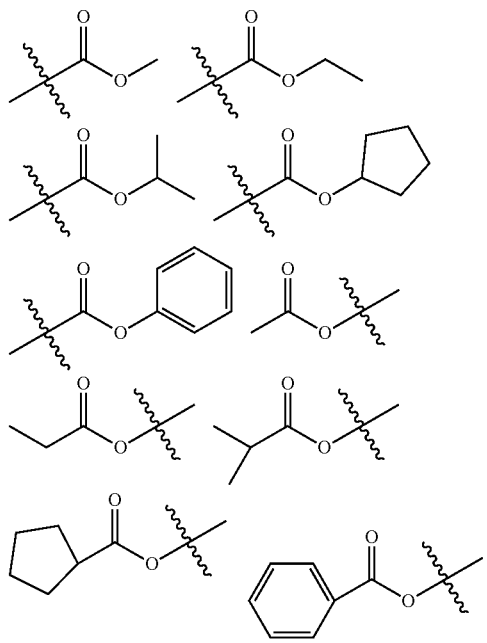

In the present specification, the number of carbon atoms of an imide group is not particularly limited, but is preferably 1 to 25. Specifically, the imide group may be a compound having the following structures, but is not limited thereto.

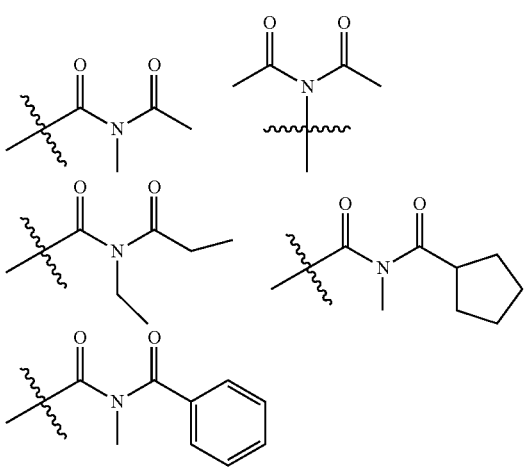

In the present specification, specific examples of a silyl group include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but are not limited thereto.

In the present specification, specific examples of a boron group include a trimethylboron group, a triethylboron group, a t-butyldimethylboron group, a triphenylboron group, a phenylboron group, and the like, but are not limited thereto.

In the present specification, examples of a halogen group include fluorine, chlorine, bromine or iodine.

In the present specification, the alkyl group may be straight-chained or branched, and the number of carbon atoms thereof is not particularly limited, but is preferably 1 to 40. According to an exemplary embodiment, the number of carbon atoms of the alkyl group is 1 to 20. According to another exemplary embodiment, the number of carbon atoms of the alkyl group is 1 to 10. According to still another exemplary embodiment, the number of carbon atoms of the alkyl group is 1 to 6. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 4-methylhexyl, 5-methylhexyl, and the like, but are not limited thereto.

In the present specification, the alkenyl group may be straight-chained or branched, and the number of carbon atoms thereof is not particularly limited, but is preferably 2 to 40. According to an exemplary embodiment, the number of carbon atoms of the alkenyl group is 2 to 20. According to another exemplary embodiment, the number of carbon atoms of the alkenyl group is 2 to 10. According to still another exemplary embodiment, the number of carbon atoms of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, a cycloalkyl group is not particularly limited, but has preferably 3 to 60 carbon atoms, and according to an exemplary embodiment, the number of carbon atoms of the cycloalkyl group is 3 to 30. According to another exemplary embodiment, the number of carbon atoms of the cycloalkyl group is 3 to 20. According to another exemplary embodiment, the number of carbon atoms of the cycloalkyl group is 3 to 6. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, examples of an arylamine group mean a substituted or unsubstituted monocyclic diarylamine group, a substituted or unsubstituted polycyclic diarylamine group, or a substituted or unsubstituted monocyclic and polycyclic diarylamine group.

In the present specification, an aryl group is not particularly limited, but has preferably 6 to 60 carbon atoms, and may be a monocyclic aryl group or a polycyclic aryl group. According to an exemplary embodiment, the number of carbon atoms of the aryl group is 6 to 30. According to an exemplary embodiment, the number of carbon atoms of the aryl group is 6 to 20. Specific examples of the monocyclic aryl group include a phenyl group, a biphenyl group, a terphenyl group, and the like, but are not limited thereto. Examples of the polycyclic aryl group include a naphthyl group, an anthracenyl group, a phenanthryl group, a pyrenyl group, a perylenyl group, a chrysenyl group, a fluorenyl group, and the like, but are not limited thereto.

In the present specification, a fluorenyl group may be substituted, and two substituents may combine with each other to form a spiro structure.

When the fluorenyl group is substituted, the fluorenyl group may be

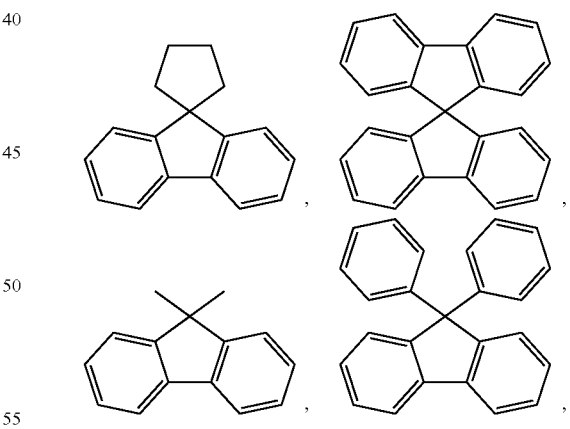

and the like. However, the fluorenyl group is not limited thereto.

In the present specification, a hetero-cyclic group is a hetero-cyclic group including one or more of N, O, S, Si, and Se as a hetero atom, and the number of carbon atoms thereof is not particularly limited, but is preferably 2 to 60. Examples of the hetero-cyclic group include a thiophene group, a furan group, a pyrrole group, an imidazole group, a triazole group, an oxazole group, an oxadiazole group, a triazole group, a pyridyl group, a bipyridyl group, a pyrimidyl group, a triazine group, an acridyl group, a pyridazine group, a pyrazinyl group, a qinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group, and the like, but are not limited thereto.

In the present specification, the description on the above-described hetero-cyclic group may be applied to a heteroaryl group except for an aromatic group.

In the present specification, the description on the above-described aryl group may be applied to an aryl group of an aryloxy group, an arylthioxy group, an arylsulfoxy group, an arylphosphine group, an aralkyl group, an aralkylamine group, an aralkenyl group, an alkylaryl group, and an arylamine group.

In the present specification, the description on the above-described alkyl group may be applied to an alkyl group of an alkylthioxy group, an alkylsulfoxy group, an aralkyl group, an aralkylamine group, an alkylaryl group, and an alkylamine group.

In the present specification, the description on the above-described hetero-cyclic group may be applied to a heteroaryl group of a heteroaryl group and a heteroarylamine group.

In the present specification, the description on the above-described alkenyl group may be applied to an alkenyl group of an aralkenyl group.

In the present specification, the description on the above-described aryl group may be applied to an arylene except for a divalent arylene group.

In the present specification, the description on the above-described hetero-cyclic group may be applied to a heteroarylene except for a divalent heteroarylene group.

In the present specification, the meaning of combining with an adjacent group to form a ring means combining with an adjacent group to form a substituted or unsubstituted aliphatic hydrocarbon ring; a substituted or unsubstituted aromatic hydrocarbon ring; a substituted or unsubstituted aliphatic hetero ring; a substituted or unsubstituted aromatic hetero ring; and a condensed ring thereof.

In the present specification, the aliphatic hydrocarbon ring means a ring composed only of carbon and hydrogen atoms as a ring which is not an aromatic group.

In the present specification, examples of the aromatic hydrocarbon ring include a phenyl group, a naphthyl group, an anthracenyl group, and the like, but are not limited thereto.

In the present specification, the aliphatic hetero ring means an aliphatic ring including one or more of hetero atoms.

In the present specification, the aromatic hetero ring means an aromatic ring including one or more of hetero atoms.

In the present specification, the aliphatic hydrocarbon ring, the aromatic hydrocarbon ring, the aliphatic hetero ring, and the aromatic hetero ring may be monocyclic or polycyclic.

According to an exemplary embodiment of the present specification, Chemical Formula 1 may be represented by any one of the following Chemical Formulae 2 to 4.

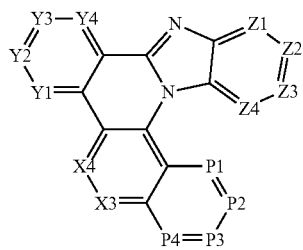

[Chemical Formula 2]

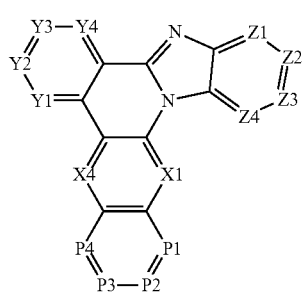

[Chemical Formula 3]

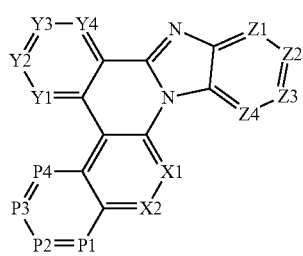

[Chemical Formula 4]

In Chemical Formulae 2 to 4,

X1 is N or CR1, X2 is N or CR2, X3 is N or CR3, and X4 is N or CR4,

Y1 is N or CR5, Y2 is N or CR6, Y3 is N or CR7, and Y4 is N or CR8,

Z1 is N or CR9, Z2 is N or CR10, Z3 is N or CR11, and Z4 is N or CR12,

P1 is N or CR13, P2 is N or CR14, P3 is N or CR15, and P4 is N or CR16,

R1 to R16 are the same as or different from each other, and are each independently hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylphosphine group; a substituted or unsubstituted phosphine oxide group; a substituted or unsubstituted aryl group; or a substituted or unsubstituted hetero-cyclic group, or may combine with an adjacent group to form a substituted or unsubstituted ring, at least one of R1 to R16 is

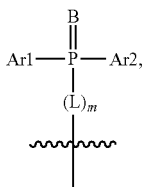

B is O, S, or Se, and

Ar1 and Ar2 are the same as or different from each other, and are each independently a substituted or unsubstituted aryl group; or a substituted or unsubstituted hetero-cyclic group, L is a substituted or unsubstituted bicyclic or more arylene; or a substituted or unsubstituted heteroarylene, m is an integer of 1 to 5, and when m is 2 or more, L's are the same as or different from each other.

According to an exemplary embodiment of the present specification, Chemical Formula 1 may be represented by any one of the following Chemical Formulae 5 to 7.

[Chemical Formula 5]

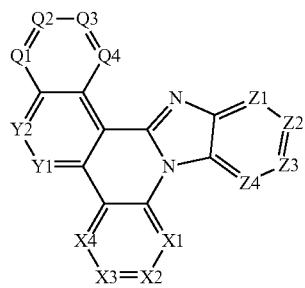

[Chemical Formula 6]

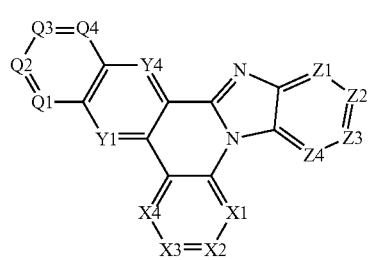

[Chemical Formula 7]

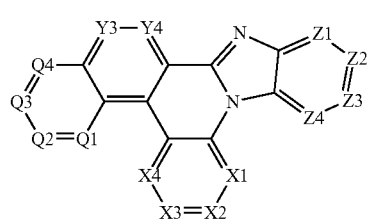

In Chemical Formulae 5 to 7,

X1 is N or CR1, X2 is N or CR2, X3 is N or CR3, and X4 is N or CR4,

Y1 is N or CR5, Y2 is N or CR6, Y3 is N or CR7, and Y4 is N or CR8,

Z1 is N or CR9, Z2 is N or CR10, Z3 is N or CR11, and Z4 is N or CR12,

Q1 is N or CR17, Q2 is N or CR18, Q3 is N or CR19, and Q4 is N or CR20,

R1 to R12 and R17 to R20 are the same as or different from each other, and are each independently hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylphosphine group; a substituted or unsubstituted phosphine oxide group; a substituted or unsubstituted aryl group; or a substituted or unsubstituted hetero-cyclic group, or may combine with an adjacent group to form a substituted or unsubstituted ring, at least one of R1 to R12 and R17 to R20 is

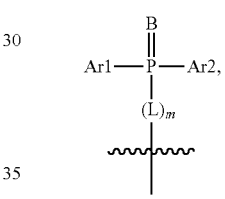

B is O, S, or Se, and

Ar1 and Ar2 are the same as or different from each other, and are each independently a substituted or unsubstituted aryl group; or a substituted or unsubstituted hetero-cyclic group, L is a substituted or unsubstituted bicyclic or more arylene; or a substituted or unsubstituted heteroarylene, m is an integer of 1 to 5, and when m is 2 or more, L's are the same as or different from each other.

According to an exemplary embodiment of the present specification, Chemical Formula 1 may be represented by any one of the following Chemical Formulae 8 to 16.

[Chemical Formula 8]

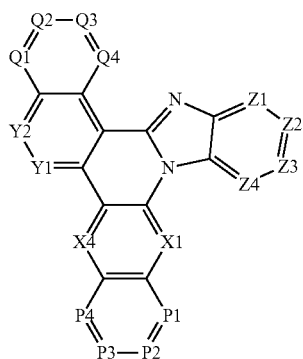

-continued

[Chemical Formula 9]
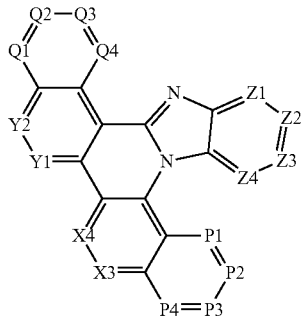

[Chemical Formula 10]
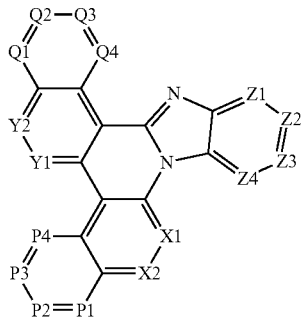

[Chemical Formula 11]
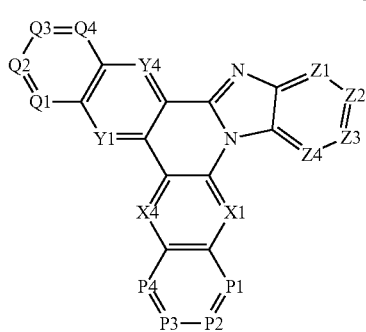

[Chemical Formula 12]
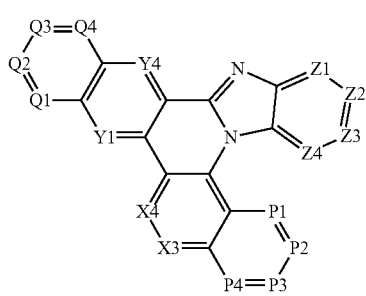

[Chemical Formula 13]
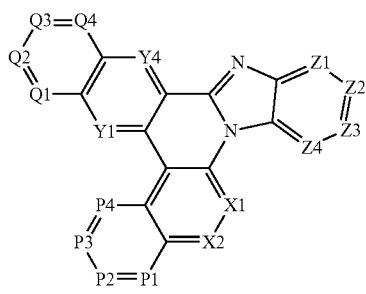

[Chemical Formula 14]
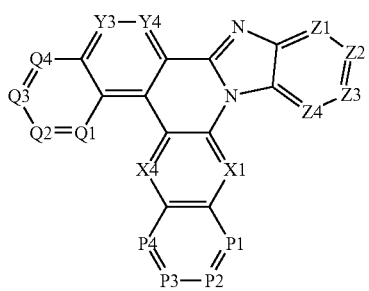

[Chemical Formula 15]
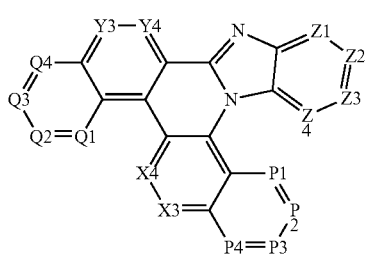

[Chemical Formula 16]
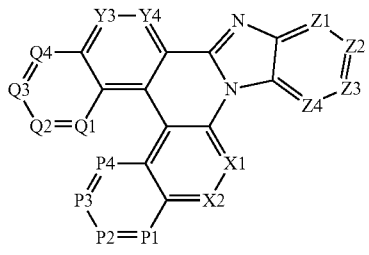

In Chemical Formulae 8 to 16,

X1 is N or CR1, X2 is N or CR2, X3 is N or CR3, and X4 is N or CR4,

Y1 is N or CR5, Y2 is N or CR6, Y3 is N or CR7, and Y4 is N or CR8,

Z1 is N or CR9, Z2 is N or CR10, Z3 is N or CR11, and Z4 is N or CR12,

P1 is N or CR13, P2 is N or CR14, P3 is N or CR15, and P4 is N or CR16,

Q1 is N or CR17, Q2 is N or CR18, Q3 is N or CR19, and Q4 is N or CR20,

R1 to R20 are the same as or different from each other, and are each independently hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylphosphine group; a substituted or unsubstituted phosphine oxide group; a substituted or unsubstituted aryl group; or a substituted or unsubstituted hetero-cyclic group, or may combine with an adjacent group to form a substituted or unsubstituted ring, at least one of R1 to R20 is

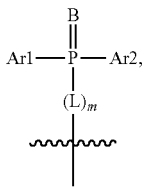

B is O, S, or Se, and

Ar1 and Ar2 are the same as or different from each other, and are each independently a substituted or unsubstituted aryl group; or a substituted or unsubstituted hetero-cyclic group, L is a substituted or unsubstituted bicyclic or more arylene; or a substituted or unsubstituted heteroarylene, m is an integer of 1 to 5, and when m is 2 or more, L's are the same as or different from each other.

According to an exemplary embodiment of the present specification, the 6-membered ring formed by combining two or more adjacent groups of R1 to R8 is a hydrocarbon ring.

According to an exemplary embodiment of the present specification, the 6-membered ring formed by combining two or more adjacent groups of R1 to R8 is a hetero ring.

According to an exemplary embodiment of the present specification, at least one of the substituent of the 6-membered ring formed by combining two or more adjacent groups of R1 to R8 is

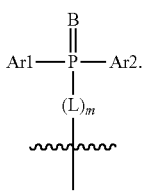

According to an exemplary embodiment of the present specification, at least one of R1 to R12 is

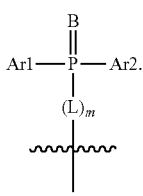

According to an exemplary embodiment of the present specification, at least two or more of the substituent of the 6-membered ring formed by combining two or more adjacent groups of R1 to R8; a group of R1 to R8, which does not form a ring; and R9 to R12 are

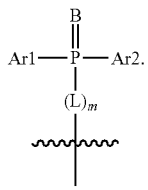

According to an exemplary embodiment of the present specification, at least two or more of the substituent of the 6-membered ring formed by combining two or more adjacent groups of R1 to R8, R1 to R4, and R9 to R12 are

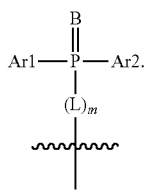

According to an exemplary embodiment of the present specification, at least one of the substituent of the 6-membered ring formed by combining two or more adjacent groups of R1 to R8, and R1 to R12 is

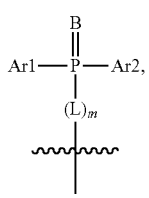

and at least one of the substituent of a 6-membered ring formed by combining two or more adjacent groups of R1 to R8 and groups which are not

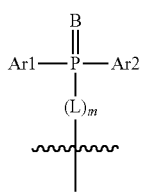

in R1 to R12 is a substituted or unsubstituted aryl group; or a substituted or unsubstituted hetero-cyclic group.

According to an exemplary embodiment of the present specification, at least one of the substituent of the 6-membered ring formed by combining two or more adjacent groups of R1 to R8; a group of R1 to R8, which does not form a ring; and R9 to R12 is

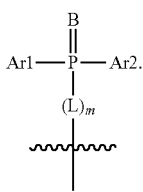

At least one of the substituent of the 6-membered ring formed by combining two or more adjacent groups of R1 to R8; a group of R1 to R8, which does not form a ring; and groups which are not

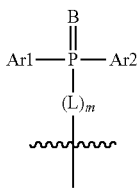

in R9 to R12 is a substituted or unsubstituted monocyclic to pentacyclic aryl group; or a substituted or unsubstituted monocyclic to pentacyclic hetero-cyclic group.

According to an exemplary embodiment of the present specification, at least one of the substituent of the 6-membered ring formed by combining two or more adjacent groups of R1 to R8; a group of R1 to R8, which does not form a ring; and R9 to R12 is

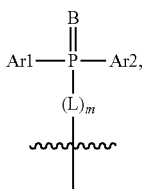

and
at least one of the substituent of the 6-membered ring formed by combining two or more adjacent groups of R1 to R8; a group of R1 to R8, which does not form a ring; and groups which are not

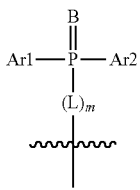

in R9 to R12 is a substituted or unsubstituted phenyl group; a substituted or unsubstituted biphenyl group; a substituted or unsubstituted naphthyl group; a substituted or unsubstituted phenanthryl group; a substituted or unsubstituted pyrenyl group; a substituted or unsubstituted fluorenyl group; a substituted or unsubstituted pyridyl group; a substituted or unsubstituted quinoline group; a substituted or unsubstituted quinazoline group; a substituted or unsubstituted quinoxaline group; a substituted or unsubstituted carbazole group; or a substituted or unsubstituted dibenzofuran group, but is not limited thereto.

According to an exemplary embodiment of the present specification, at least one of the substituent of the 6-membered ring formed by combining two or more adjacent groups of R1 to R8; a group of R1 to R8, which does not form a ring; and R9 to R12 is

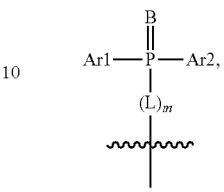

and at least one of the substituent of the 6-membered ring formed by combining two or more adjacent groups of R1 to R8; a group of R1 to R8, which does not form a ring; and groups which are not

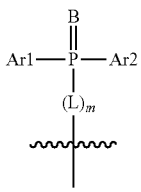

in R9 to R12 is a phenyl group; a biphenyl group; a naphthyl group; a phenanthryl group; a pyrenyl group; a fluorenyl group; a pyridyl group; a quinoline group; a quinazoline group; a quinoxaline group; a carbazole group; or a dibenzofuran group, but is not limited thereto.

According to an exemplary embodiment of the present specification, at least one of R9 to R12 is a substituted or unsubstituted aryl group; or a substituted or unsubstituted hetero-cyclic group.

According to an exemplary embodiment of the present specification, at least one of R9 to R12 is a substituted or unsubstituted monocyclic to pentacyclic aryl group; or a substituted or unsubstituted monocyclic to pentacyclic hetero-cyclic group.

According to an exemplary embodiment of the present specification, at least one of R9 to R12 is a substituted or unsubstituted aryl group; or a substituted or unsubstituted heteroaryl group.

According to an exemplary embodiment of the present specification, at least one of R9 to R12 is an aryl group; or a hetero-cyclic group.

According to an exemplary embodiment of the present specification, at least one of R9 to R12 is a monocyclic to pentacyclic aryl group; or a monocyclic to pentacyclic hetero-cyclic group.

According to an exemplary embodiment of the present specification, at least one of R9 to R12 is an aryl group; or a heteroaryl group.

According to an exemplary embodiment of the present specification, at least one of R9 to R12 is a substituted or unsubstituted phenyl group; a substituted or unsubstituted naphthyl group; a substituted or unsubstituted phenanthryl group, or a substituted or unsubstituted pyridyl group.

According to an exemplary embodiment of the present specification, at least one of R9 to R12 is a phenyl group; a naphthyl group; a phenanthryl group, or a pyridyl group.

According to an exemplary embodiment of the present specification, the aryl group is a substituted or unsubstituted phenyl group; a substituted or unsubstituted biphenyl group; a substituted or unsubstituted naphthyl group; a substituted or unsubstituted phenanthryl group, or a substituted or unsubstituted pyrenyl group; or a substituted or unsubstituted fluorenyl group, but is not limited thereto.

According to an exemplary embodiment of the present specification, the hetero-cyclic group is a substituted or unsubstituted pyridyl group; a substituted or unsubstituted quinoline group; a substituted or unsubstituted quinazoline group; a substituted or unsubstituted quinoxaline group; a substituted or unsubstituted carbazole group; or a substituted or unsubstituted dibenzofuran group, but is not limited thereto.

According to an exemplary embodiment of the present specification, B is O.

According to an exemplary embodiment of the present specification, B is S or Se.

According to an exemplary embodiment of the present specification, Ar1 and Ar2 are the same as or different from each other, and are each independently a substituted or unsubstituted monocyclic to pentacyclic aryl group; or a substituted or unsubstituted monocyclic to pentacyclic hetero-cyclic group, or combine with each other to form a ring.

According to an exemplary embodiment of the present specification, Ar1 and Ar2 are the same as or different from each other, and are each independently a substituted or unsubstituted phenyl group; a substituted or unsubstituted biphenyl group; a substituted or unsubstituted naphthyl group; a substituted or unsubstituted phenanthryl group; a substituted or unsubstituted fluorenyl group; a substituted or unsubstituted pyrenyl group; a substituted or unsubstituted pyridyl group; a substituted or unsubstituted quinoline group; a substituted or unsubstituted quinazoline group; a substituted or unsubstituted quinoxaline group; a substituted or unsubstituted carbazole group; a substituted or unsubstituted phenanthroline group; or a substituted or unsubstituted dihydroacenaphthalene, or combine with each other to form a ring.

According to an exemplary embodiment of the present specification, Ar1 and Ar2 are the same as or different from each other, and are each independently a monocyclic to pentacyclic aryl group.

According to an exemplary embodiment of the present specification, Ar1 and Ar2 are the same as or different from each other, and are each independently a substituted or unsubstituted monocyclic to pentacyclic aryl group.

According to an exemplary embodiment of the present specification, Ar1 and Ar2 are the same as or different from each other, and are each independently a substituted or unsubstituted phenyl group.

According to an exemplary embodiment of the present specification, Ar1 and Ar2 are the same as or different from each other, and are each independently a phenyl group; a biphenyl group; a naphthyl group; a phenanthryl group; a fluorenyl group; a pyrenyl group; a pyridyl group; a quinoline group; a quinazoline group; a qunoxaline group; a carbazole group; a phenanthroline group; or a dihydroacenaphthalene group, or combine with each other to form a ring.

According to an exemplary embodiment of the present specification,

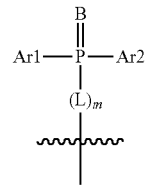

may be

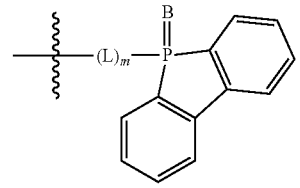

In an exemplary embodiment of the present specification, Ar1 and Ar2 are a phenyl group.

According to an exemplary embodiment of the present specification, L is a substituted or unsubstituted arylene having 10 or more carbon atoms; or a substituted or unsubstituted monocyclic to pentacyclic heteroarylene.

According to an exemplary embodiment of the present specification, L is a substituted or unsubstituted divalent naphthyl group; a substituted or unsubstituted divalent biphenyl group; a substituted or unsubstituted divalent pyridyl group; or a substituted or unsubstituted divalent quinoline group, but is not limited thereto.

According to an exemplary embodiment of the present specification, L is a divalent naphthyl group; a divalent biphenyl group; a divalent pyridyl group; or a divalent quinoline group, but is not limited thereto.

According to an exemplary embodiment of the present specification, X1 is N.

According to an exemplary embodiment of the present specification, X2 is N.

According to an exemplary embodiment of the present specification, X3 is N.

According to an exemplary embodiment of the present specification, X4 is N.

According to an exemplary embodiment of the present specification, Y1 is N.

According to an exemplary embodiment of the present specification, Y2 is N.

According to an exemplary embodiment of the present specification, Y3 is N.

According to an exemplary embodiment of the present specification, Y4 is N.

According to an exemplary embodiment of the present specification, Z1 is N.

According to an exemplary embodiment of the present specification, Z2 is N.

According to an exemplary embodiment of the present specification, Z3 is N.

According to an exemplary embodiment of the present specification, Z4 is N.

According to an exemplary embodiment of the present specification, the compound of Chemical Formula 1 may be any one selected from the following compounds. However, the compound of Chemical Formula 1 is not limited to the following structures.

[Compound 1-1]
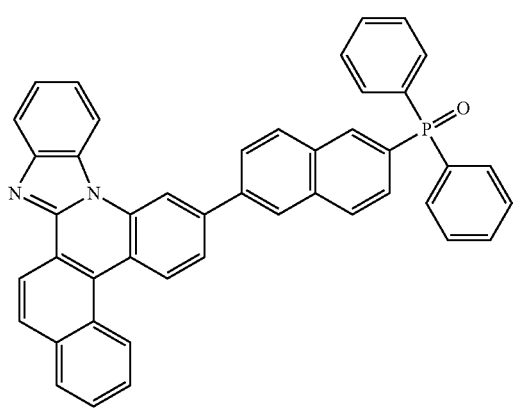
[Compound 1-2]
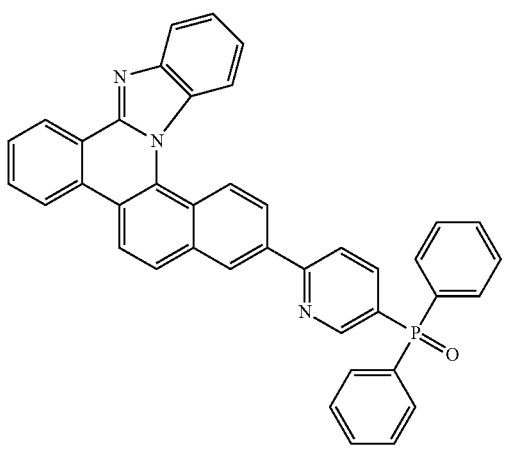
[Compound 1-3]
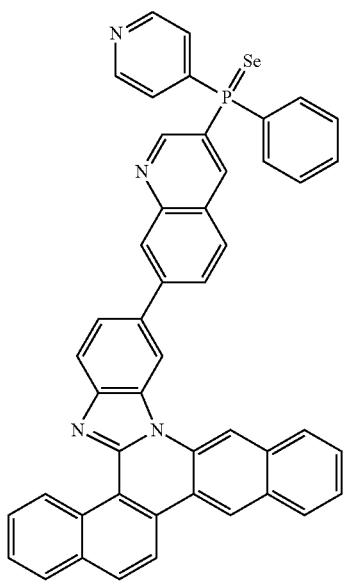
[Compound 1-4]
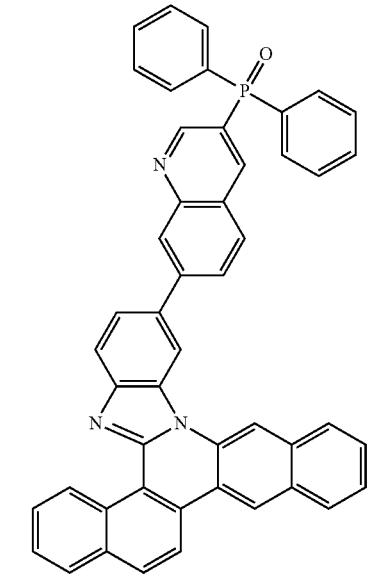
[Compound 1-5]
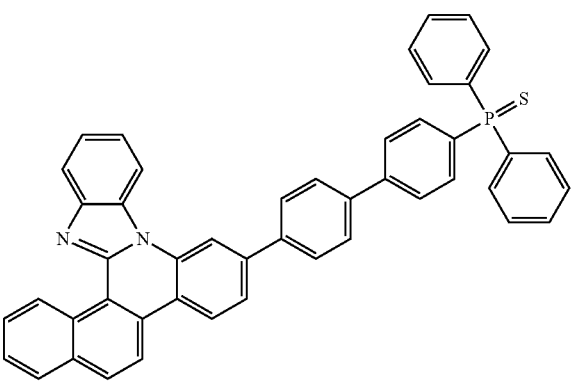
[Compound 1-6]
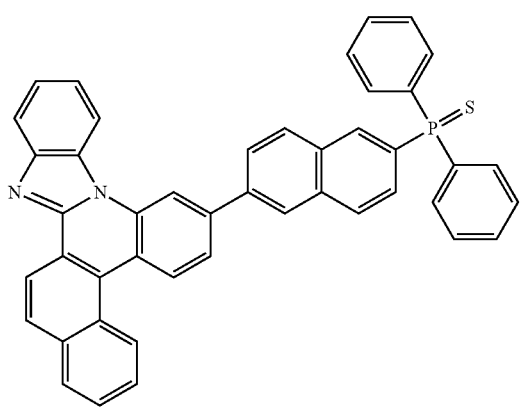

[Compound 1-7]
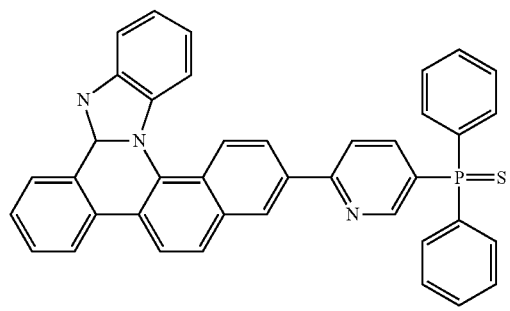
[Compound 1-10]
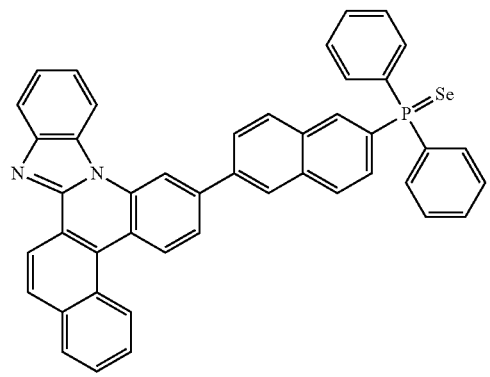
[Compound 1-8]
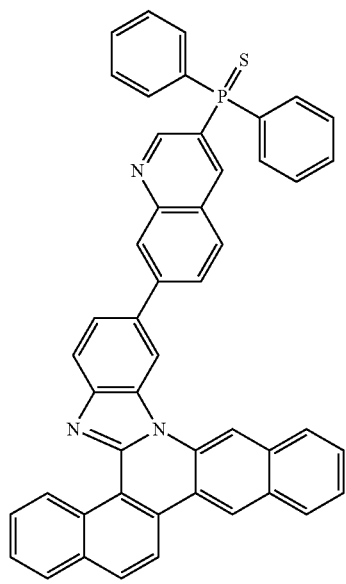
[Compound 1-11]
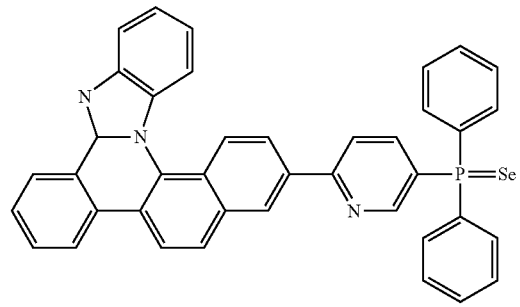
[Compound 1-9]
[Compound 1-12]
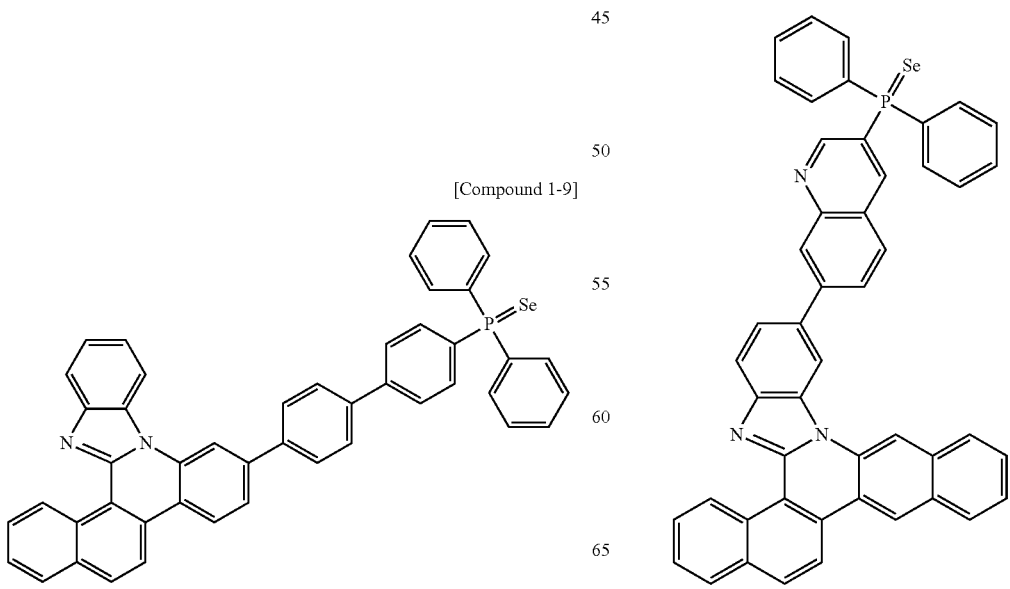

[Compound 1-13]
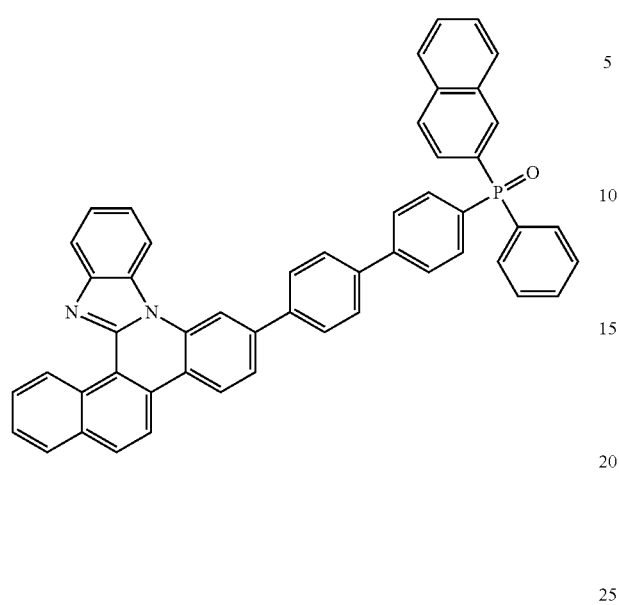
[Compound 1-14]
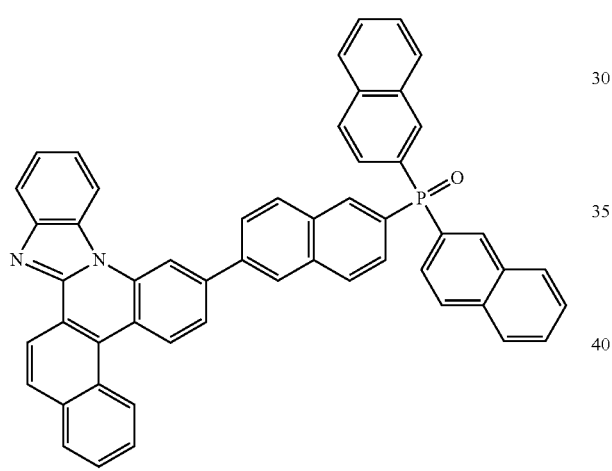
[Compound 1-15]
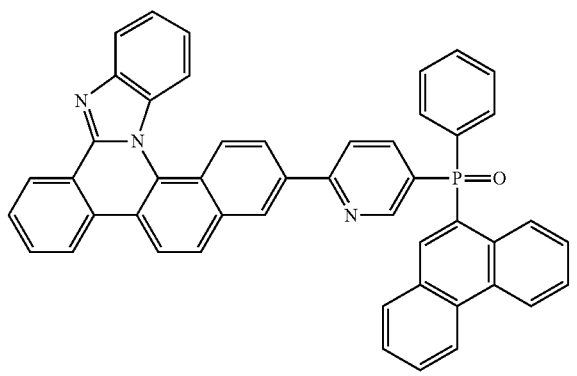
[Compound 1-16]
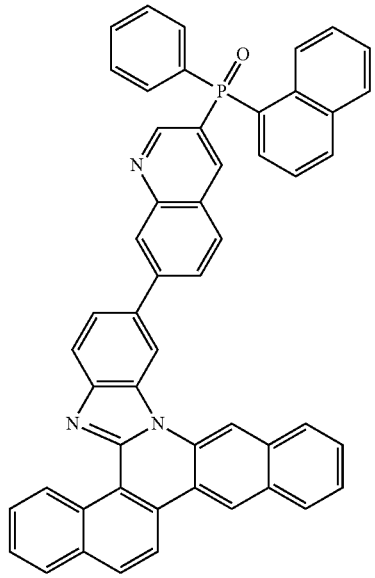
[Compound 1-17]
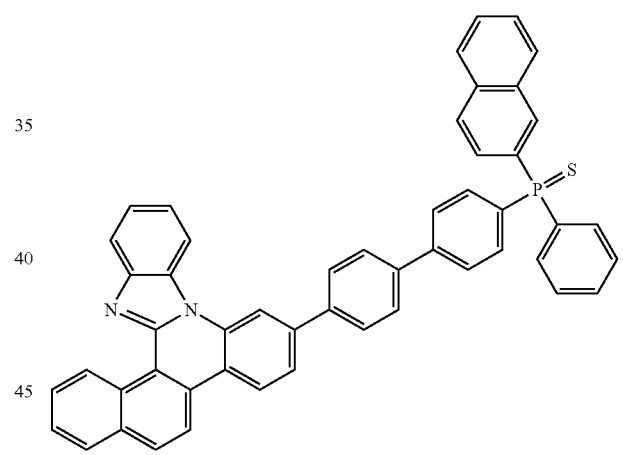
[Compound 1-18]
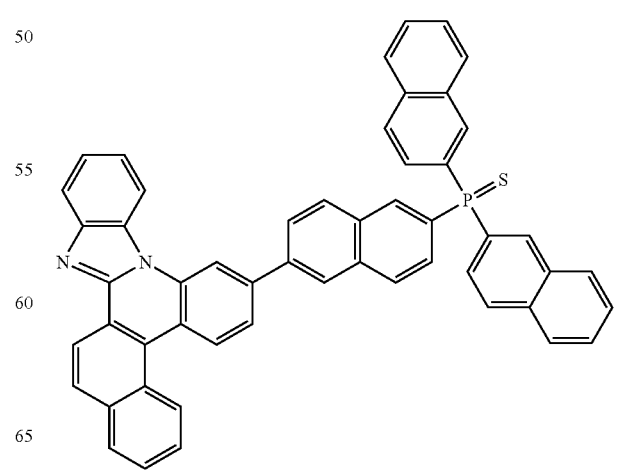

[Compound 1-19]
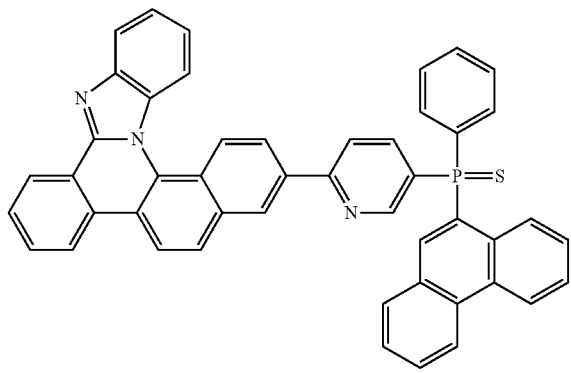
[Compound 1-20]
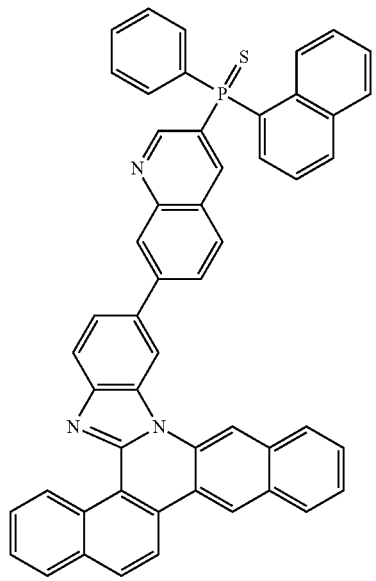
[Compound 1-21]
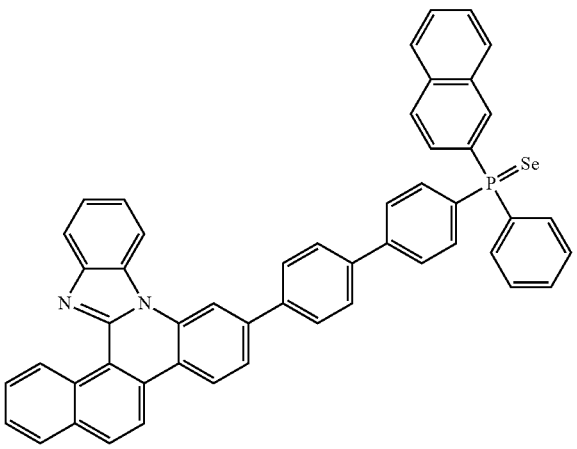
[Compound 1-22]
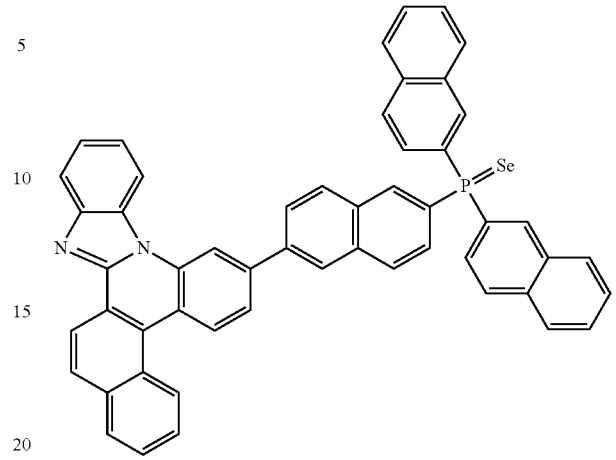
[Compound 1-23]
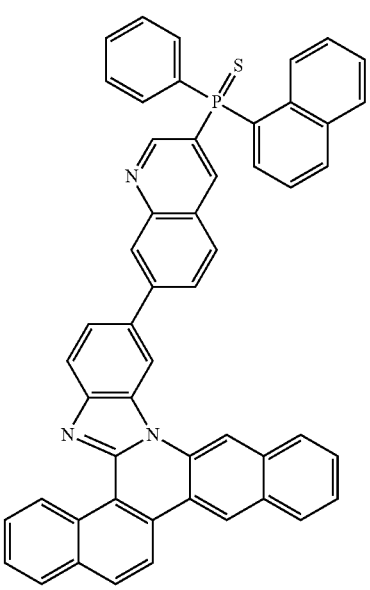
[Compound 1-24]

[Compound 1-25]
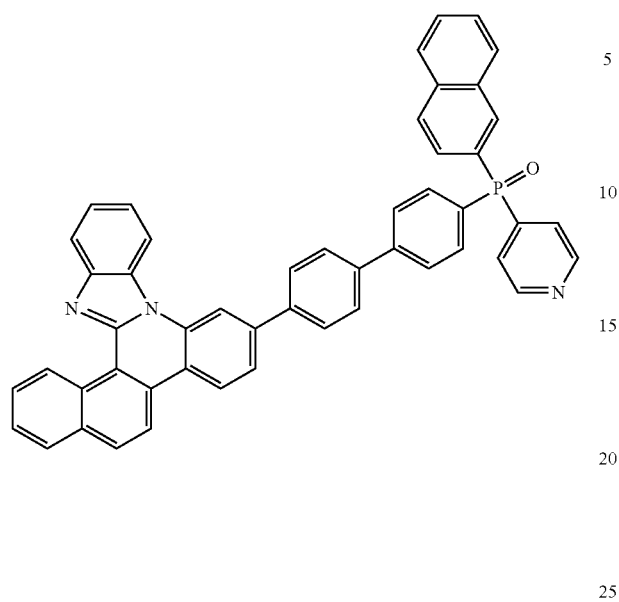
[Compound 1-26]
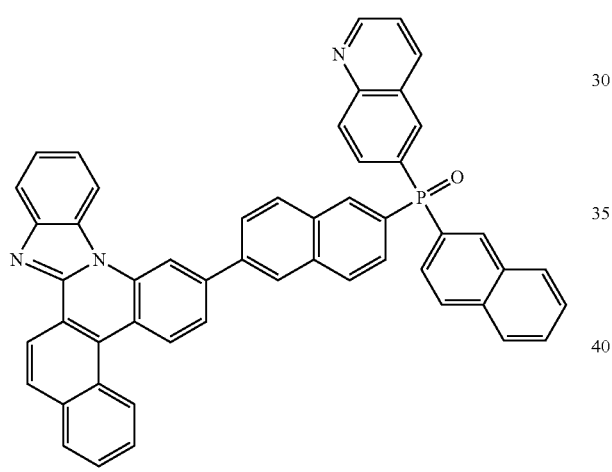
[Compound 1-27]
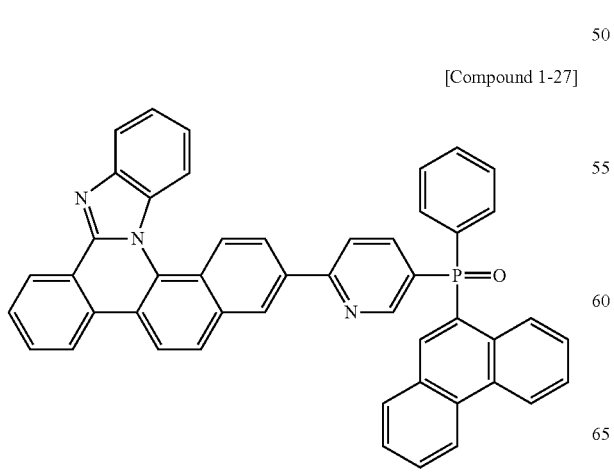
[Compound 1-28]
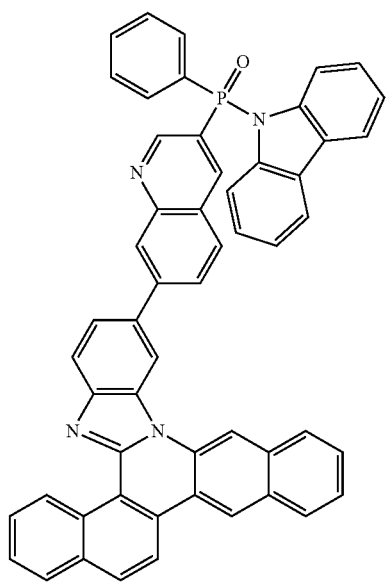
[Compound 1-29]
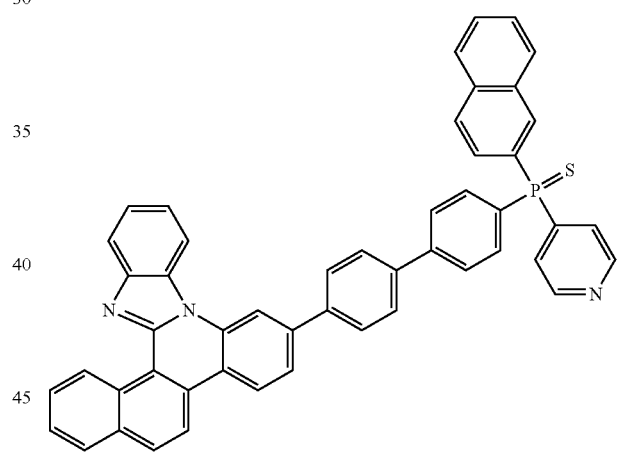
[Compound 1-30]
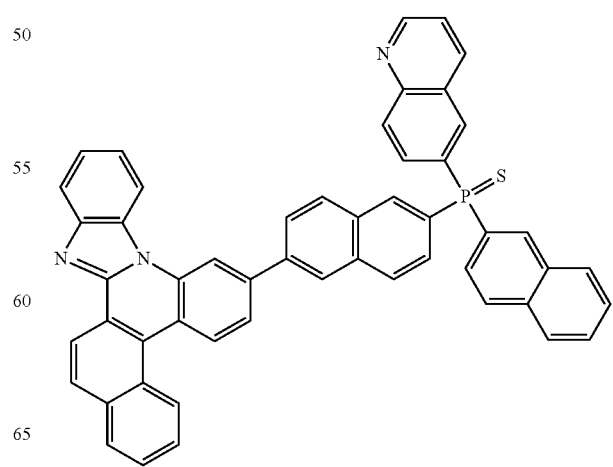

[Compound 1-31]
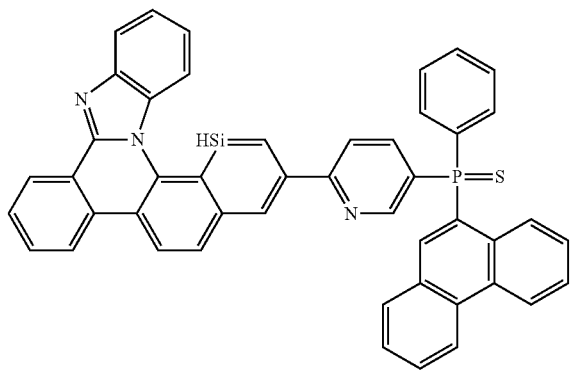
[Compound 1-34]
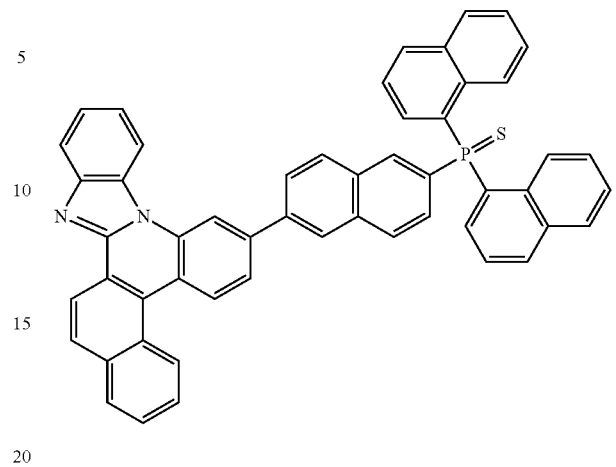
[Compound 1-32]
[Compound 1-35]
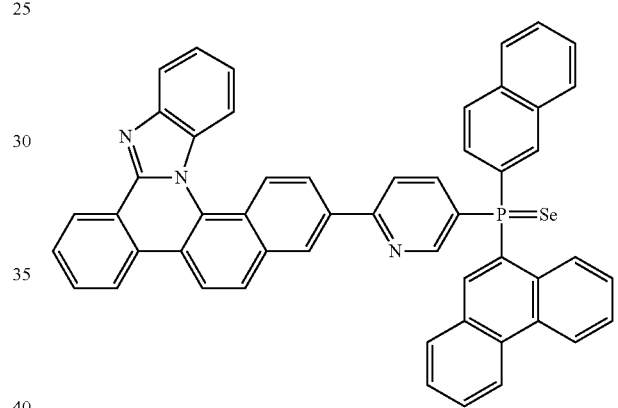
[Compound 1-36]
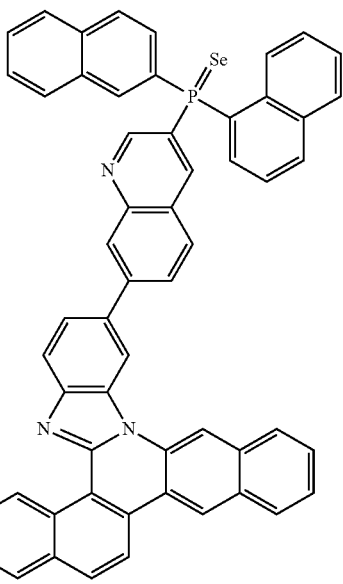
[Compound 1-33]

[Compound 1-37]
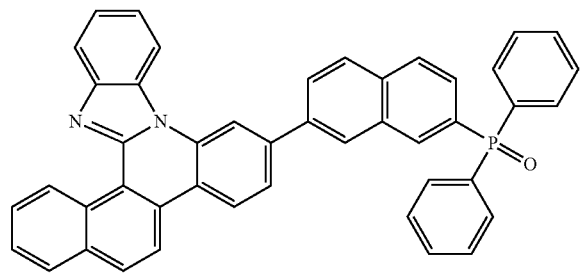
[Compound 1-41]
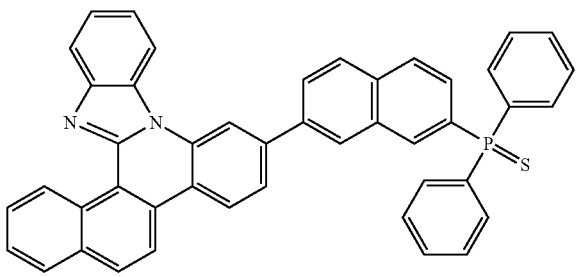
[Compound 1-38]
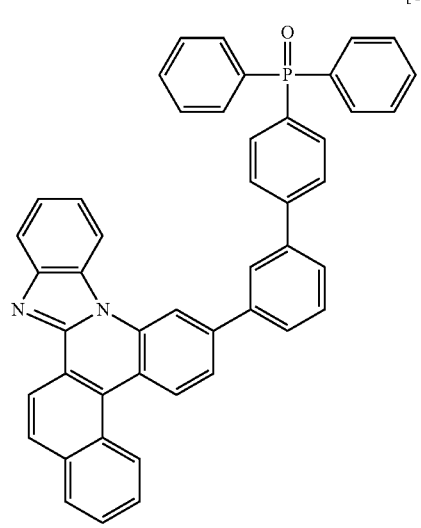
[Compound 1-42]
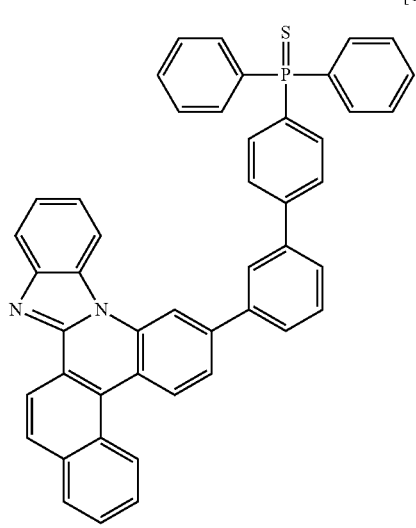
[Compound 1-39]
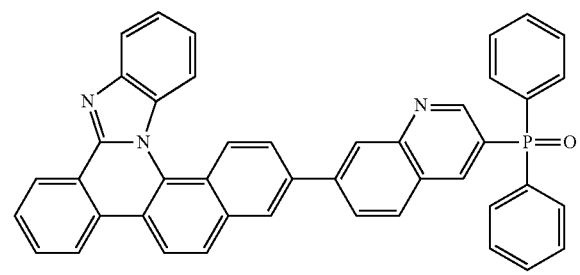
[Compound 1-43]
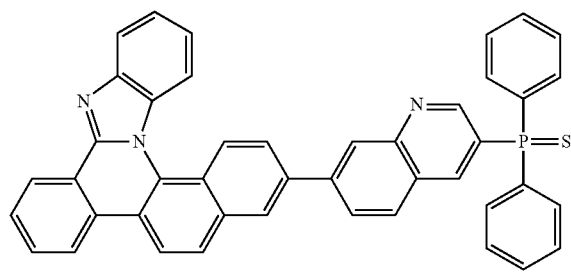
[Compound 1-40]
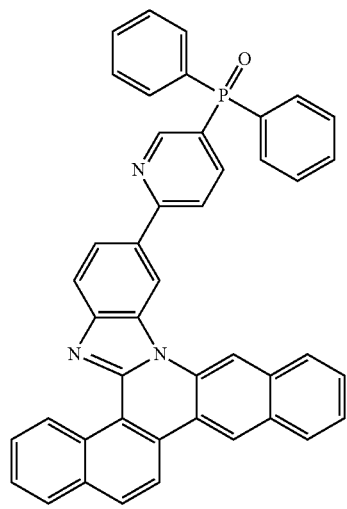
[Compound 1-44]
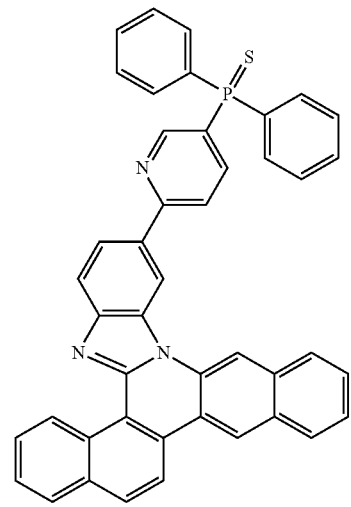

[Compound 1-45]
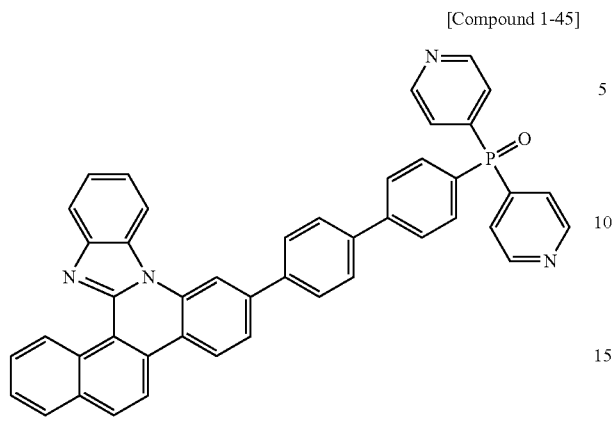
[Compound 1-46]
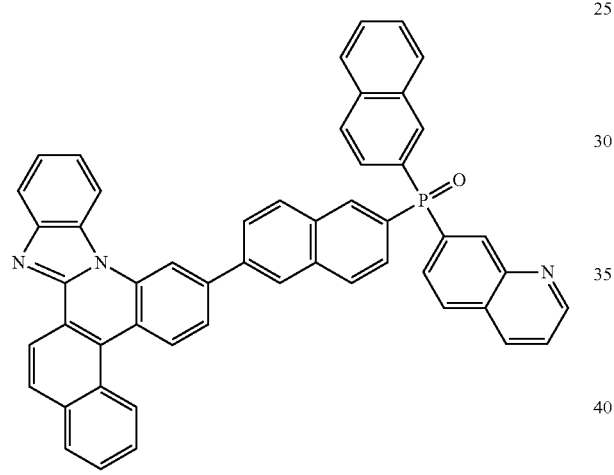
[Compound 1-47]
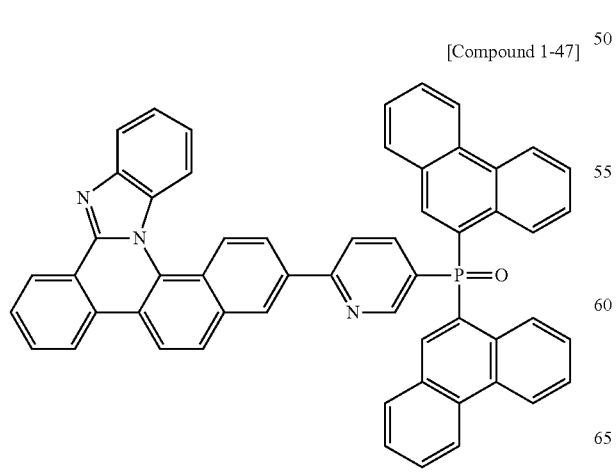
[Compound 1-48]
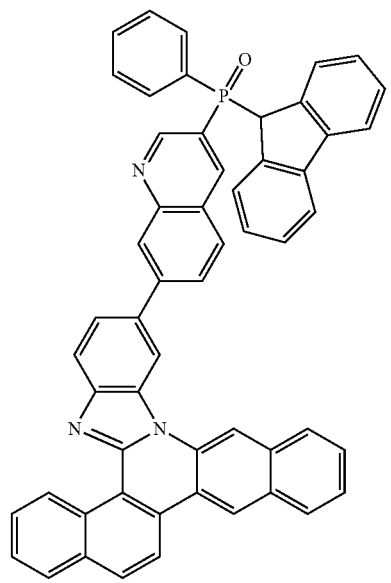
[Compound 1-49]
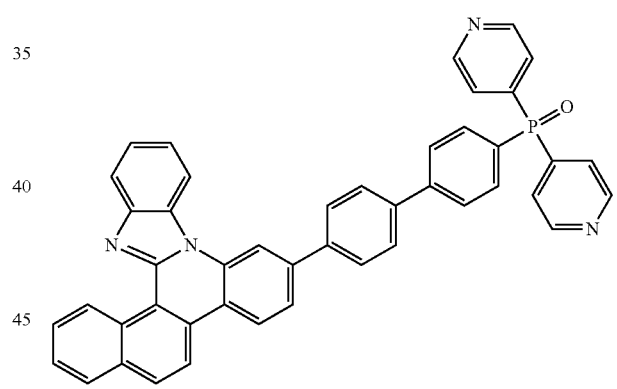
[Compound 1-50]
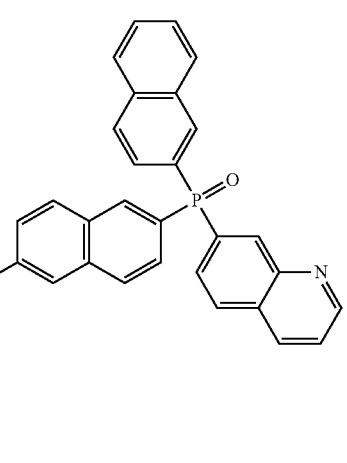

[Compound 1-51]
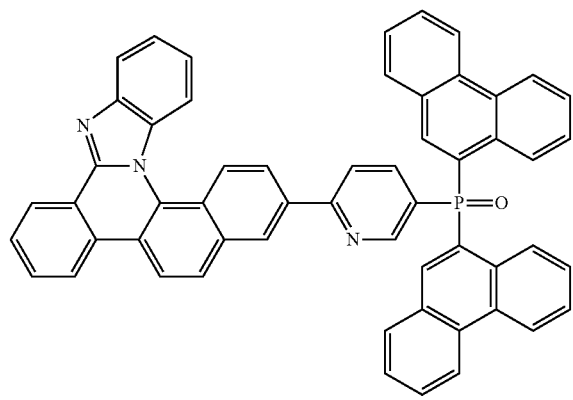
[Compound 1-52]
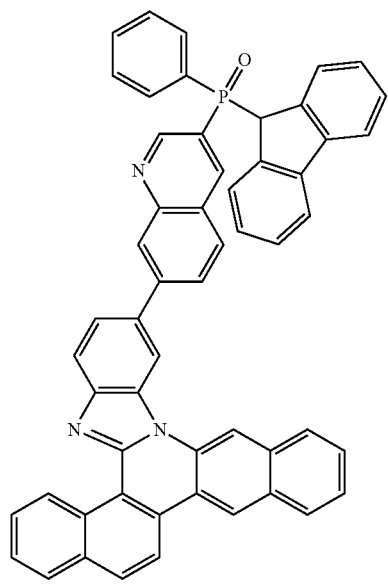
[Compound 1-53]
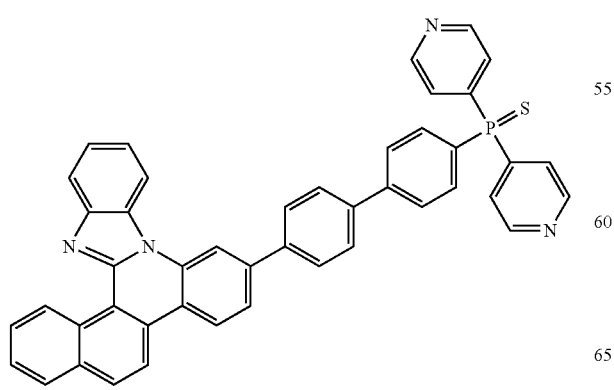
[Compound 1-54]
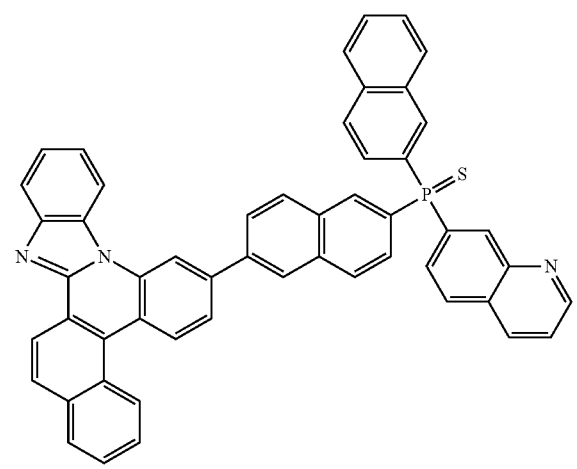
[Compound 1-55]
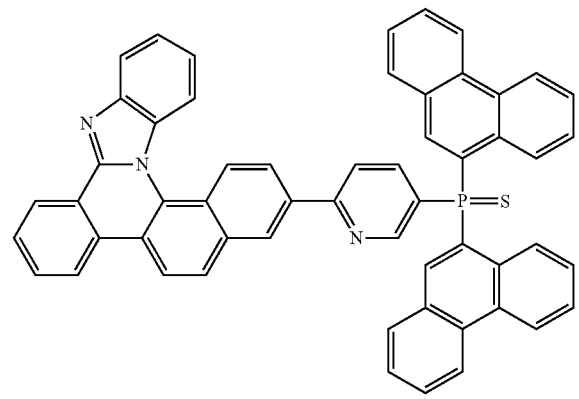
[Compound 1-56]
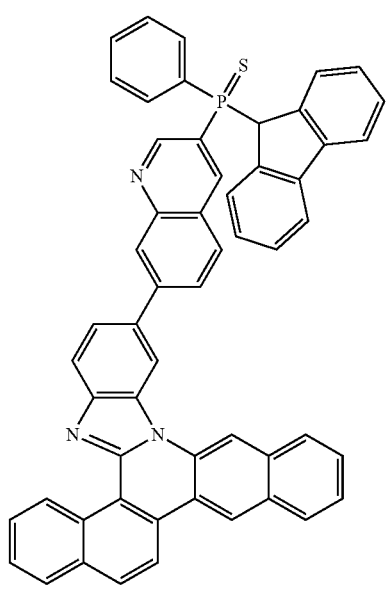

[Compound 1-57]
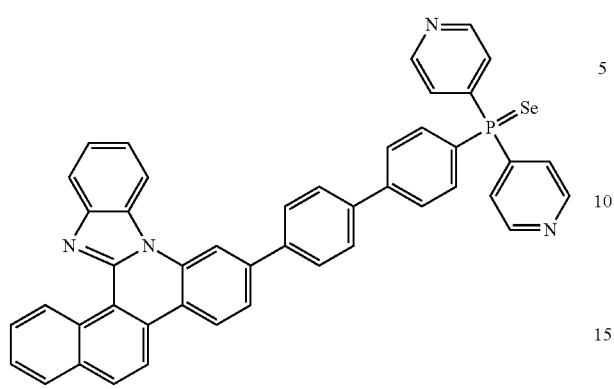
[Compound 1-58]
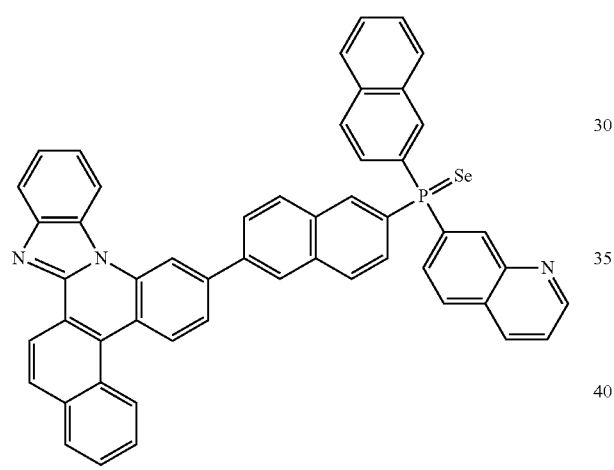
[Compound 1-59]
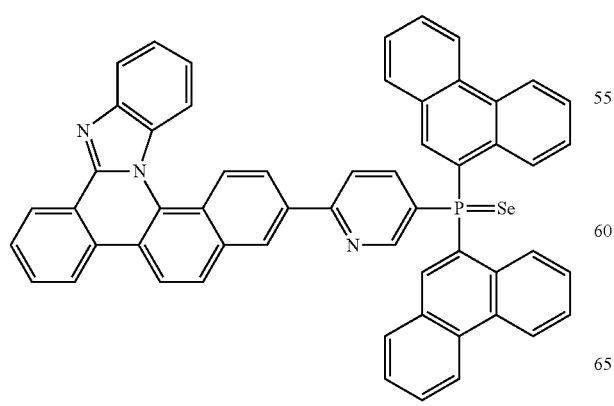
[Compound 1-60]
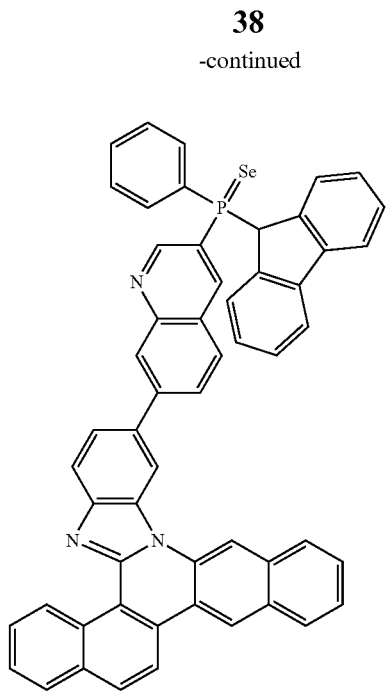
[Compound 1-61]
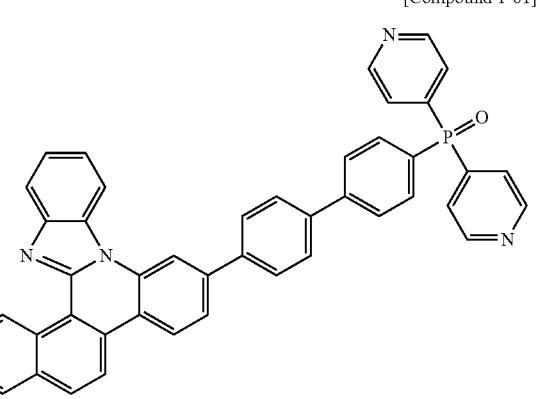
[Compound 1-62]
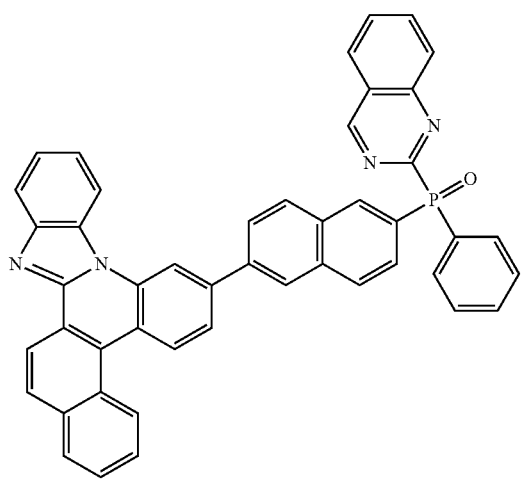

[Compound 1-63]
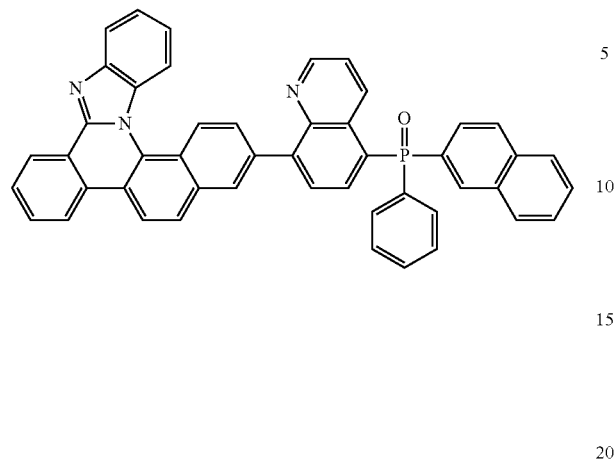
[Compound 1-64]
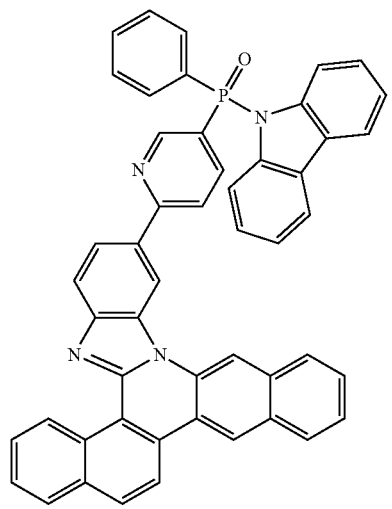
[Compound 1-65]
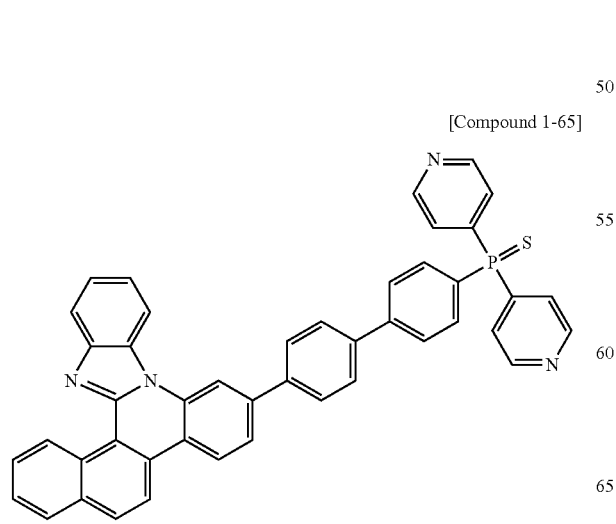
[Compound 1-66]
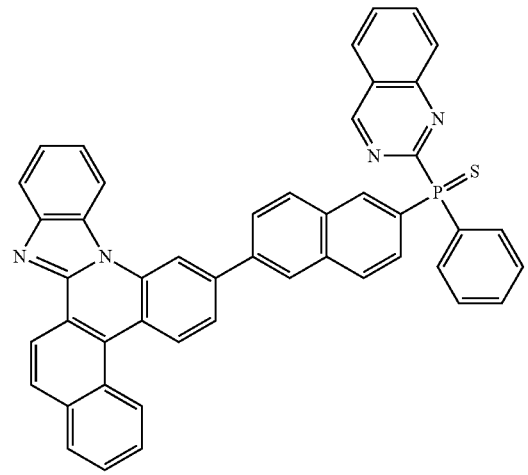
[Compound 1-67]
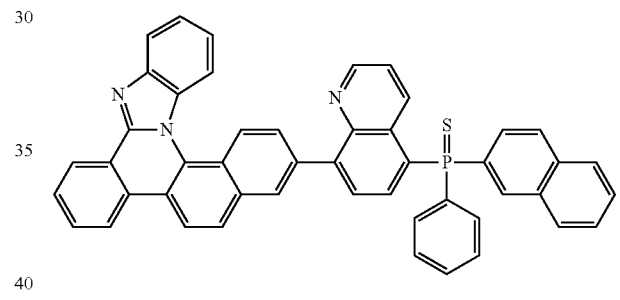
[Compound 1-68]
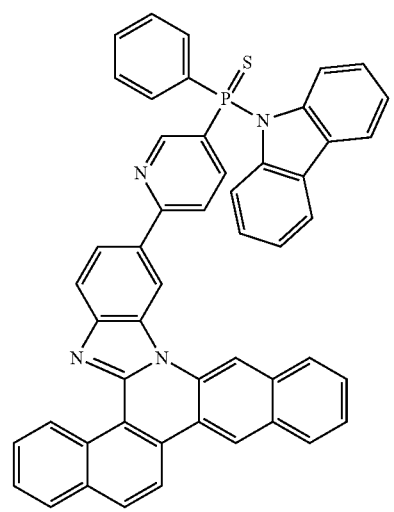

[Compound 1-69]
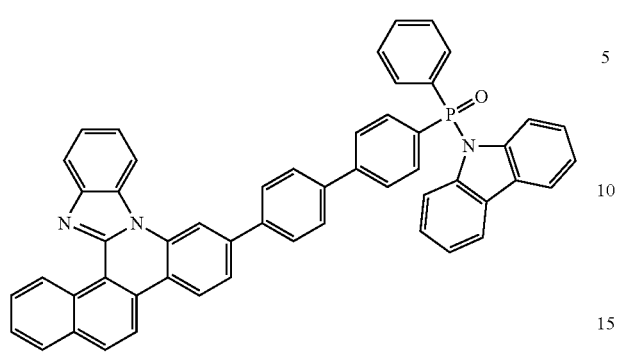
[Compound 1-70]
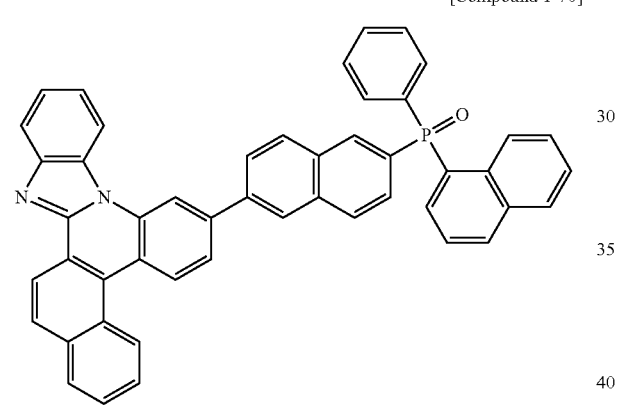
[Compound 1-71]
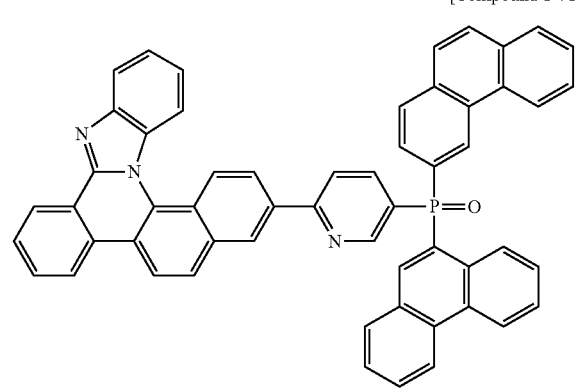
[Compound 1-72]
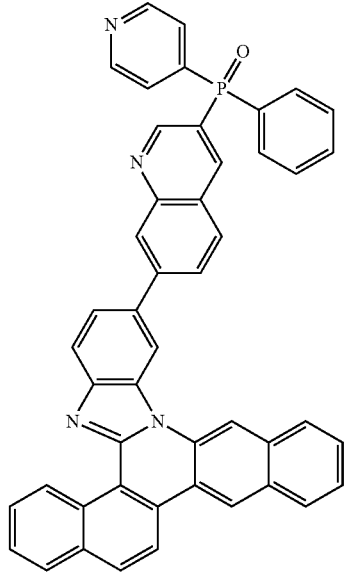
[Compound 1-73]
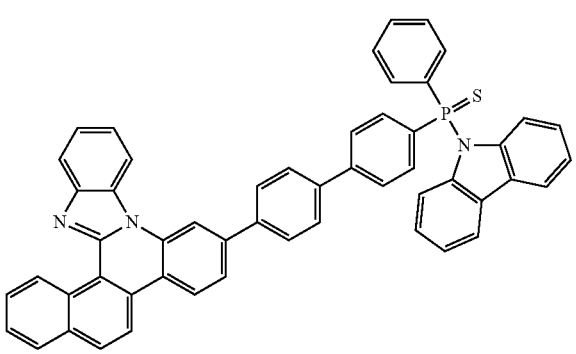
[Compound 1-74]
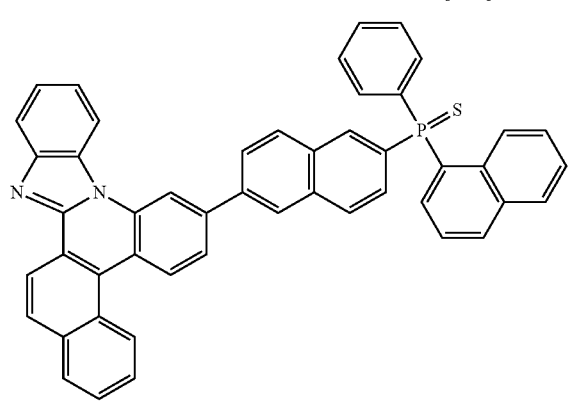

[Compound 1-75]
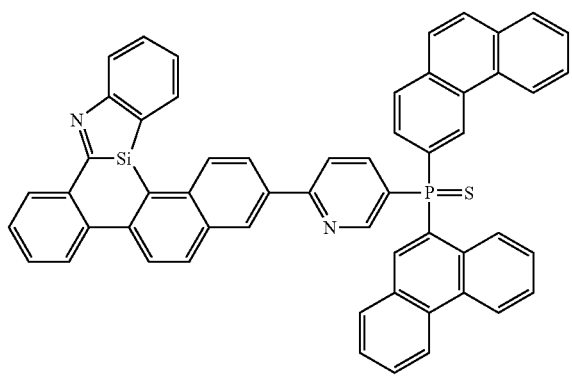
[Compound 1-78]
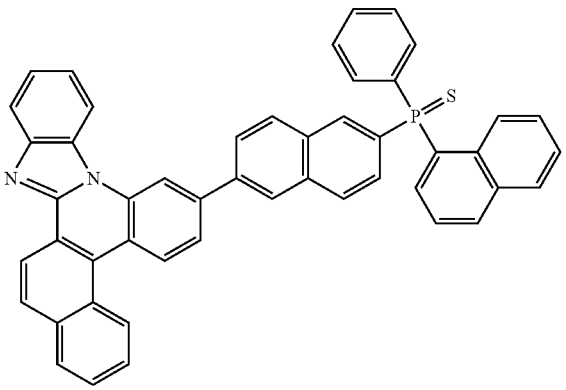
[Compound 1-76]
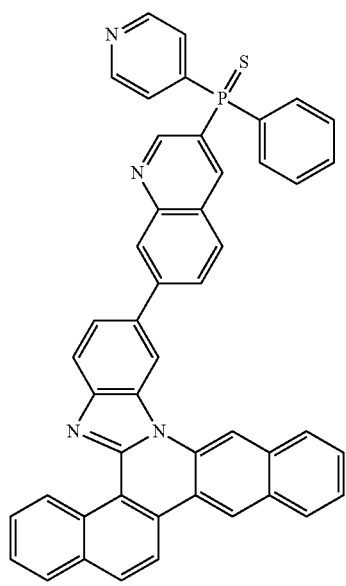
[Compound 1-79]
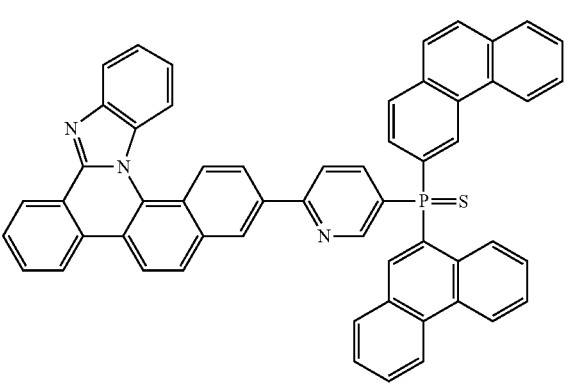
[Compound 1-77]
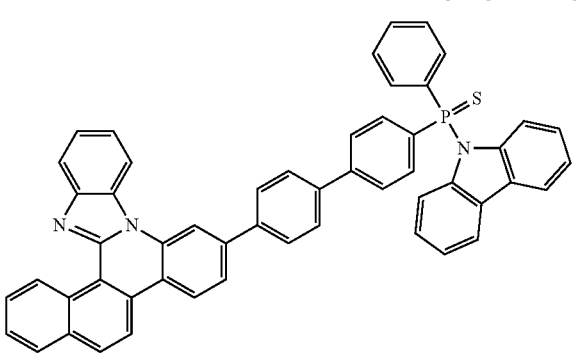
[Compound 1-80]
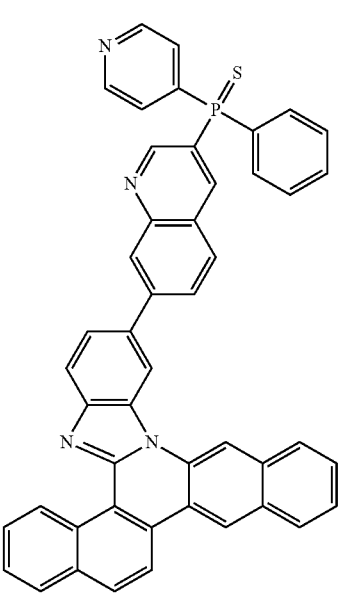

[Compound 1-81]
[Compound 1-82]
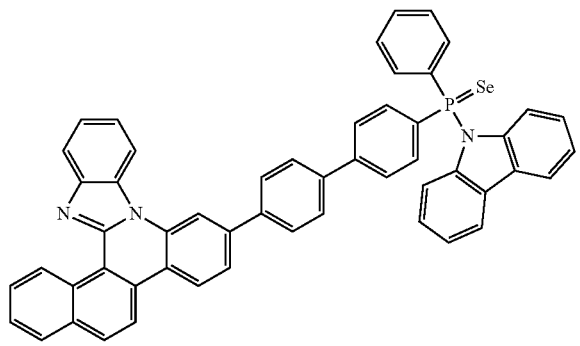
[Compound 1-83]
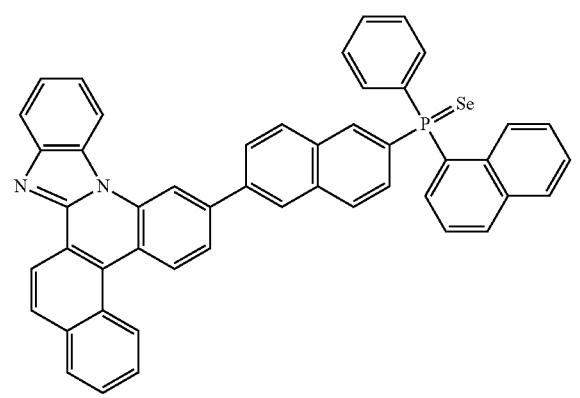
[Compound 1-84]
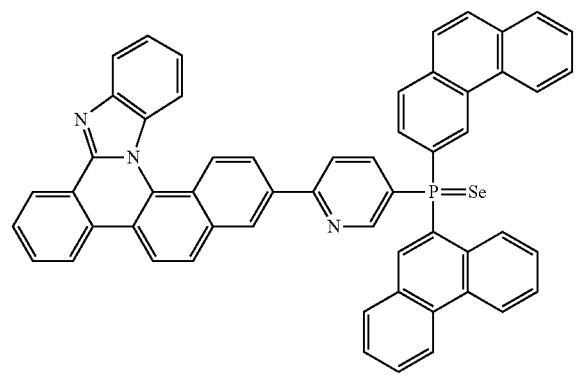
[Compound 1-85]
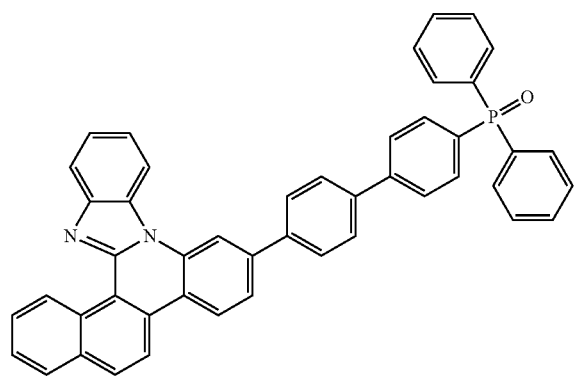
[Compound 1-86]
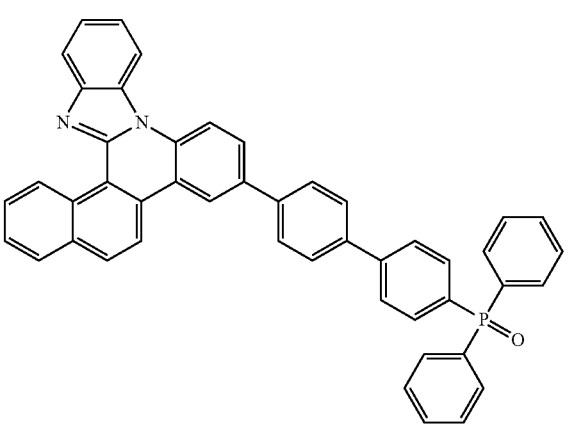
[Compound 1-87]
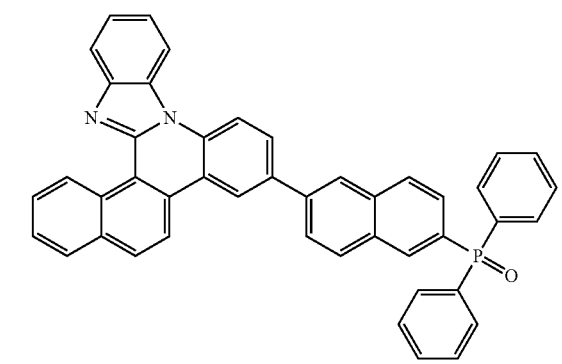
[Compound 1-88]
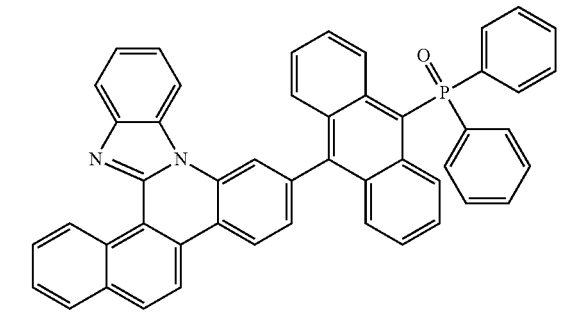

[Compound 1-89]
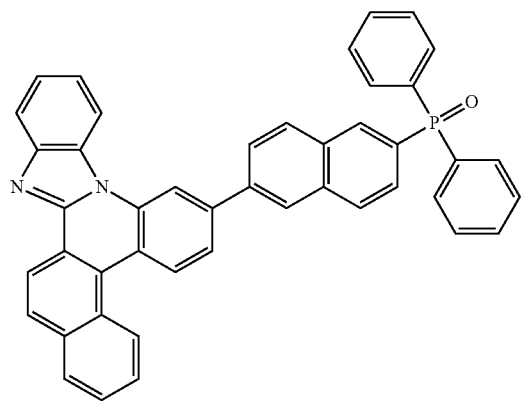
[Compound 1-90]
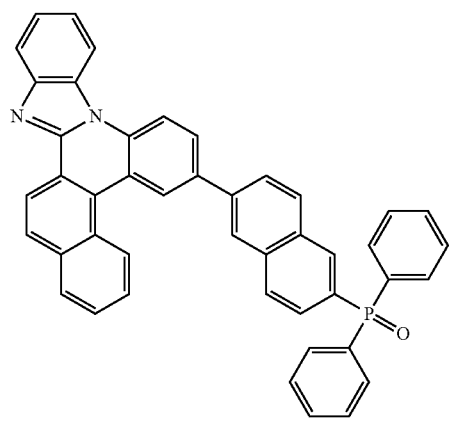
[Compound 1-91]
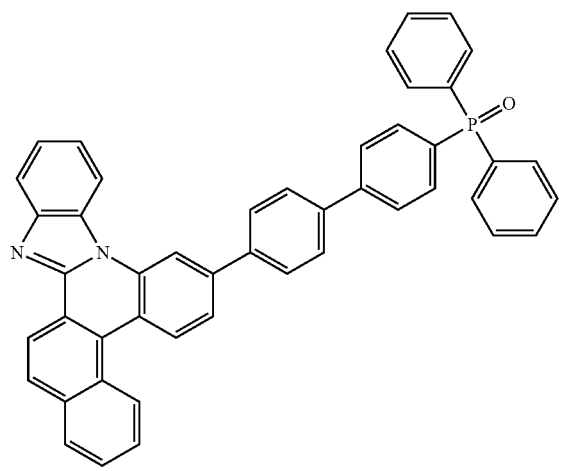
[Compound 1-92]
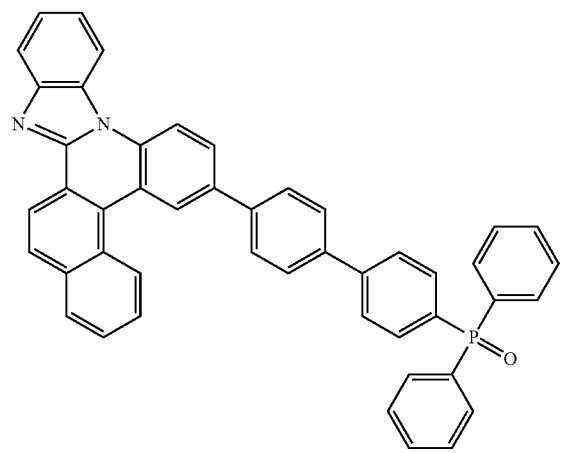
[Compound 1-93]
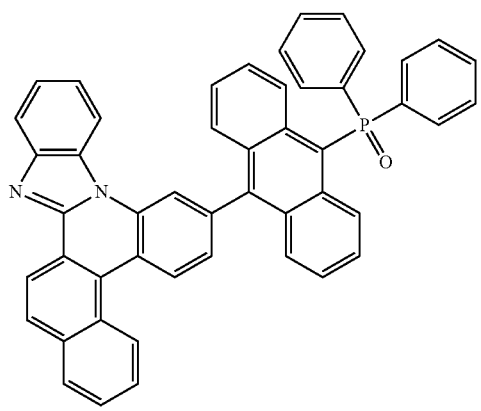
[Compound 1-94]
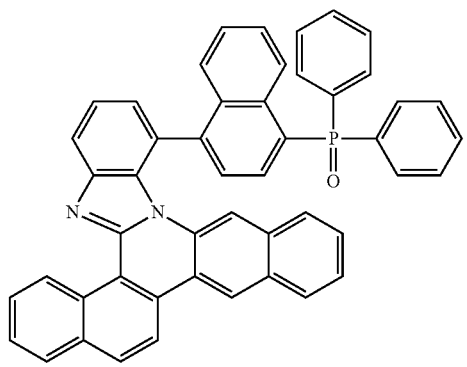

[Compound 1-95]
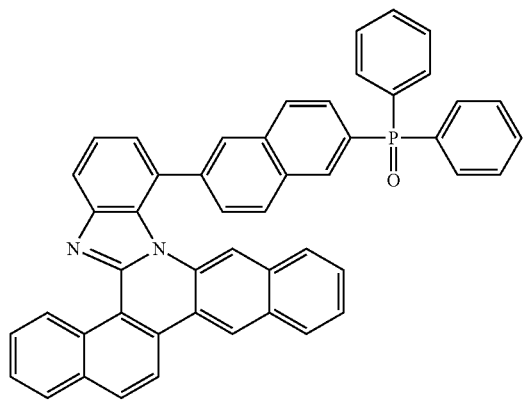
[Compound 1-98]
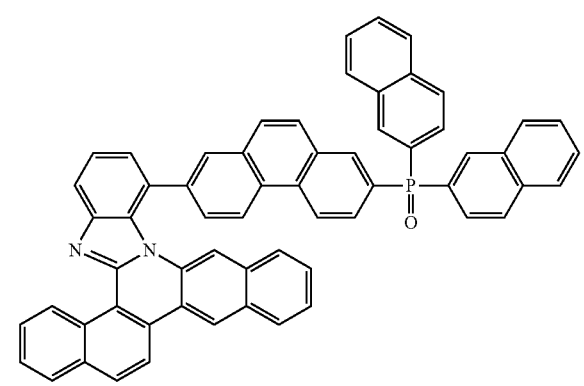
[Compound 1-96]
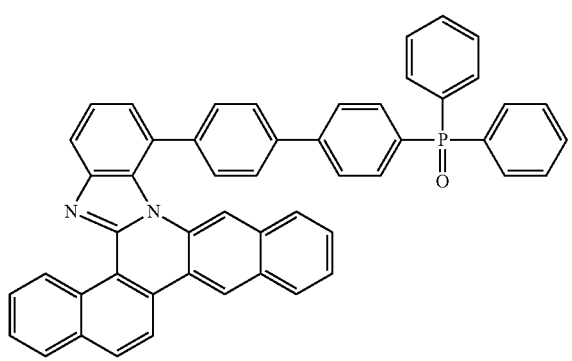
[Compound 1-99]
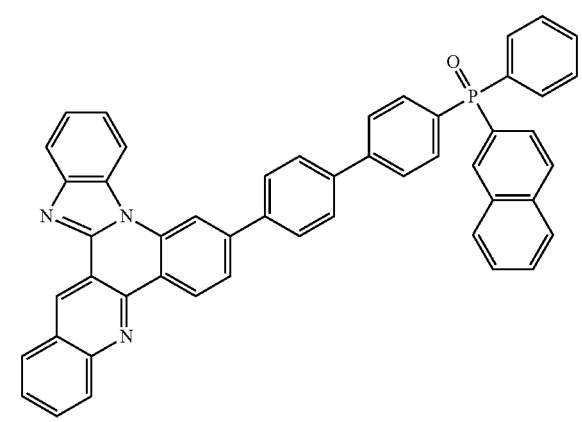
[Compound 1-97]
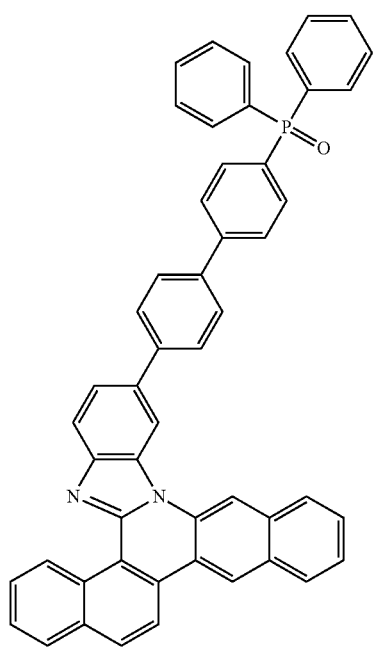
[Compound 1-100]
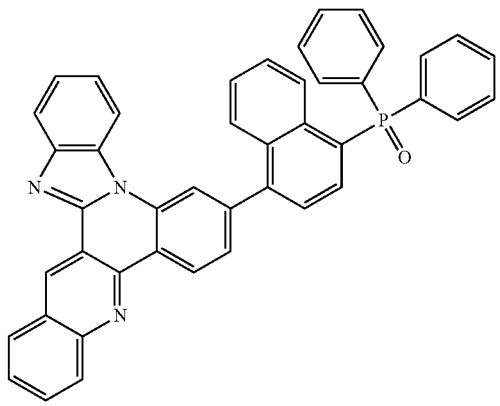

[Compound 1-101]
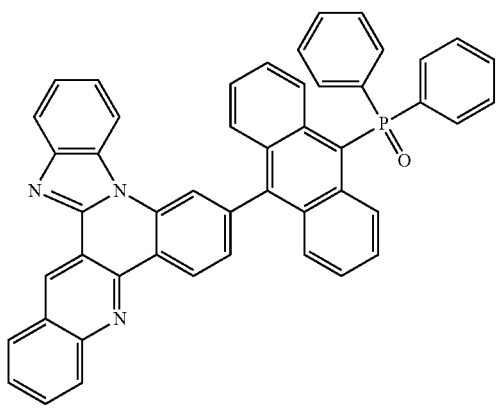
[Compound 1-104]
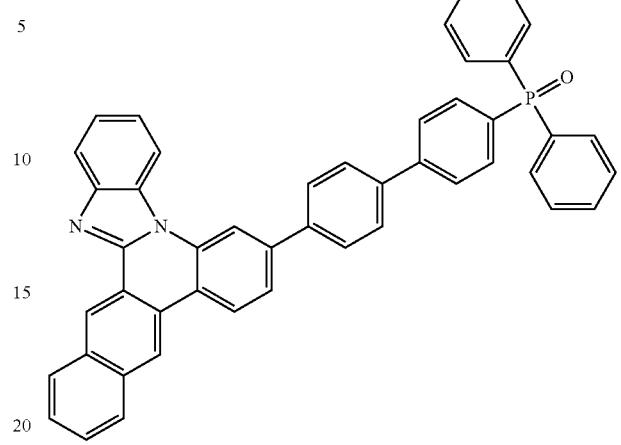
[Compound 1-102]
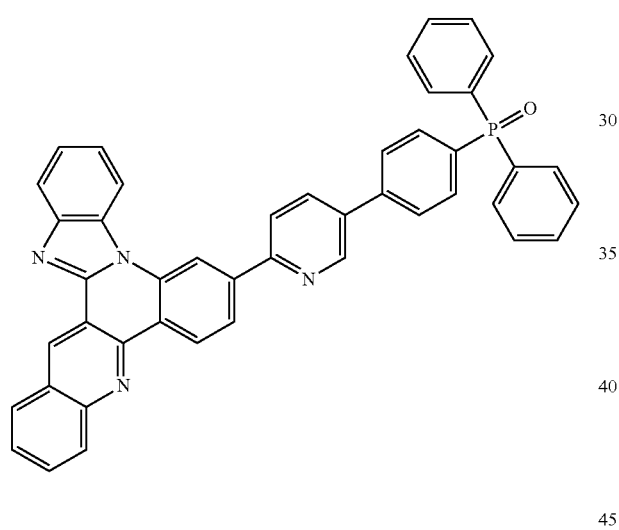
[Compound 1-105]
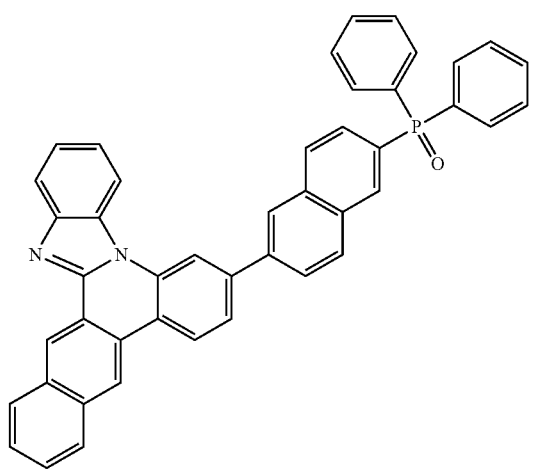
[Compound 1-103]
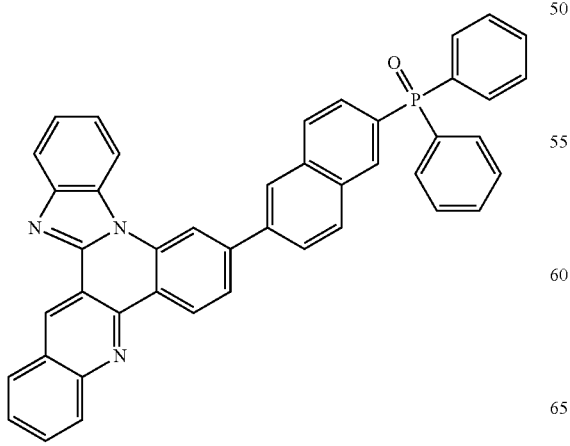
[Compound 1-106]
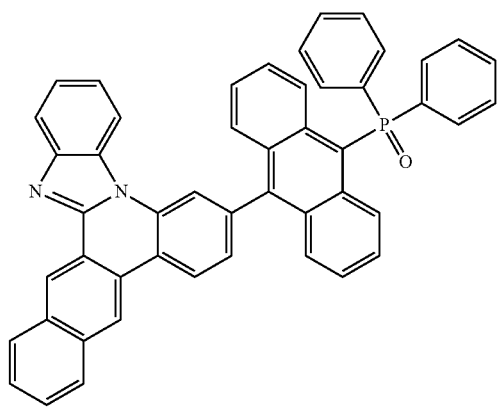

[Compound 1-107]
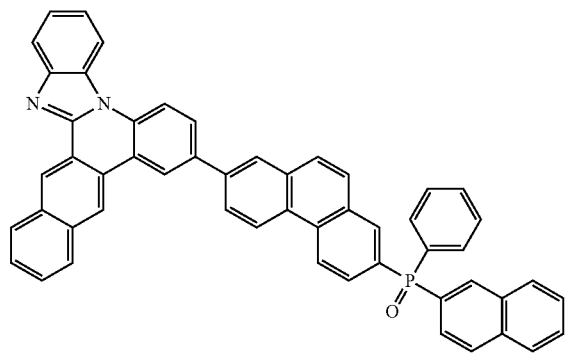
[Compound 1-108]
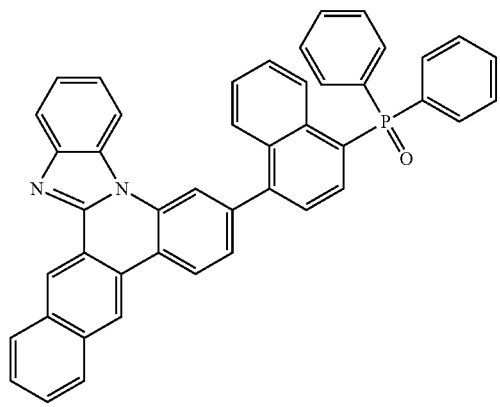
[Compound 1-109]
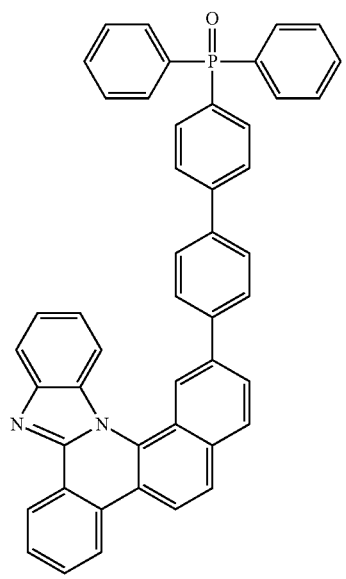
[Compound 1-110]
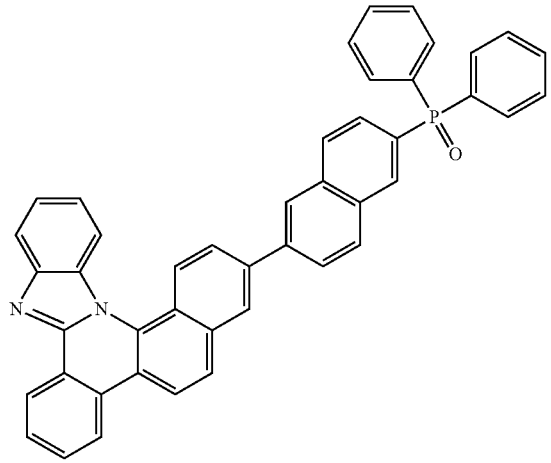
[Compound 1-111]
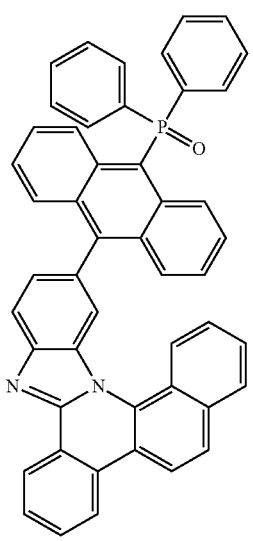
[Compound 1-112]
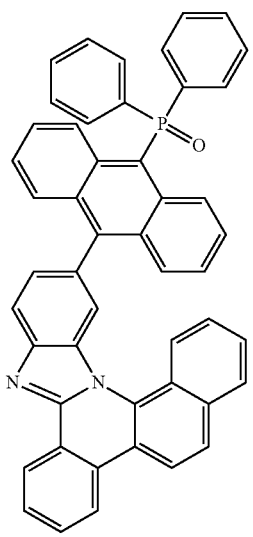

[Compound 1-113]
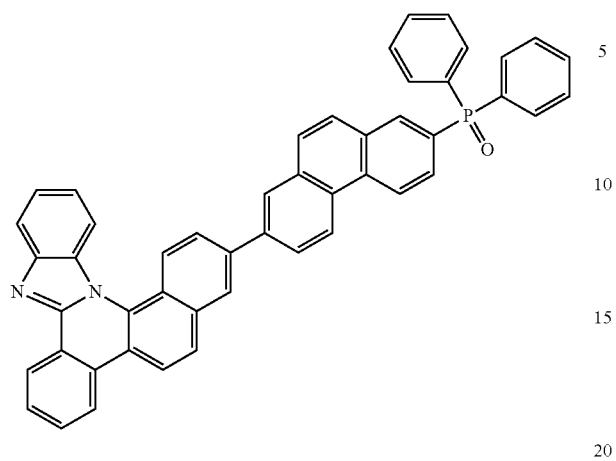
According to an exemplary embodiment of the present specification, the compound of Chemical Formula 1 may be any one selected from the following compounds. However, the compound of Chemical Formula 1 is not limited to the following structures.
[Compound 2-1]
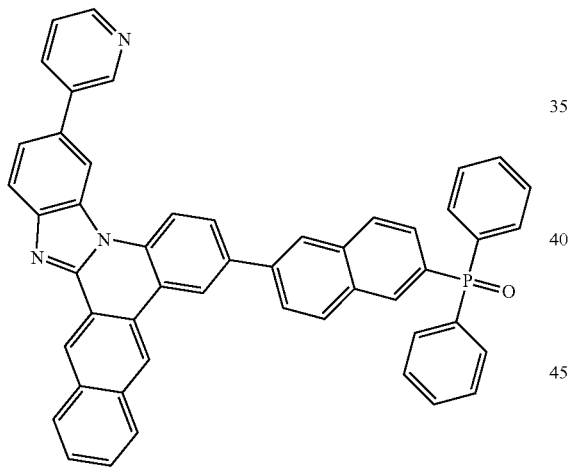
[Compound 2-2]
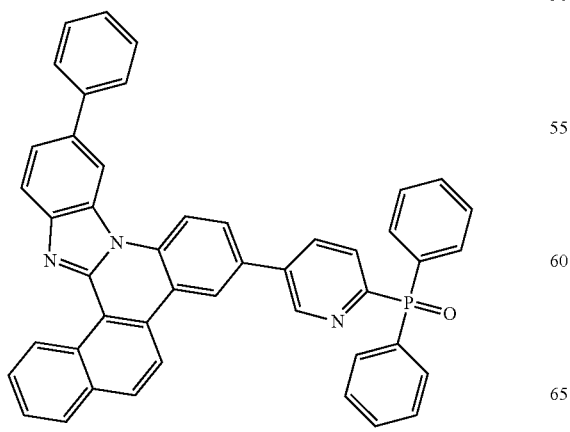
[Compound 2-3]
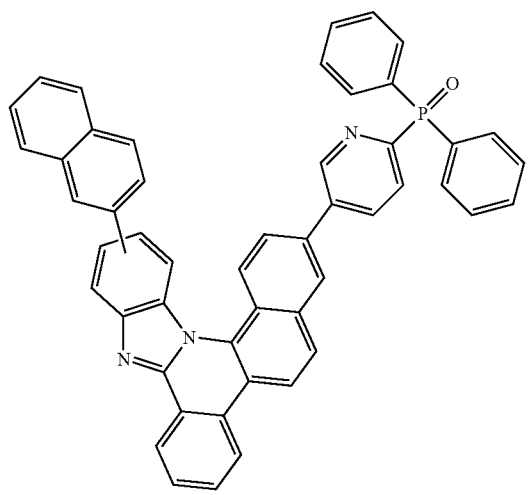
[Compound 2-4]
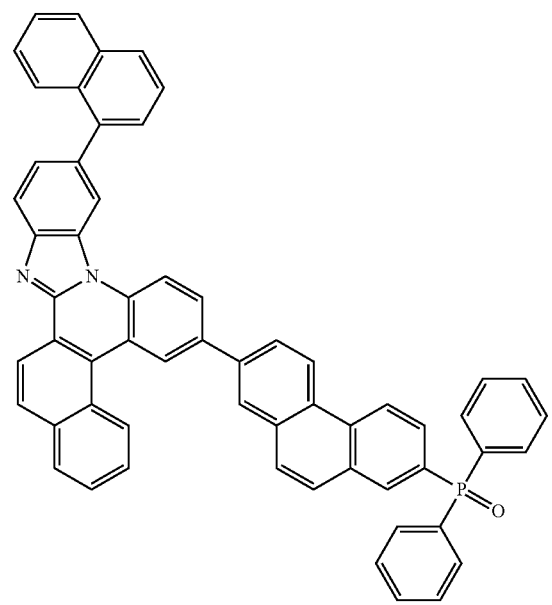

[Compound 2-5]
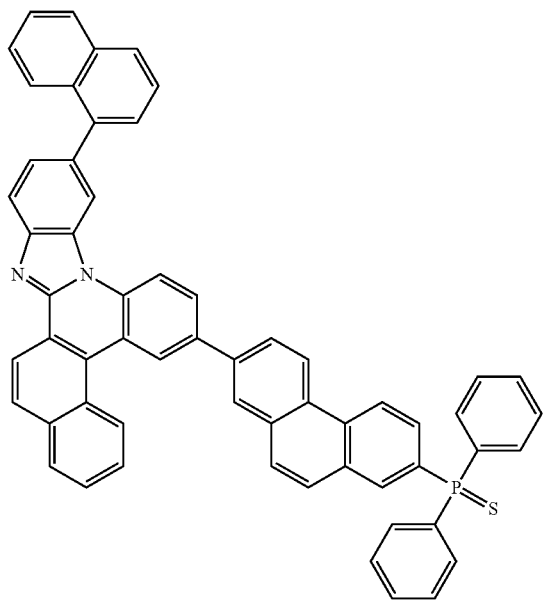
[Compound 2-6]
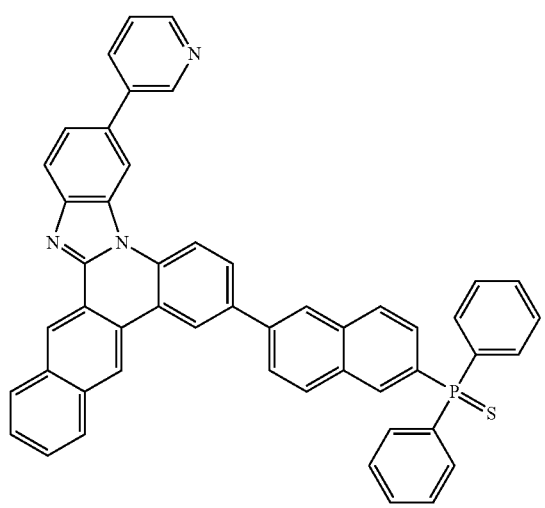
[Compound 2-7]
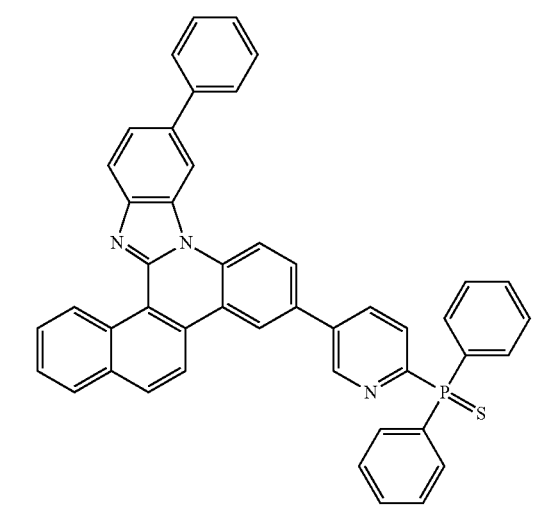
[Compound 2-8]
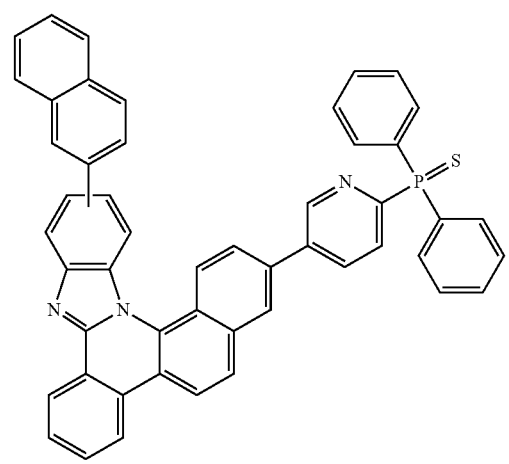
[Compound 2-9]
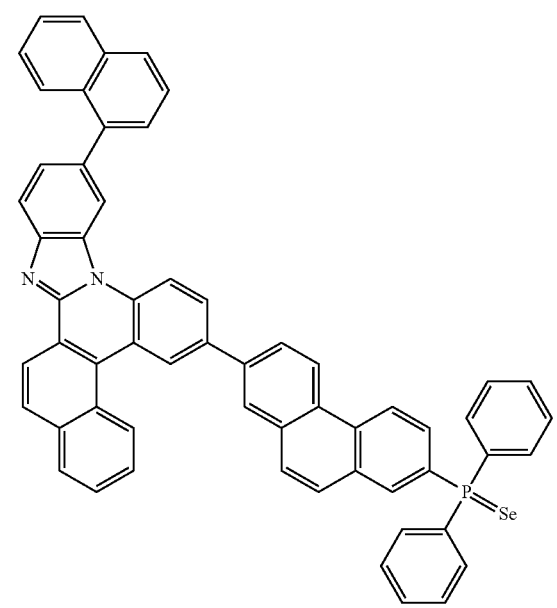
[Compound 2-10]
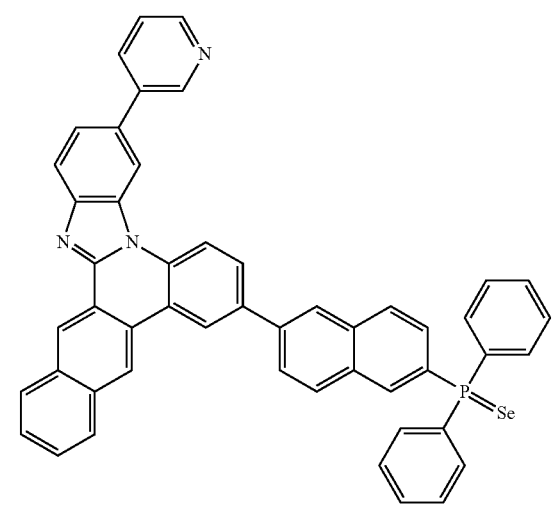

[Compound 2-11]
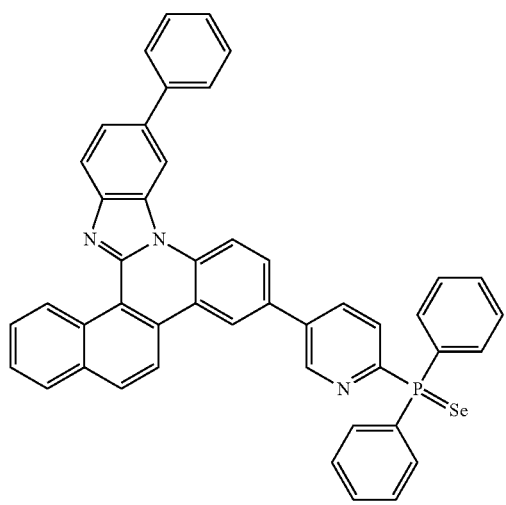
[Compound 2-12]
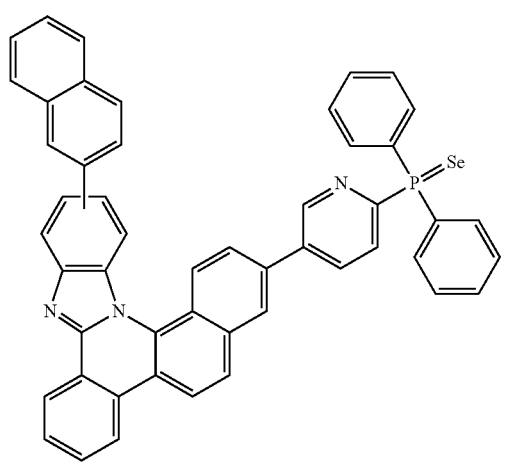
[Compound 2-13]
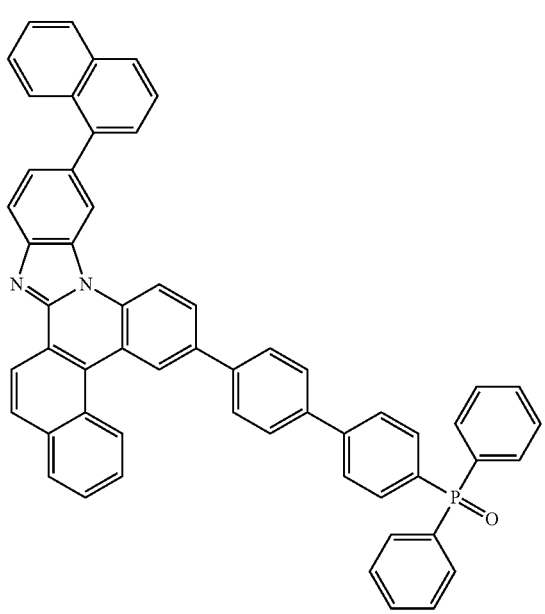
[Compound 2-14]
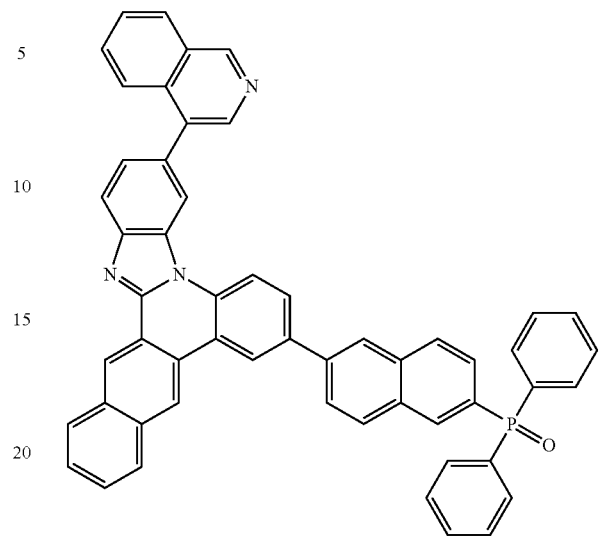
[Compound 2-15]
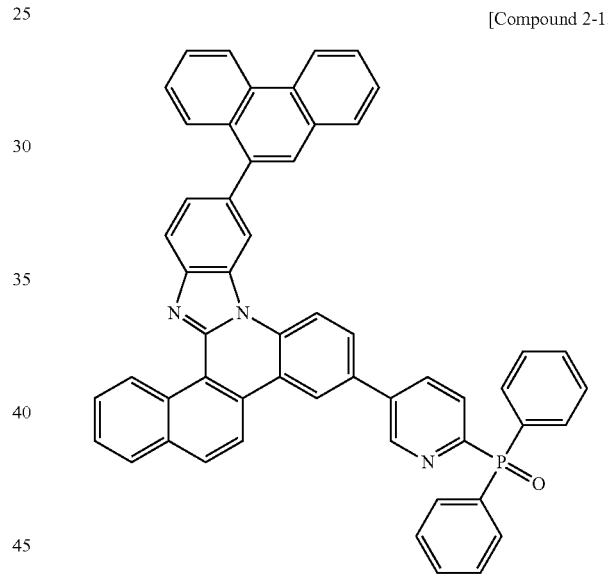
[Compound 2-16]
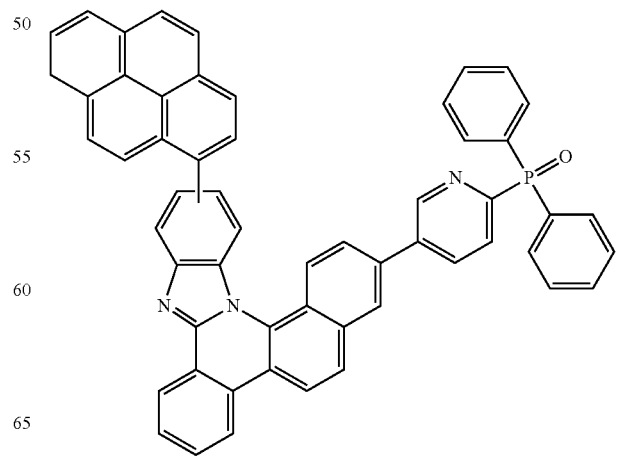

[Compound 2-17]
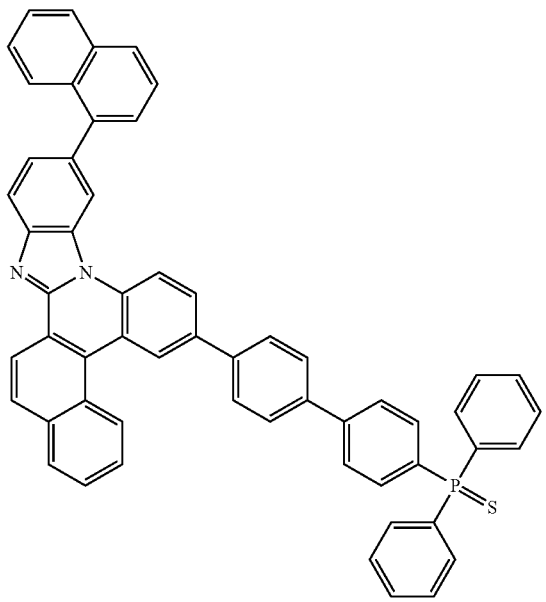
[Compound 2-18]
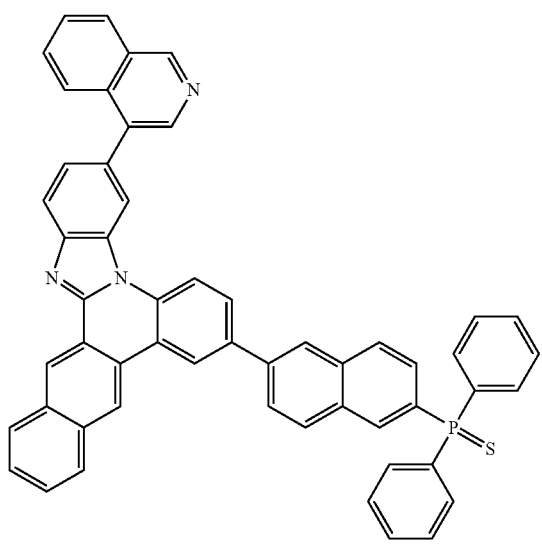
[Compound 2-19]
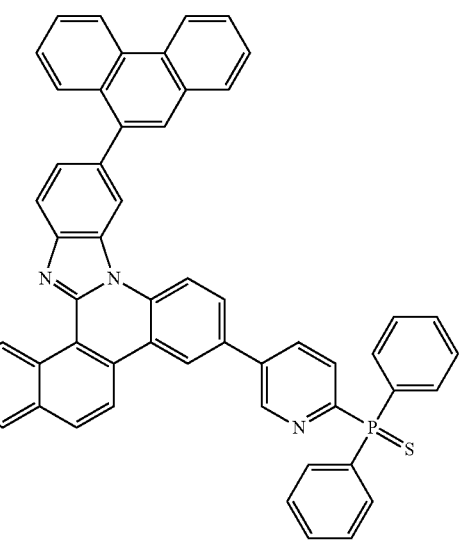
[Compound 2-20]
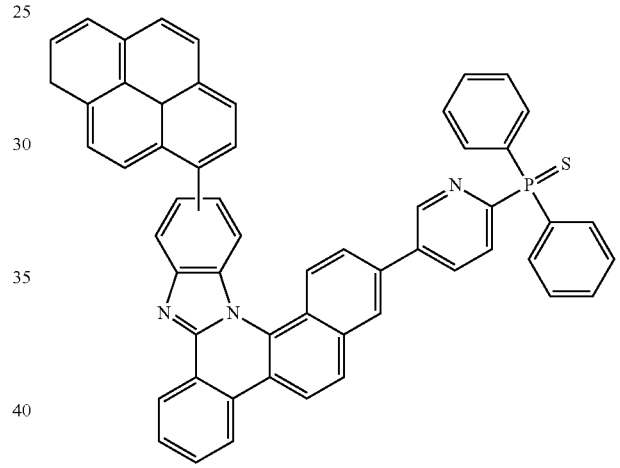
[Compound 2-21]
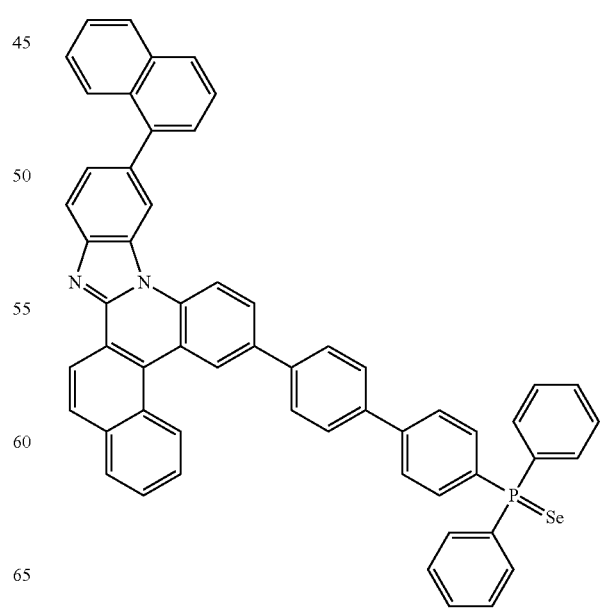

[Compound 2-22]
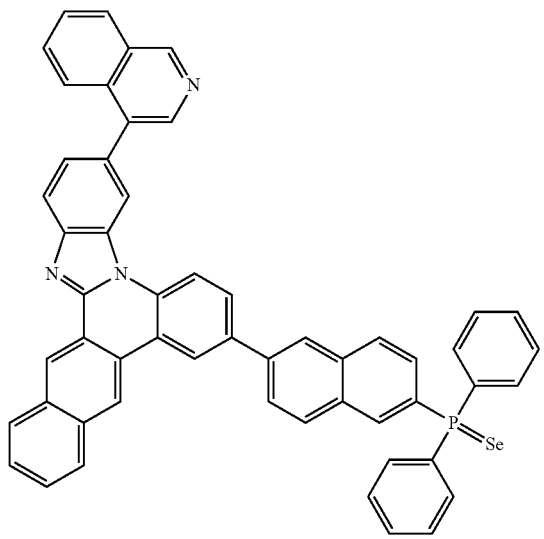
[Compound 2-25]
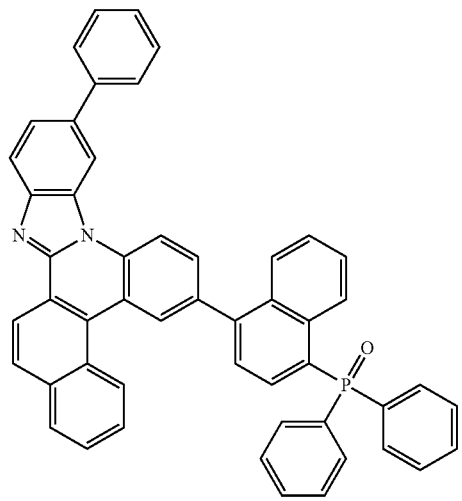
[Compound 2-23]
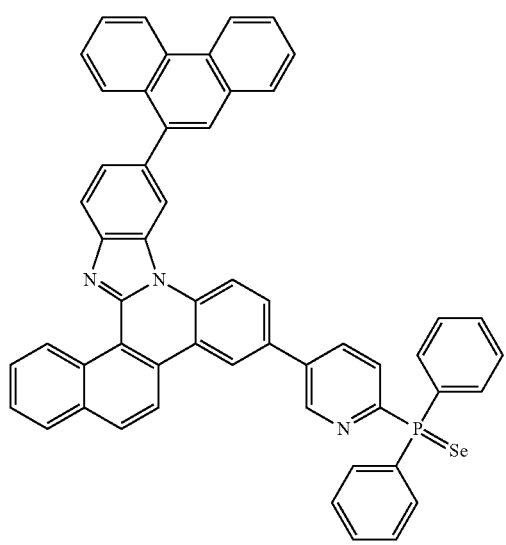
[Compound 2-26]
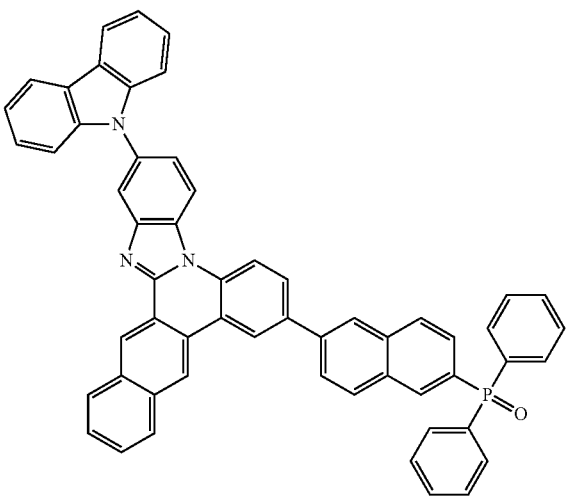
[Compound 2-24]
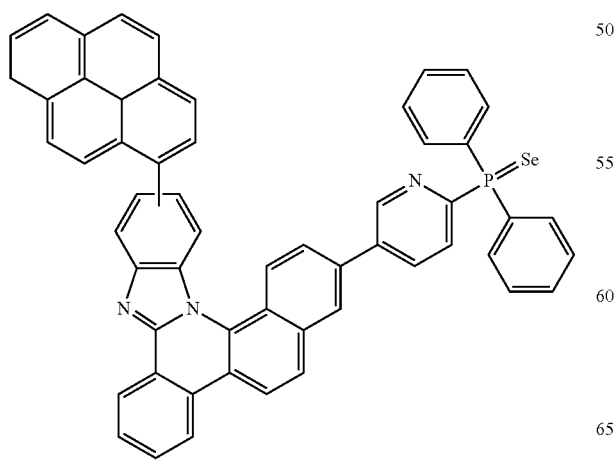
[Compound 2-27]
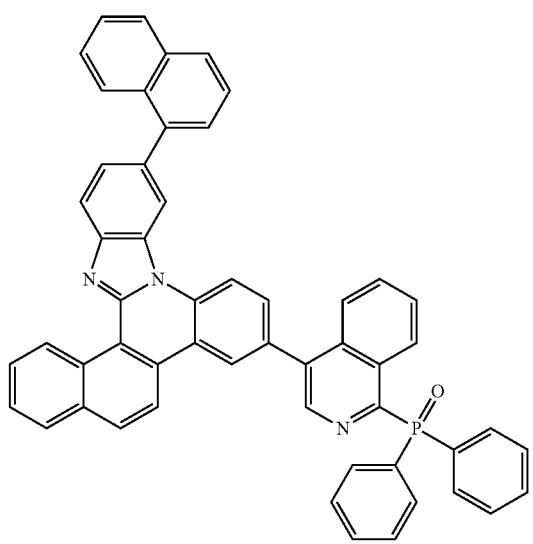

[Compound 2-28]
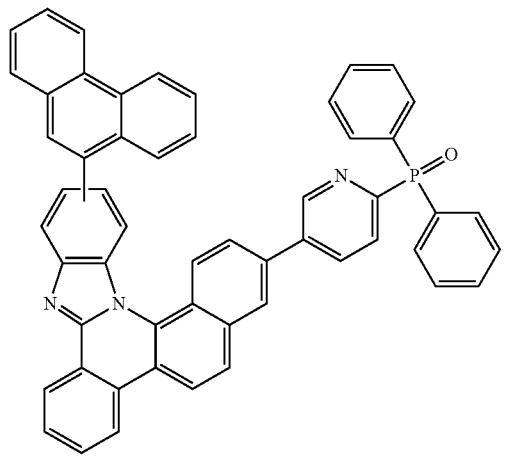
[Compound 2-29]
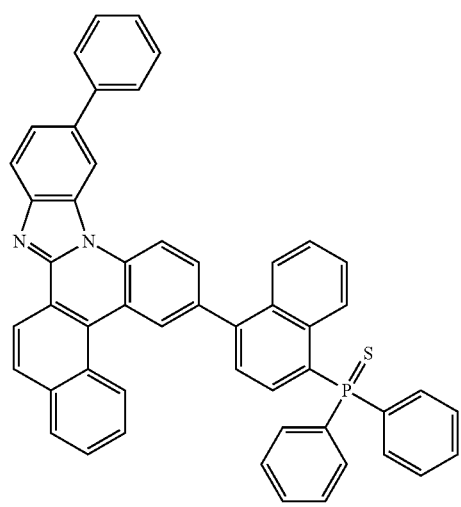
[Compound 2-30]
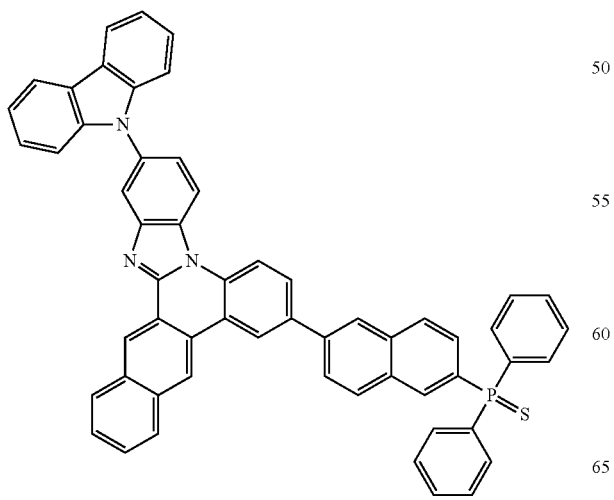
[Compound 2-31]
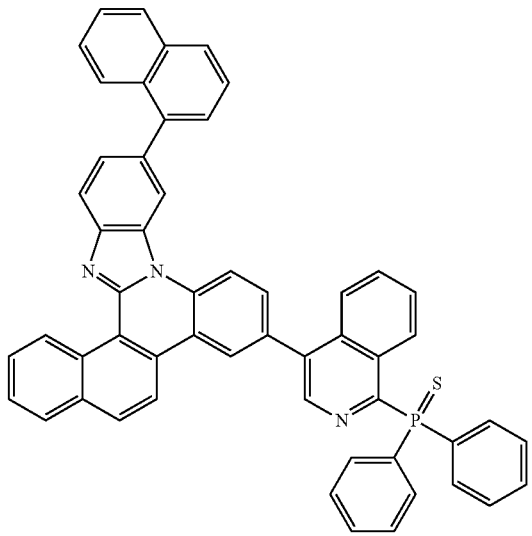
[Compound 2-32]
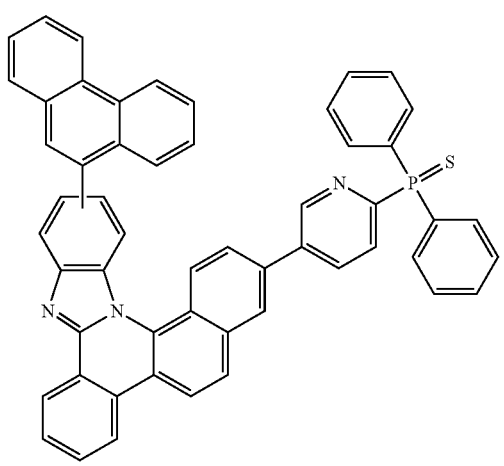
[Compound 2-33]
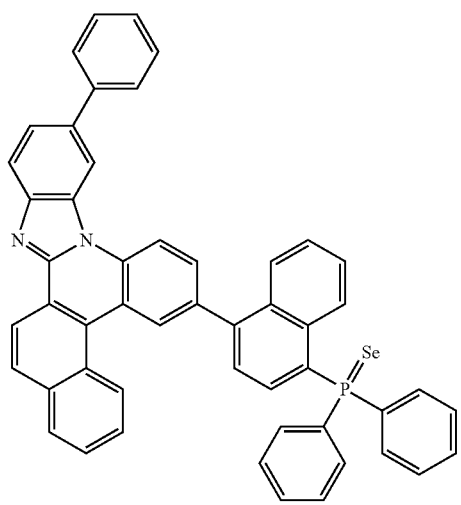

[Compound 2-34]
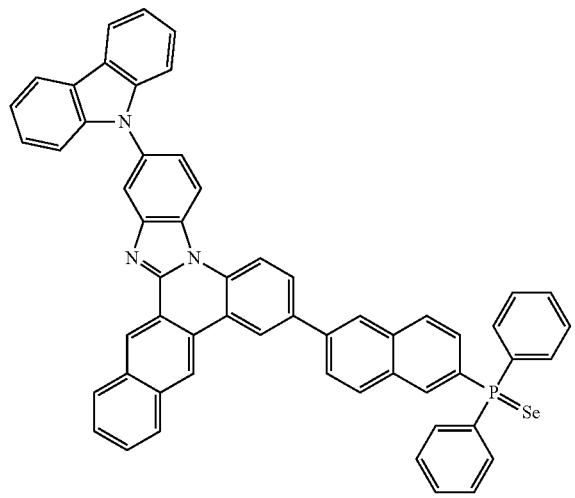
[Compound 2-35]
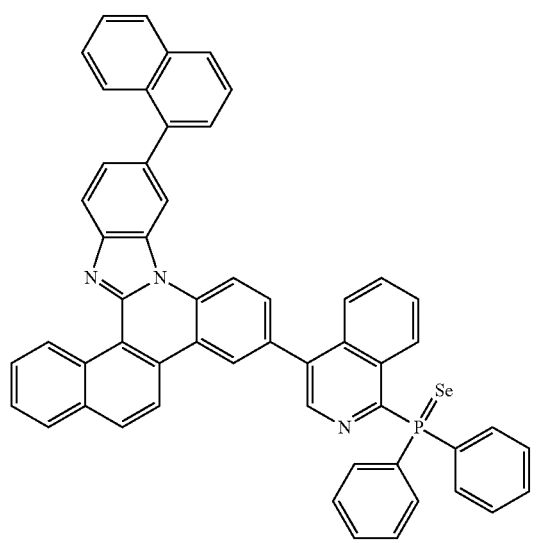
[Compound 2-36]
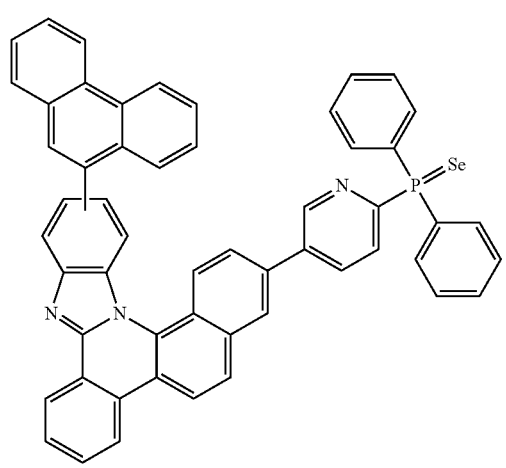
[Compound 2-37]
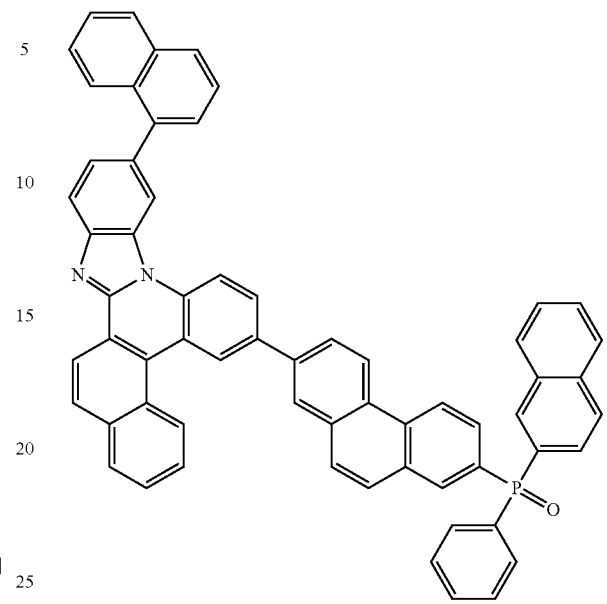
[Compound 2-38]

[Compound 2-39]
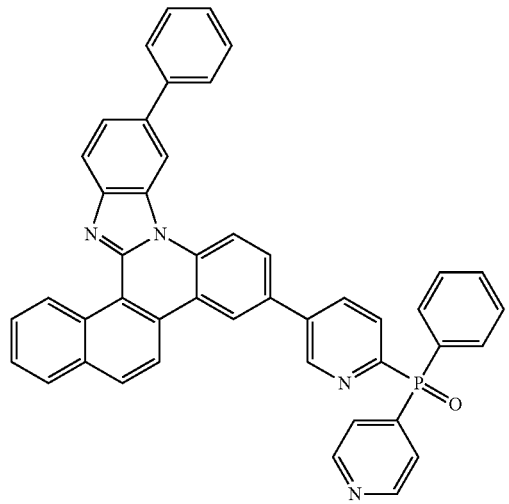
[Compound 2-40]
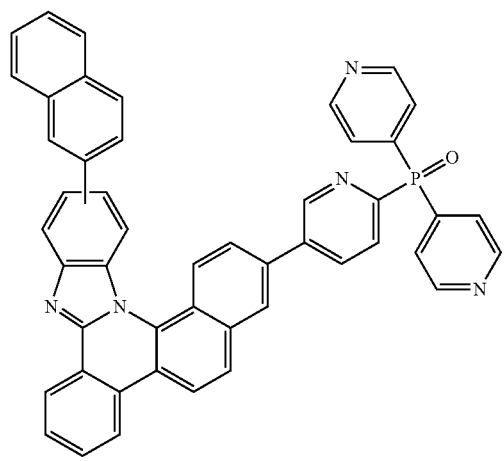
[Compound 2-41]
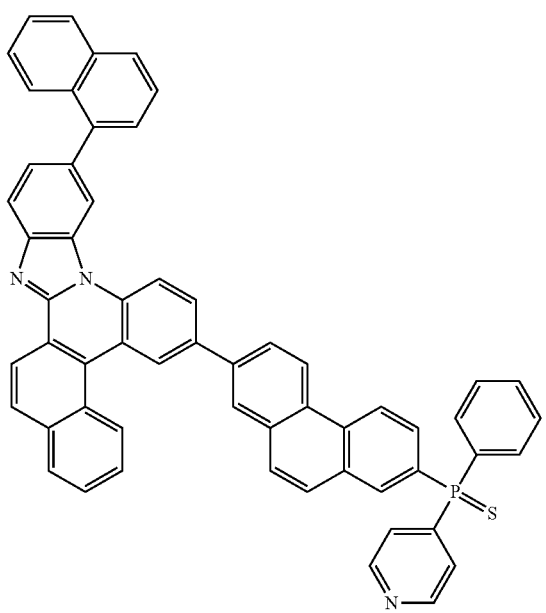
[Compound 2-42]
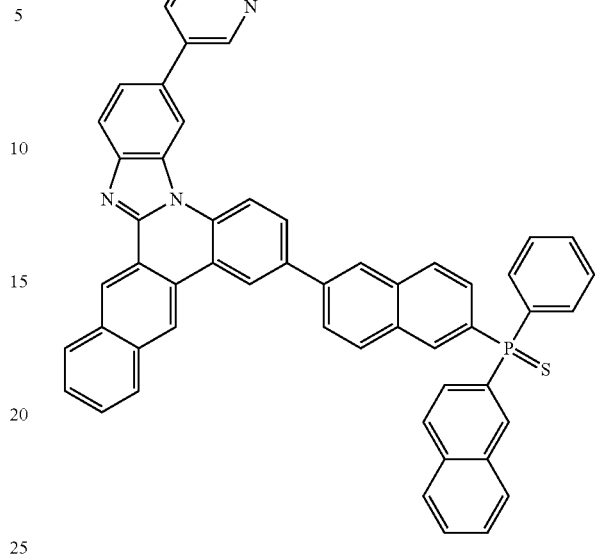
[Compound 2-43]
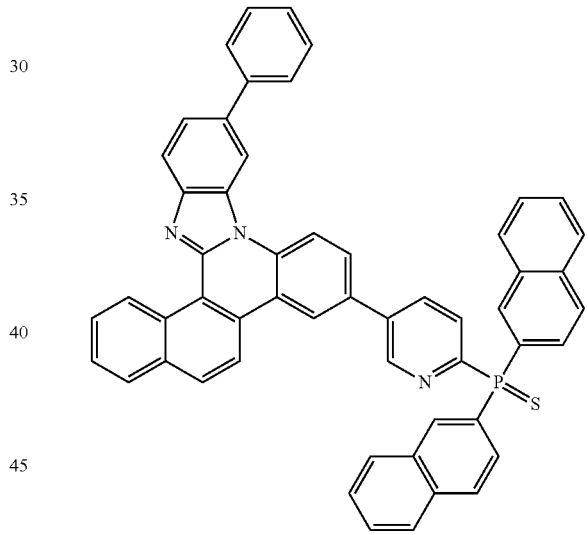
[Compound 2-44]
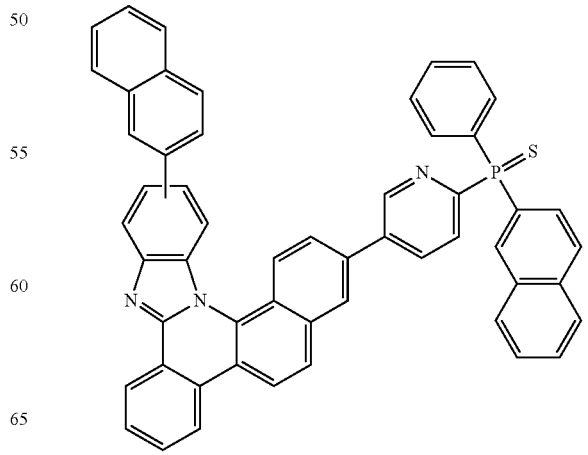

[Compound 2-45]
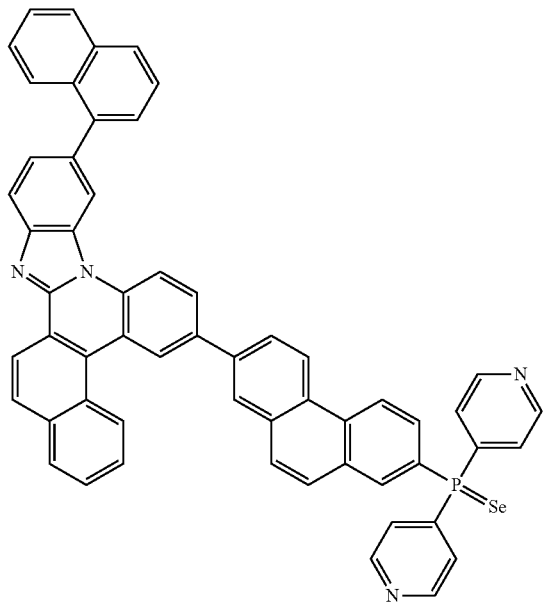
[Compound 2-47]
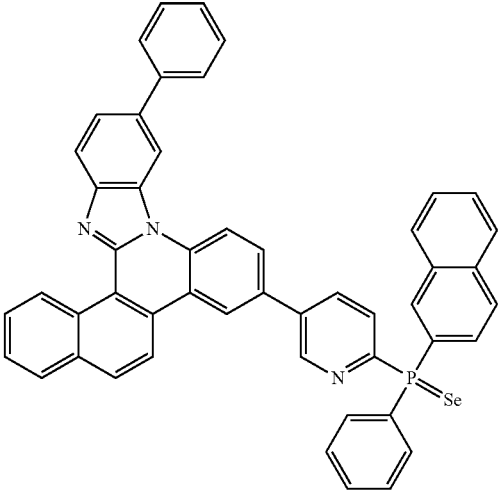
[Compound 2-48]
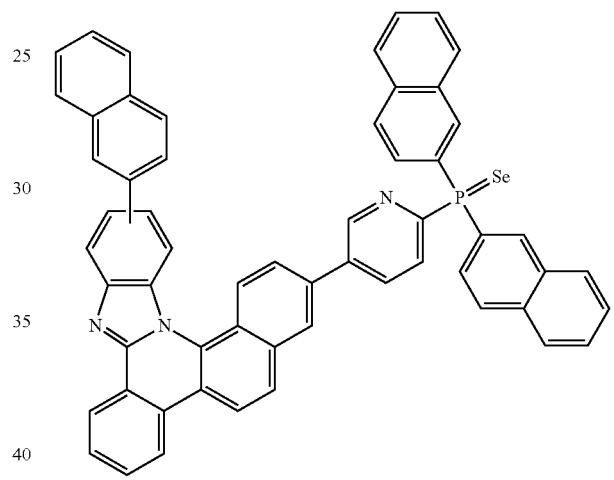
[Compound 2-46]
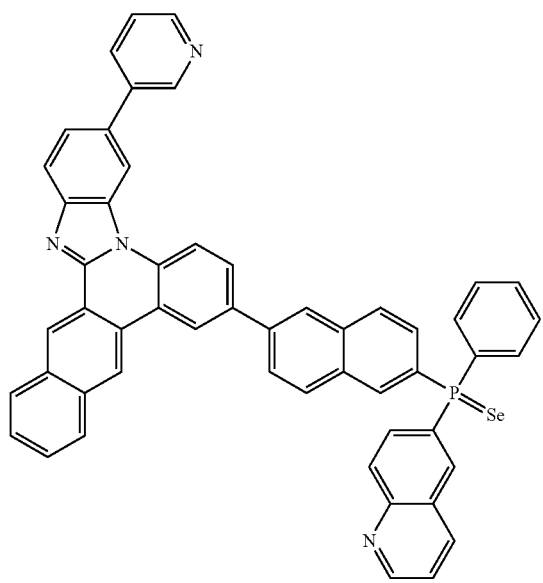
[Compound 2-49]
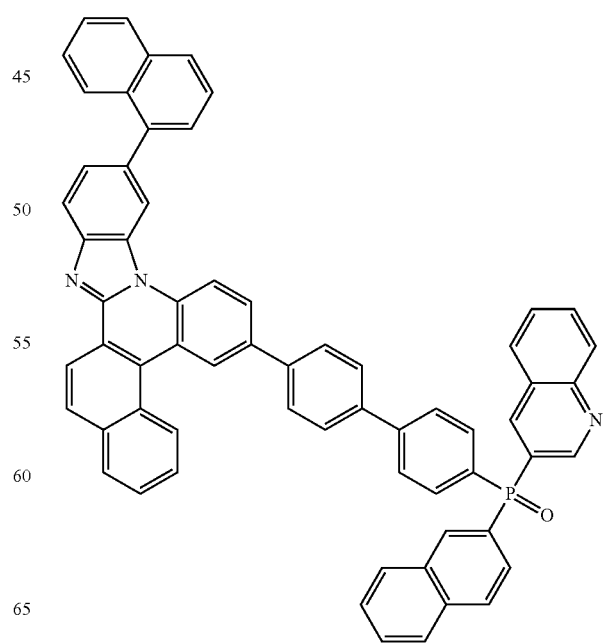

[Compound 2-50]
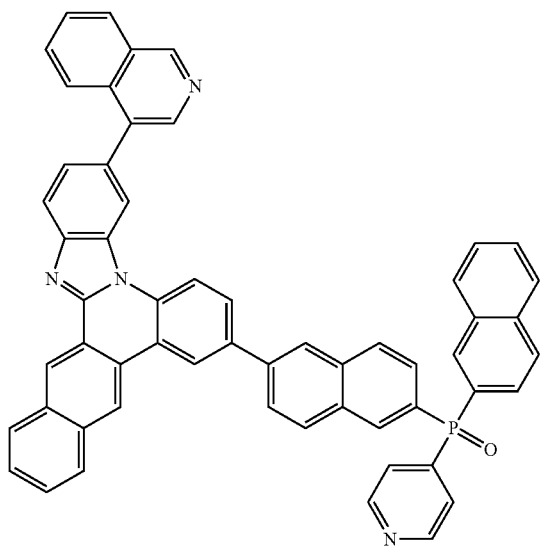
[Compound 2-52]
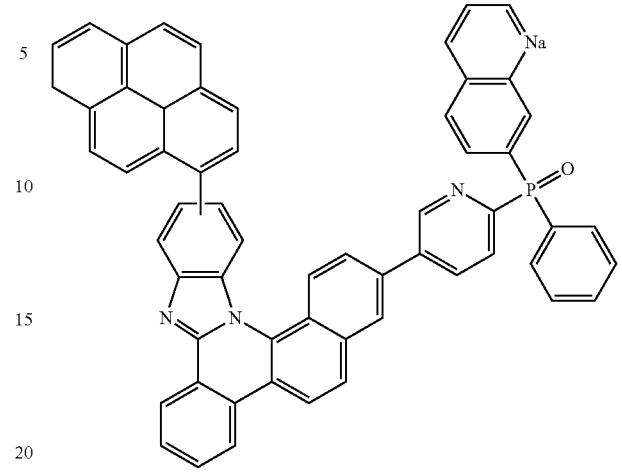
According to an exemplary embodiment of the present specification, the compound of Chemical Formula 1 may be any one selected from the following compounds. However, the compound of Chemical Formula 1 is not limited to the following structures.
[Compound 2-51]
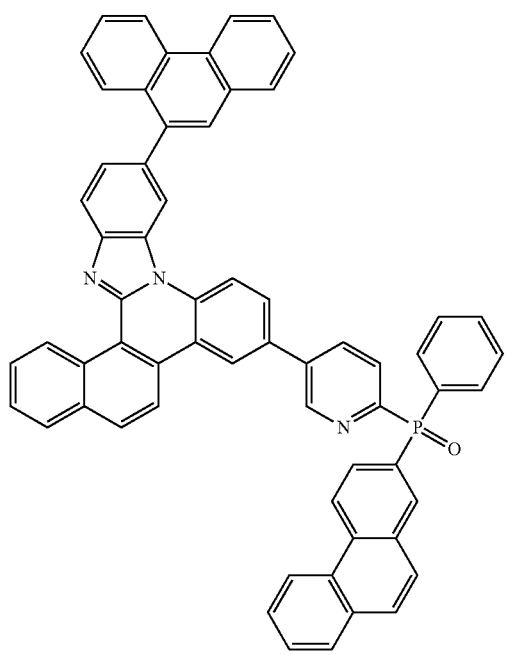
[Compound 3-1]
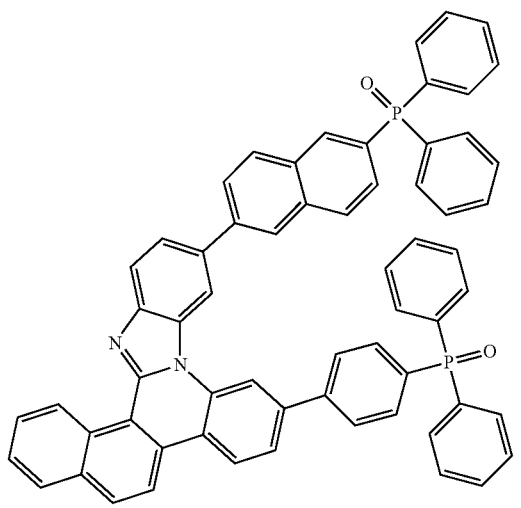

-continued
[Compound 3-2]
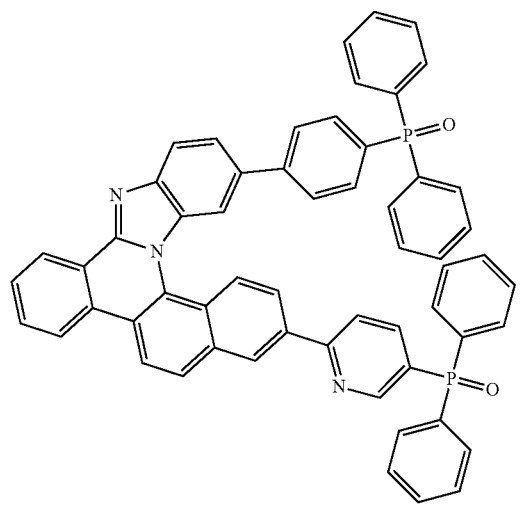
[Compound 3-3]
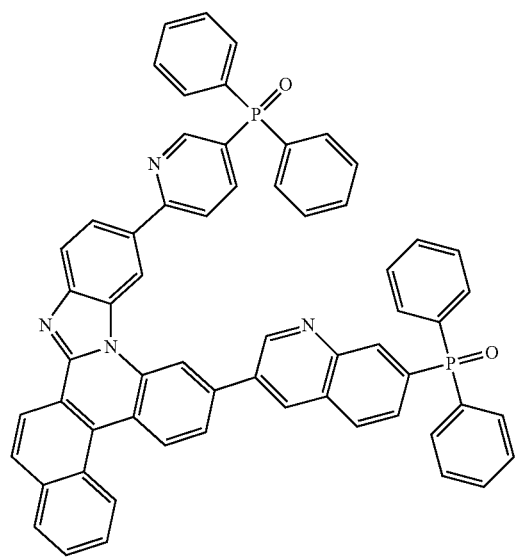
[Compound 3-4]
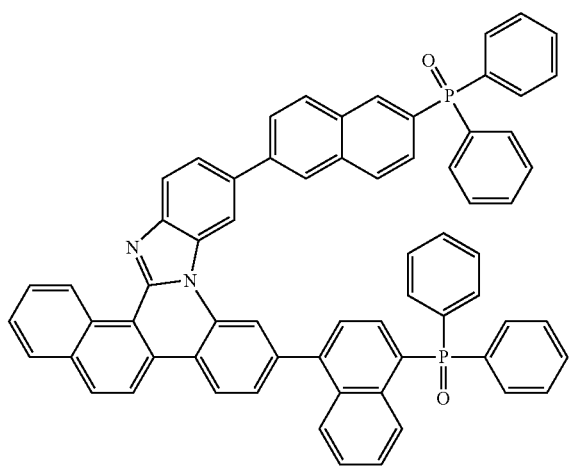
[Compound 3-5]
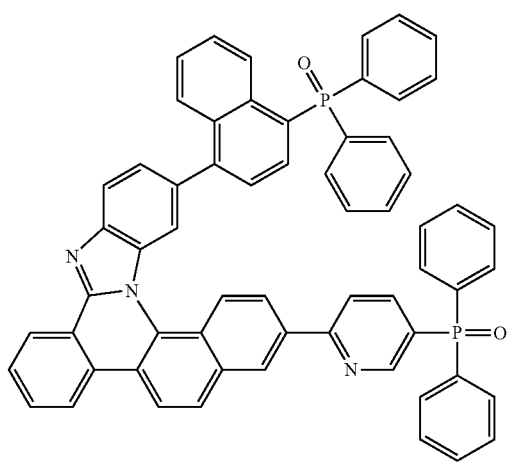
[Compound 3-6]
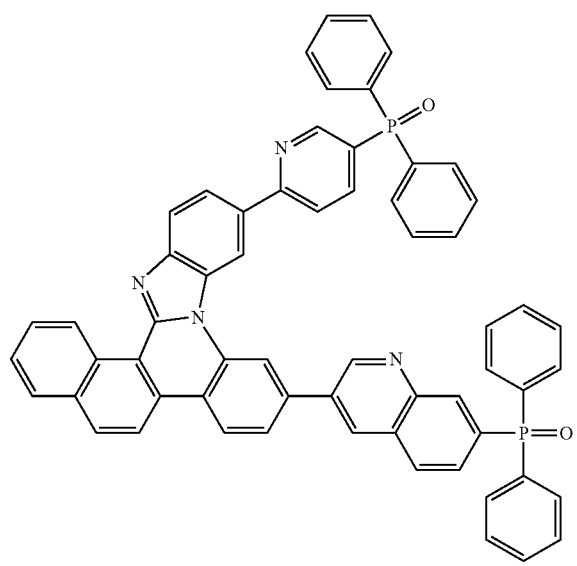
[Compound 3-7]
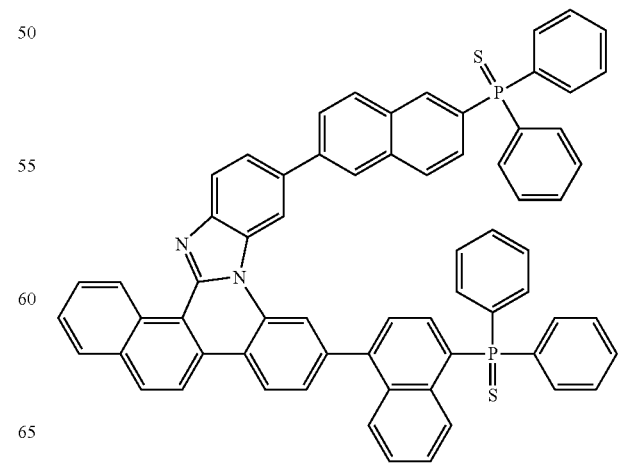

[Compound 3-8]
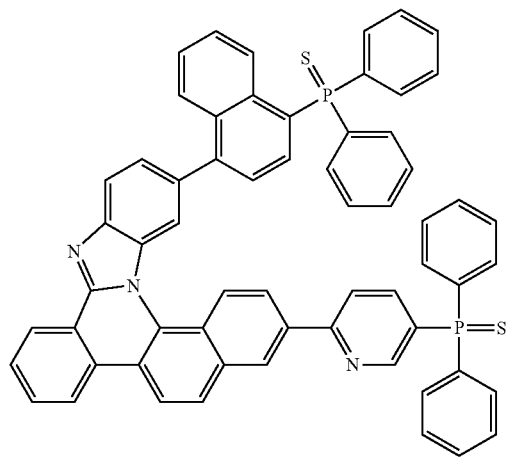
[Compound 3-11]
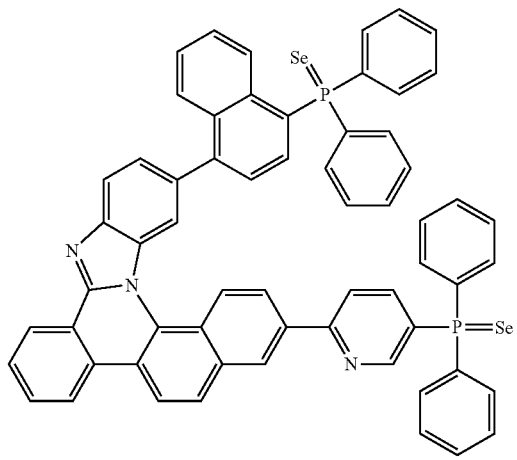
[Compound 3-9]
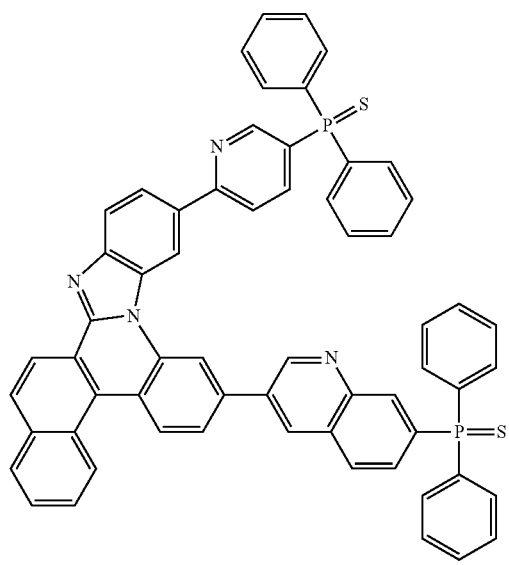
[Compound 3-12]
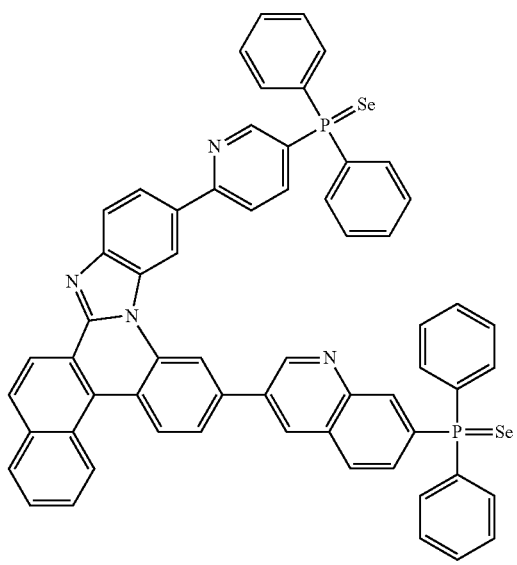
[Compound 3-10]
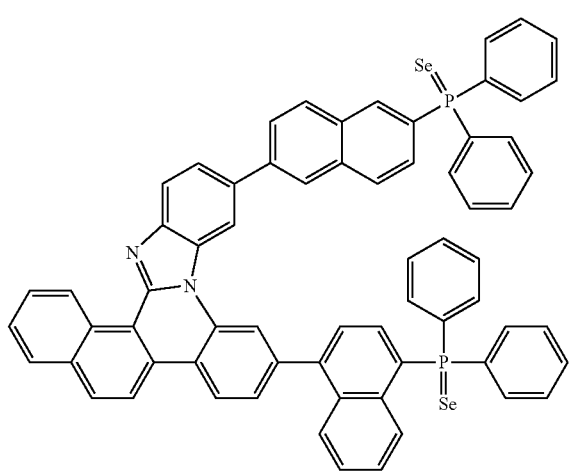
[Compound 3-13]
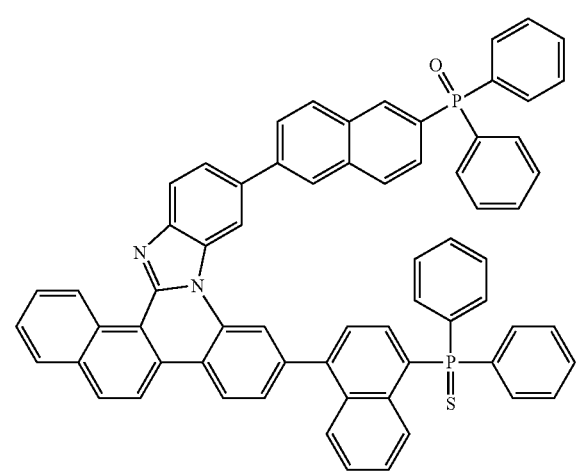

-continued
[Compound 3-14]
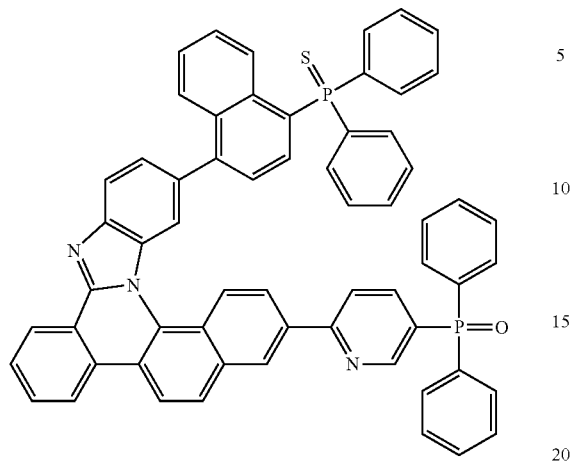
[Compound 3-15]
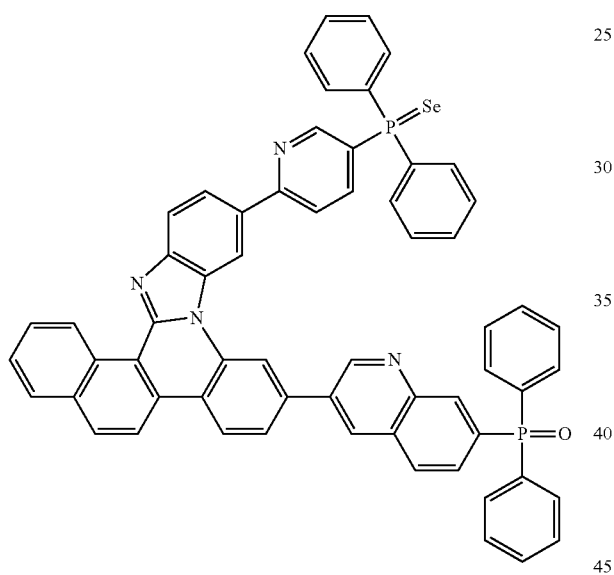
[Compound 3-16]
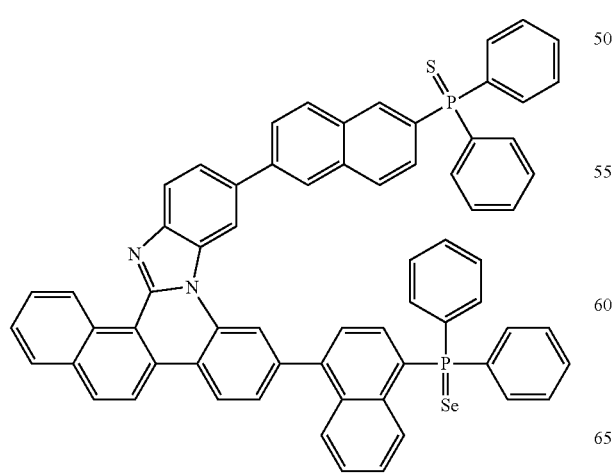
-continued
[Compound 3-17]
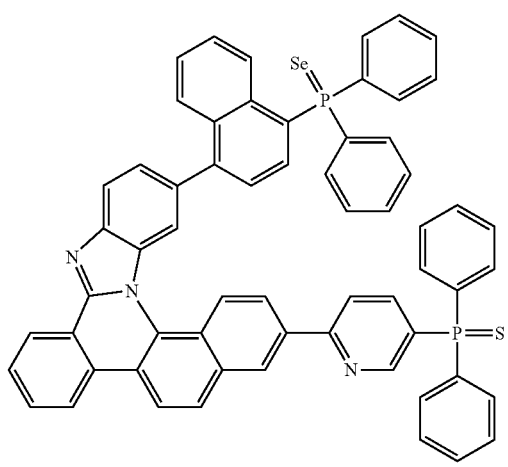
[Compound 3-18]
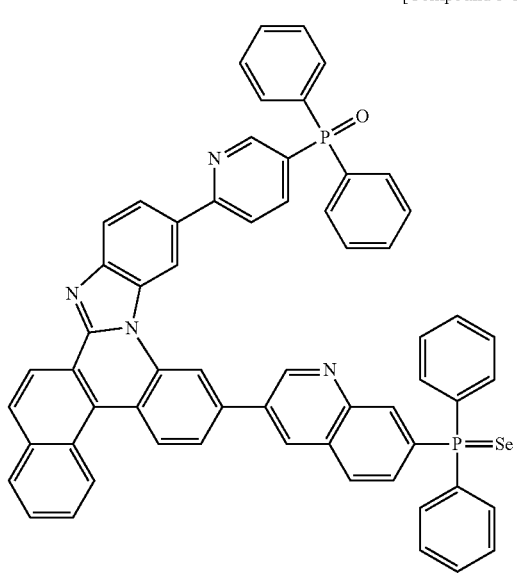
[Compound 3-19]
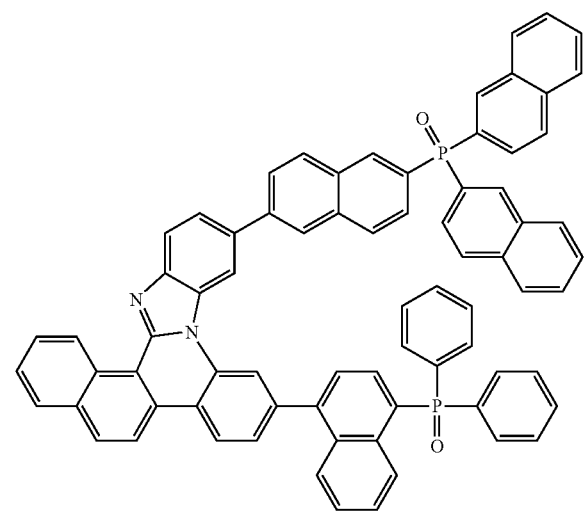

[Compound 3-20]
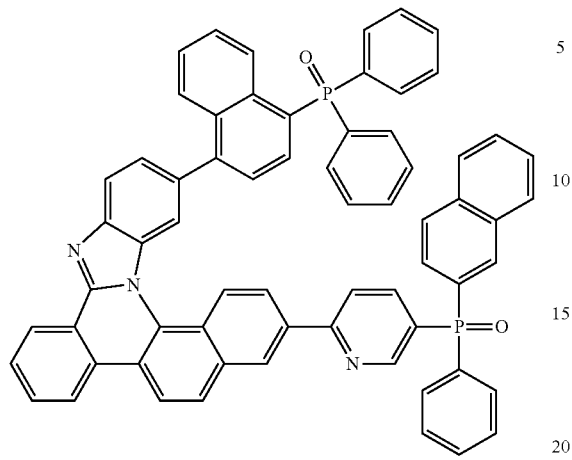
[Compound 3-21]
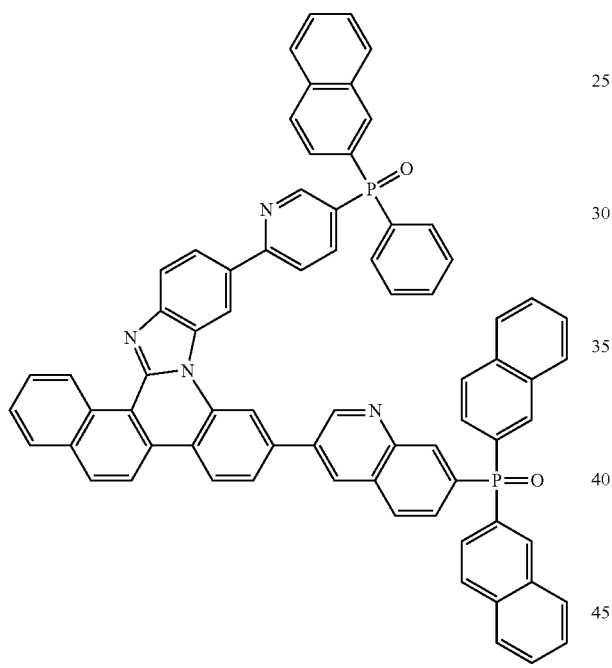
[Compound 3-22]
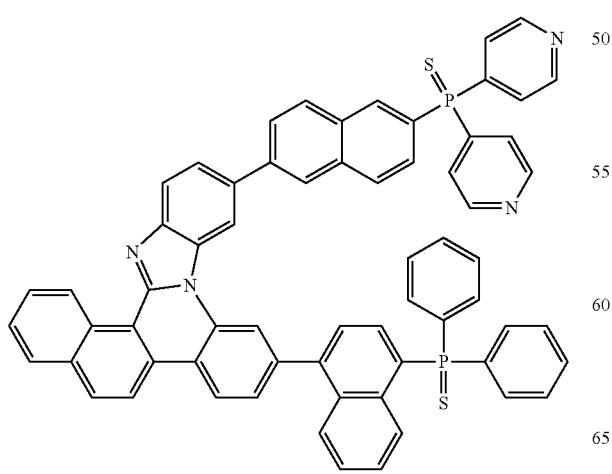
[Compound 3-23]
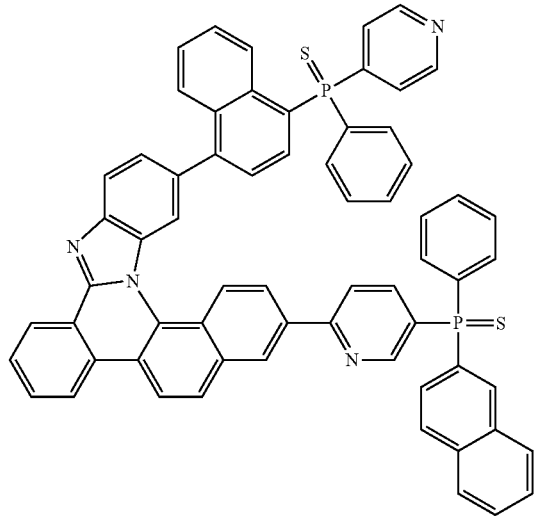
[Compound 3-24]
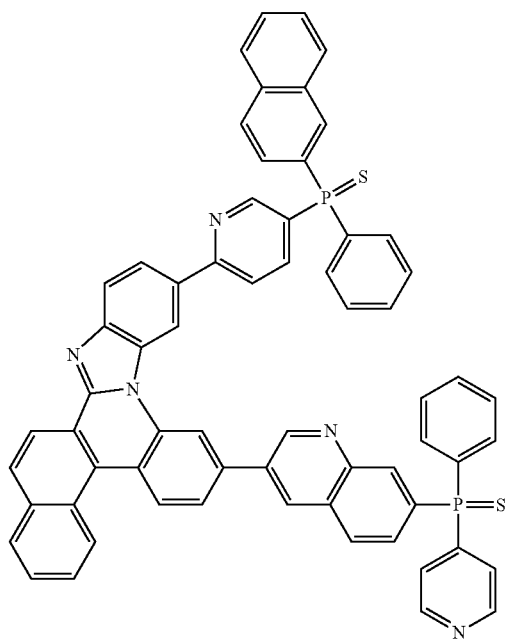

[Compound 3-25]
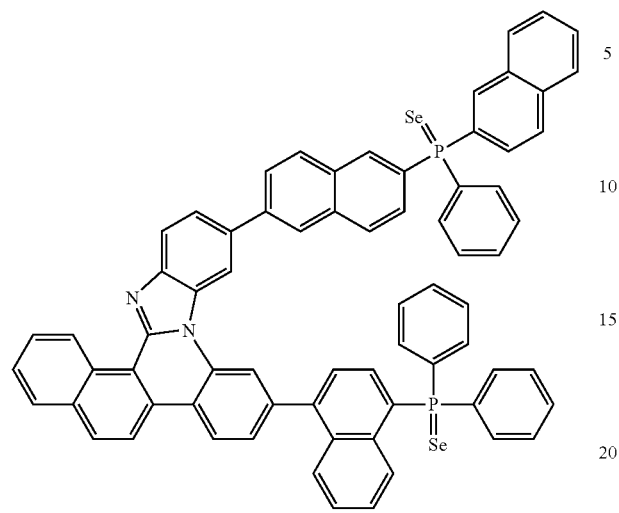
[Compound 3-26]
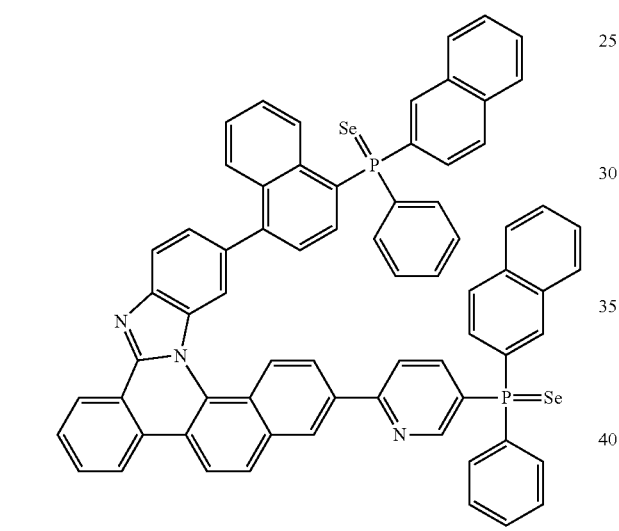
[Compound 3-27]
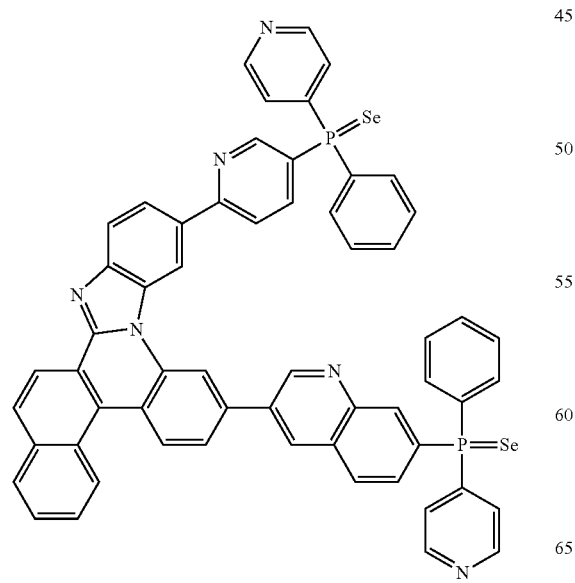
[Compound 3-28]
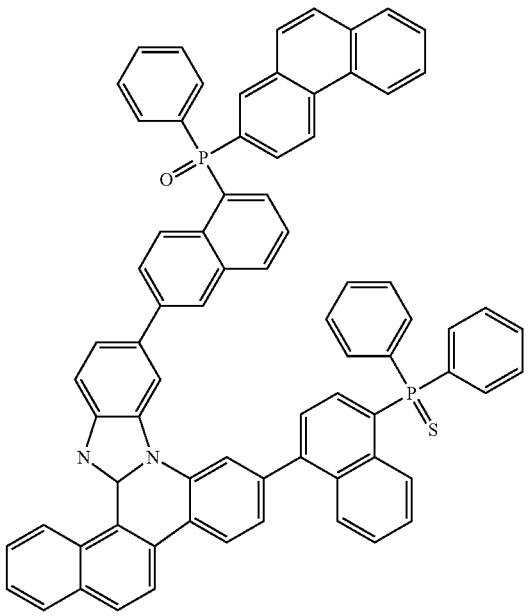
[Compound 3-29]
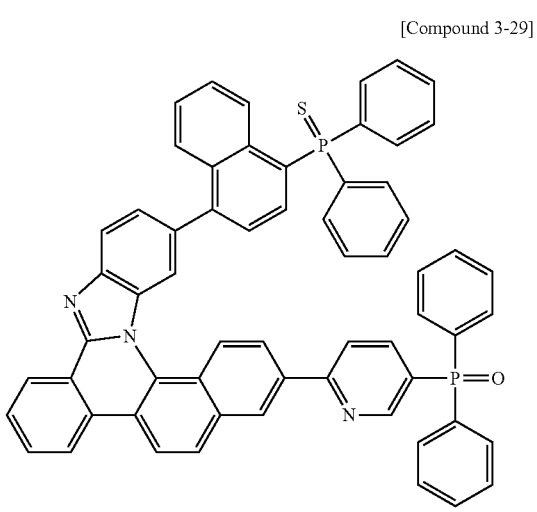

[Compound 3-30]
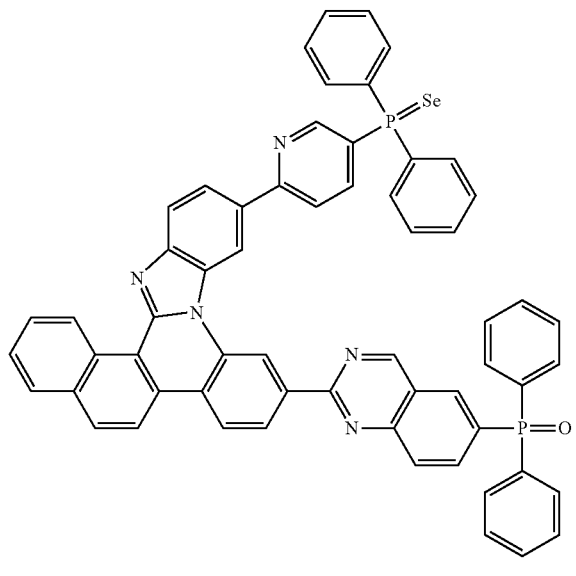
[Compound 3-32]
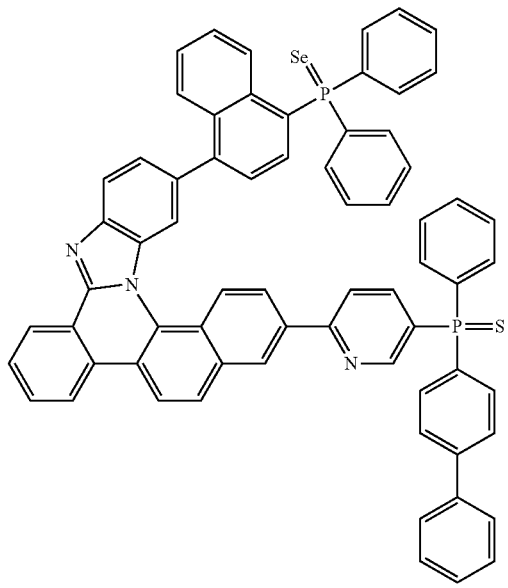
[Compound 3-31]
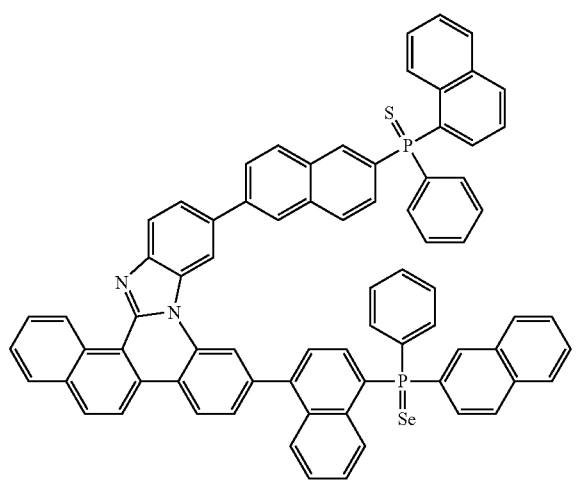
[Compound 3-33]
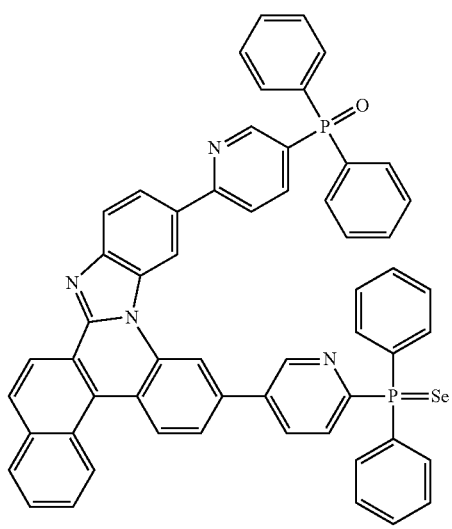
According to an exemplary embodiment of the present specification, the compound of Chemical Formula 1 may be any one selected from the following compounds. However, the compound of Chemical Formula 1 is not limited to the following structures.

-continued
[Compound 4-1]
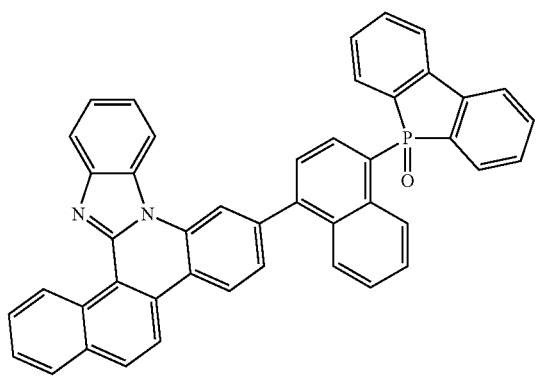
[Compound 4-2]
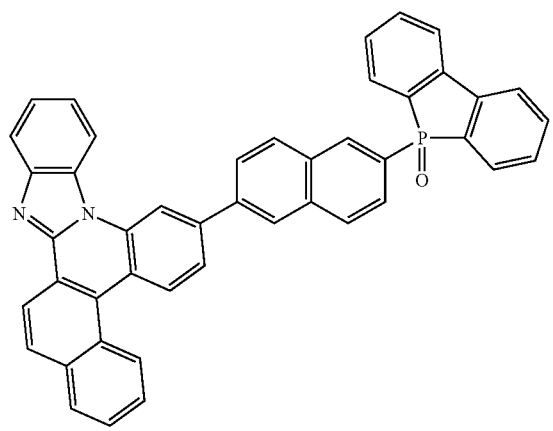
[Compound 4-3]
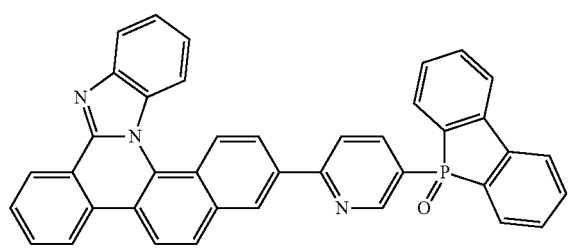
[Compound 4-4]
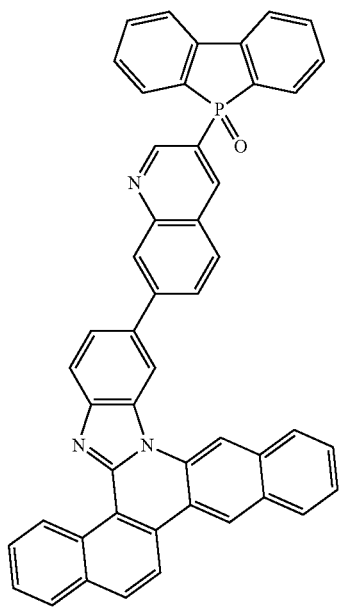
[Compound 4-5]
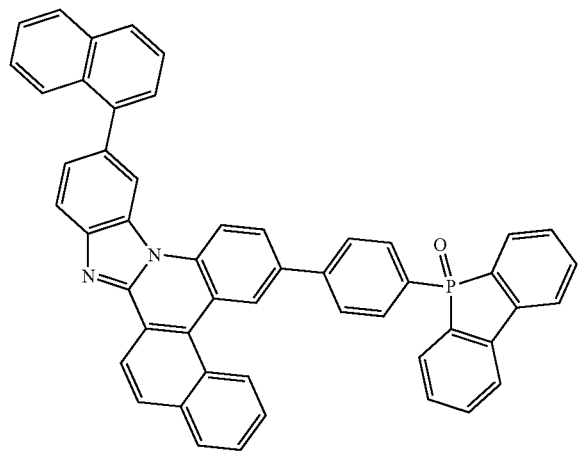
[Compound 4-6]
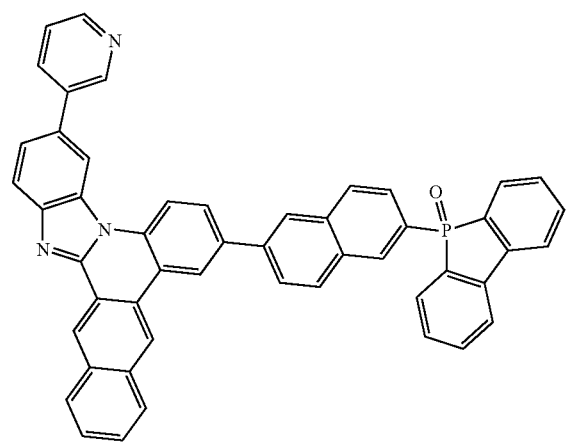

[Compound 4-7]
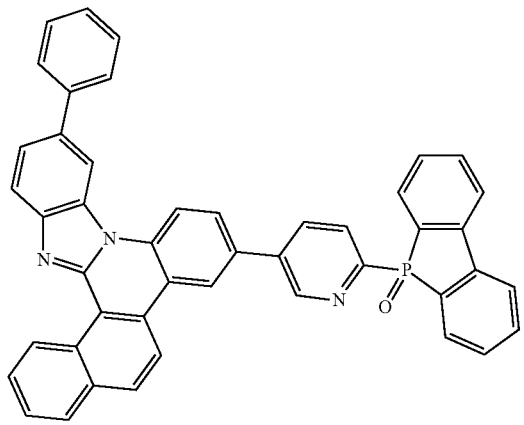
[Compound 4-8]
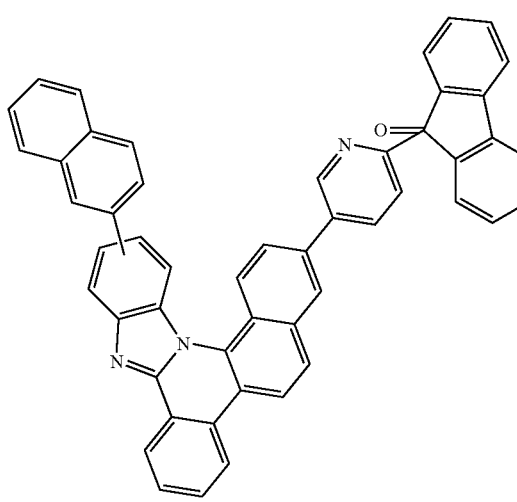
[Compound 4-9]
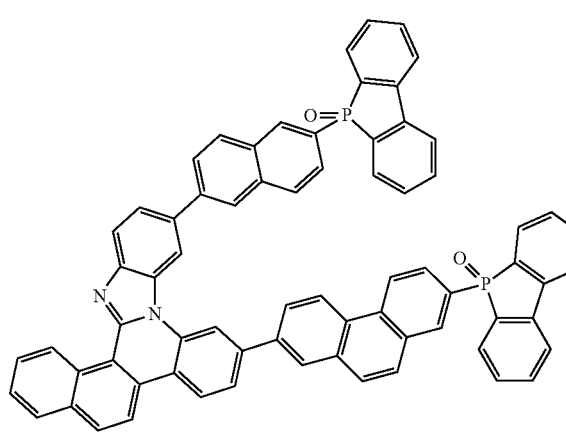
[Compound 4-10]
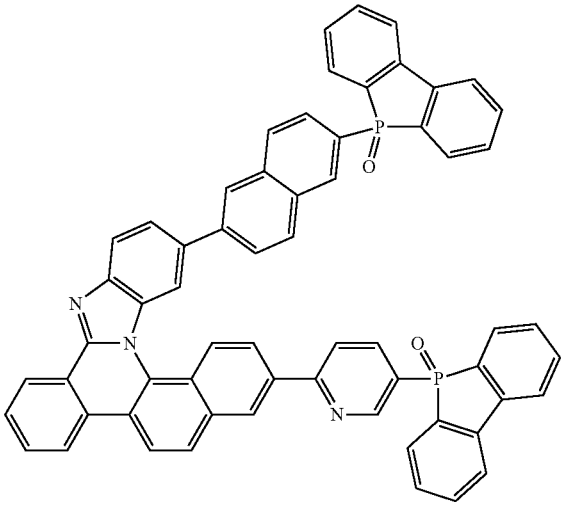
[Compound 4-11]
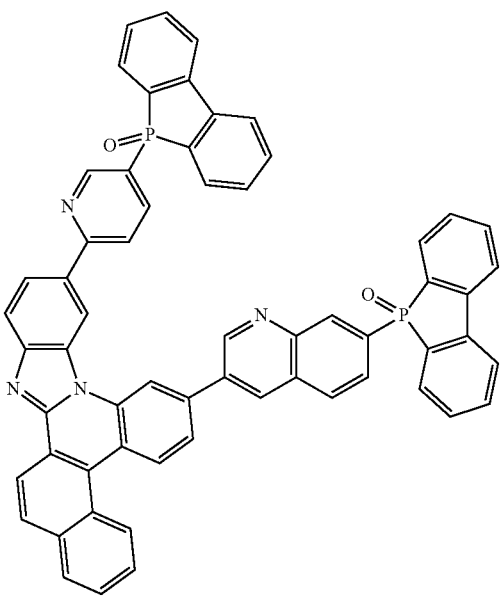
The compound represented by Chemical Formula 1 may be prepared based on the Preparation Examples to be described below. According to an exemplary embodiment, the compound may be prepared by the method such as the following Reaction Formulae 1 to 3.

[Reaction Formula 1]
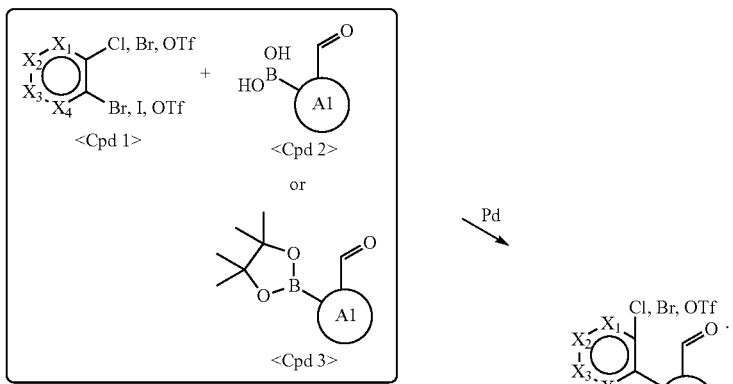
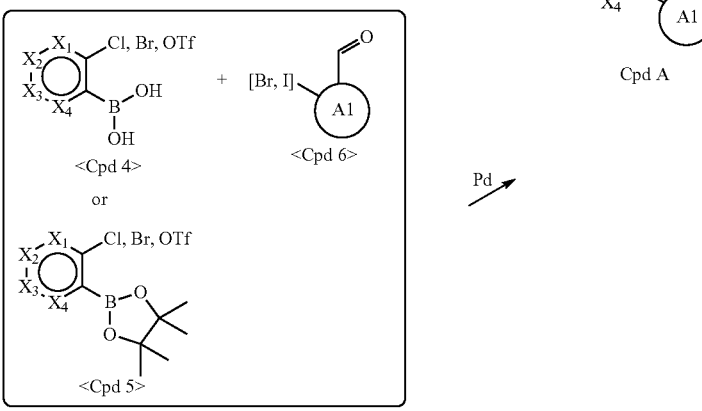
[Reaction Formula 2]
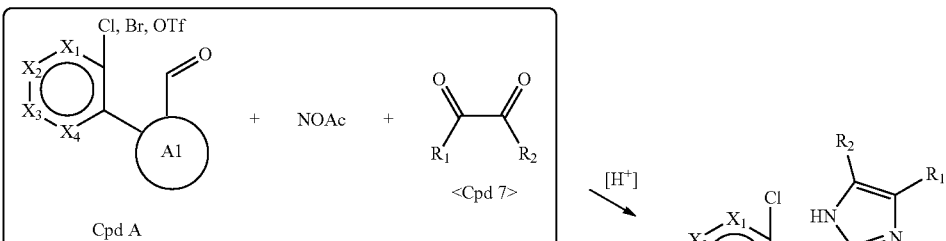
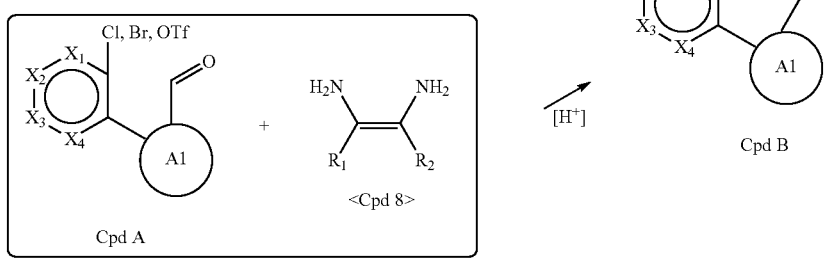
[Reaction Formula 3]
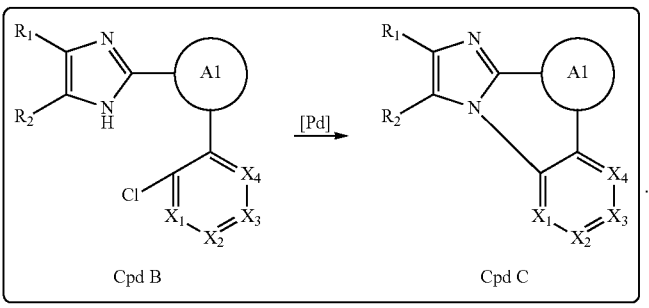

In Reaction Formulae 1 to 3, the definitions of X1 to X4 are the same as those in Chemical Formula 1, Al represents a ring, and R1 and R2 combine with each other to form a ring.

Specifically, for a compound represented by Cpd B, an imidazole group may be prepared via an acid catalyst by mixing the compound represented by Cpd B, Cpd A in which a halogen group and a formyl group are substituted, a diketo derivative (Cpd 7) having R1 and R2 substituents, and ammonium acetate. Furthermore, an imidazole group may be prepared via an acid catalyst by mixing Cpd A in which a halogen group and a formyl group are substituted, and a diamine derivative (Cpd 8) having R1 and R2 substituents.

Further, for the compound represented by Cpd C, Cpd C (a Compound represented by Chemical Formula 1) may be prepared via the cyclization reaction in the molecule from Cpd B, in which a halogen group and an imidazole group are substituted, using the Pd catalyst.

Further, the present specification provides an organic light emitting device including the compound represented by Chemical Formula 1.

An exemplary embodiment of the present specification provides an organic light emitting device including: a first electrode; a second electrode provided to face the first electrode; and one or more organic material layers provided between the first electrode and the second electrode, in which one or more layers of the organic material layers include the compound of Chemical Formula 1.

The organic material layer of the organic light emitting device of the present specification may also be composed of a single-layered structure, but may be composed of a multi-layered structure in which two or more organic material layers are stacked. For example, the organic light emitting device of the present invention may have a structure including a hole injection layer, a hole transporting layer, a light emitting layer, an electron transporting layer, an electron injection layer, and the like as organic material layers. However, the structure of the organic light emitting device is not limited thereto, and may include a fewer number of organic layers.

In an exemplary embodiment of the present specification, the organic material layer includes a hole injection layer, a hole transporting layer, or a layer which simultaneously injects and transports holes, and the hole injection layer, the hole transporting layer, or the layer which simultaneously injects and transports holes includes the compound of Chemical Formula 1.

In another exemplary embodiment, the organic material layer includes a light emitting layer, and the light emitting layer includes the compound of Chemical Formula 1. In an exemplary embodiment of the present specification, the organic material layer includes an electron transporting layer or an electron injection layer, and the electron transporting layer or the electron injection layer includes the compound of Chemical Formula 1.

In an exemplary embodiment of the present specification, the electron transporting layer, the electron injection layer, or the layer which simultaneously transports and injects electrons includes the compound of Chemical Formula 1.

In another exemplary embodiment, the organic material layer includes a light emitting layer and an electron transporting layer, and the electron transporting layer includes the compound of Chemical Formula 1.

In still another exemplary embodiment, the organic light emitting device may be an organic light emitting device having a structure (normal type) in which a positive electrode, one or more organic material layers, and a negative electrode are sequentially stacked on a substrate.

In yet another exemplary embodiment, the organic light emitting device may be an organic light emitting device having a reverse-direction structure (inverted type) in which a negative electrode, one or more organic material layers, and a positive electrode are sequentially stacked on a substrate.

For example, the structure of the organic light emitting device according to an exemplary embodiment of the present specification is illustrated in FIGS. 1 and 2.

FIG. 1 illustrates an example of an organic light emitting device composed of a substrate 1, a positive electrode 2, a light emitting layer 3, and a negative electrode 4. In the structure, the compound may be included in the light emitting layer.

FIG. 2 illustrates an example of an organic light emitting device composed of a substrate 1, a positive electrode 2, a hole injection layer 5, a hole transporting layer 6, a light emitting layer 7, an electron transporting layer 8, and a negative electrode 4. In the structure, the compound may be included in one or more layers of the hole injection layer, the hole transporting layer, the light emitting layer, and the electron transporting layer.

The organic light emitting device of the present specification may be manufactured by the materials and methods known in the art, except that one or more layers of the organic material layers include the compound of the present specification, that is, the compound of Chemical Formula 1.

When the organic light emitting device includes a plurality of organic material layers, the organic material layers may be formed of the same material or different materials.

The organic light emitting device of the present specification may be manufactured by the materials and methods known in the art, except that one or more layers of the organic material layers include the compound of Chemical Formula 1, that is, the compound represented by Chemical Formula 1.

For example, the organic light emitting device of the present specification may be manufactured by sequentially stacking a first electrode, an organic material layer, and a second electrode on a substrate. In this case, the organic light emitting device may be manufactured by depositing a metal or a metal oxide having conductivity, or an alloy thereof on a substrate to form a positive electrode, forming an organic material layer including a hole injection layer, a hole transporting layer, a light emitting layer, and an electron transporting layer thereon, and then depositing a material, which may be used as a negative electrode, thereon, by using a physical vapor deposition (PVD) method such as sputtering or e-beam evaporation. In addition to the method as described above, an organic light emitting device may be made by sequentially depositing a negative electrode material, an organic material layer, and a positive electrode material on a substrate.

Further, the compound of Chemical Formula 1 may be formed as an organic material layer by not only a vacuum deposition method, but also a solution application method when an organic light emitting device is manufactured. Here, the solution application method means spin coating, dip coating, doctor blading, inkjet printing, screen printing, a spray method, roll coating, and the like, but is not limited thereto.

In addition to the method as described above, an organic light emitting device may also be made by sequentially depositing a negative electrode material, an organic material layer, and a positive electrode material on a substrate (International Publication No. 2003/012890). However, the manufacturing method is not limited thereto. In an exemplary embodiment of the present specification, the first electrode is a positive electrode, and the second electrode is a negative electrode.

In another exemplary embodiment, the first electrode is a negative electrode, and the second electrode is a positive electrode.

As the positive electrode material, a material having a large work function is usually preferred so as to smoothly inject holes into an organic material layer.

Specific examples of the positive electrode material which may be used in the present invention include: a metal, such as vanadium, chromium, copper, zinc, and gold, or alloys thereof; a metal oxide, such as zinc oxide, indium oxide, indium tin oxide (ITO), and indium zinc oxide (IZO); a combination of metal and oxide, such as ZnO:Al or $SnO_2$:Sb; an electrically conductive polymer, such as poly(3-methylthiophene), poly[3,4-(ethylene-1,2-dioxy)thiophene] (PEDOT), polypyrrole, and polyaniline, and the like, but are not limited thereto.

As the negative electrode material, a material having a small work function is usually preferred so as to smoothly inject electrons into an organic material layer. Specific examples of the negative electrode material include: a metal, such as magnesium, calcium, sodium, potassium, titanium, indium, yttrium, lithium, gadolinium, aluminum, silver, tin, and lead, or alloys thereof; a multi-layered structural material, such as LiF/Al or $LiO_2$/Al, and the like, but are not limited thereto.

The hole injection material is a layer which injects holes from an electrode, and is preferably a compound which has a capability of transporting holes and thus has an effect of injecting holes at a positive electrode and an excellent effect of injecting holes for a light emitting layer or a light emitting material, prevents excitons produced from the light emitting layer from moving to an electron injection layer or an electron injection material, and is also excellent in the ability to form a thin film. It is preferred that the highest occupied molecular orbital (HOMO) of the hole injection material is between the work function of the positive electrode material and the HOMO of a peripheral organic material layer. Specific examples of the hole injection material include metal porphyrin, oligothiophene, an arylamine-based organic material, a hexanitrile hexaazatriphenylene-based organic material, a quinacridone-based organic material, a perylene-based organic material, anthraquinone, a polyaniline and polythiophene-based electrically conductive polymer, and the like, but are not limited thereto.

The hole transporting layer is a layer which receives holes from a hole injection layer and transports holes to a light emitting layer, and a hole transporting material is suitably a material which may receive holes from a positive electrode or a hole injection layer to transfer holes to a light emitting layer, and has a large mobility for the holes. Specific examples thereof include an arylamine-based organic material, an electrically conductive polymer, a block copolymer in which a conjugate portion and a non-conjugate portion are present together, and the like, but are not limited thereto.

The light emitting material is a material which may receive holes and electrons from a hole transporting layer and an electron transporting layer, respectively, and combine the holes and the electrons to emit light in a visible ray region, and is preferably a material having good quantum efficiency to fluorescence or phosphorescence. Specific examples thereof include: a 8-hydroxy-quinoline aluminum complex ($Alq_3$); a carbazole-based compound; a dimerized styryl compound; BAlq; a 10-hydroxybenzoquinoline-metal compound; a benzoxazole, benzthiazole and benzimidazole-based compound; a poly(p-phenylenevinylene (PPV)-based polymer; a spiro compound; polyfluorene, lubrene, and the like, but are not limited thereto.

The light emitting layer may include a host material and a dopant material. Examples of the host material include a condensed aromatic ring derivative, or a hetero ring-containing compound, and the like. Specifically, examples of the condensed aromatic ring derivative include an anthracene derivative, a pyrene derivative, a naphthalene derivative, a pentacene derivative, a phenanthrene compound, a fluoranthene compound, and the like, and examples of the hetero ring-containing compound include a carbazole derivative, a dibenzofuran derivative, a ladder-type furan compound, a pyrimidine derivative, and the like, but the examples thereof are not limited thereto.

Examples of the dopant material include an aromatic amine derivative, a styrylamine compound, a boron complex, a fluoranthene compound, a metal complex, and the like. Specifically, the aromatic amine derivative is a condensed aromatic ring derivative having a substituted or unsubstituted arylamino group, and examples thereof include a pyrene, an anthracene, a chrysene, a periflanthene, and the like, which have an arylamino group, and the styrylamine compound is a compound in which a substituted or unsubstituted arylamine is substituted with at least one arylvinyl group, and one or two or more substituents selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, examples of the metal complex include an iridium complex, a platinum complex, and the like, but are not limited thereto.

The electron transporting material is a material which receives electrons from an electron injection layer and transports the electrons to a light emitting layer, and an electron transporting material is a material which may inject electrons well from a negative electrode and may transfer the electrons to a light emitting layer, and is suitably a material which has large mobility for the electrons. Specific examples thereof include: an Al complex of 8-hydroxyquinoline; a complex including $Alq_3$; an organic radical compound; a hydroxyflavone-metal complex, and the like, but are not limited thereto. The electron transporting layer may be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and is preferably a compound which has a capability of transporting electrons, has an effect of injecting electrons from a negative electrode and an excellent effect of injecting electrons into a light emitting layer or a light emitting material, prevents excitons produced from the light emitting layer from moving to a hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris(2-methyl-8-hydroxyquinolinato) aluminum, tris(8-hydroxyquinolinato) gallium, bis(10-hydroxybenzo[h]quinolinato) beryllium, bis(10-hydroxybenzo[h]quinolinato) zinc, bis(2-methyl-8-quinolinato) chlorogallium, bis(2-methyl-8-quinolinato) (o-cresolato) gallium, bis(2-methyl-8-quinolinato) (1-naphtholato) aluminum, bis(2-methyl-8-quinolinato) (2-naphtholato) gallium, and the like, but are not limited thereto.

The organic light emitting device according to the present specification may be a top emission type, a bottom emission type, or a dual emission type according to the material to be used.

In an exemplary embodiment of the present specification, the compound of Chemical Formula 1 may be included in an organic solar cell or an organic transistor in addition to an organic light emitting device.

MODE FOR INVENTION

The preparation of the compound represented by Chemical Formula 1 and the organic light emitting device including the same will be specifically described in the following Examples. However, the following Examples are provided for exemplifying the present specification, and the scope of the present specification is not limited thereby.

PREPARATION EXAMPLES

<Preparation Example 1> Synthesis of the Following Compound 1-1

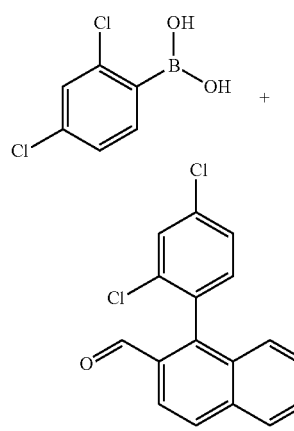

[Structural Formula 1-1A]

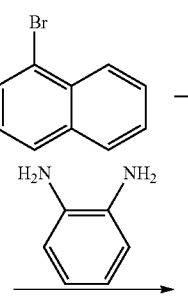

[Structural Formula 1-1B]

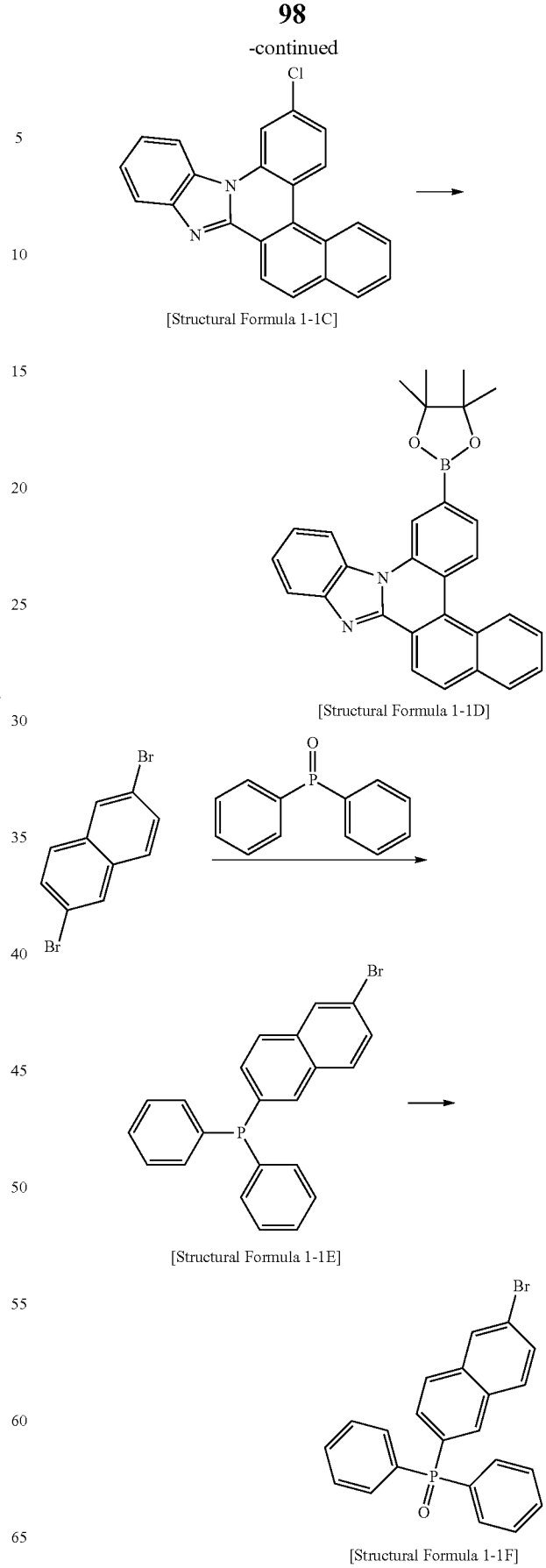

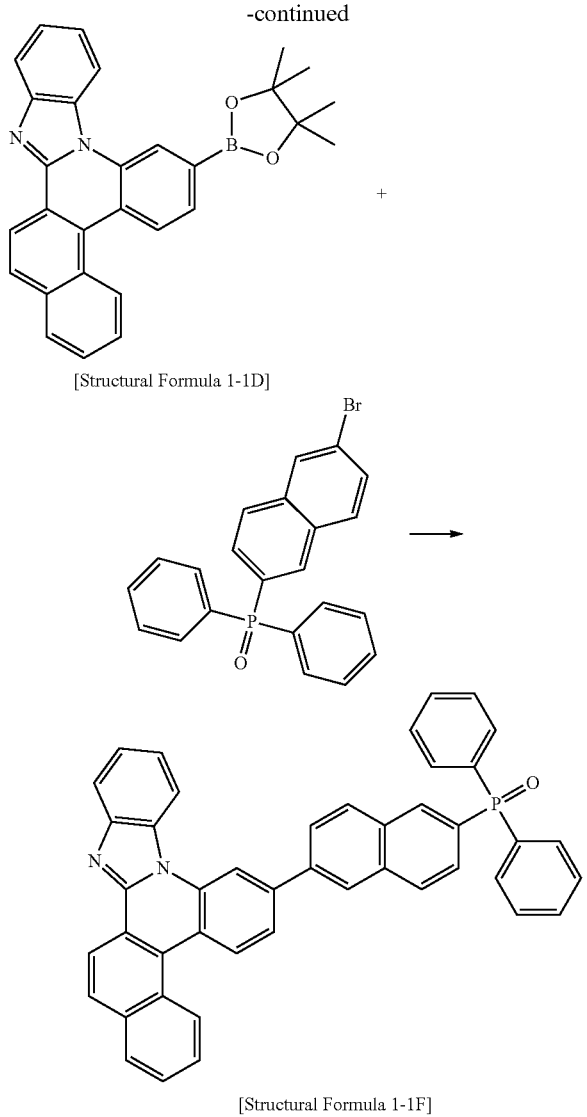

[Structural Formula 1-1D]

[Structural Formula 1-1F]

[Compound 1-1]

Preparation of Structural Formula 1-1A

After 2,4-dichlorophenylboronic acid (18.3 g, 95.8 mmol) and 1-bromo-2-naphthaldehyde (20.5 g, 87.2 mmol) were completely dissolved in tetrahydrofuran (THF) (300 mL), a 2 M potassium carbonate aqueous solution (180 mL) was added thereto, tetrakistriphenylphosphinopalladium (Pd(PPh3)4) (2.0 g, 2 mol %) was added thereto, and then the resulting mixture was stirred and refluxed for 5 hours. The temperature was lowered to normal temperature, the aqueous layer was removed, and the organic layer was dried over anhydrous magnesium sulfate (MgSO$_4$), and then filtered. The filtrate was concentrated under reduced pressure and subjected to column chromatographic purification at a ratio of tetrahydrofuran:hexane=1:10 to prepare Structural Formula 1-1A (21.0 g, 80%).

MS: [M+H]+=301

Preparation of Structural Formula 1-1B

Structural Formula 1-1A (26.2 g, 87.0 mmol) and diaminobenzene (9.4 g, 87.0 mmol) were suspended in dioxane (1,4-dioxane) (200 mL) and acetic acid (AcOH) (20 mL). The obtained mixture was stirred and refluxed for about 6 hours, and cooled to normal temperature. The mixture was diluted with water (100 mL), and then the produced solid was filtered, and washed with water and ethyl ether to prepare Structural Formula 1-1B (19.3 g, 57%).

MS: [M+H]+=389

Preparation of Structural Formula 1-1C

Compound 1-1B (1.99 g, 5.10 mmol), sodium-tertiary-butoxide (NaOt-Bu) (0.58 g, 6.01 mmol), and Pd[P(t-Bu)3]2 (51 mg, 2 mol %) were suspended in toluene (50 mL). The obtained mixture was stirred and refluxed for about 6 hours, and cooled to normal temperature. Distilled water was added to the reaction solution, the reaction was terminated, and the organic layer was extracted, dried over anhydrous magnesium sulfate, and then filtered. The filtrate was concentrated under reduced pressure and subjected to column chromatographic purification at a ratio of tetrahydrofuran:hexane=1:5 to prepare Structural Formula 1-1C (0.756 g, 42%).

MS: [M+H]+=353

Preparation of Structural Formula 1-1D

After Structural Formula 1-1C (12 g, 34 mmol), bis(pinacolato)diboron (12 g, 47 mmol), and potassium acetate (12 g, 118 mmol) were dissolved in dioxane (150 mL), the temperature was increased to 50° C., Pd(DBA)$_2$ (0.23 g, 0.4 mmol) and P(Cy)3 (0.22 g, 0.8 mmol) were added thereto, and then the resulting mixture was heated and stirred for 12 hours. After the reaction solution was cooled to room temperature, distilled water (100 mL) was added thereto, and extraction was performed using methylene chloride (100 mL×3). The organic layer was concentrated and recrystallized with ethanol to obtain Structural Formula 1-1D (14 g, yield 90%).

MS: [M+H]+=445

Preparation of Structural Formula 1-1E 2,6-dibromonaphthalene (20 g, 69.94 mmol) was dissolved in tetrahydrofuran (100 ml), and then the resulting solution was cooled to −78° C. n-BuLi (2.5 M, 37 ml, 93 mmol) was slowly added dropwise thereto, and then the resulting mixture was stirred for 30 minutes. After chlorodiphenylphosphine (17 g, 76 mmol) was slowly added dropwise thereto, the resulting mixture was stirred for 3 hours, and then the temperature was increased to normal temperature, and then water (100 mL) was added thereto, and extraction was performed using tetrahydrofuran. The organic layer was concentrated and recrystallized with hexane to obtain Structural Formula 1-1E (21 g, yield 76.8%).

MS: [M+H]+=391

Preparation of Structural Formula 1-1F

After structural Formula 1-1E (20 g, 51 mmol) was dissolved in trichloromethane (200 ml), a hydrogen peroxide solution (20 ml) was added thereto, and then the resulting mixture was stirred for 12 hours. MgSO$_4$ was added thereto, the resulting mixture was stirred to remove water, and then the resulting product was filtered, concentrated, and recrystallized with hexane to obtain Structural Formula 1-1F (18 g, yield 86.5%).

MS: [M+H]+=407

Preparation of Compound 1-1

Structural Formula 1-1D (9.0 g, 20.3 mmol) and Structural Formula 1-1F (9.1 g, 22.4 mmol) were completely dissolved in tetrahydrofuran (200 ml) while being heated, and then 100 ml of a 2M potassium carbonate aqueous solution was added thereto, Pd(PPh$_3$)$_4$ (0.26 g, 0.22 mmol) was added thereto, and the resulting mixture was stirred for 12 hours. The temperature was lowered to normal temperature, and then the aqueous layer was removed, and the produced solid was filtered. The filtered solid was recrystallized with tetrahydrofuran and acetone to obtain Compound 1-1 (8.5 g, yield 65%).
MS: [M+H]+=645
<Preparation Example 2> Synthesis of the Following Compound 1-38
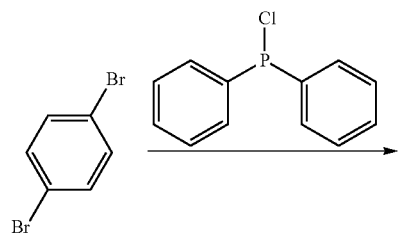
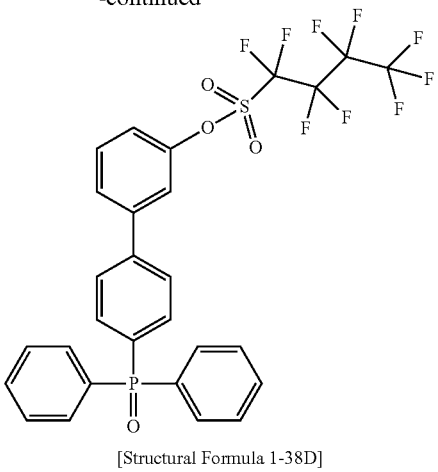
[Structural Formula 1-38D]
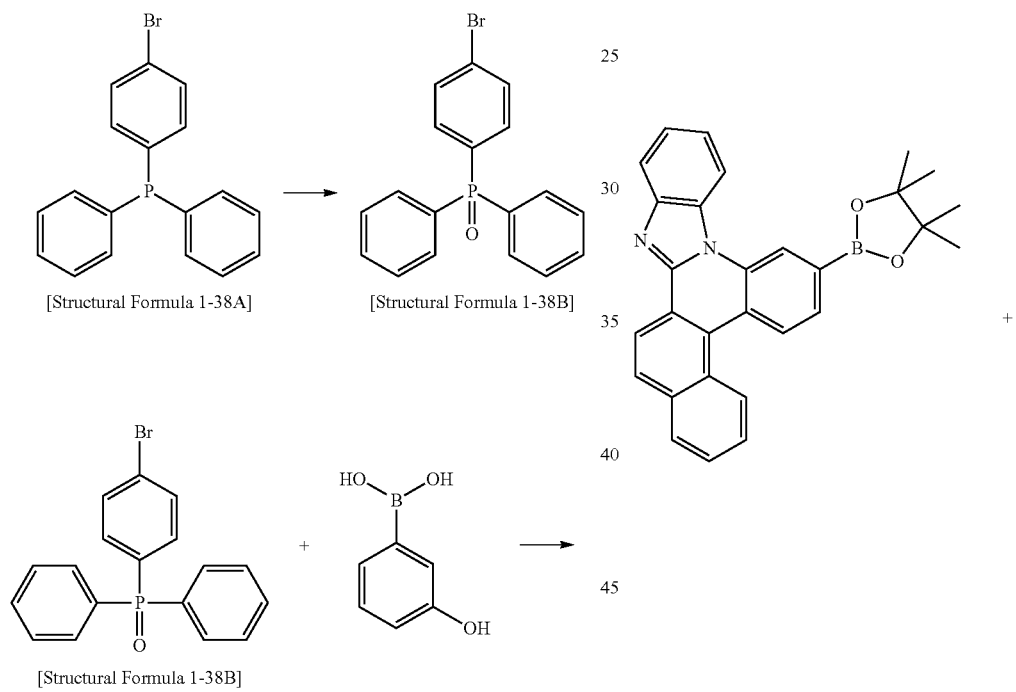
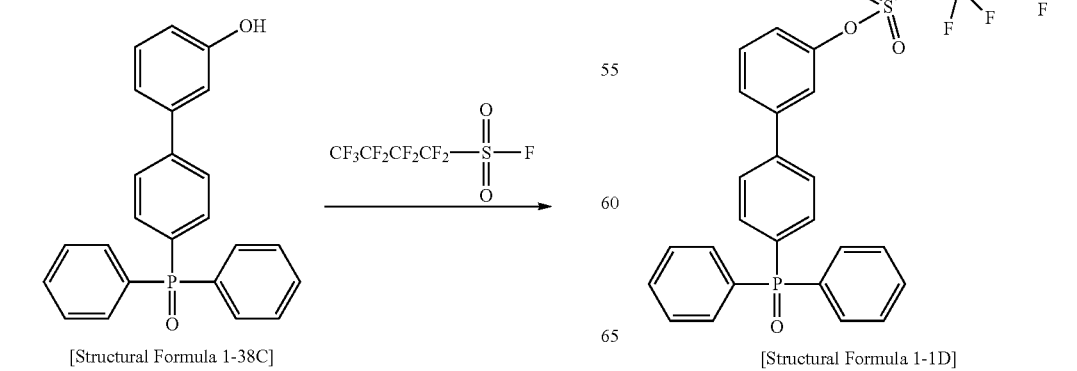
[Structural Formula 1-1D]

-continued

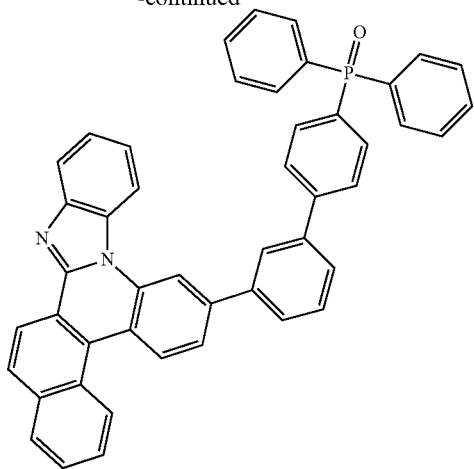

[Structural Formula 1-38D]

[Compound 1-38]
Preparation of Structural Formula 1-38A

Dibromobenzene (20 g, 85 mmol) was dissolved in tetrahydrofuran (100 ml), and then the resulting solution was cooled to −78° C. n-BuLi (2.5 M, 37 ml, 93 mmol) was slowly added dropwise thereto, and then the resulting mixture was stirred for 30 minutes. After chlorodiphenylphosphine (17 g, 76 mmol) was slowly added dropwise thereto, the resulting mixture was stirred for 3 hours, and then the temperature was increased to normal temperature, and then water (100 ml) was added thereto, and extraction was performed using tetrahydrofuran. The organic layer was concentrated and recrystallized with hexane to obtain Structural Formula 1-38A (20 g, yield 70%).

MS: [M+H]+=341

Preparation of Structural Formula 1-38B

After structural Formula 1-38A (20 g, 58 mmol) was dissolved in trichloromethane (200 ml), a hydrogen peroxide solution (20 ml) was added thereto, and then the resulting mixture was stirred for 12 hours. $MgSO_4$ was added thereto, the resulting mixture was stirred to remove water, and then the resulting product was filtered, concentrated, and recrystallized with hexane to obtain Structural Formula 1-38B (18 g, yield 85%).

MS: [M+H]+=357

Preparation of Structural Formula 1-38C

Structural Formula 1-38B (8 g, 22.4 mmol) and 3-hydroxyphenylboronic acid (3.1 g, 22.4 mmol) were completely dissolved in tetrahydrofuran (200 ml) while being heated, and then 100 ml of a 2M potassium carbonate aqueous solution was added thereto, $Pd(PPh_3)_4$ (0.26 g, 0.22 mmol) was added thereto, and the resulting mixture was stirred for 12 hours. After the temperature was lowered to normal temperature, the organic layer was extracted, and then the solvent was evaporated, and the produced solid was filtered. The filtered solid was recrystallized with tetrahydrofuran and hexane to obtain Structural Formula 1-38C (7 g, yield 84%).

MS: [M+H]+=371

Preparation of Structural Formula 1-38D

After Structural Formula 1-38C (7 g, 18.9 mmol) was dissolved in acetonitrile (200 ml), perchlorobutanesulfonyl fluoride (2.9 g, 20.8 mmol) and 100 ml of a 2 M potassium carbonate aqueous solution were added thereto and heated, and then the resulting mixture was stirred for 12 hours. After the temperature was lowered to normal temperature, the organic layer was extracted, and then the solvent was evaporated, and the produced solid was filtered. The filtered solid was recrystallized with chloroform and hexane to obtain Structural Formula 1-38D (9.5 g, yield 75%).

MS: [M+H]+=653

Preparation of Compound 1-38

Compound 1-38 was obtained in the same manner as in the preparation method of Compound 1-1, except that Structural Formula 1-38D was used instead of Structural Formula 1-1F.

MS: [M+H]+=671

<Preparation Example 3> Synthesis of the Following Compound 1-84

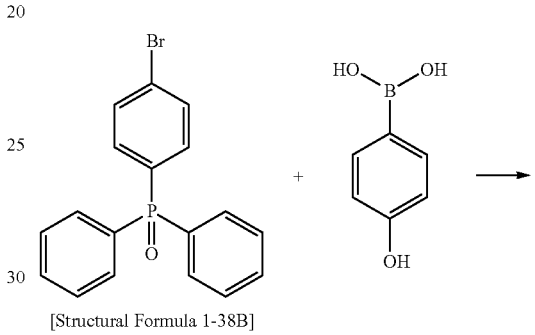

[Structural Formula 1-38B]

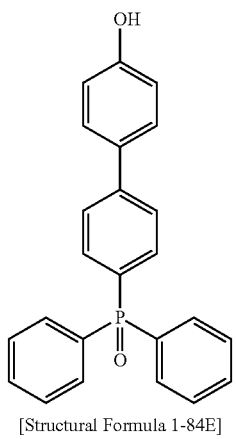

[Structural Formula 1-84E]

-continued
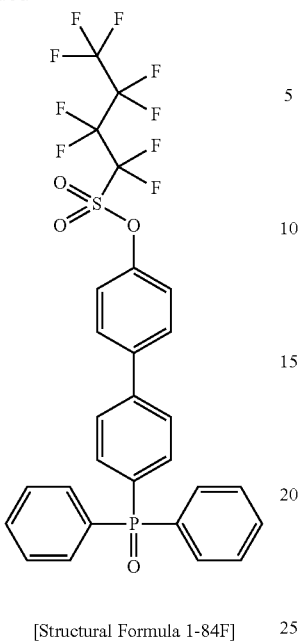
[Structural Formula 1-84F]
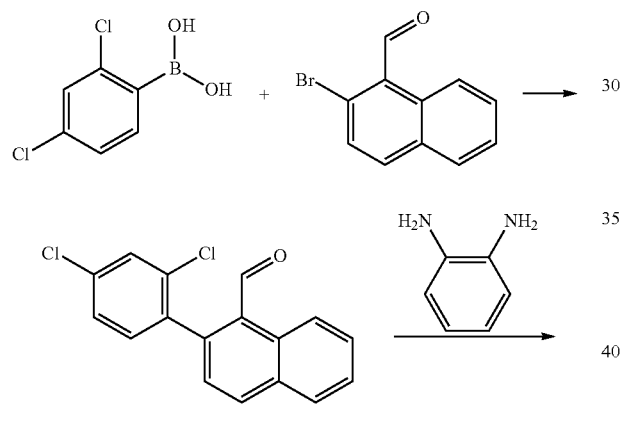
[Structural Formula 1-84A]
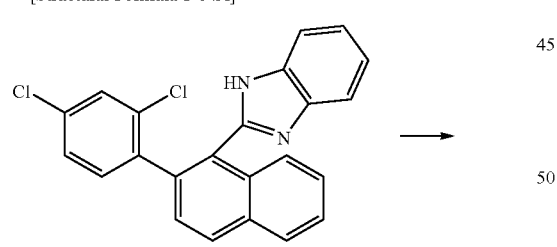
[Structural Formula 1-84B]
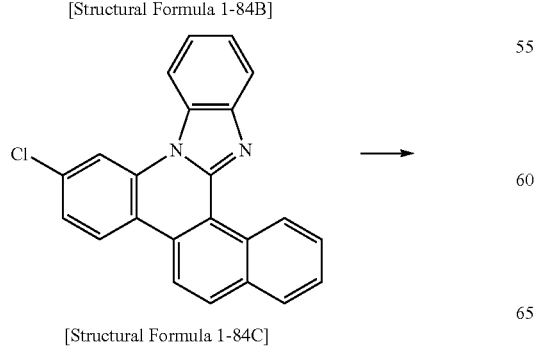
[Structural Formula 1-84C]
-continued
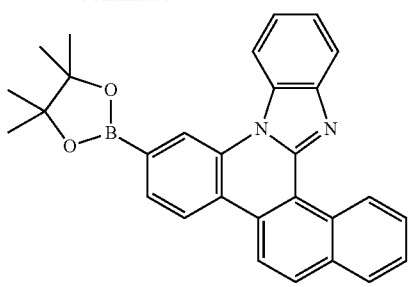
[Structural Formula 1-84D]
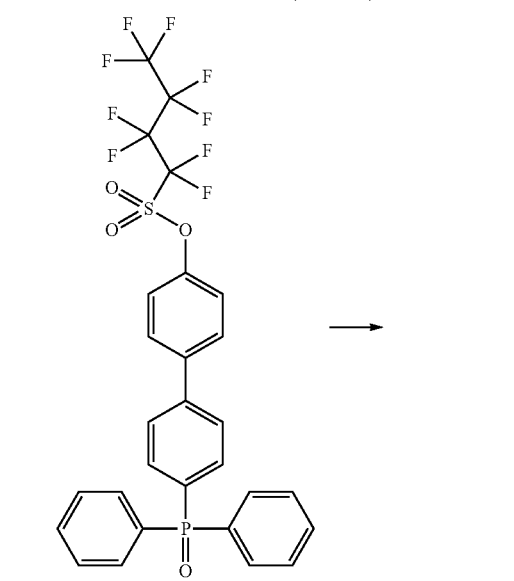
[Structural Formula 1-84D]
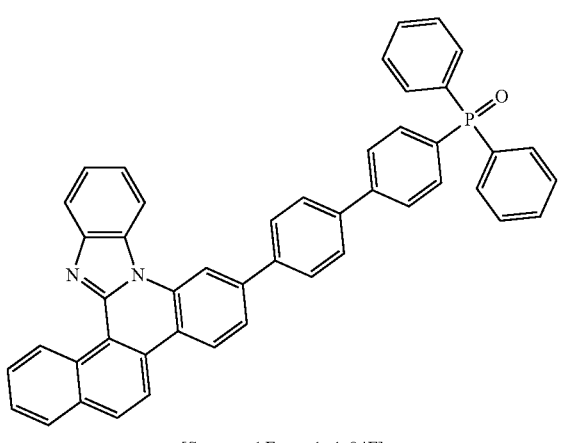
[Structural Formula 1-84F]

[Compound 1-84]

Preparation of Structural Formula 1-84E

Structural Formula 1-84E was obtained in the same manner as in the preparation method of Chemical Formula 1-38C, except that 4-hydroxyphenylboronic acid was used instead of 3-hydroxyphenylboronic acid.

MS: [M+H]+=371

Preparation of Structural Formula 1-84F

Structural Formula 1-84F was obtained in the same manner as in the preparation method of Chemical Formula 1-38D, except that Structural Formula 1-84E was used instead of Structural Formula 1-38C.

MS: [M+H]+=653

Preparation of Structural Formula 1-84A

After 2,4-dichlorophenylboronic acid (18.3 g, 95.8 mmol) and 2-bromo-1-naphthaldehyde (20.5 g, 87.2 mmol) were completely dissolved in tetrahydrofuran (THF) (300 mL), a 2 M potassium carbonate aqueous solution (180 mL) was added thereto, tetrakistriphenylphosphinopalladium (Pd (PPh3)4) (2.0 g, 2 mol %) was added thereto, and then the resulting mixture was stirred and refluxed for 5 hours. The temperature was lowered to normal temperature, the aqueous layer was removed, and the organic layer was dried over anhydrous magnesium sulfate (MgSO$_4$), and then filtered. The filtrate was concentrated under reduced pressure and subjected to column chromatographic purification at a ratio of tetrahydrofuran:hexane=1:10 to prepare Structural Formula 1-84A (21.0 g, 80%).

MS: [M+H]+=301

Preparation of Structural Formula 1-84B

Structural Formula 1-84A (26.2 g, 87.0 mmol) and diaminobenzene (9.4 g, 87.0 mmol) were suspended in dioxane (1,4-dioxane) (200 mL) and acetic acid (AcOH) (20 mL). The obtained mixture was stirred and refluxed for about 6 hours, and cooled to normal temperature. The mixture was diluted with water (100 mL), and then the produced solid was filtered, and washed with water and ethyl ether to prepare Structural Formula 1-84B (19.3 g, 57%).

MS: [M+H]+=389

Preparation of Structural Formula 1-84C

Structural Formula 1-84B (1.99 g, 5.10 mmol), sodium-tertiary-butoxide (NaOt-Bu) (0.58 g, 6.01 mmol), and Pd[P(t-Bu)3]2 (51 mg, 2 mol %) were suspended in toluene (50 mL). The obtained mixture was stirred and refluxed for about 6 hours, and cooled to normal temperature. Distilled water was added to the reaction solution, the reaction was terminated, and the organic layer was extracted, dried over anhydrous magnesium sulfate, and then filtered. The filtrate was concentrated under reduced pressure and subjected to column chromatographic purification at a ratio of tetrahydrofuran:hexane=1:5 to prepare Structural Formula 1-84C (0.756 g, 42%).

MS: [M+H]+=353

Preparation of Structural Formula 1-84D

After Structural Formula 1-84C (12 g, 34 mmol), bis(pinacolato)diboron (12 g, 47 mmol), and potassium acetate (12 g, 118 mmol) were dissolved in dioxane (150 mL), the temperature was increased to 50° C., Pd(DBA)$_2$ (0.23 g, 0.4 mmol) and P(Cy)3 (0.22 g, 0.8 mmol) were added thereto, and then the resulting mixture was heated and stirred for 12 hours. After the reaction solution was cooled to room temperature, distilled water (100 mL) was added thereto, and extraction was performed using methylene chloride (100 mL×3). The organic layer was concentrated and recrystallized with ethanol to obtain Structural Formula 1-84D (14 g, yield 90%).

MS: [M+H]+=445

Preparation of Compound 1-84

Compound 1-84 was obtained in the same manner as in the preparation method of Compound 1-1, except that Structural Formula 1-84D and Structural Formula 1-84F were used instead of Structural Formula 1-1D and Structural Formula 1-1F, respectively.

MS: [M+H]+=671

<Preparation Example 4> Synthesis of the Following Compound 1-85

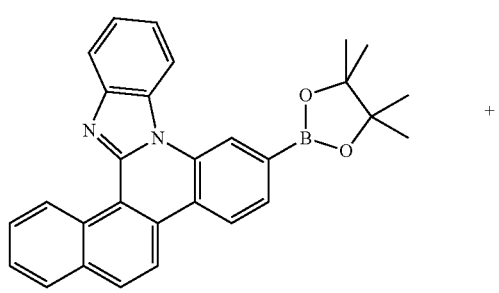

+

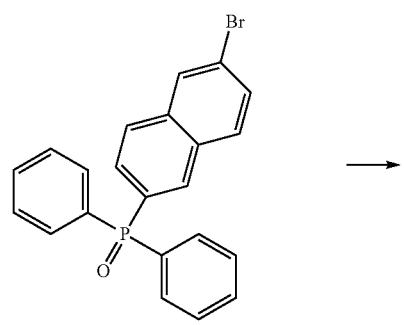

[Structural Formula 1-84D]

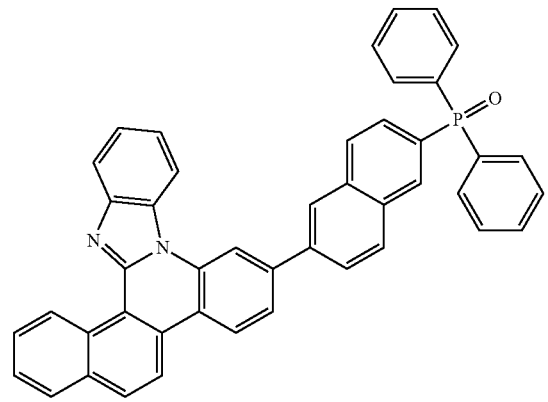

[Structural Formula 1-1F]

[Compound 1-85]

Compound 1-85 was obtained in the same manner as in the preparation method of Compound 1-1, except that Structural Formula 1-84D was used instead of Structural Formula 1-1D.

MS: [M+H]+=645

<Preparation Example 5> Synthesis of the Following Compound 1-86

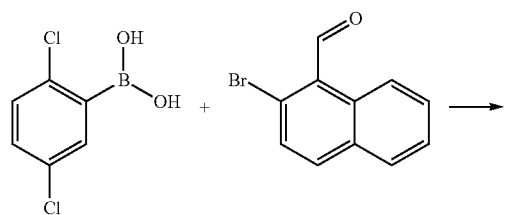

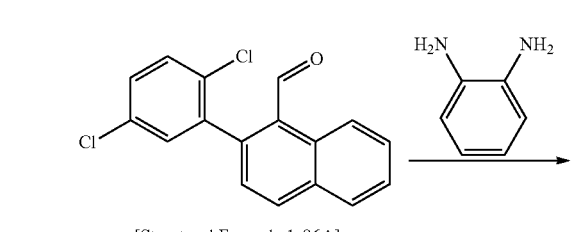

[Structural Formula 1-86A]

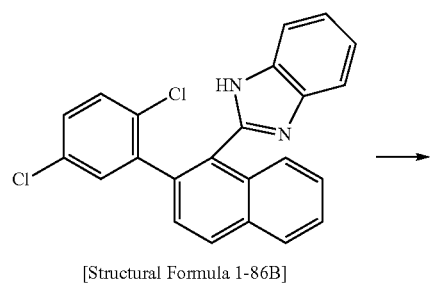

[Structural Formula 1-86B]

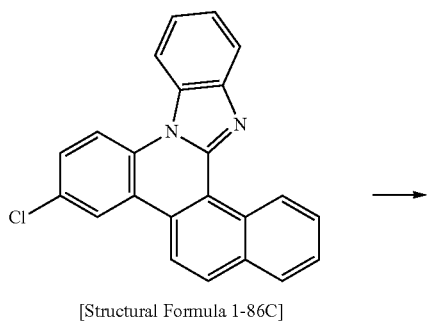

[Structural Formula 1-86C]

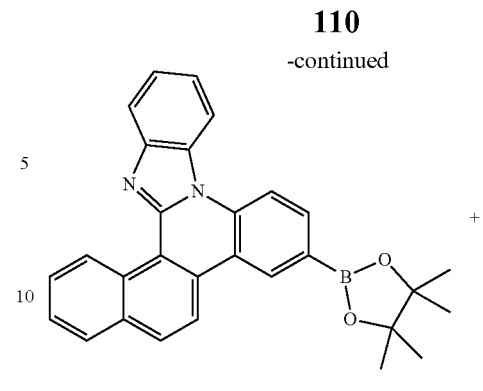

[Structural Formula 1-86D]

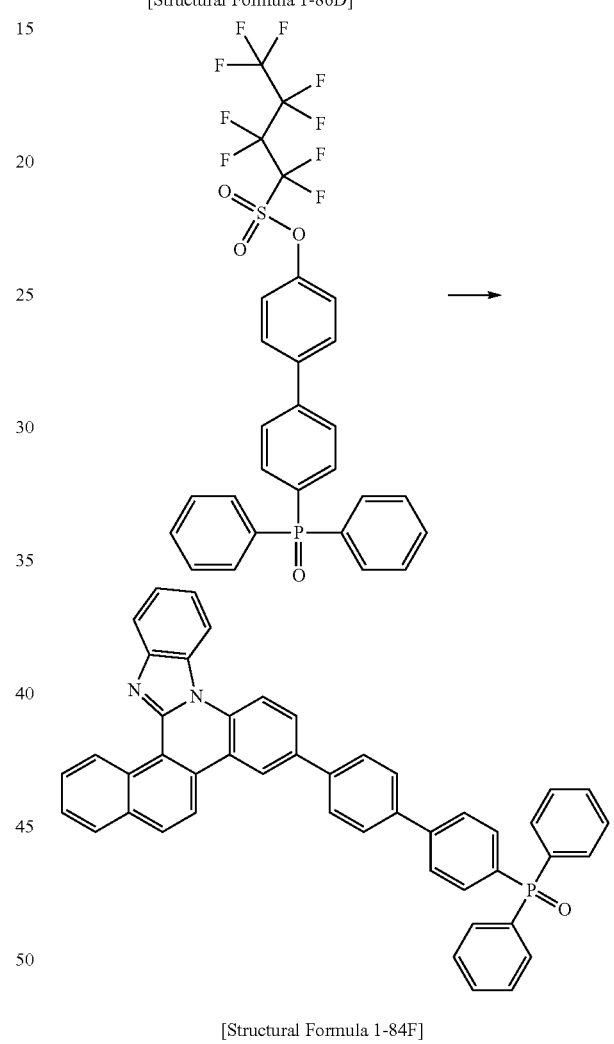

[Structural Formula 1-84F]

[Compound 1-86]

Preparation of Structural Formula 1-86A

Structural Formula 1-86A was obtained in the same manner as in the preparation method of Chemical Formula 1-84A, except that 2,5-dichlorophenylboronic acid was used instead of 2,4-dichlorophenylboronic acid.

MS: [M+H]+=301

Preparation of Structural Formula 1-86B

Structural Formula 1-86B was obtained in the same manner as in the preparation method of Structural Formula 1-84B, except that Structural Formula 1-86A was used instead of Structural Formula 1-84A.

MS: [M+H]+=389

Preparation of Structural Formula 1-86C

Structural Formula 1-86C was obtained in the same manner as in the preparation method of Structural Formula 1-84C, except that Structural Formula 1-86B was used instead of Structural Formula 1-84B.

MS: [M+H]+=353

Preparation of Structural Formula 1-86D

Structural Formula 1-86D was obtained in the same manner as in the preparation method of Structural Formula 1-84D, except that Structural Formula 1-86C was used instead of Structural Formula 1-84C.

MS: [M+H]+=445

Preparation of Compound 1-86

Compound 1-86 was obtained in the same manner as in the preparation method of Compound 1-1, except that Structural Formula 1-86D and Structural Formula 1-84F were used instead of Structural Formula 1-1D and Structural Formula 1-1F, respectively.

MS: [M+H]+=671

<Preparation Example 6> Synthesis of the Following Compound 1-87

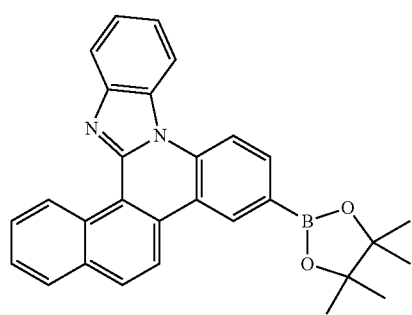

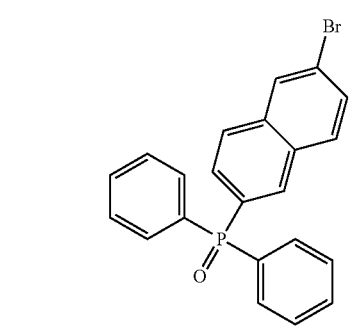

[Structural Formula 1-86D]

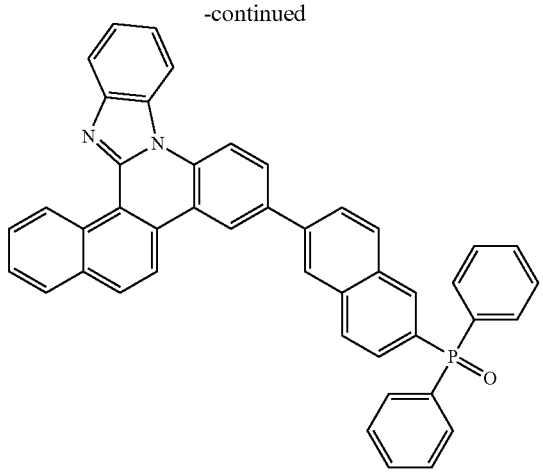

[Structural Formula 1-1F]

[Compound 1-87]

Preparation of Compound 1-87 Chemical Formula 1-87 was obtained in the same manner as in the preparation method of Chemical Formula 1-1, except that Structural Formula 1-86D was used instead of Structural Formula 1-1D.

MS: [M+H]+=645

<Preparation Example 7> Synthesis of the Following Compound 1-37

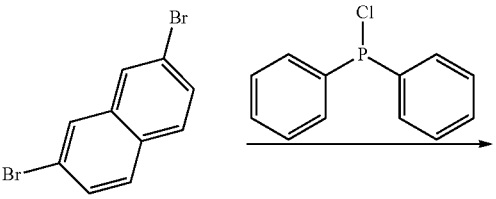

[Structural Formula 1-37F]

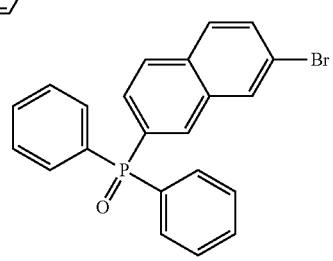

[Structural Formula 1-37E]

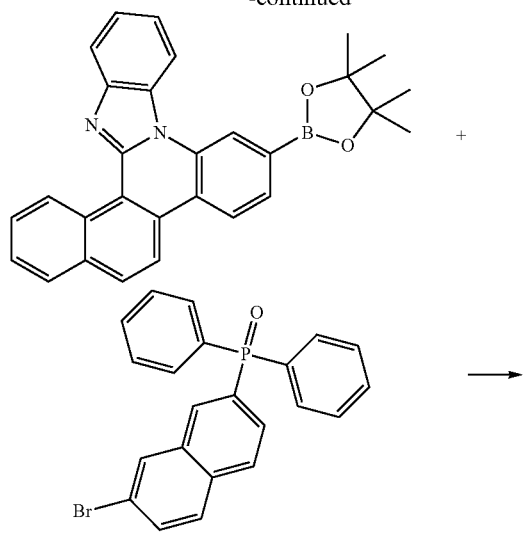

[Structural Formula 1-84D]

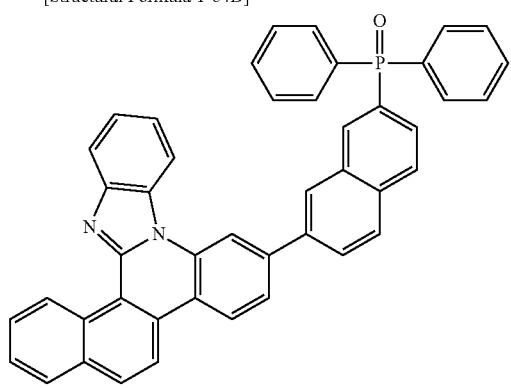

[Structural Formula 1-37F]

[Compound 1-37]
Preparation of Structural Formula 1-37E 2.7-dibromonaphthalene (20 g, 69.94 mmol) was dissolved in tetrahydrofuran (100 ml), and then the resulting solution was cooled to −78° C. n-BuLi (2.5 M, 37 ml, 93 mmol) was slowly added dropwise thereto, and then the resulting mixture was stirred for 30 minutes. After chlorodiphenylphosphine (17 g, 76 mmol) was slowly added dropwise thereto, the resulting mixture was stirred for 3 hours, and then the temperature was increased to normal temperature, and then water (100 mL) was added thereto, and extraction was performed using tetrahydrofuran. The organic layer was concentrated and recrystallized with hexane to obtain Structural Formula 1-37E (21 g, yield 76.8%).

MS: [M+H]+=391

Preparation of Structural Formula 1-37F

Structural Formula 1-37F was obtained in the same manner as in the preparation method of Chemical Formula 1-1F, except that Structural Formula 1-37E was used instead of Structural Formula 1-1E.

MS: [M+H]+=407

Preparation of Compound 1-37

Compound 1-37 was obtained in the same manner as in the preparation method of Compound 1-1, except that Structural Formula 1-84D and Structural Formula 1-37F were used instead of Structural Formula 1-1D and Structural Formula 1-1F, respectively.

MS: [M+H]+=645

EXPERIMENTAL EXAMPLES

Example 1

A glass substrate (Corning 7059 glass) thinly coated with indium tin oxide (ITO) to have a thickness of 1,000 Å was put into distilled water in which a dispersant was dissolved, and ultrasonically washed. A product manufactured by Fischer Co. was used as the detergent, and distilled water twice filtered using a filter manufactured by Millipore Co. was used as the distilled water. After the ITO was washed for 30 minutes, ultrasonic washing was conducted repeatedly twice using distilled water for 10 minutes. After the washing using distilled water was completed, ultrasonic washing was conducted using isopropyl alcohol, acetone, and methanol solvents in this order, and drying was then conducted. Hexanitrile hexaazatriphenylene was thermally vacuum deposited to have a thickness of 500 Å on a transparent ITO electrode thus prepared, thereby forming a hole injection layer. NPB (400 Å), which is a material transporting holes, was vacuum deposited thereon, and then a host H1 compound and a dopant D1 compound were vacuum deposited to have a thickness of 300 Å as a light emitting layer. Next, Compound 1-1 synthesized in Preparation Example 1 and LiQ were thermally vacuum deposited together (200 Å) as an electron injection layer and an electron transporting layer, respectively. Lithium quinolate (LiQ) and aluminum were sequentially deposited on the electron transporting layer to have a thickness of 12 Å and a thickness of 2,000 Å, respectively, to form a negative electrode, thereby manufacturing an organic light emitting device.

E1 was used as a comparative example of the electron transporting layer. In the aforementioned procedure, the deposition rate of the organic material, lithium quinolate, and aluminum were maintained at 1 Å/sec, 0.2 Å/sec, and 3 to 7 Å/sec, respectively.

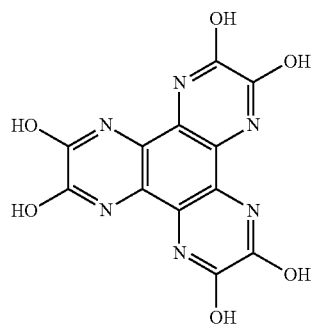

[Hexanitrile hexaazatriphenylene]

115
-continued

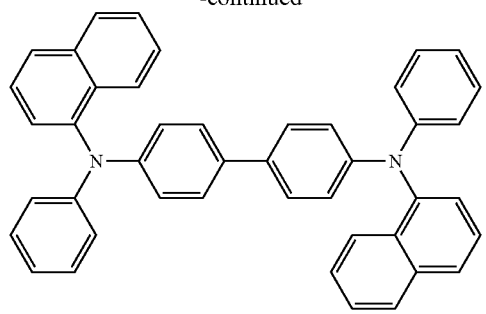

[NPB]

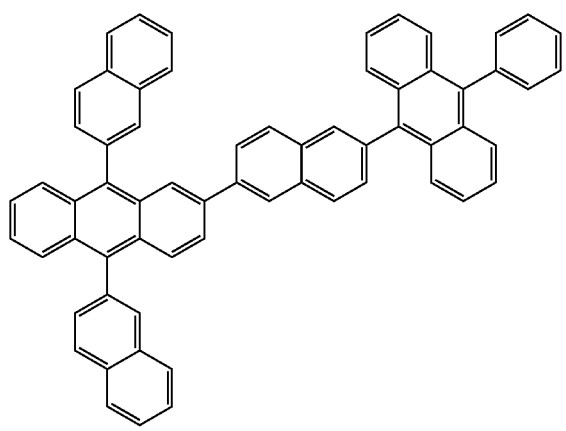

[H1]

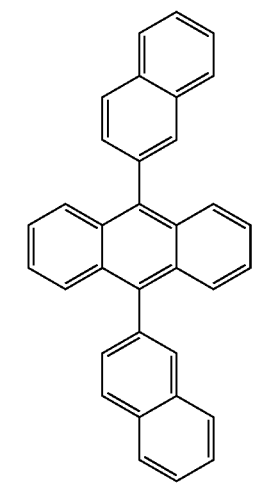

[H2]

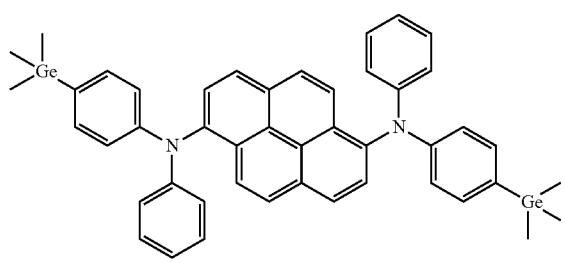

[D1]

116
-continued

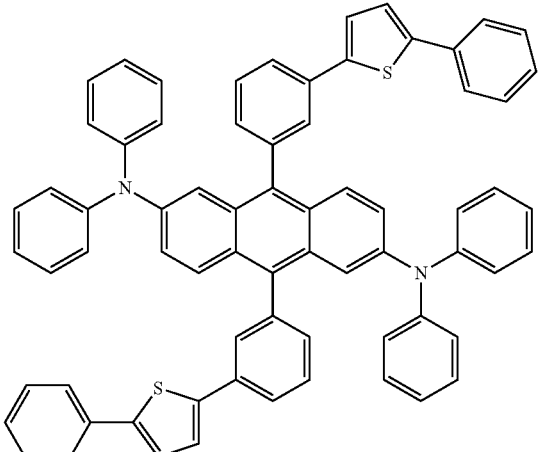

[D2]

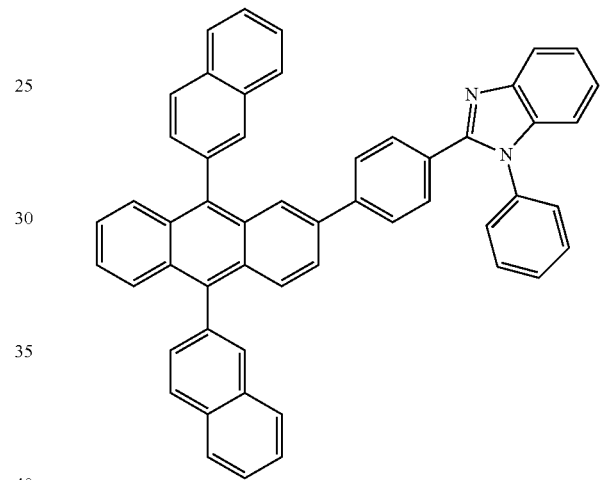

[B1]

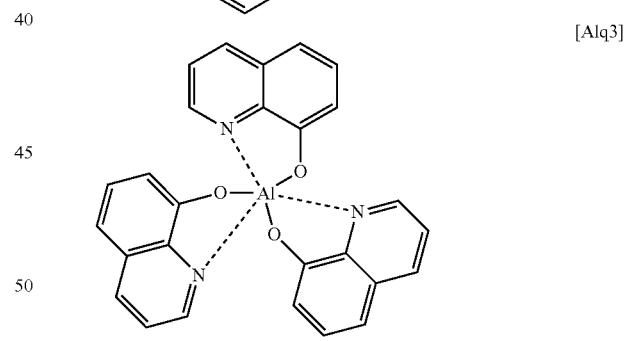

[Alq3]

Example 2

An experiment was performed in the same manner as in Example 1, except that as the electron transporting layer, Chemical Formula 1-38 was used instead of Chemical Formula 1-1.

Example 3

An experiment was performed in the same manner as in Example 1, except that as the electron transporting layer, Chemical Formula 1-84 was used instead of Chemical Formula 1-1.

Example 4

An experiment was performed in the same manner as in Example 1, except that as the electron transporting layer, Chemical Formula 1-85 was used instead of Chemical Formula 1-1.

Example 5

An experiment was performed in the same manner as in Example 1, except that as the electron transporting layer, Chemical Formula 1-86 was used instead of Chemical Formula 1-1.

Example 6

An experiment was performed in the same manner as in Example 1, except that as the electron transporting layer, Chemical Formula 1-87 was used instead of Chemical Formula 1-1.

Example 7

An experiment was performed in the same manner as in Example 1, except that as the electron transporting layer, Chemical Formula 1-37 was used instead of Chemical Formula 1-1.

Comparative Example 1

An experiment was performed in the same manner as in Example 1, except that as the electron transporting layer, E1 was used instead of Chemical Formula 1-1.

Comparative Example 2

An experiment was performed in the same manner as in Example 1, except that as the electron transporting layer, E2 was used instead of Chemical Formula 1-1.

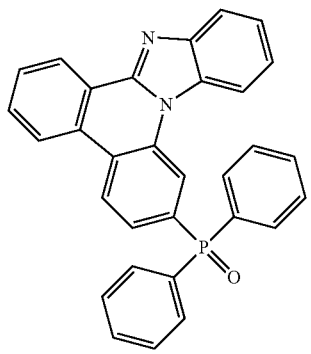

[E2]

Comparative Example 3

An experiment was performed in the same manner as in Example 1, except that as the electron transporting layer, E3 was used instead of Chemical Formula 1-1.

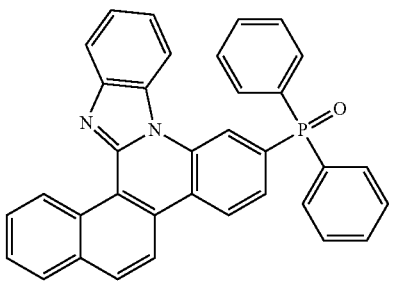

[E3]

Comparative Example 4

An experiment was performed in the same manner as in Example 1, except that as the electron transporting layer, E4 was used instead of Chemical Formula 1-1.

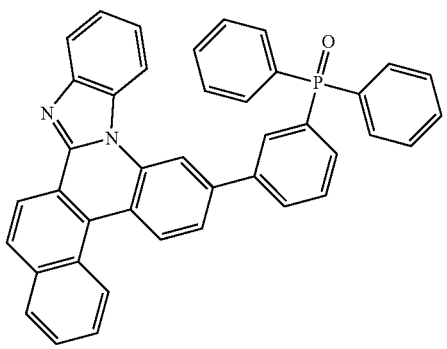

[E4]

The results in which an organic light emitting device manufactured by using each compound as an electron transporting layer material as in the Examples was experimented are shown in Table 1.

TABLE 1

| Experimental Example (5 mA/cm$^2$) | ETL Material | Voltage (V) | Efficiency (Cd/A) | Lifespan (Td5) (hr) |
|---|---|---|---|---|
| Comparative Example 1 | E1 | 3.98 | 5.51 | 96.1 |
| Comparative Example 2 | E2 | 3.17 | 4.9 | 112 |
| Comparative Example 3 | E3 | 4.34 | 5.35 | 206.6 |
| Comparative Example 4 | E4 | 4.37 | 5.26 | 170.3 |
| Experimental Example 1 | Compound 1-1 | 4.31 | 5.42 | 204.3 |
| Experimental Example 2 | Compound 1-38 | 4.28 | 4.98 | 210.2 |
| Experimental Example 3 | Compound 1-84 | 4.16 | 5.37 | 202 |
| Experimental Example 4 | Compound 1-85 | 4.5 | 5.11 | 205.3 |
| Experimental Example 5 | Compound 1-86 | 4.27 | 5.25 | 198.7 |
| Experimental Example 6 | Compound 1-87 | 4.35 | 5.51 | 201.1 |
| Experimental Example 7 | Compound 1-37 | 4.3 | 5.64 | 211.6 |

As in the results, the novel compound according to the present invention may be used as a material for an organic material layer of an organic electronic device including an organic light emitting device by introducing various substituents, and the like. The organic electronic device including the organic light emitting device using the compound represented by Chemical Formula 1 according to the present invention as a material for an organic material layer exhibits excellent efficiency characteristics and particularly, lifespan characteristics (long lifespan) compared to the existing materials and E1, E2, E3, and E4 in the Comparative Examples.

The invention claimed is:

1. A compound represented by the following Chemical Formula 1:

[Chemical Formula 1]

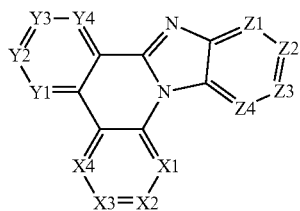

in Chemical Formula 1,

X1 is N or CR1, X2 is N or CR2, X3 is N or CR3, and X4 is N or CR4,

Y1 is N or CR5, Y2 is N or CR6, Y3 is N or CR7, and Y4 is N or CR8,

Z1 is N or CR9, Z2 is N or CR10, Z3 is N or CR11, and Z4 is N or CR12,

X1 to X4, Y1 to Y4, and Z1 to Z4 are not simultaneously N,

R1 to R12 are the same as or different from each other, and are each independently hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylphosphine group; a substituted or unsubstituted phosphine oxide group; a substituted or unsubstituted aryl group; or a substituted or unsubstituted hetero-cyclic group, or optionally combine with an adjacent group to form a substituted or unsubstituted ring, two or more adjacent groups of R1 to R8 combine with each other to form a substituted or unsubstituted 6-membered ring, at least one of a substituent of the 6-membered ring formed by combining two or more adjacent groups of R1 to R8; a group of R1 to R8, which does not form a ring; and R9 to R12 is

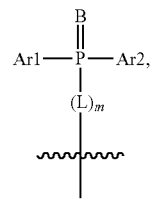

B is O, S, or Se, and

Ar1 and Ar2 are the same as or different from each other, and are each independently a substituted or unsubstituted aryl group; or a substituted or unsubstituted hetero-cyclic group, or combine with each other to form a substituted or unsubstituted ring, L is a substituted or unsubstituted divalent naphthyl group; a substituted or unsubstituted divalent biphenyl group; a substituted or unsubstituted divalent pyridyl group; a substituted or unsubstituted divalent quinoline group; a substituted or unsubstituted divalent anthracene group; or a substituted or unsubstituted divalent phenanthrene group, m is an integer of 1 to 5, and when m is 2 or more, L's are the same as or different from each other.

2. The compound of claim 1, wherein Chemical Formula 1 is represented by any one of the following Chemical Formulae 2 to 4:

[Chemical Formula 2]

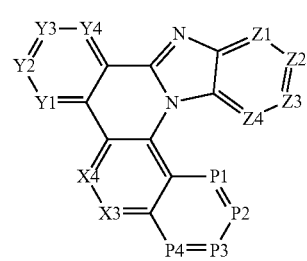

[Chemical Formula 3]

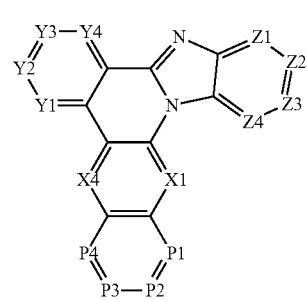

-continued

[Chemical Formula 4]

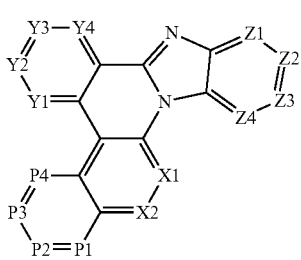

in Chemical Formulae 2 to 4,
X1 is N or CR1, X2 is N or CR2, X3 is N or CR3, and X4 is N or CR4,
Y1 is N or CR5, Y2 is N or CR6, Y3 is N or CR7, and Y4 is N or CR8,
Z1 is N or CR9, Z2 is N or CR10, Z3 is N or CR11, and Z4 is N or CR12,
P1 is N or CR13, P2 is N or CR14, P3 is N or CR15, and P4 is N or CR16,
R1 to R16 are the same as or different from each other, and are each independently hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylphosphine group; a substituted or unsubstituted phosphine oxide group; a substituted or unsubstituted aryl group; or a substituted or unsubstituted hetero-cyclic group, or optionally combine with an adjacent group to form a substituted or unsubstituted ring,
at least one of R1 to R16 is

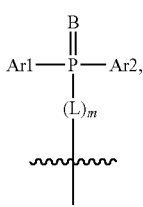

B is O, S, or Se, and
Ar1 and Ar2 are the same as or different from each other, and are each independently a substituted or unsubstituted aryl group; or a substituted or unsubstituted hetero-cyclic group,
L is a substituted or unsubstituted divalent naphthyl group; a substituted or unsubstituted divalent biphenyl group; a substituted or unsubstituted divalent pyridyl group; a substituted or unsubstituted divalent quinoline group; a substituted or unsubstituted divalent anthracene group; or a substituted or unsubstituted divalent phenanthrene group,
m is an integer of 1 to 5, and
when m is 2 or more, L's are the same as or different from each other.

3. The compound of claim 1, wherein Chemical Formula 1 is represented by any one of the following Chemical Formulae 5 to 7:

[Chemical Formula 5]

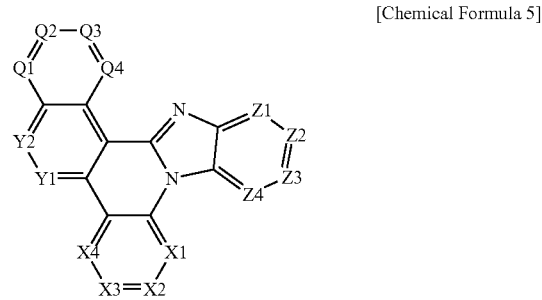

[Chemical Formula 6]

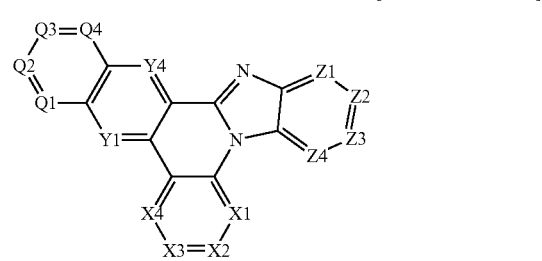

[Chemical Formula 7]

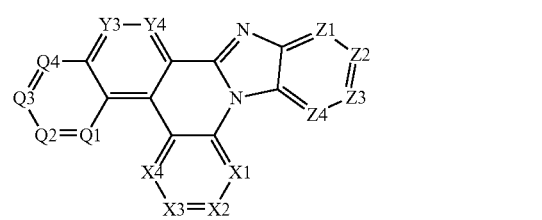

in Chemical Formulae 5 to 7,
X1 is N or CR1, X2 is N or CR2, X3 is N or CR3, and X4 is N or CR4,
Y1 is N or CR5, Y2 is N or CR6, Y3 is N or CR7, and Y4 is N or CR8,
Z1 is N or CR9, Z2 is N or CR10, Z3 is N or CR11, and Z4 is N or CR12,
Q1 is N or CR17, Q2 is N or CR18, Q3 is N or CR19, and Q4 is N or CR20,
R1 to R12 and R17 to R20 are the same as or different from each other, and are each independently hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylphosphine group; a substituted or unsubstituted phosphine oxide group; a substituted or unsubstituted aryl group; or a substituted or unsubstituted heterocyclic group, or optionally combine with an adjacent group to form a substituted or unsubstituted ring, at least one of R1 to R12 and R17 to R20 is

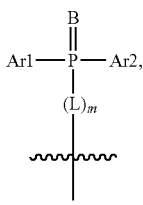

B is O, S, or Se,

Ar1 and Ar2 are the same as or different from each other, and are each independently a substituted or unsubstituted aryl group; or a substituted or unsubstituted hetero-cyclic group, L is a substituted or unsubstituted divalent naphthyl group; a substituted or unsubstituted divalent biphenyl group; a substituted or unsubstituted divalent pyridyl group; a substituted or unsubstituted divalent quinoline group; a substituted or unsubstituted divalent anthracene group; or a substituted or unsubstituted divalent phenanthrene group, m is an integer of 1 to 5, and when m is 2 or more, L's are the same as or different from each other.

4. The compound of claim 1, wherein Chemical Formula 1 is represented by any one of the following Chemical Formulae 8 to 16:

[Chemical Formula 8]

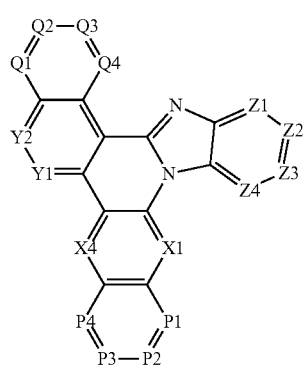

[Chemical Formula 9]

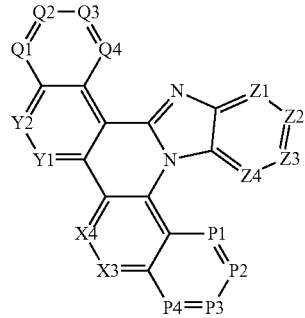

[Chemical Formula 10]

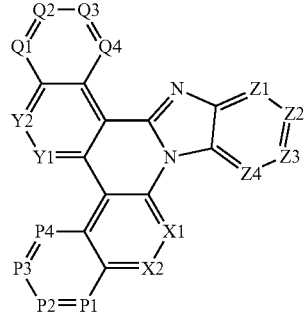

[Chemical Formula 11]

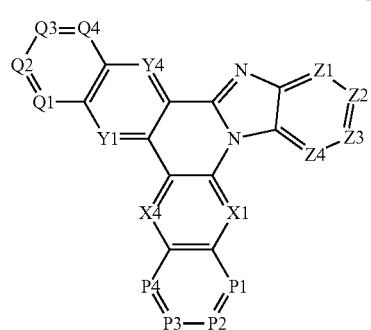

[Chemical Formula 12]

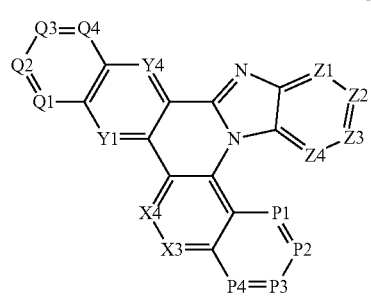

[Chemical Formula 13]

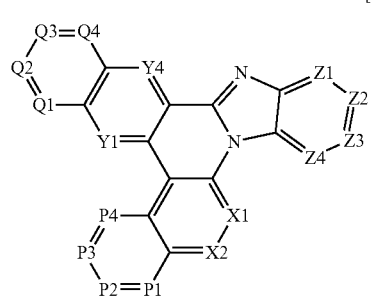

[Chemical Formula 14]

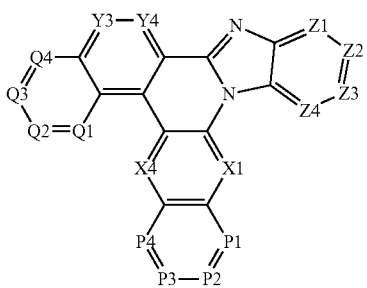

[Chemical Formula 15]

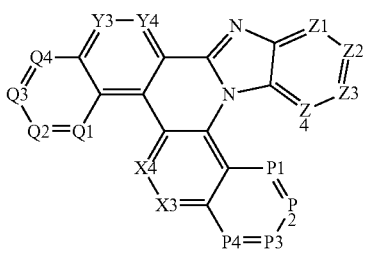

[Chemical Formula 16]

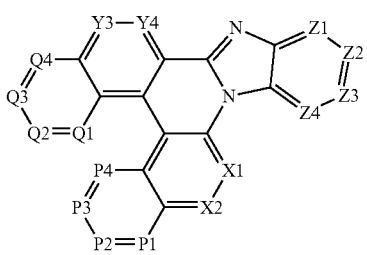

in Chemical Formulae 8 to 16,

X1 is N or CR1, X2 is N or CR2, X3 is N or CR3, and X4 is N or CR4,

Y1 is N or CR5, Y2 is N or CR6, Y3 is N or CR7, and Y4 is N or CR8,

Z1 is N or CR9, Z2 is N or CR10, Z3 is N or CR11, and Z4 is N or CR12,

P1 is N or CR13, P2 is N or CR14, P3 is N or CR15, and P4 is N or CR16,

Q1 is N or CR17, Q2 is N or CR18, Q3 is N or CR19, and Q4 is N or CR20,

R1 to R20 are the same as or different from each other, and are each independently hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylphosphine group; a substituted or unsubstituted phosphine oxide group; a substituted or unsubstituted aryl group; or a substituted or unsubstituted hetero-cyclic group, or optionally combine with an adjacent group to form a substituted or unsubstituted ring, at least one of R1 to R20 is

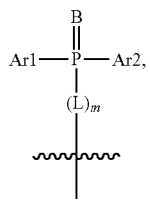

B is O, S, or Se,

Ar1 and Ar2 are the same as or different from each other, and are each independently a substituted or unsubstituted aryl group; or a substituted or unsubstituted hetero-cyclic group, L is a substituted or unsubstituted divalent naphthyl group; a substituted or unsubstituted divalent biphenyl group; a substituted or unsubstituted divalent pyridyl group; a substituted or unsubstituted divalent quinoline group; a substituted or unsubstituted divalent anthracene group; or a substituted or unsubstituted divalent phenanthrene group, m is an integer of 1 to 5, and when m is 2 or more, L's are the same as or different from each other.

5. The compound of claim 1, wherein at least one of the substituent of the 6-membered ring formed by combining two or more adjacent groups of R1 to R8; a group of R1 to R8, which does not form a ring; and R9 to R12 is

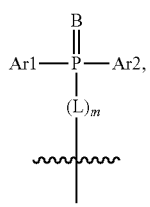

at least one of the substituent of the 6-membered ring formed by combining two or more adjacent groups among R1 to R8; a group of R1 to R8, which does not form a ring; and groups which are not

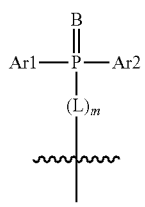

in R9 to R12, is a substituted or unsubstituted aryl group; or a substituted or unsubstituted hetero-cyclic group.

6. The compound of claim 1, wherein at least one of the substituent of the 6-membered ring formed by combining two or more adjacent groups of R1 to R8; a group of R1 to R8, which does not form a ring; and R9 to R12 is

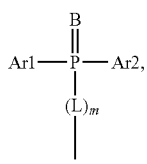

at least one of the substituent of the 6-membered ring formed by combining two or more adjacent groups of R1 to R8; a group of R1 to R8, which does not form a ring; and groups which are not

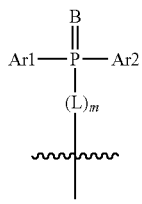

in R9 to R12 is a substituted or unsubstituted phenyl group; a substituted or unsubstituted biphenyl group; a substituted or unsubstituted naphthyl group; a substituted or unsubstituted phenanthryl group; a substituted or unsubstituted pyrenyl group; a substituted or unsubstituted fluorenyl group; a substituted or unsubstituted pyridyl group; a substituted or unsubstituted quinoline group; a substituted or unsubstituted quinazoline group; a substituted or unsubstituted quinoxaline group; a substituted or unsubstituted carbazole group; or a substituted or unsubstituted dibenzofuran group.

7. The compound of claim 1, wherein at least two or more of the substituent of the 6-membered ring formed by combining two or more adjacent groups of R1 to R8; a group of R1 to R8, which does not form a ring; and R9 to R12 are

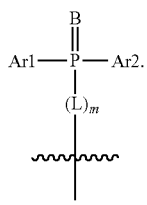

8. The compound of claim 1, wherein the compound of Chemical Formula 1 is any one selected from the following structural formulae:

[Compound 1-1]

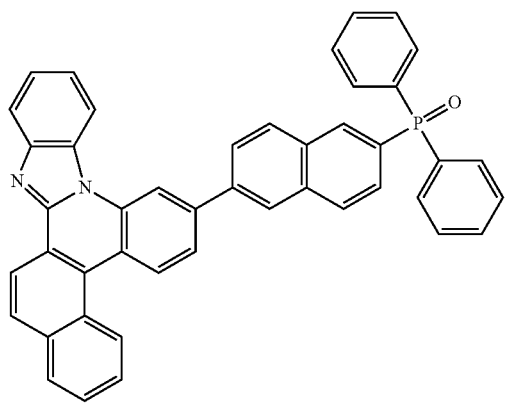

[Compound 1-2]

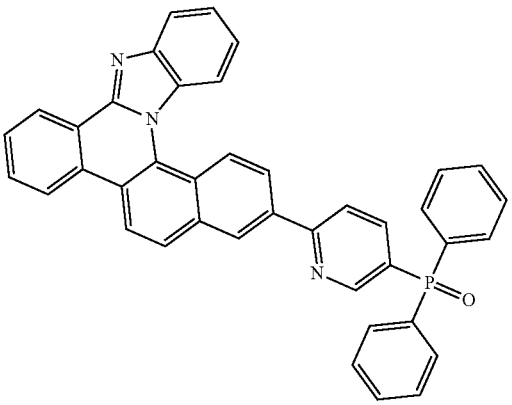

[Compound 1-3]

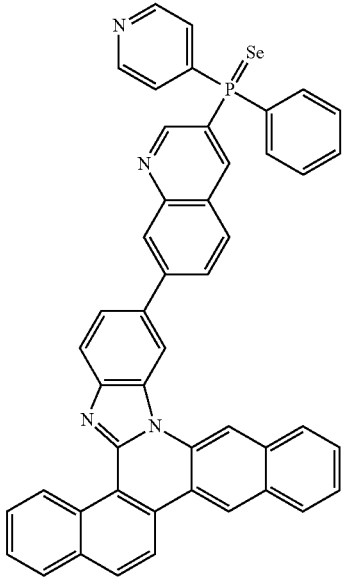

[Compound 1-4]

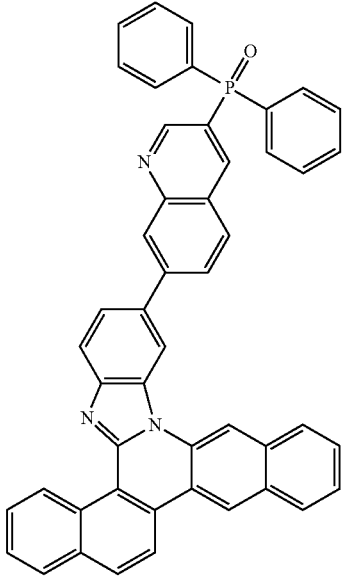

[Compound 1-5]
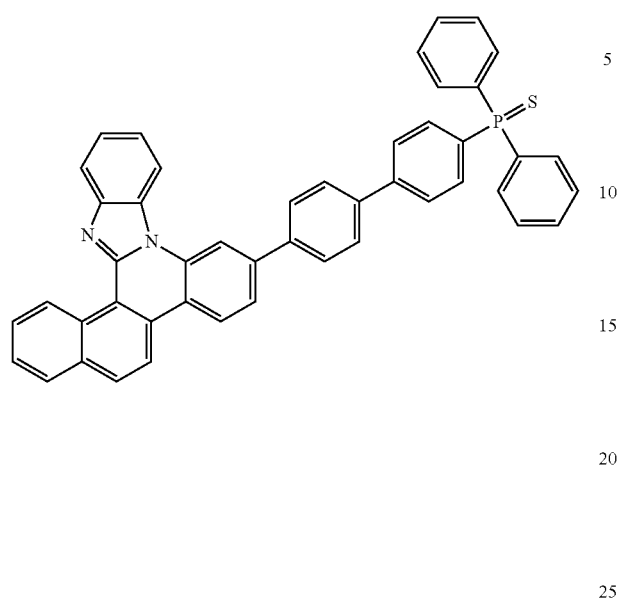
[Compound 1-8]
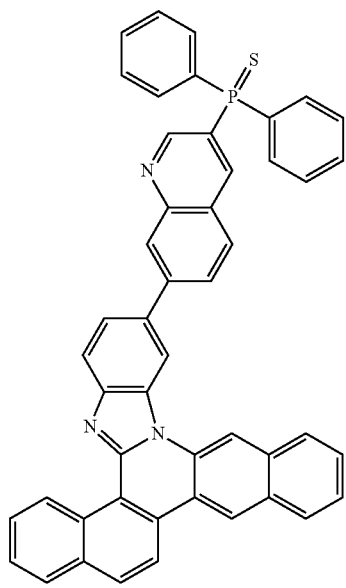
[Compound 1-6]
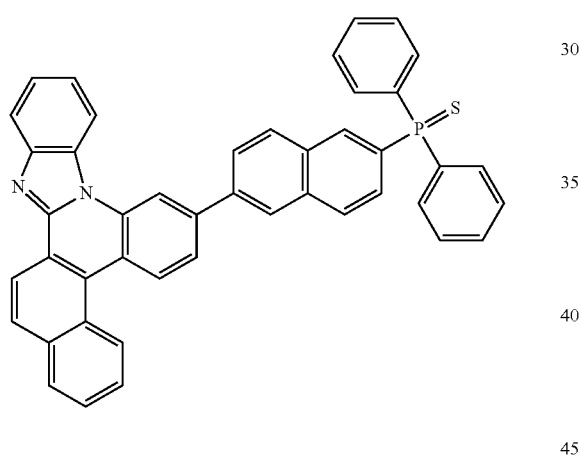
[Compound 1-9]
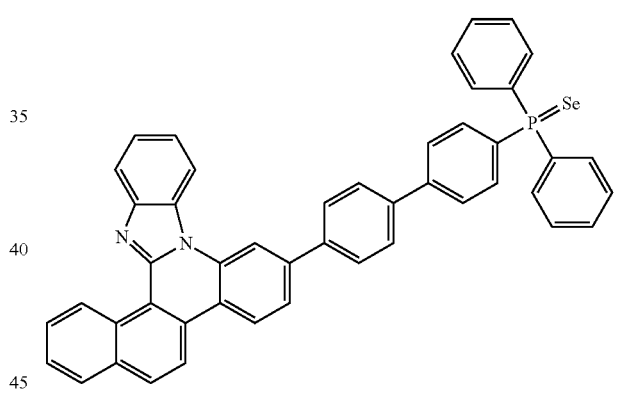
[Compound 1-7]
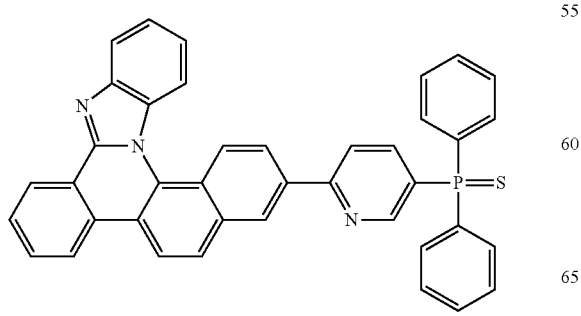
[Compound 1-10]
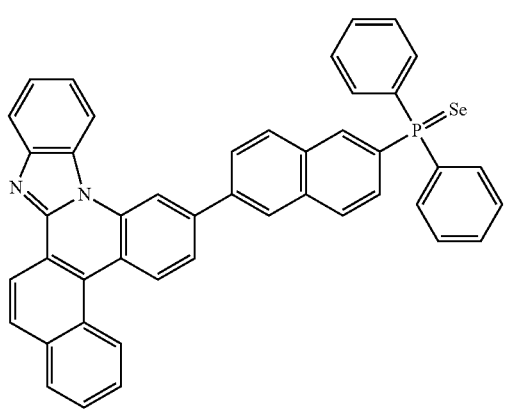

-continued
[Compound 1-11]
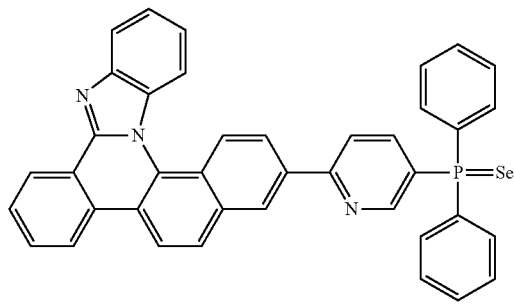
[Compound 1-12]
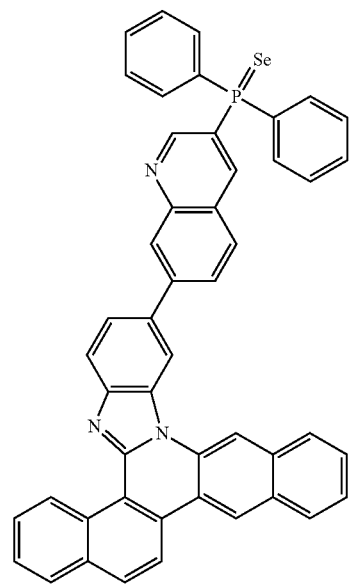
[Compound 1-13]
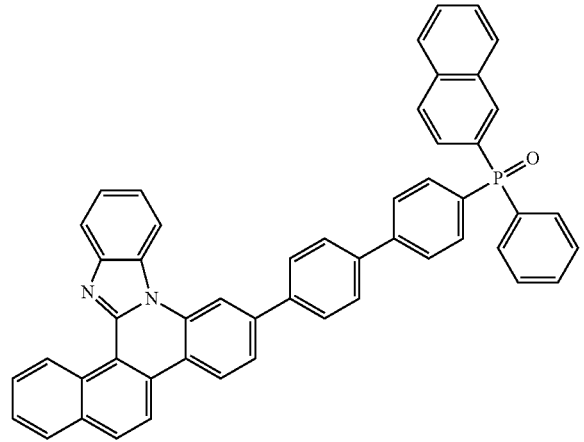
-continued
[Compound 1-14]
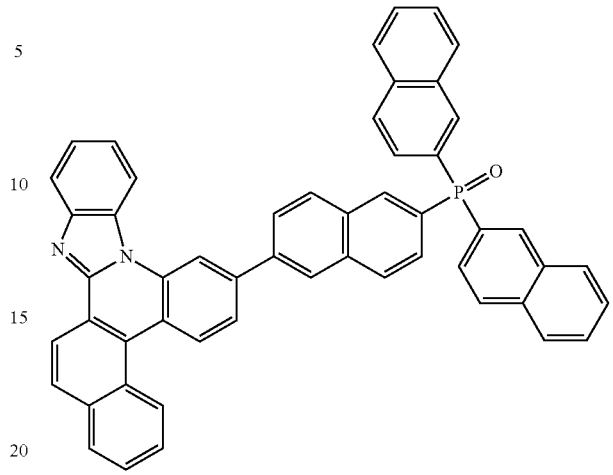
[Compound 1-15]
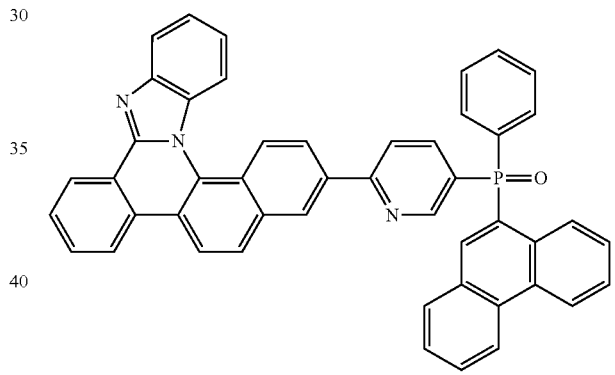
[Compound 1-16]
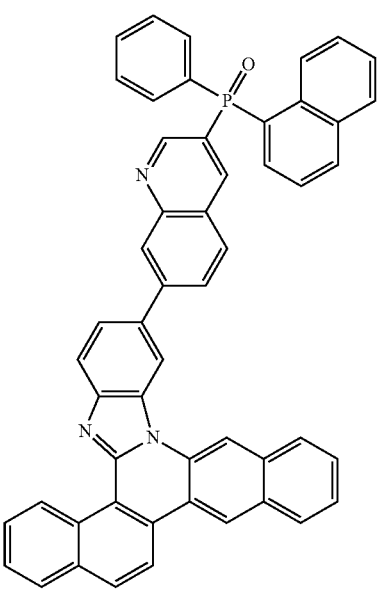

[Compound 1-17]
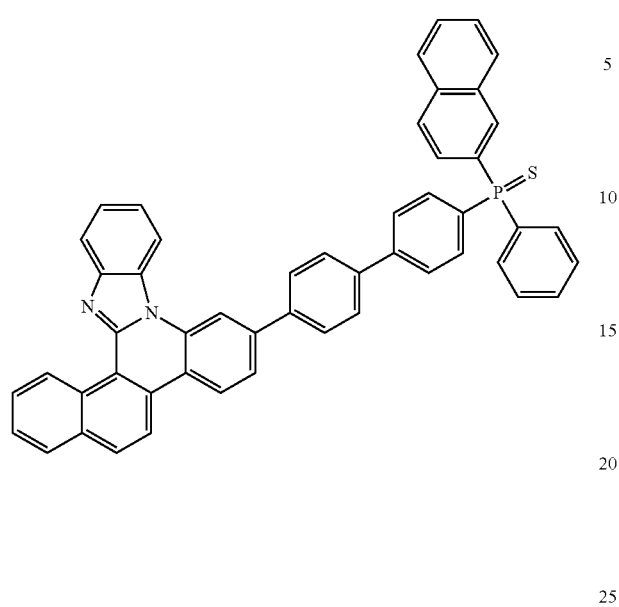
[Compound 1-18]
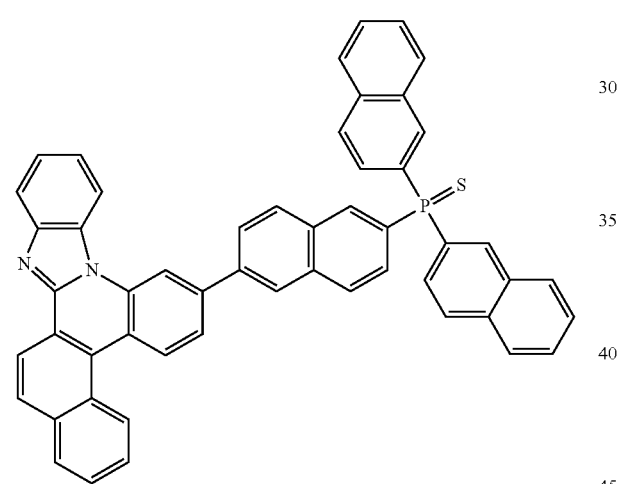
[Compound 1-19]
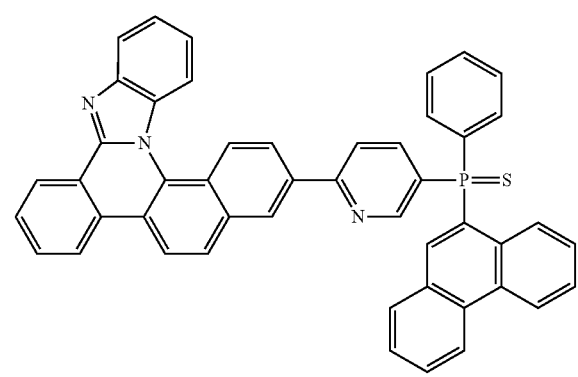
[Compound 1-20]
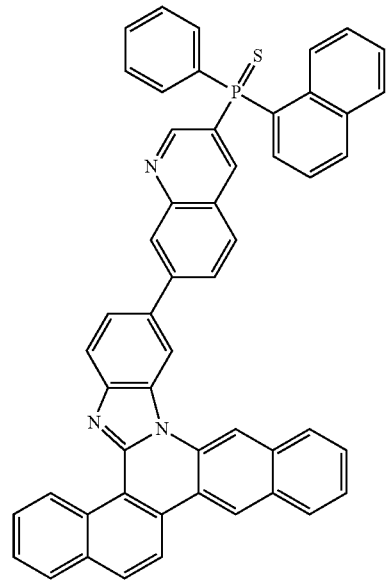
[Compound 1-21]
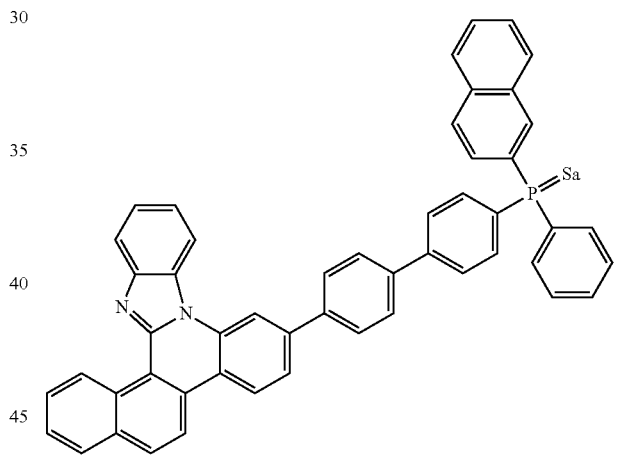
[Compound 1-22]
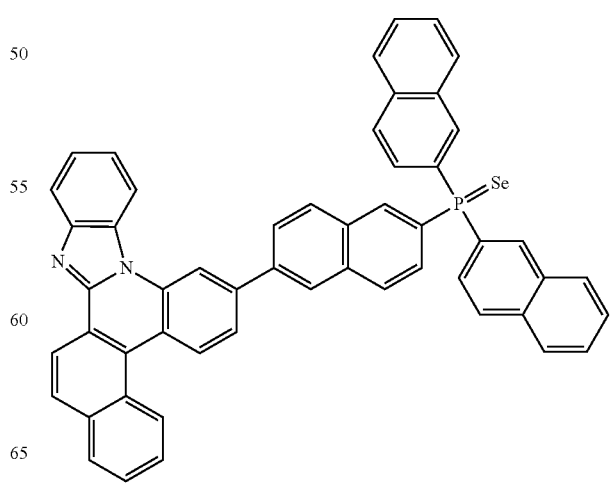

[Compound 1-23]
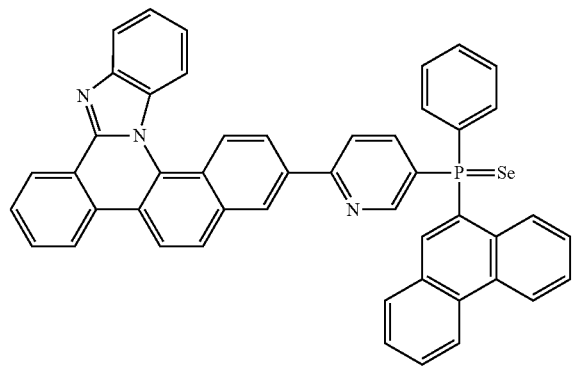
[Compound 1-24]
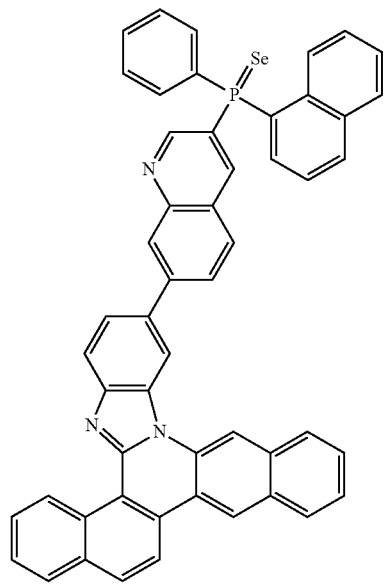
[Compound 1-25]
[Compound 1-26]
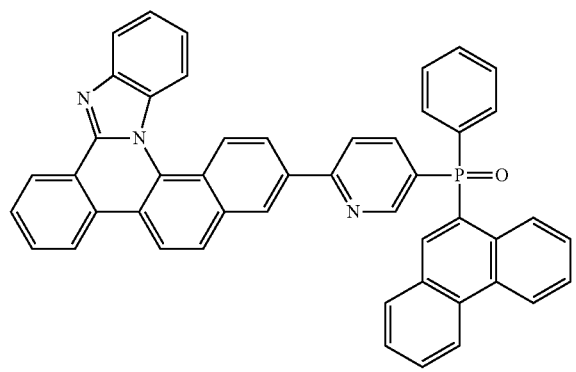
[Compound 1-27]
[Compound 1-28]
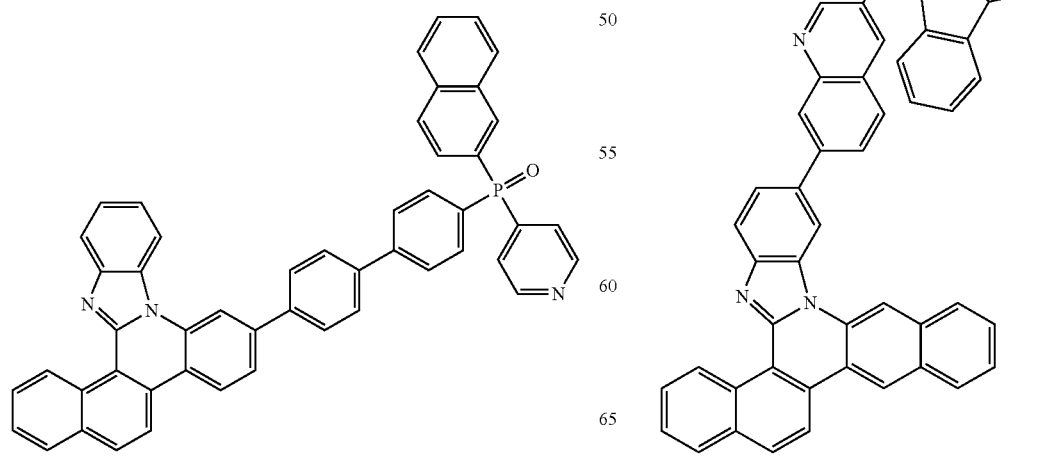

-continued
[Compound 1-29]
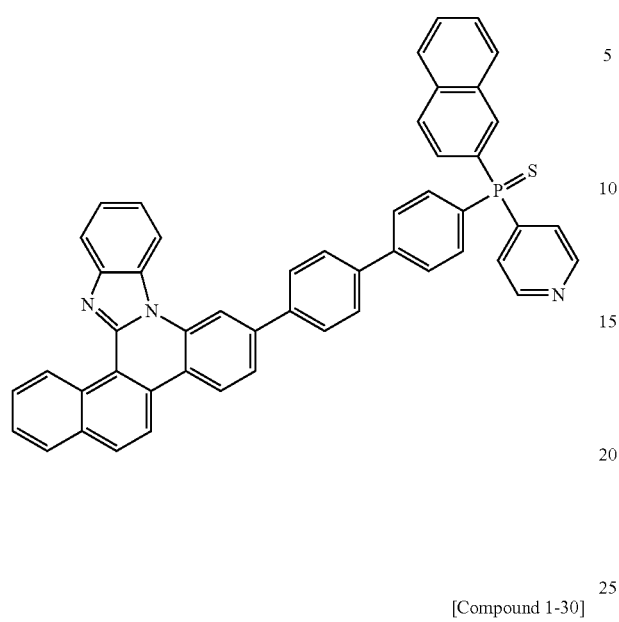
[Compound 1-30]
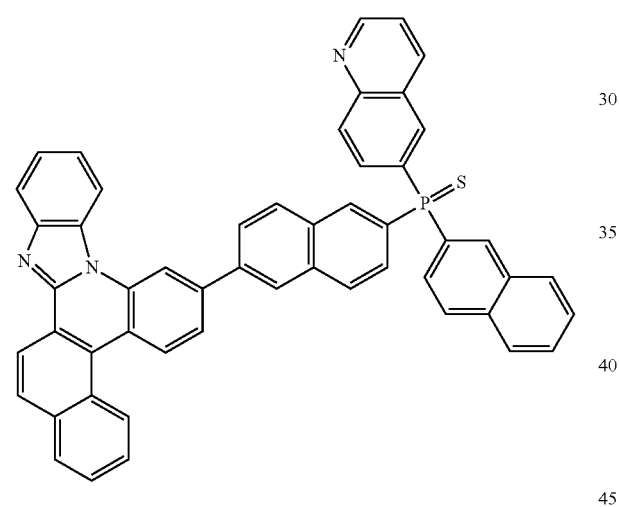
[Compound 1-31]
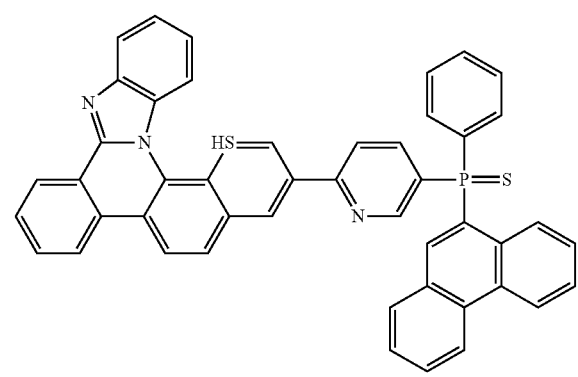
[Compound 1-32]
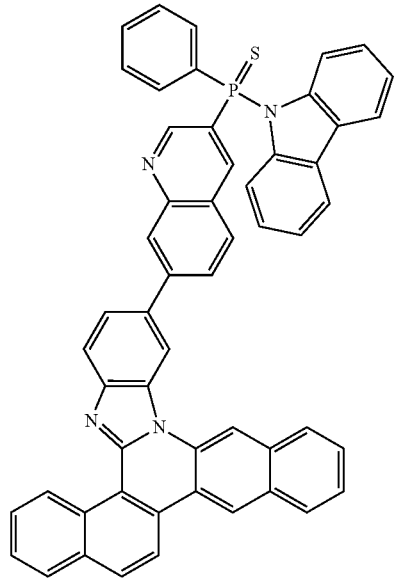
[Compound 1-33]
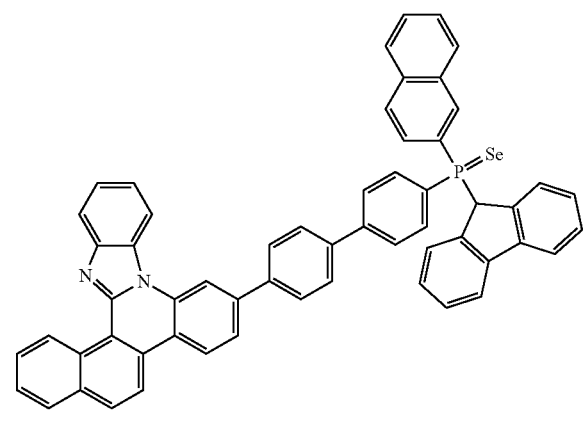
[Compound 1-34]
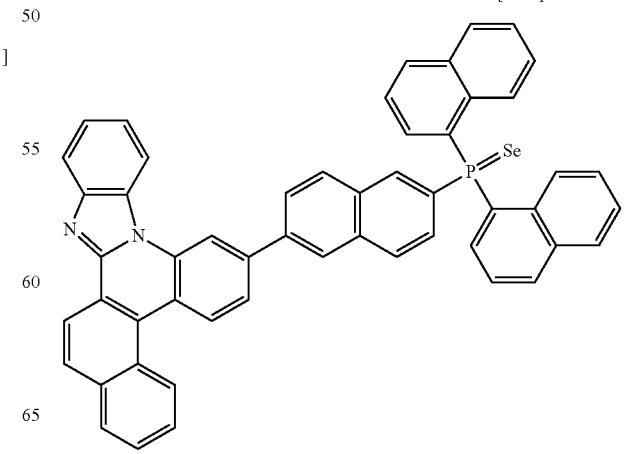

[Compound 1-35]
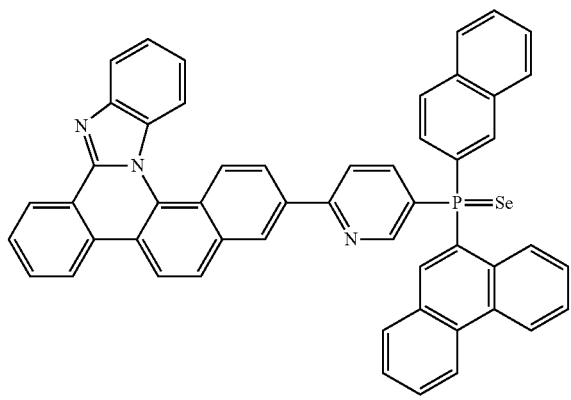
[Compound 1-36]
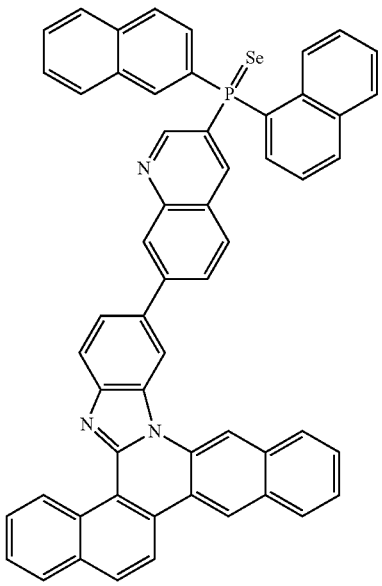
[Compound 1-37]
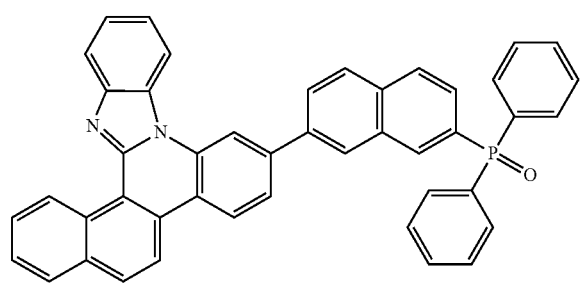
[Compound 1-38]
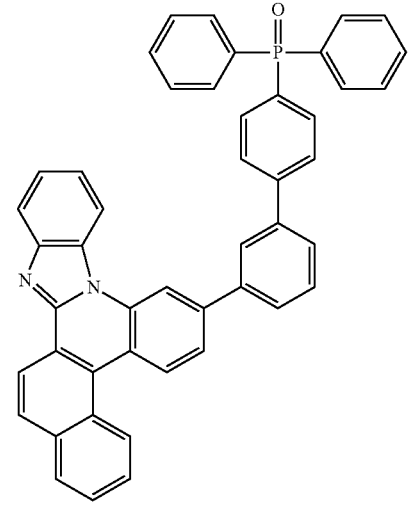
[Compound 1-39]
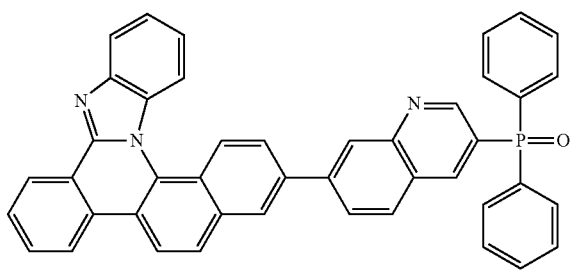
[Compound 1-40]
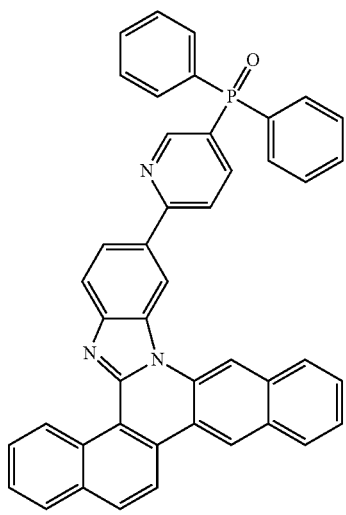
[Compound 1-41]
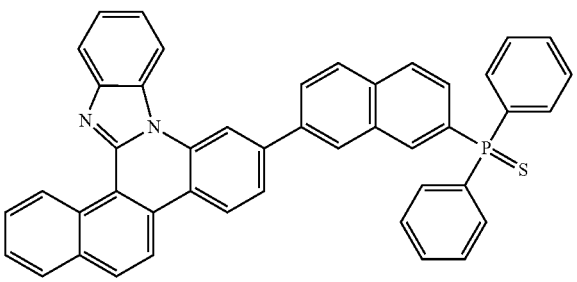

[Compound 1-42]
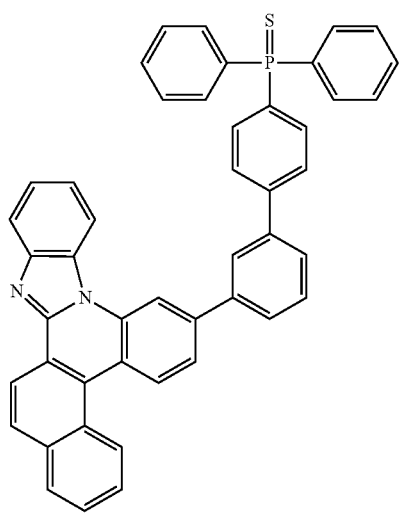
[Compound 1-45]
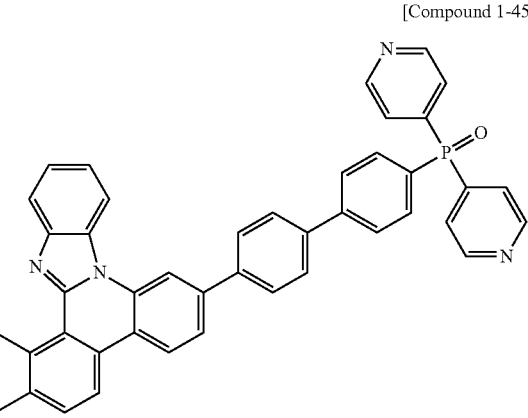
[Compound 1-43]
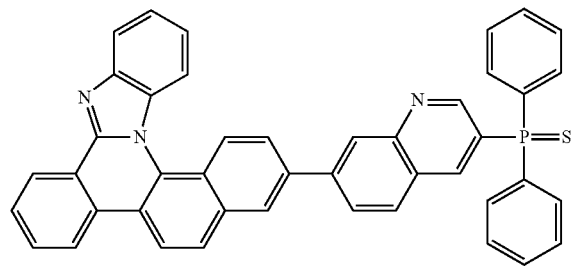
[Compound 1-46]
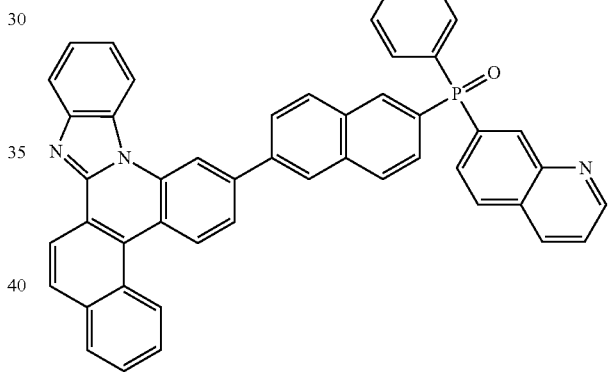
[Compound 1-44]
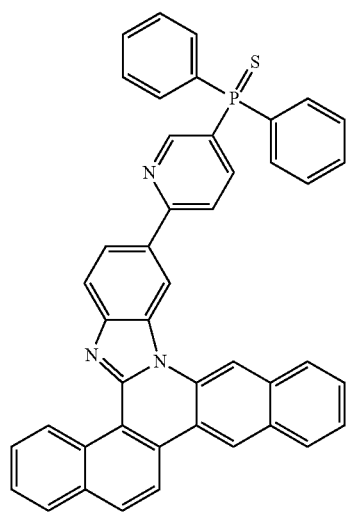
[Coumpound 1-47]
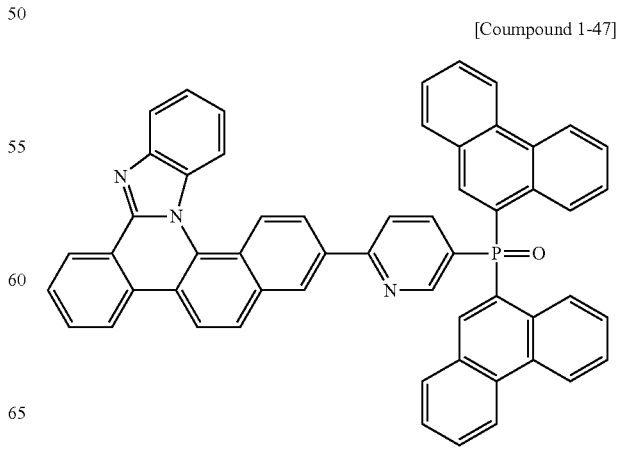

[Compound 1-48]
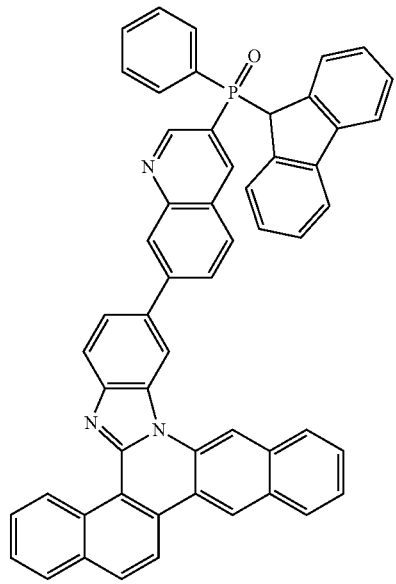
[Compound 1-51]
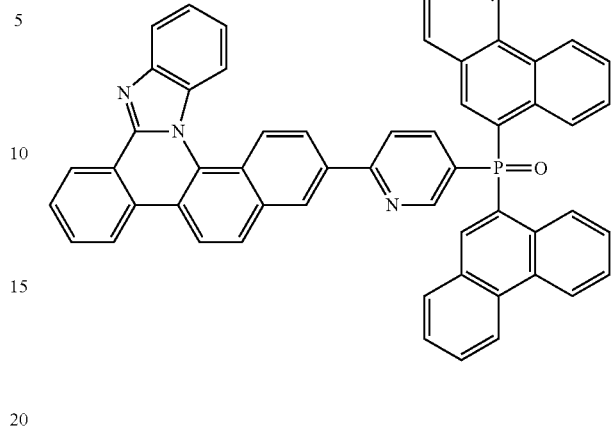
[Compound 1-49]
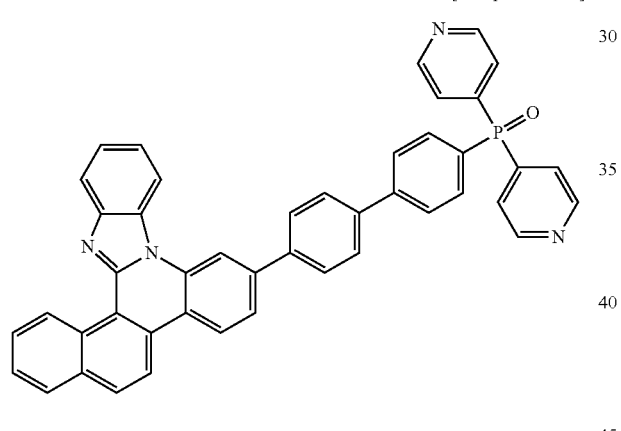
[Compound 1-52]
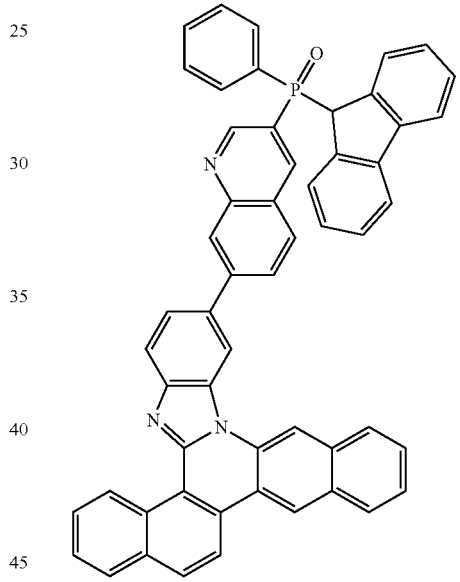
[Compound 1-50]
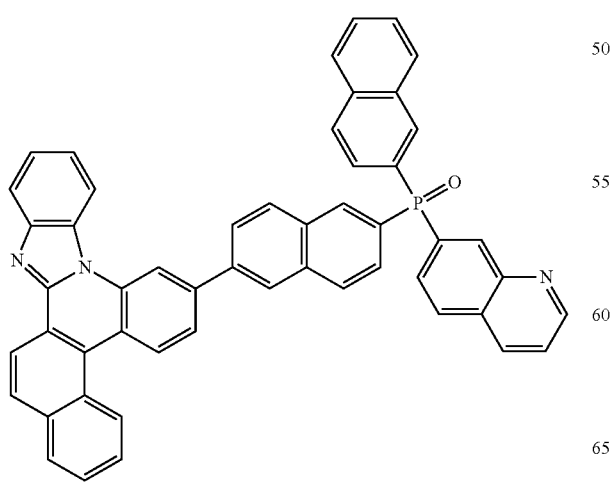
[Compound 1-53]
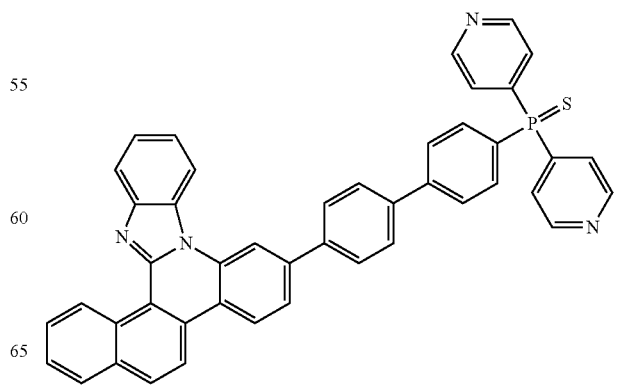

[Compound 1-54]
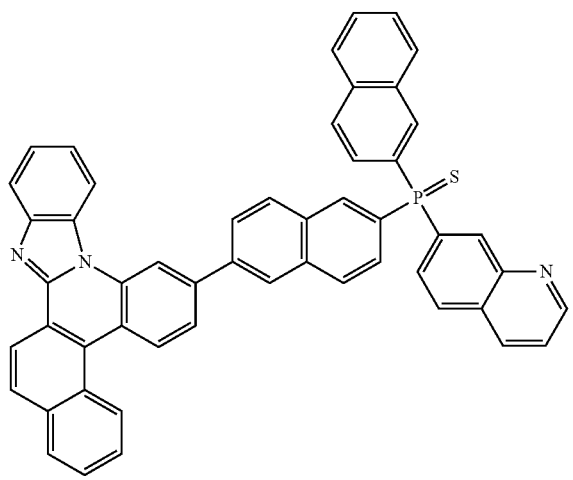
[Compound 1-55]
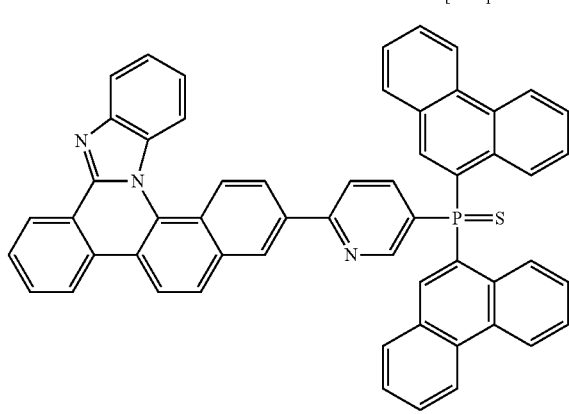
[Compound 1-56]
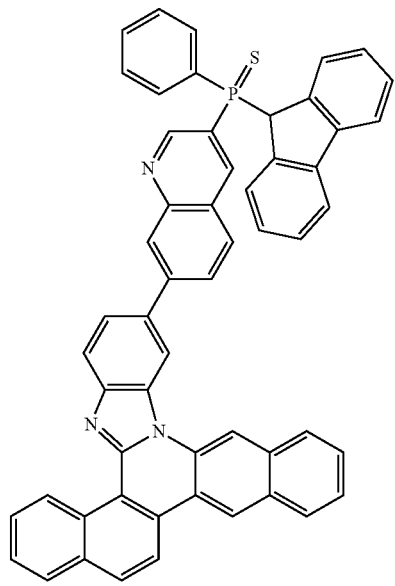
[Compound 1-57]
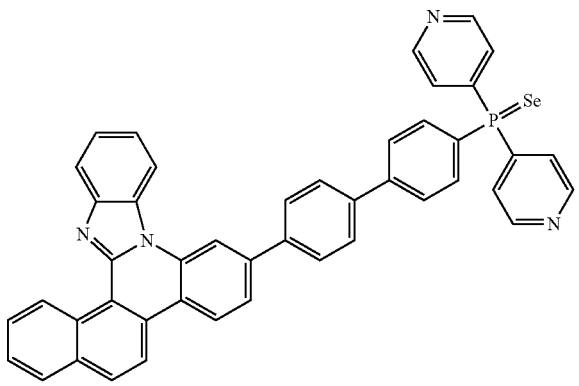
[Compound 1-58]
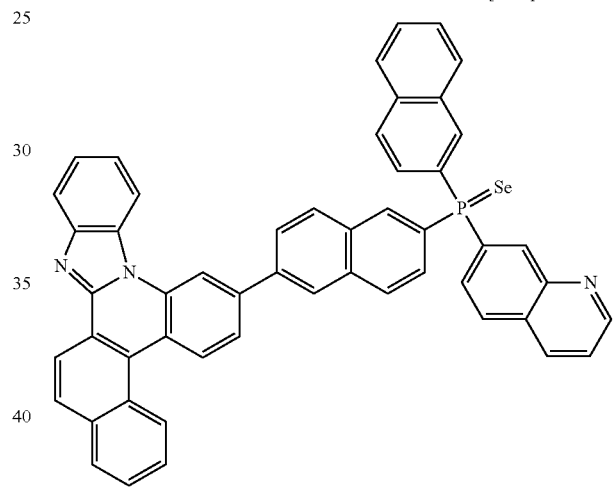
[Compound 1-59]
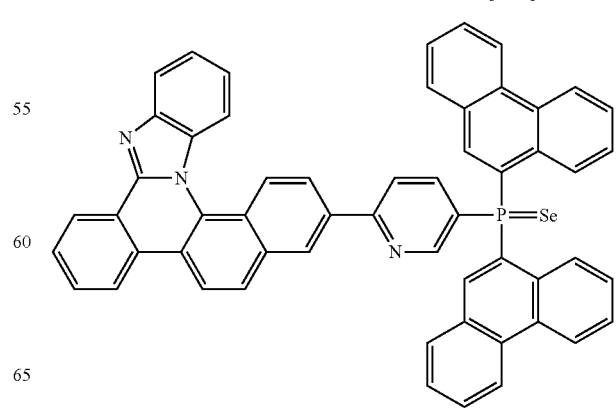

[Compound 1-60]
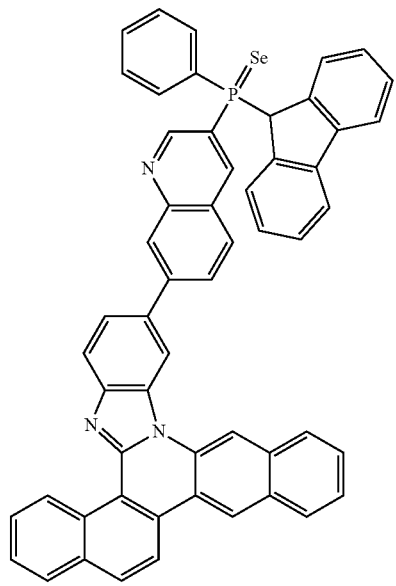
[Compound 1-63]
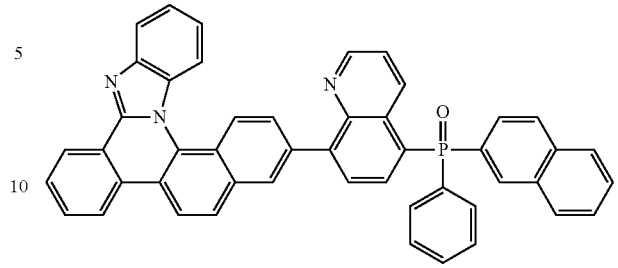
[Compound 1-61]
[Compound 1-64]
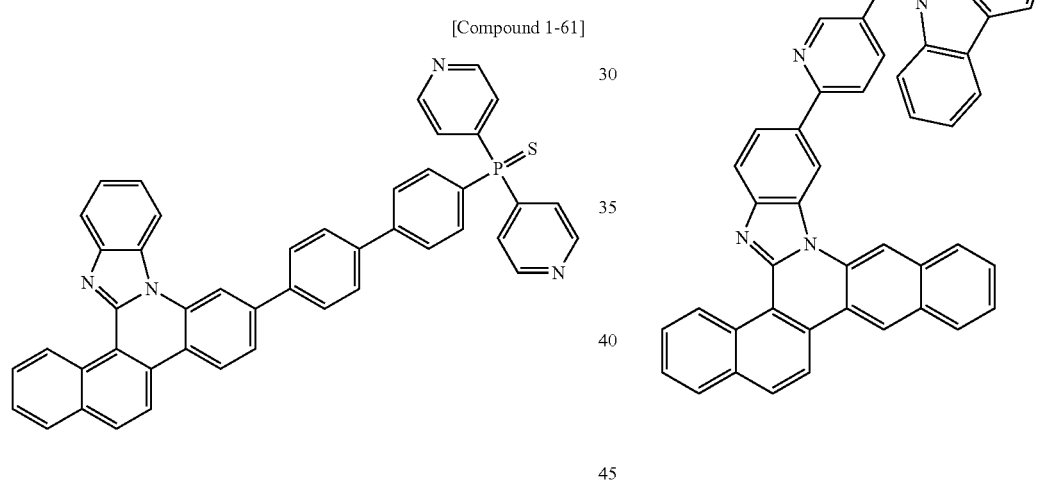
[Compound 1-62]
[Compound 1-65]
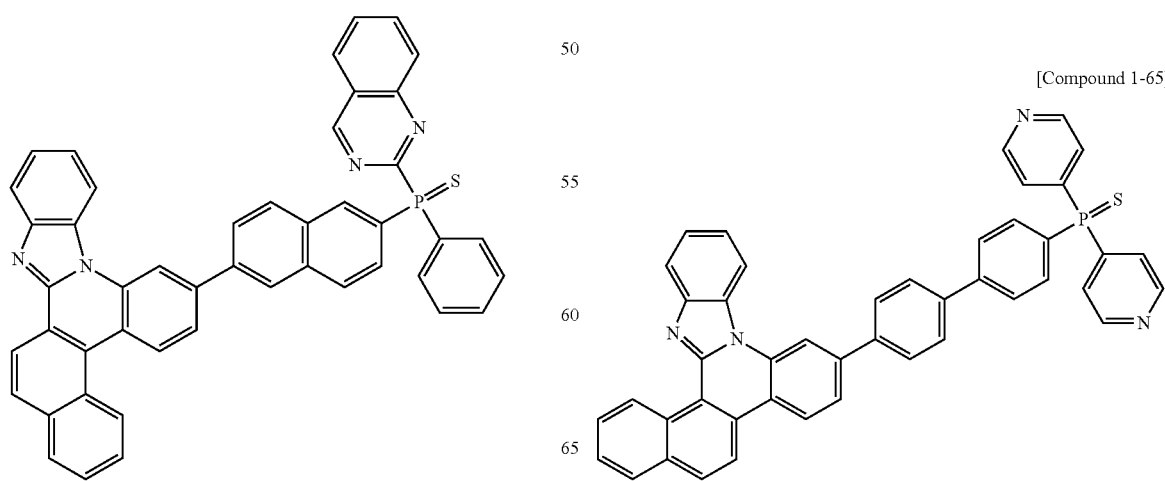

[Compound 1-66]
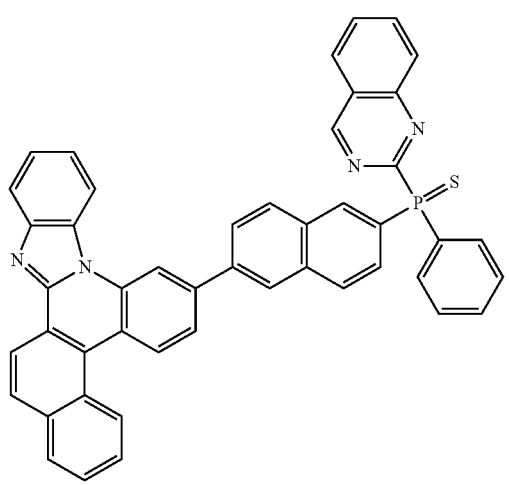
[Compound 1-69]
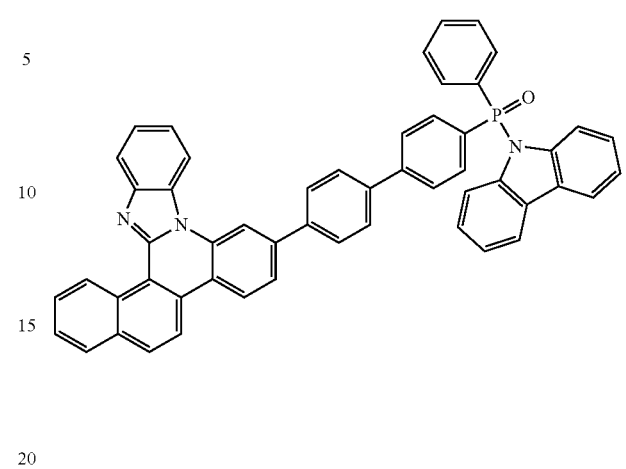
[Compound 1-67]
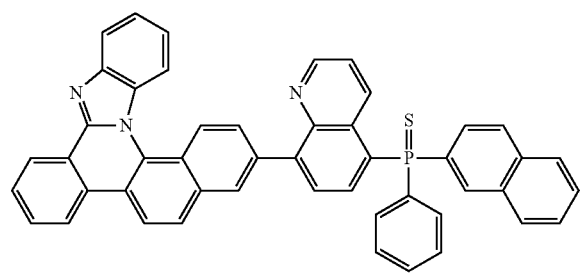
[Compound 1-70]
[Compound 1-68]
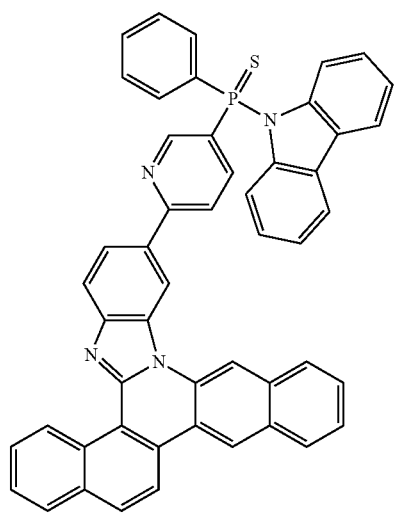
[Compound 1-71]
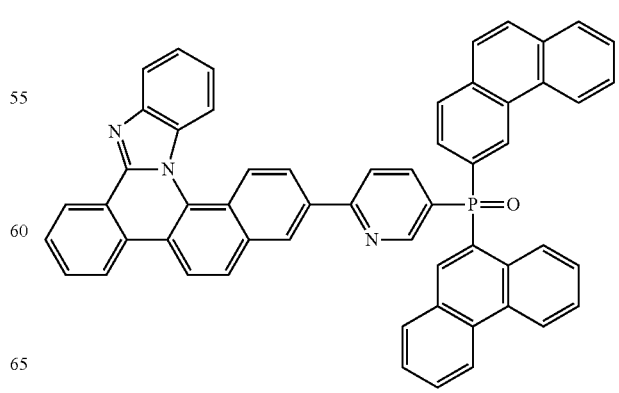

[Compound 1-72]
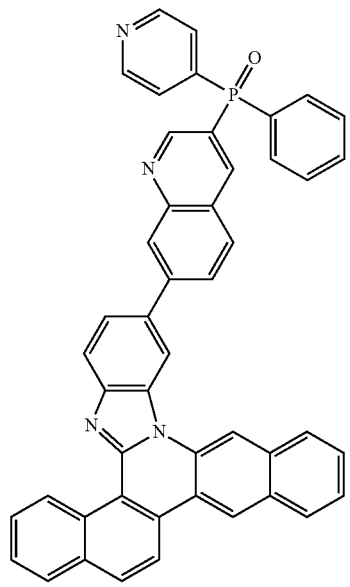
[Compound 1-76]
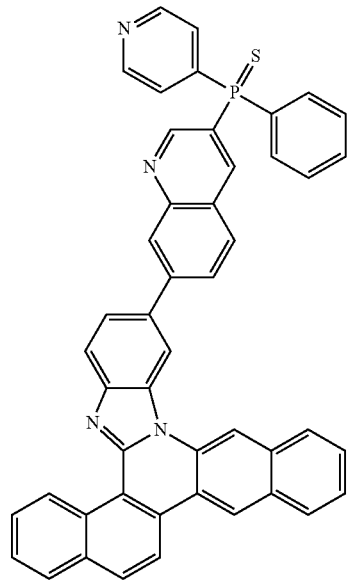
[Compound 1-73]
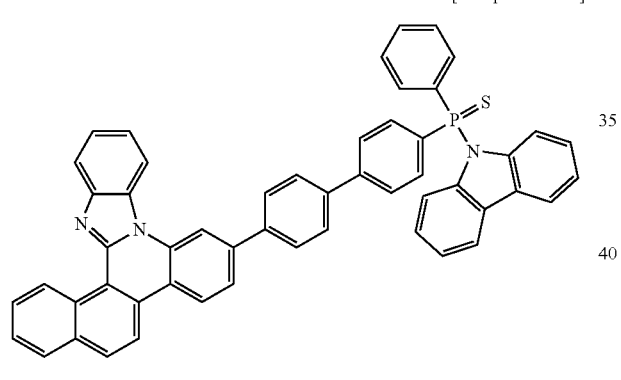
[Compound 1-77]
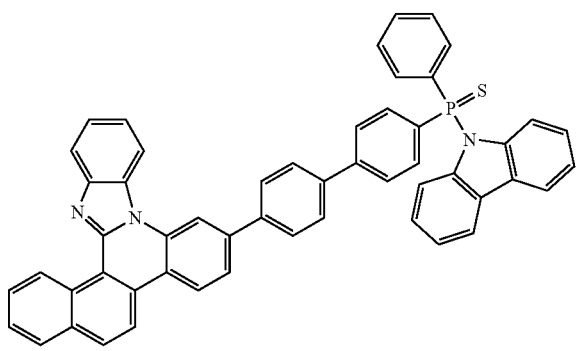
[Compound 1-74]
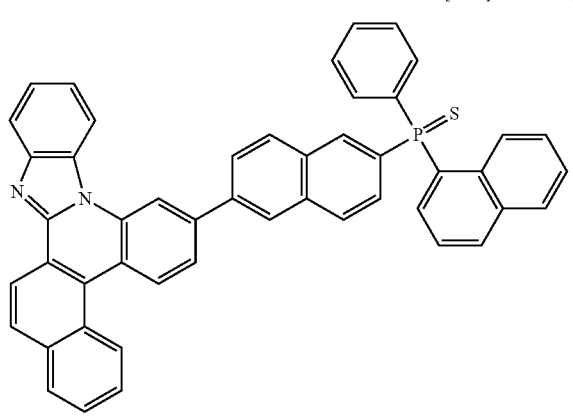
[Compound 1-78]
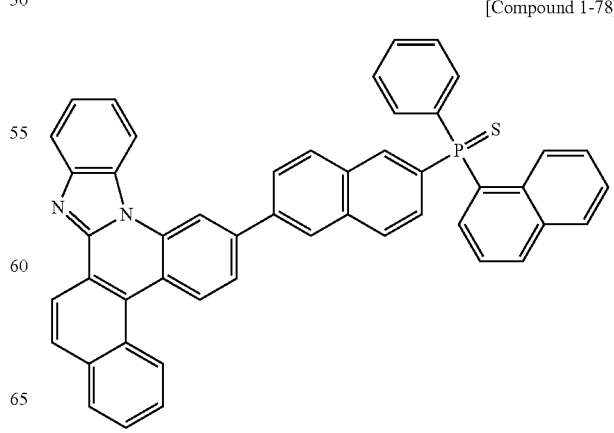

[Compound 1-80]
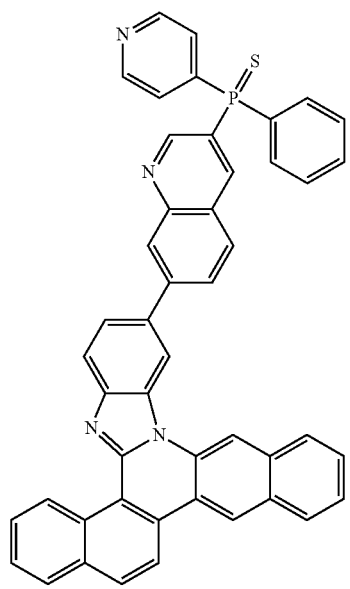
[Compound 1-84]
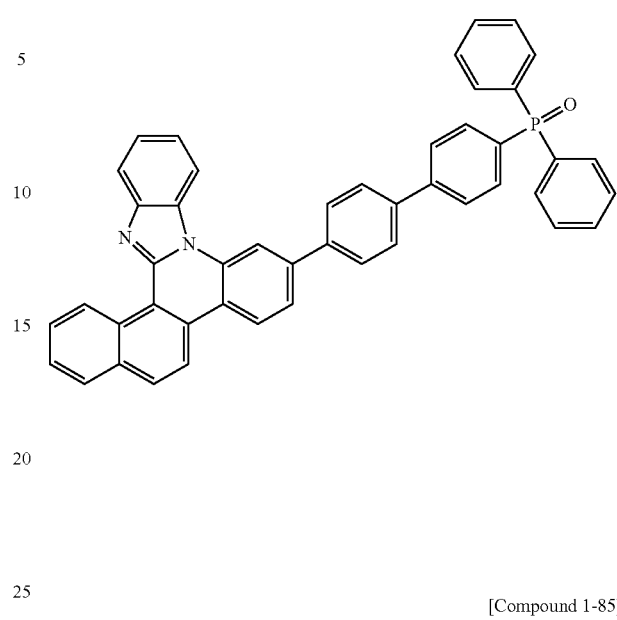
[Compound 1-81]
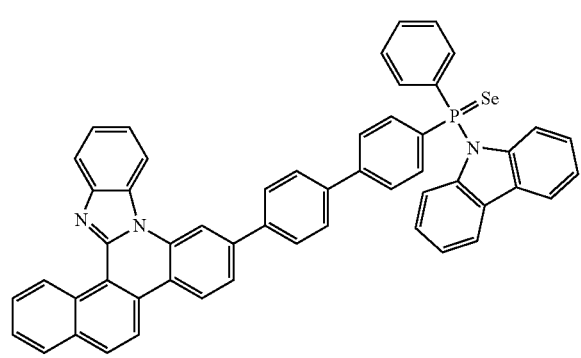
[Compound 1-85]
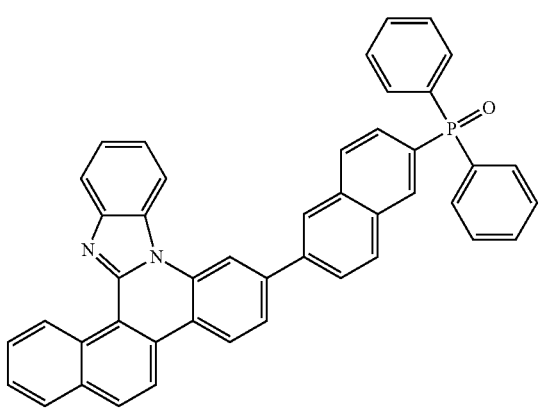
[Compound 1-82]
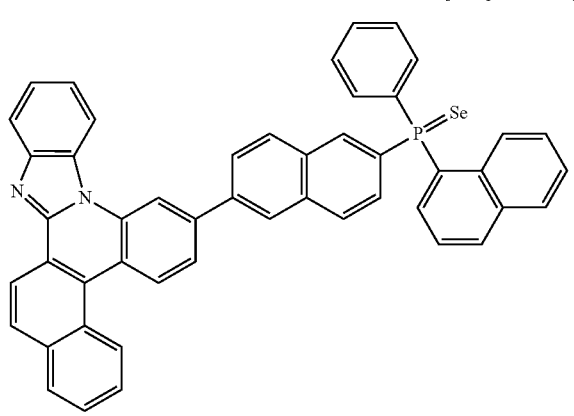
[Compound 1-86]
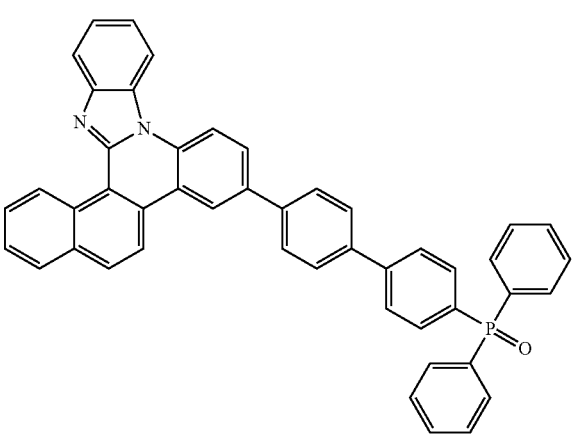

[Compound 1-87]
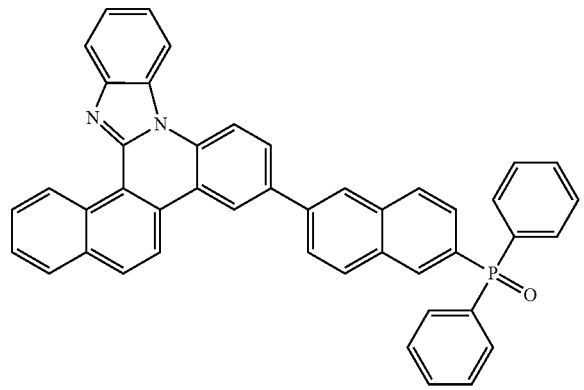
[Compound 1-88]
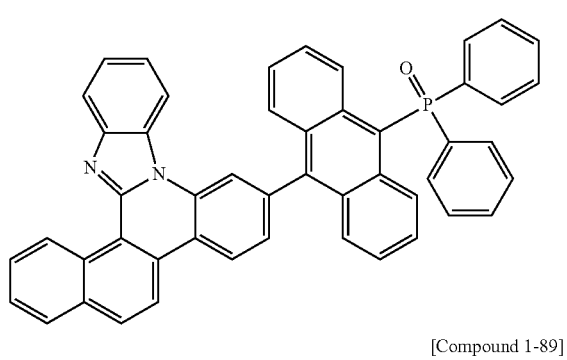
[Compound 1-89]
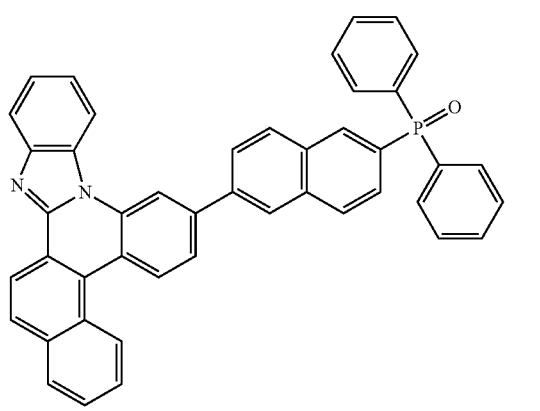
[Compound 1-90]
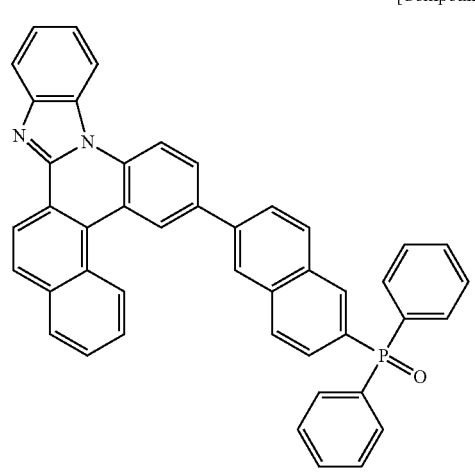
[Compound 1-91]
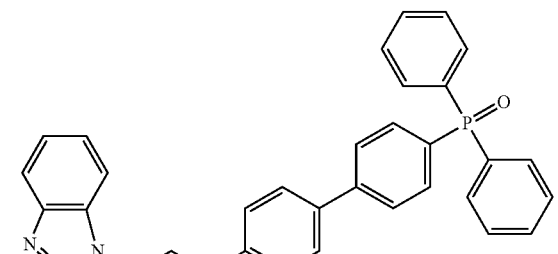
[Compound 1-92]
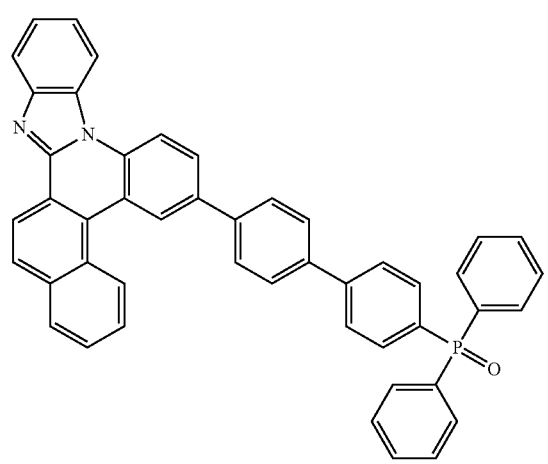
[Compound 1-93]
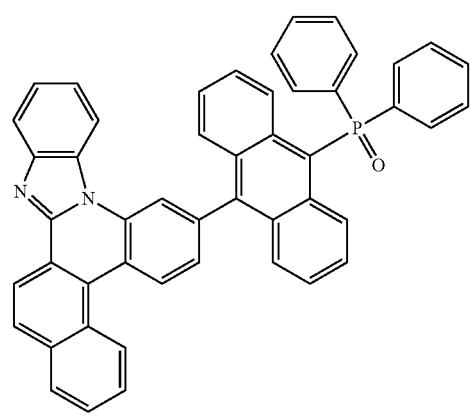

[Compound 1-94]
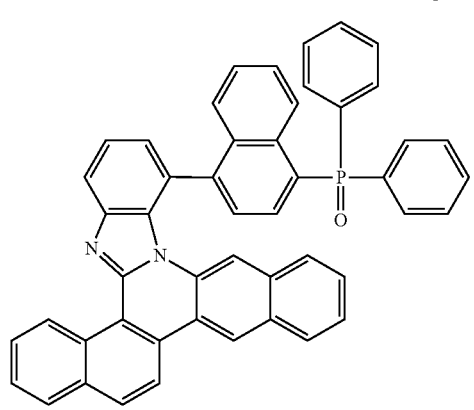
[Compound 1-95]
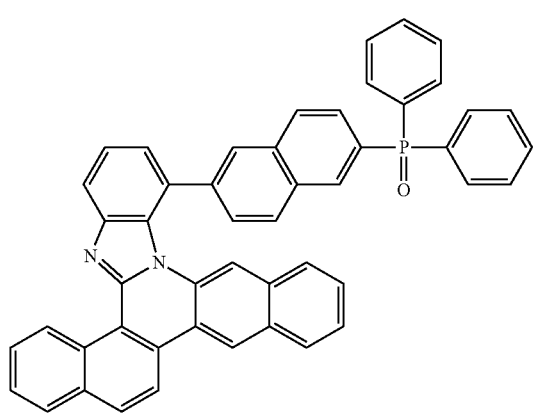
[Compound 1-96]
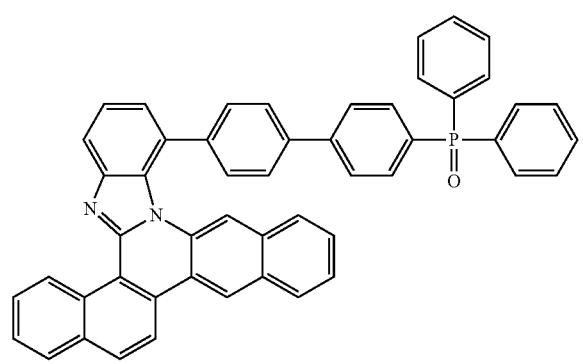
[Compound 1-97]
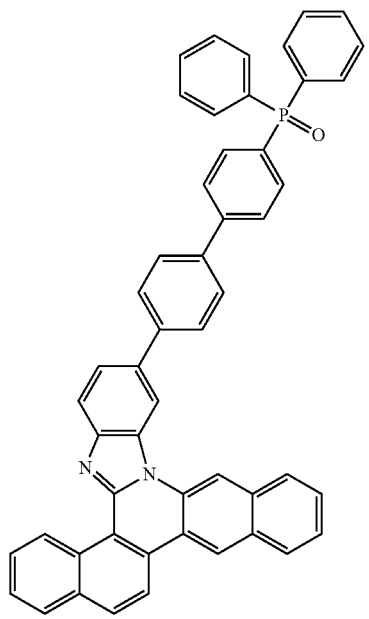
[Compound 1-98]
[Compound 1-99]
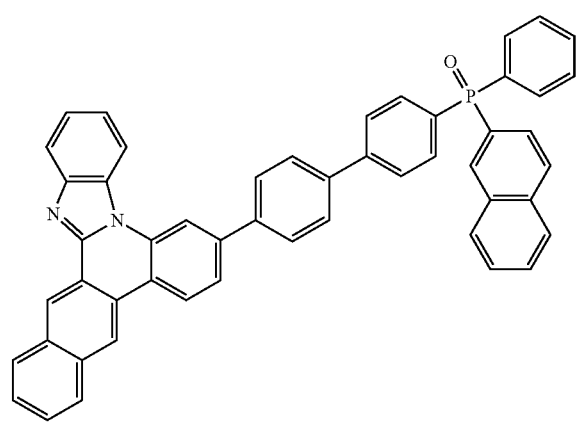

[Compound 1-100]
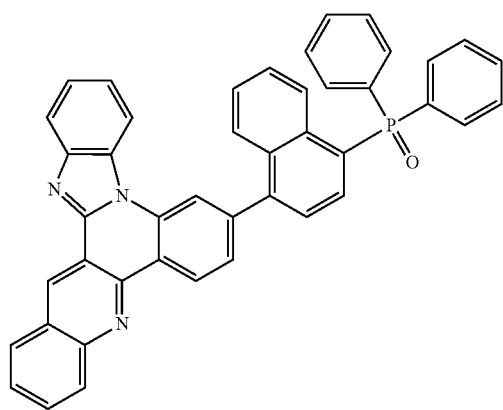
[Compound 1-104]
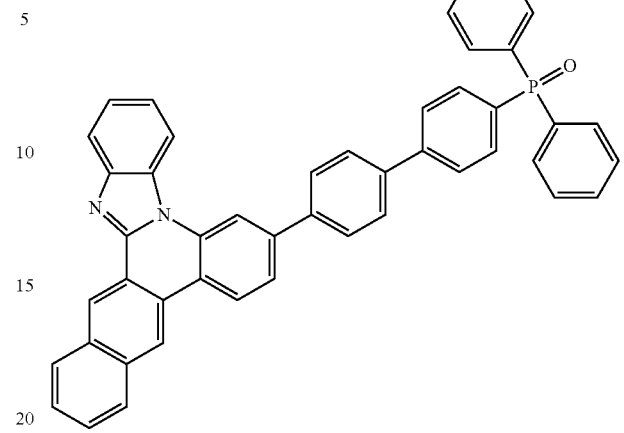
[Compound 1-101]
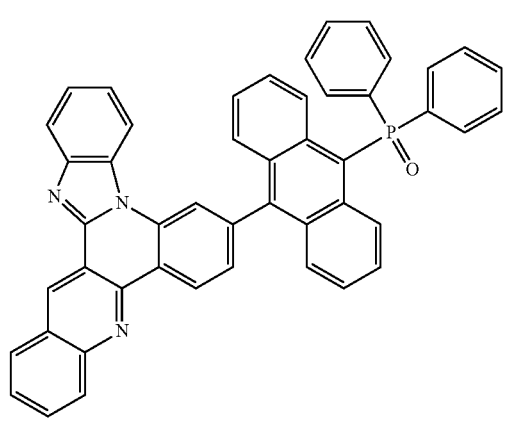
[Compound 1-105]
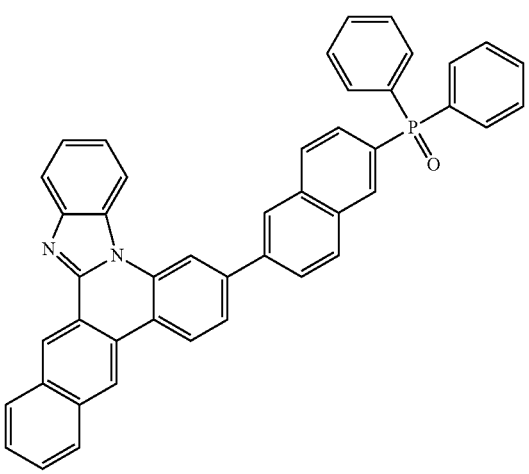
[Compound 1-103]
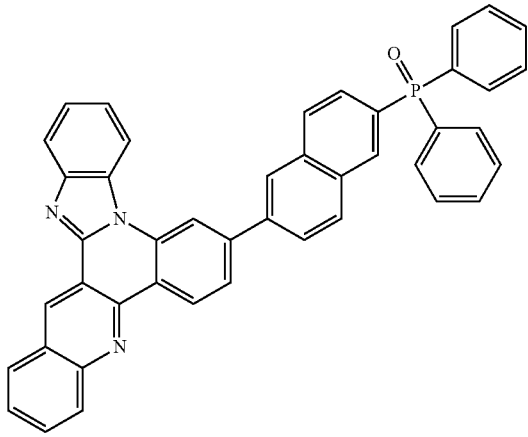
[Compound 1-106]
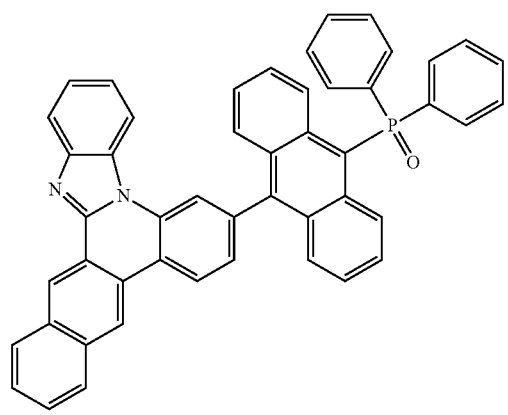

[Compound 1-107]
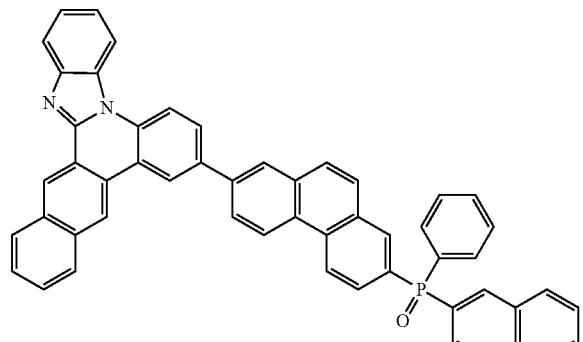
[Compound 1-108]
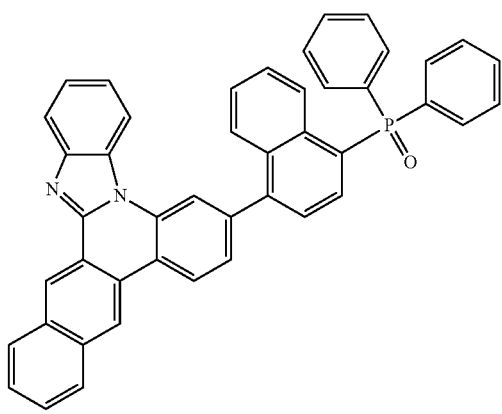
[Compound 1-109]
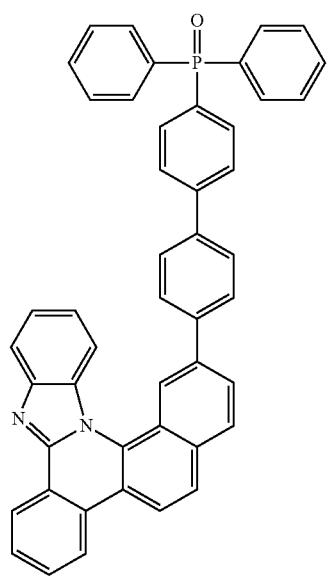
[Compound 1-110]
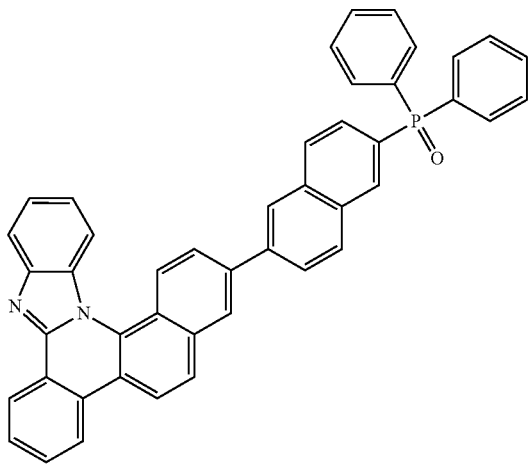
[Compound 1-111]
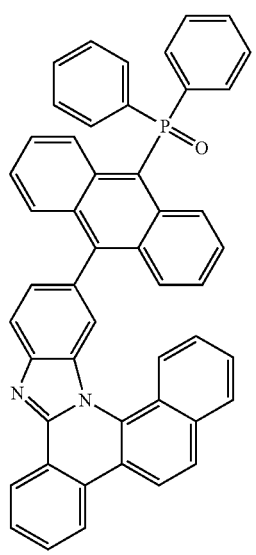
[Compound 1-112]
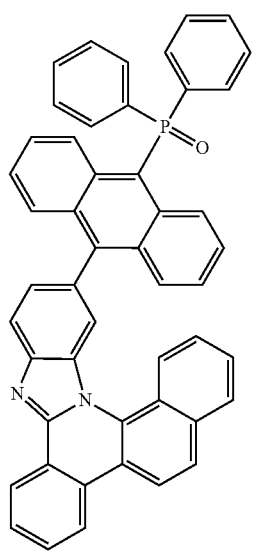

[Compound 1-113]
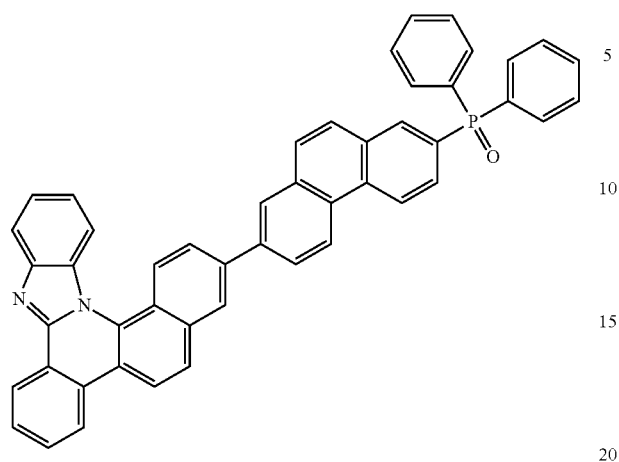
[Compound 2-1]
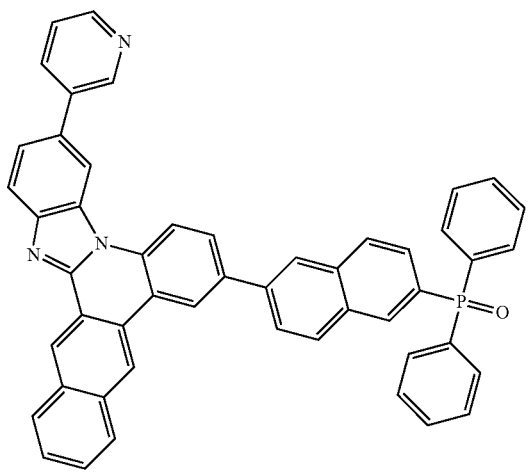
[Compound 2-2]
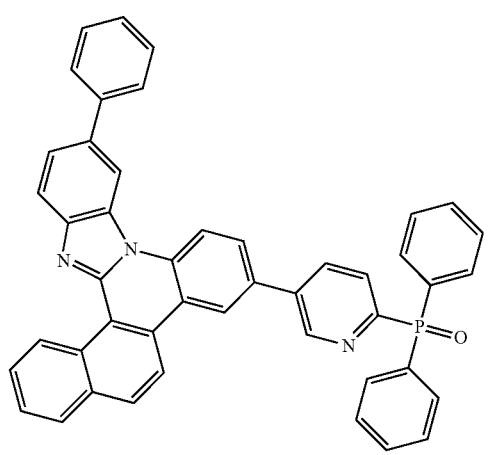
[Compound 2-3]
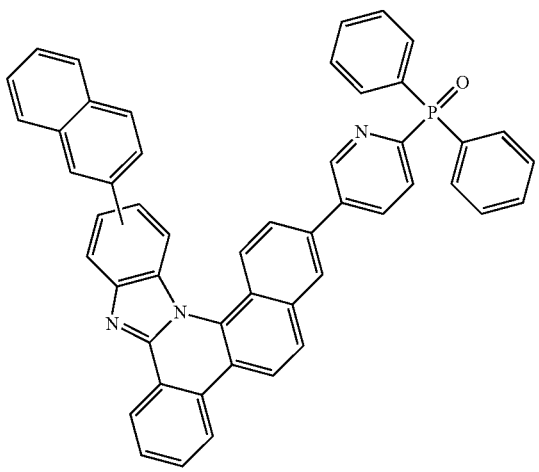
[Compound 2-4]
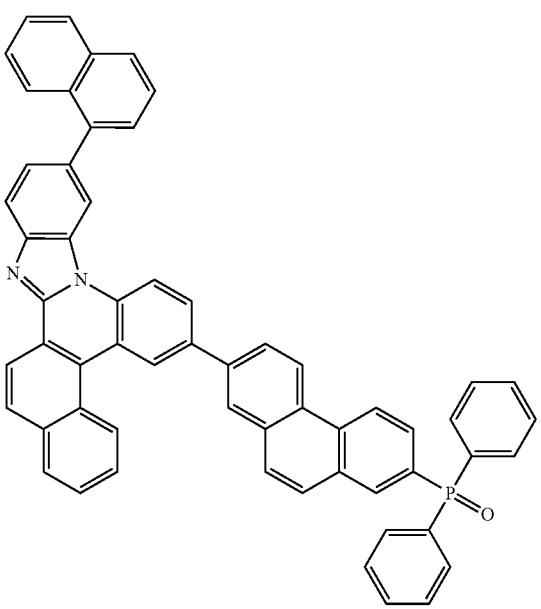

[Compound 2-5]
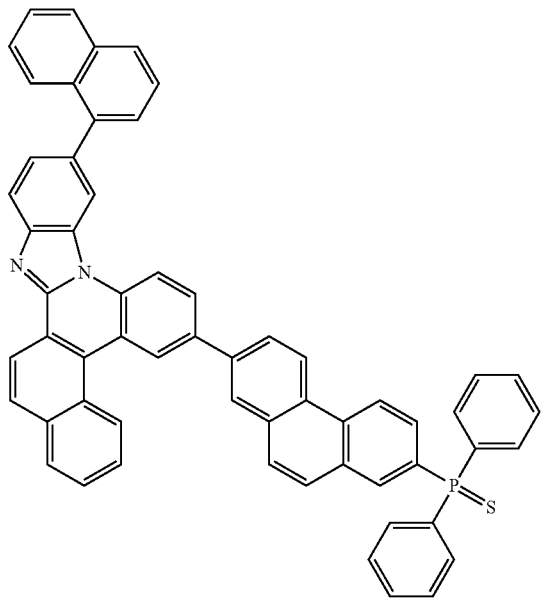
[Compound 2-6]
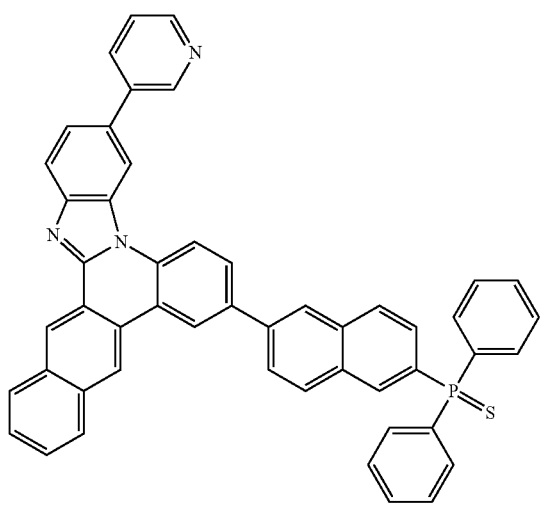
[Compound 2-7]
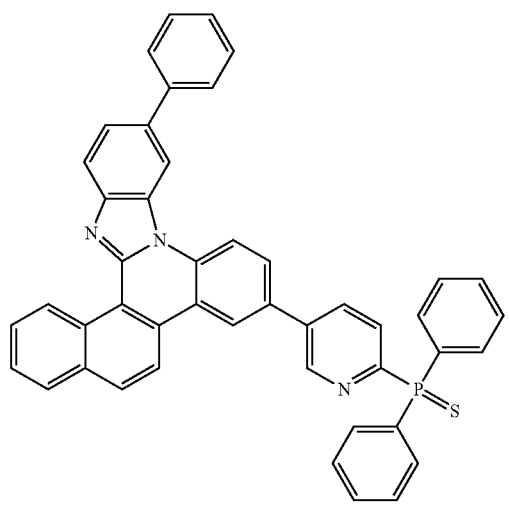
[Compound 2-8]
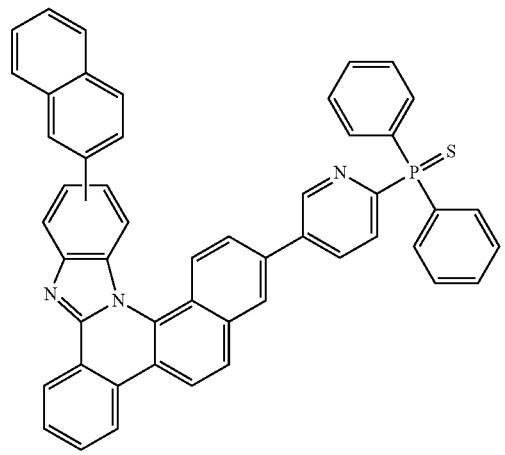
[Compound 2-9]
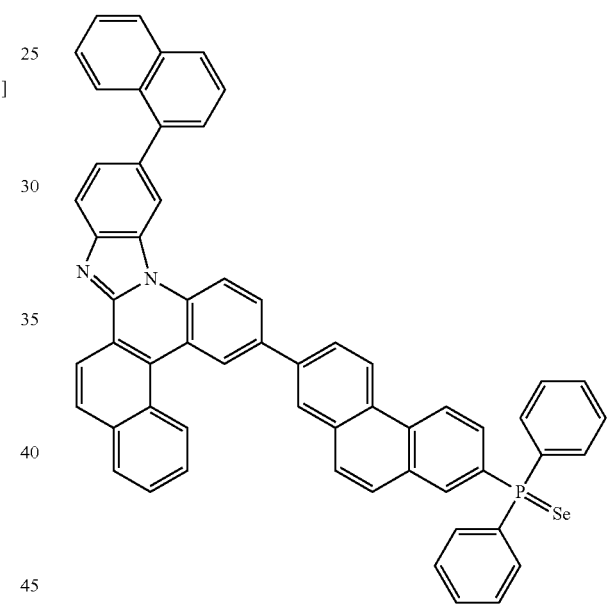
[Compound 2-10]
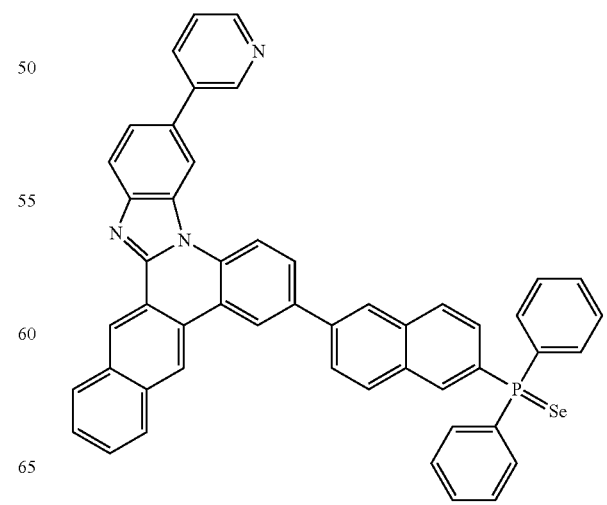

[Compound 2-11]
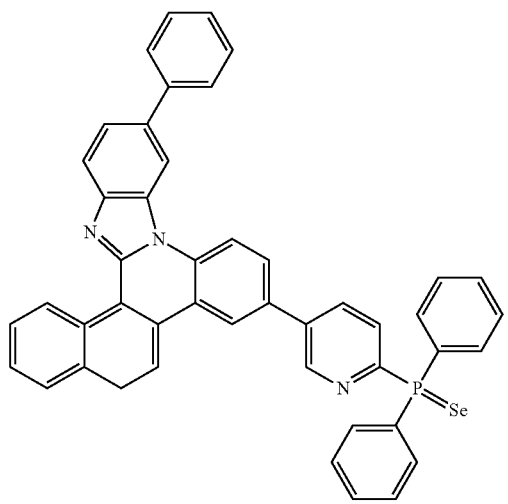
[Compound 2-12]
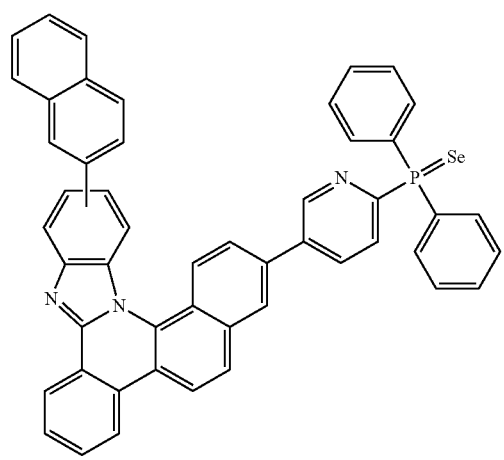
[Compound 2-13]
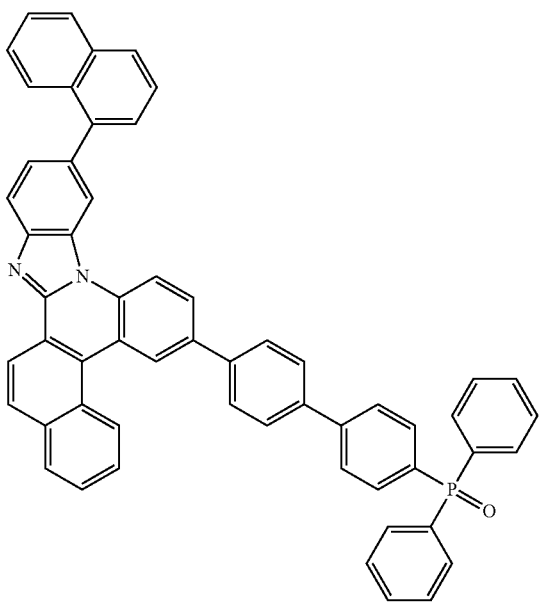
[Compound 2-14]
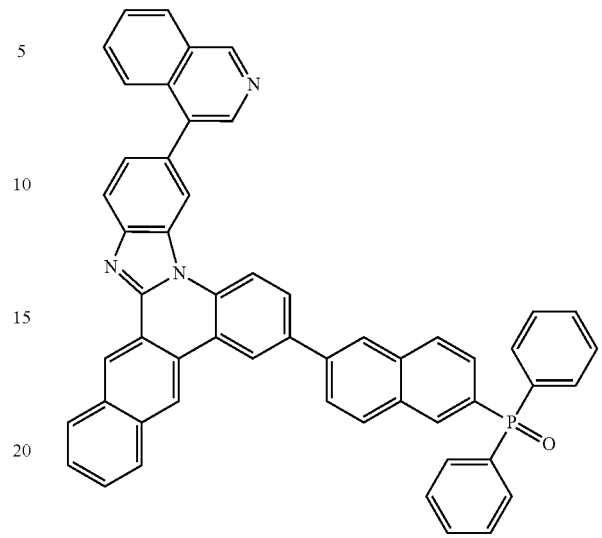
[Compound 2-15]
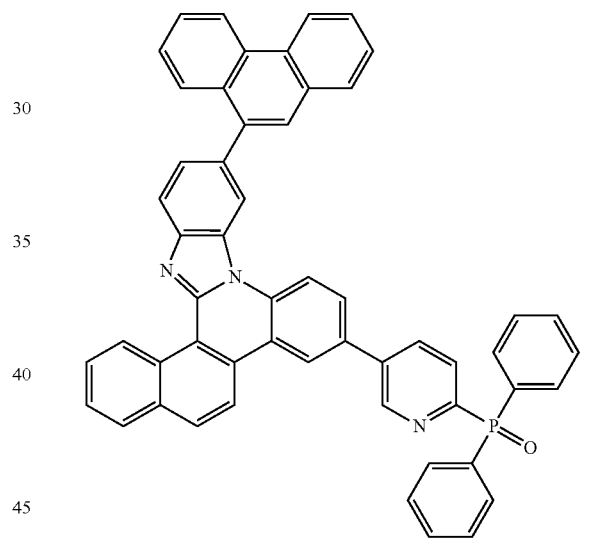
[Compound 2-16]
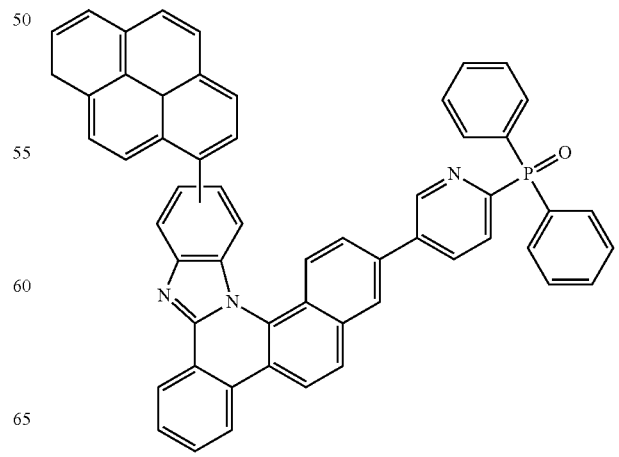

[Compound 2-17]
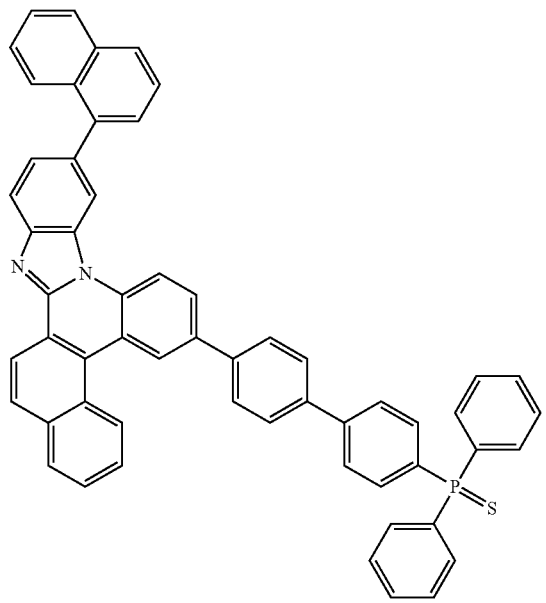
[Compound 2-18]
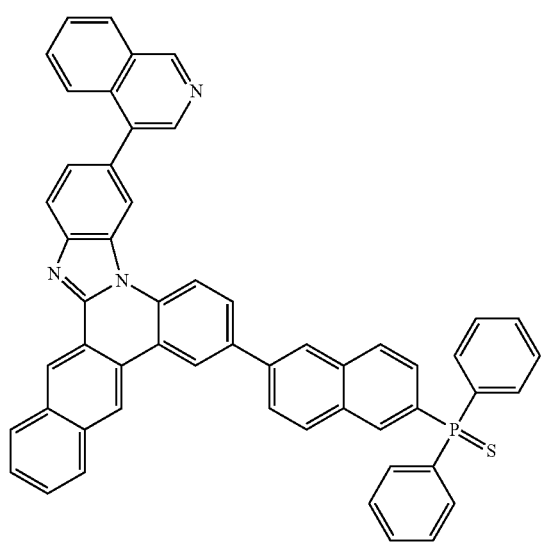
[Compound 2-19]
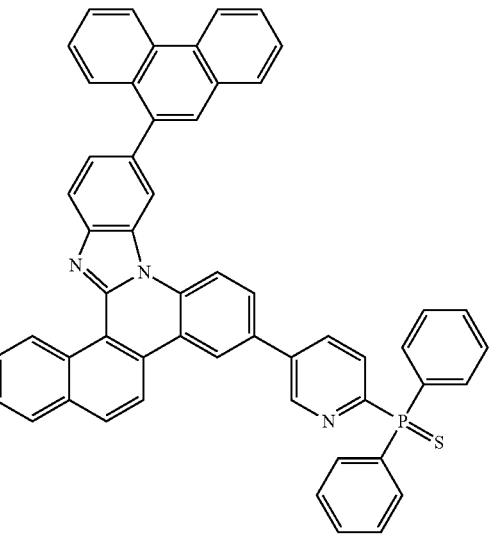
[Compound 2-20]
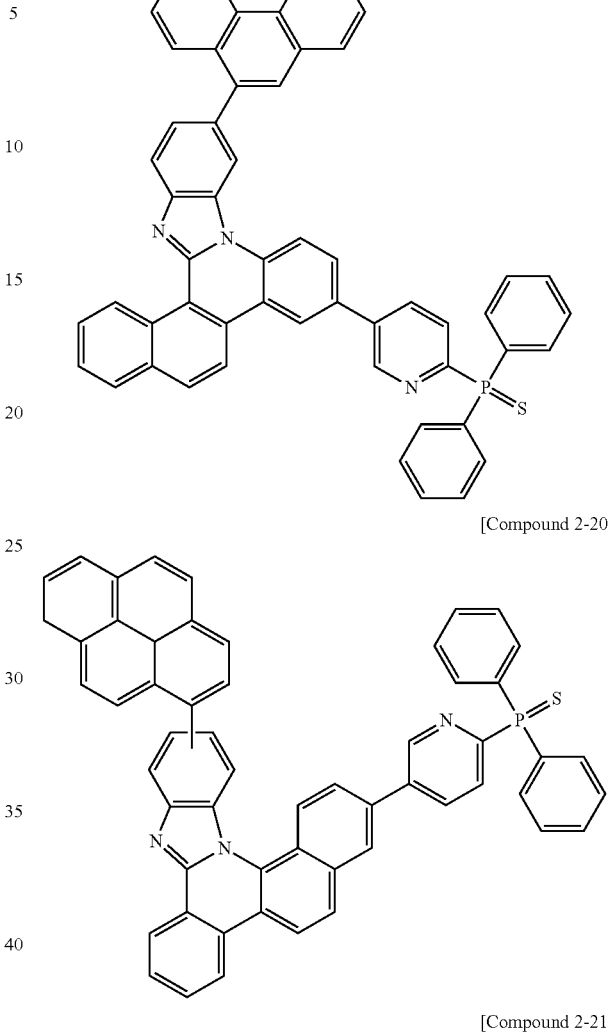
[Compound 2-21]
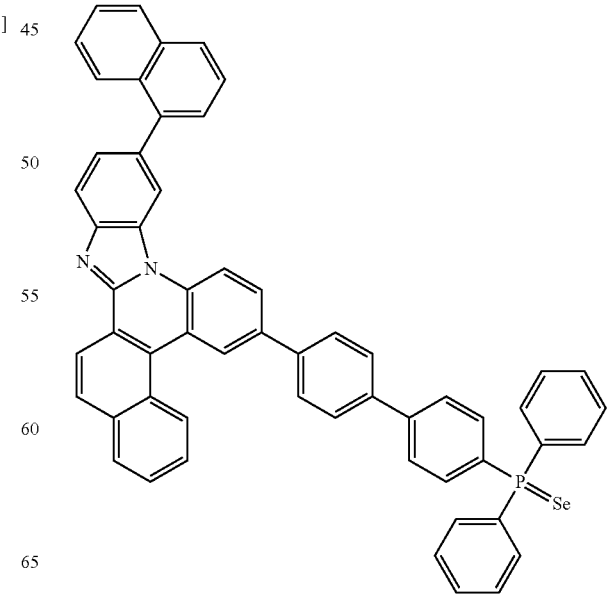

[Compound 2-22]
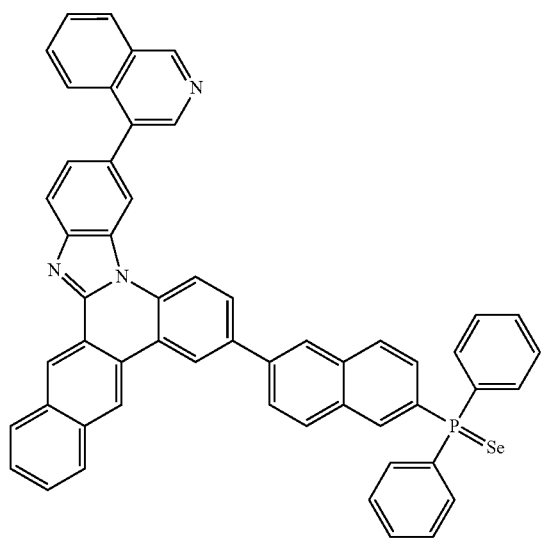
[Compound 2-25]
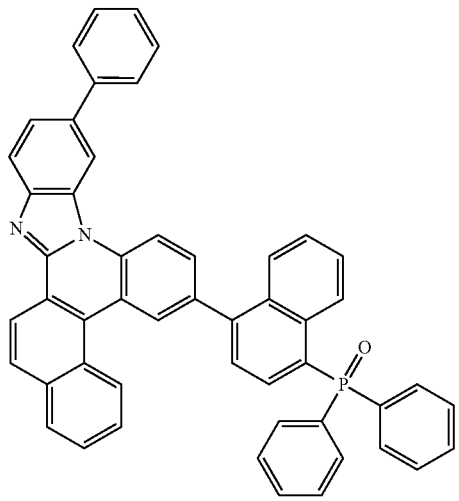
[Compound 2-23]
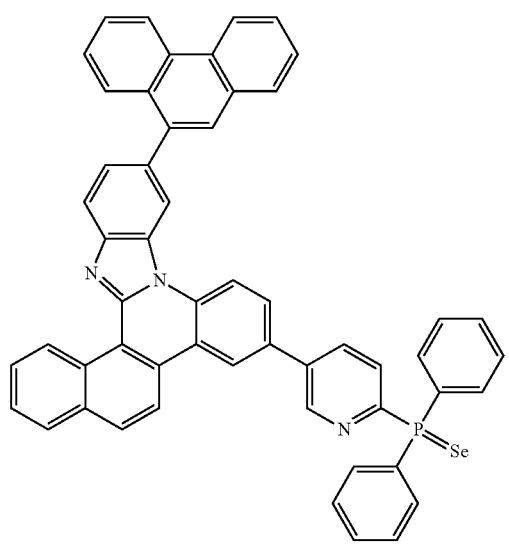
[Compound 2-26]
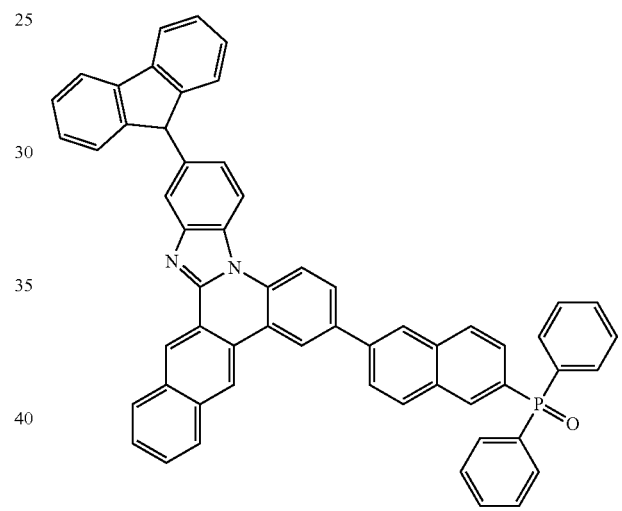
[Compound 2-24]
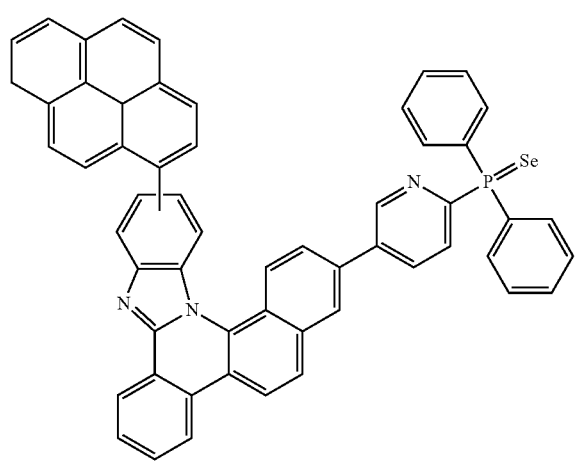
[Compound 2-27]
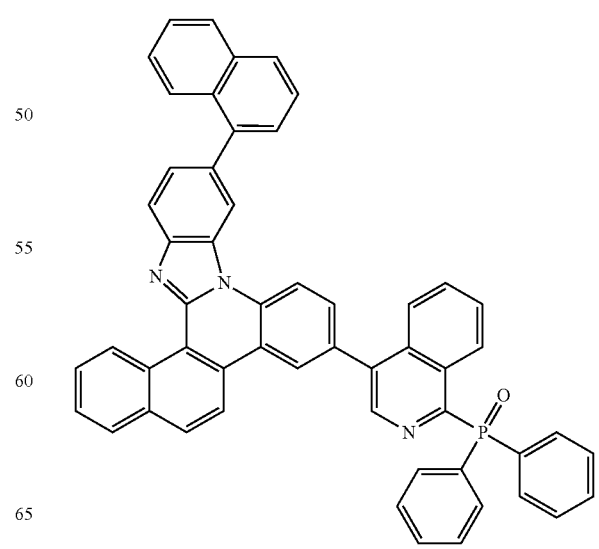

[Compound 2-28]
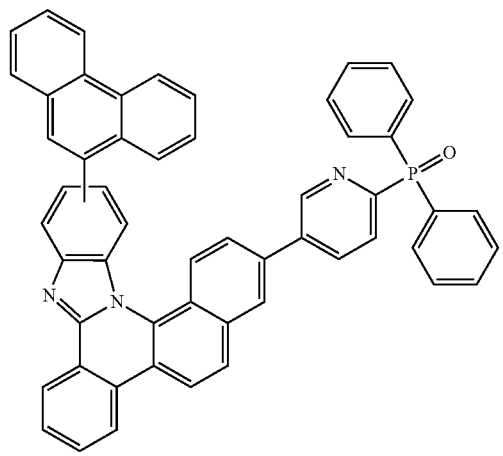
[Compound 2-31]
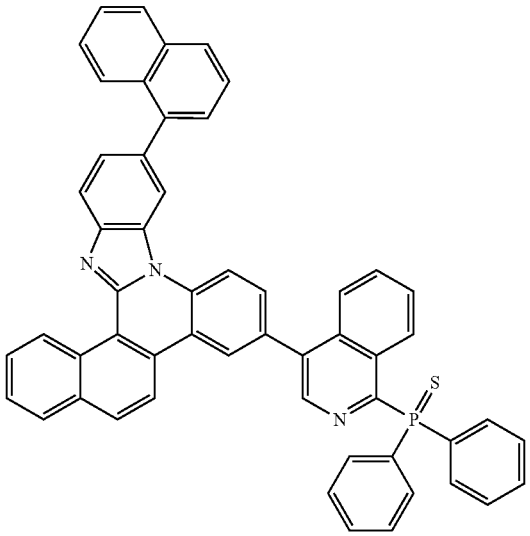
[Compound 2-29]
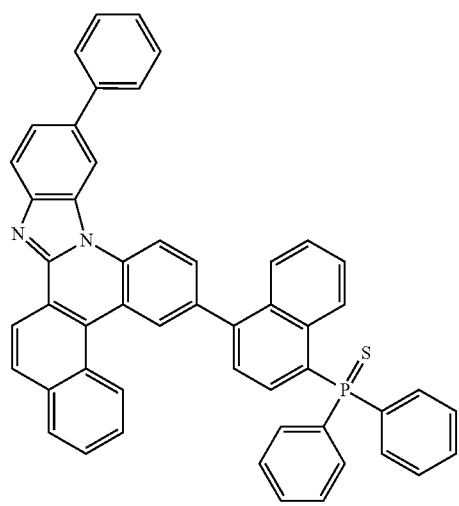
[Compound 2-32]
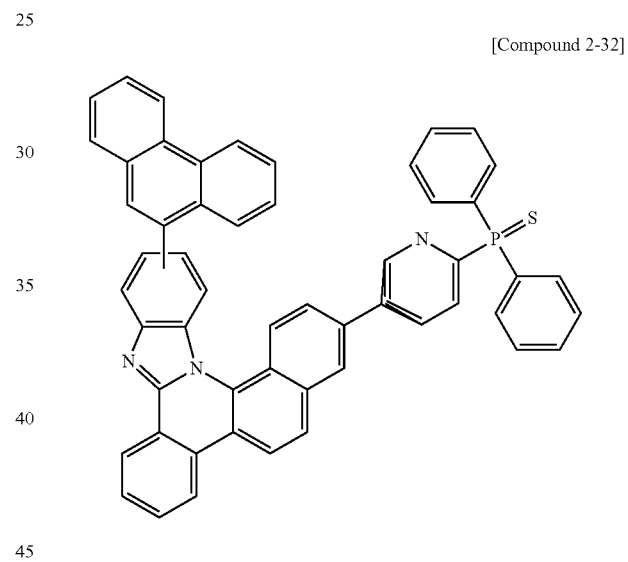
[Compound 2-30]
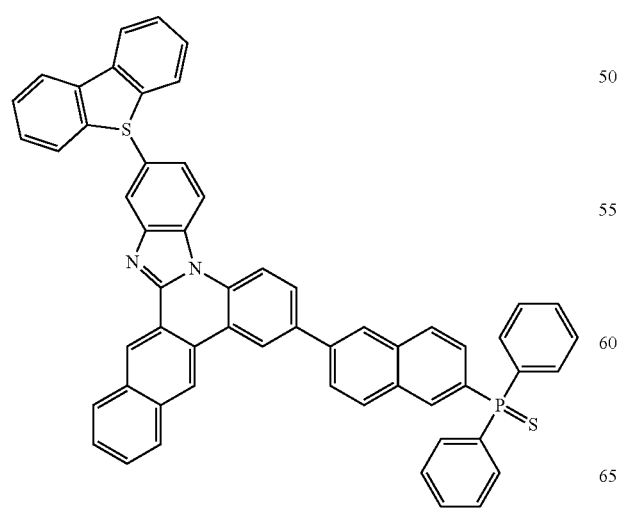
[Compound 2-33]
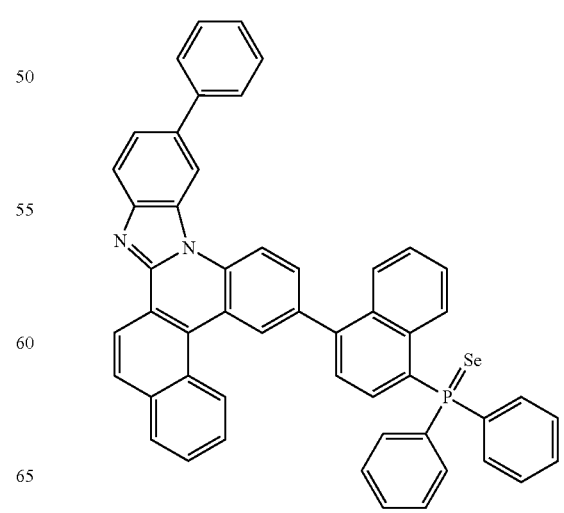

[Compound 2-34]
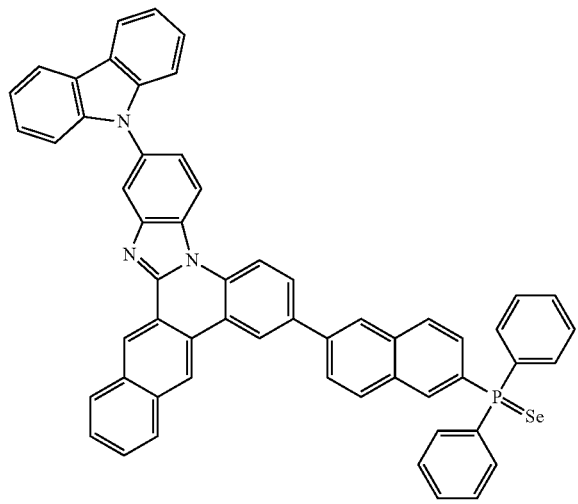
[Compound 2-35]
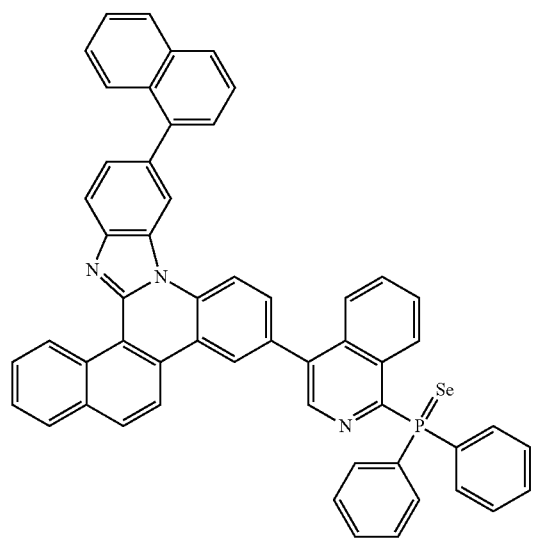
[Compound 2-36]
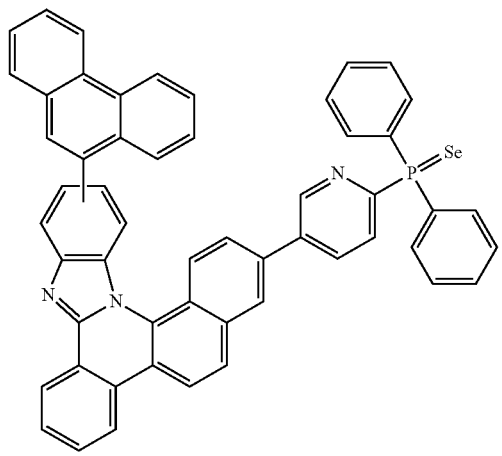
[Compound 2-37]
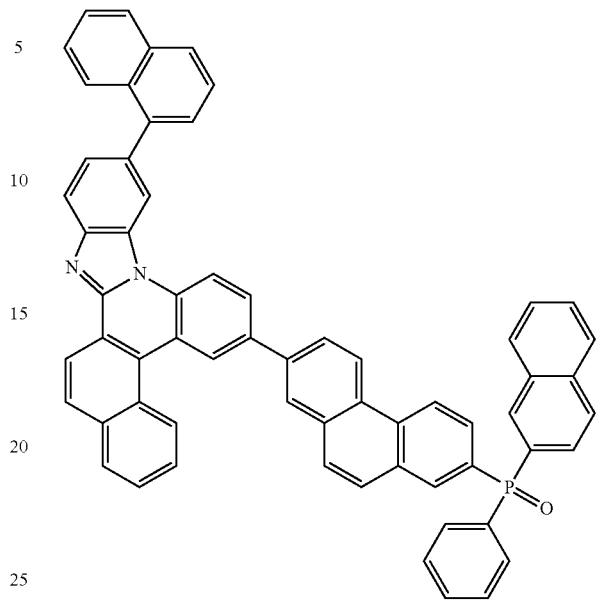
[Compound 2-38]
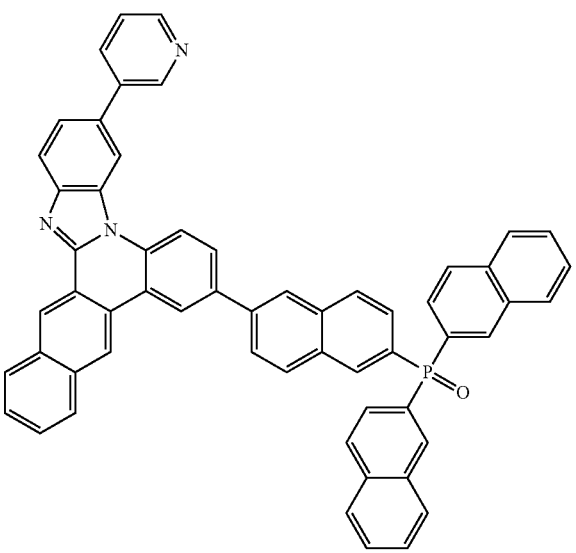

-continued
[Compound 2-39]
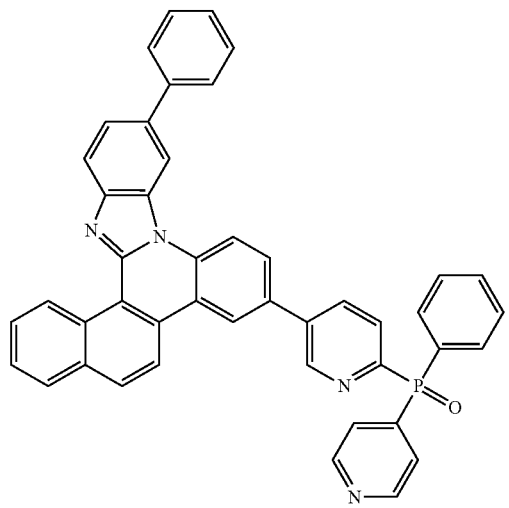
[Compound 2-40]
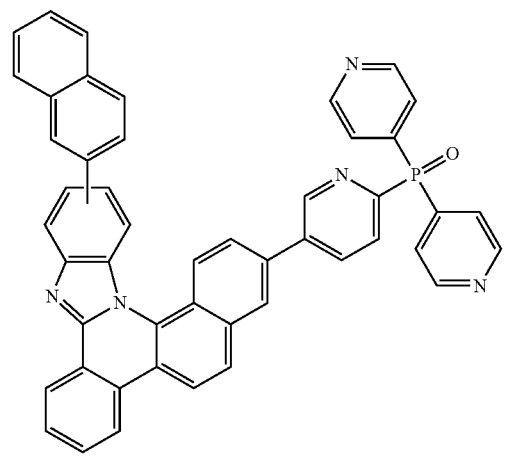
[Compound 2-41]
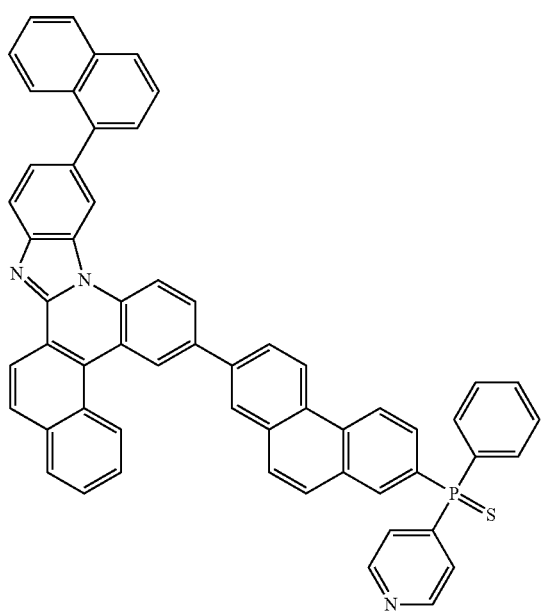
-continued
[Compound 2-42]
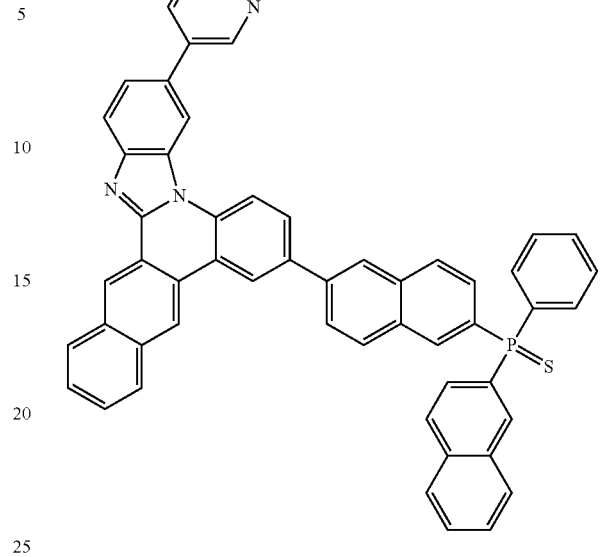
[Compound 2-43]
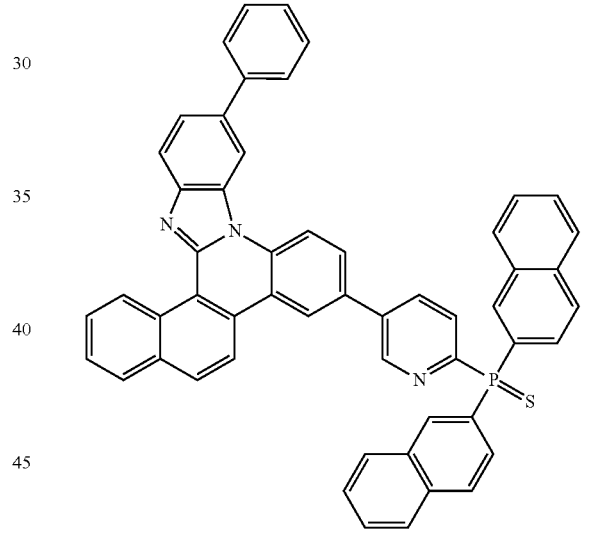
[Compound 2-44]
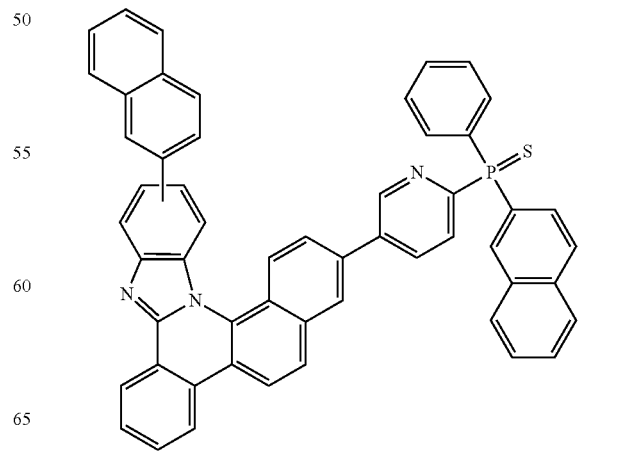

[Compound 2-45]
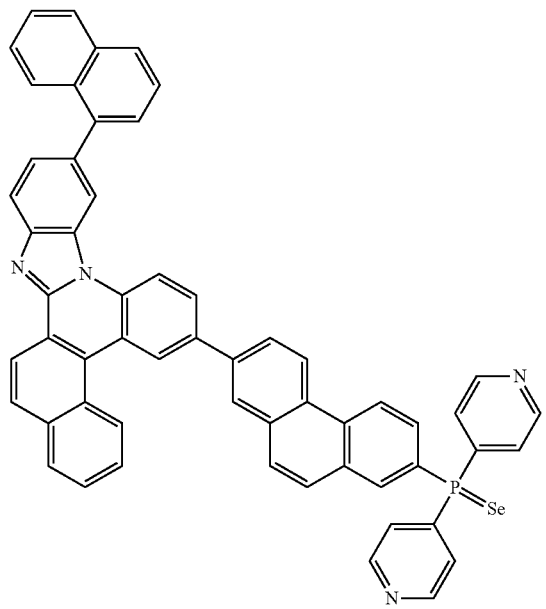
[Compound 2-47]
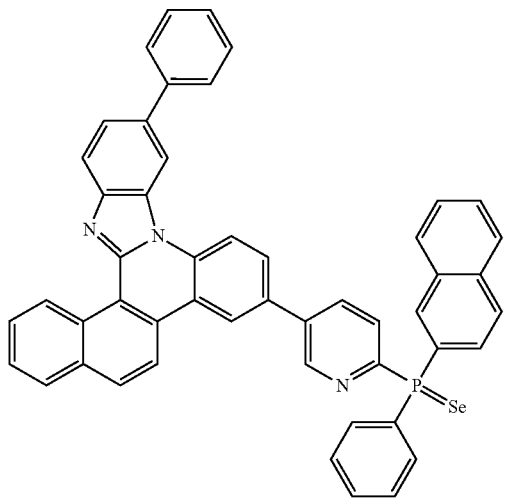
[Compound 2-48]
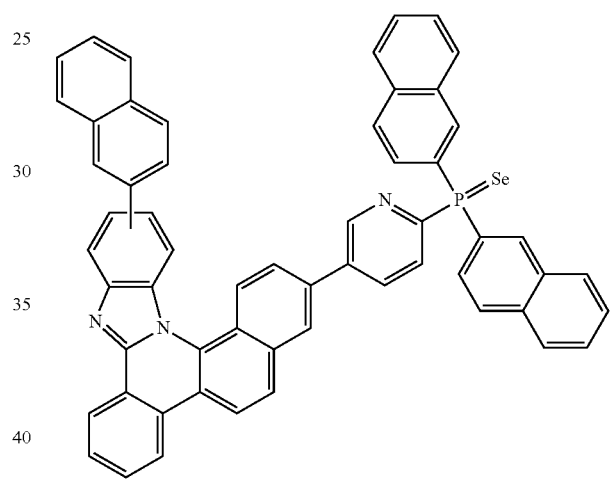
[Compound 2-46]
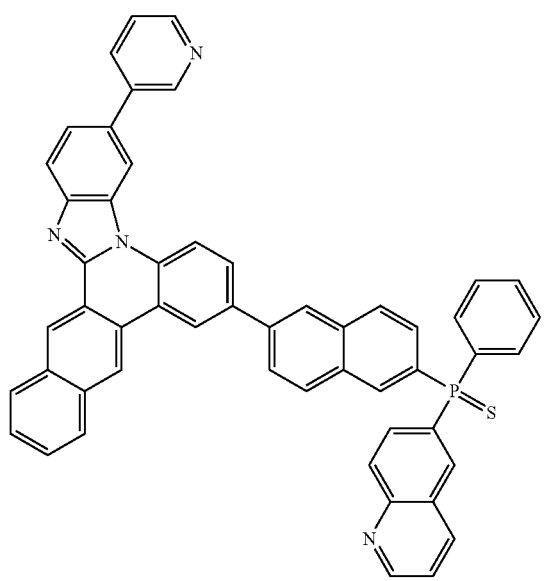
[Compound 2-49]
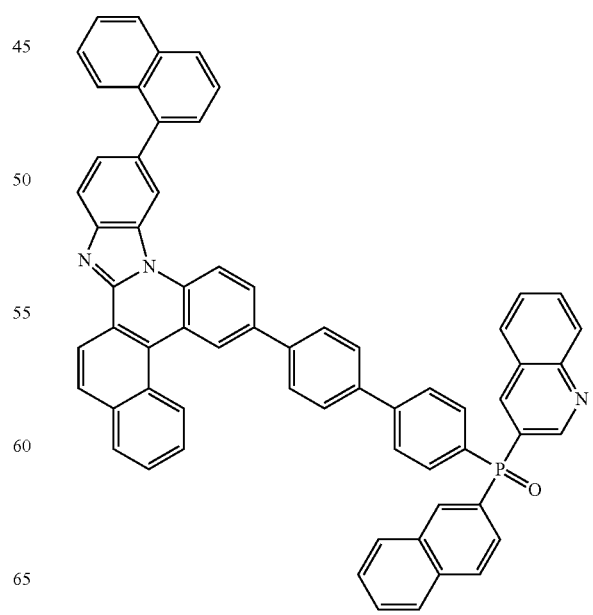

[Compound 2-50]
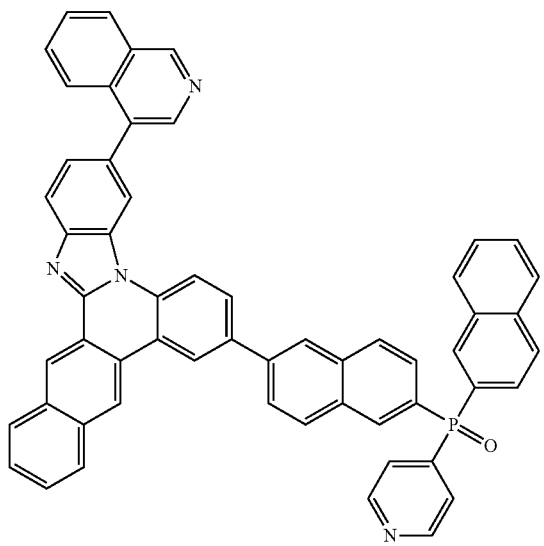
[Compound 2-52]
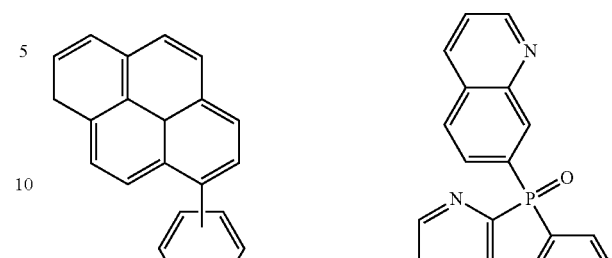
[Compound 3-1]
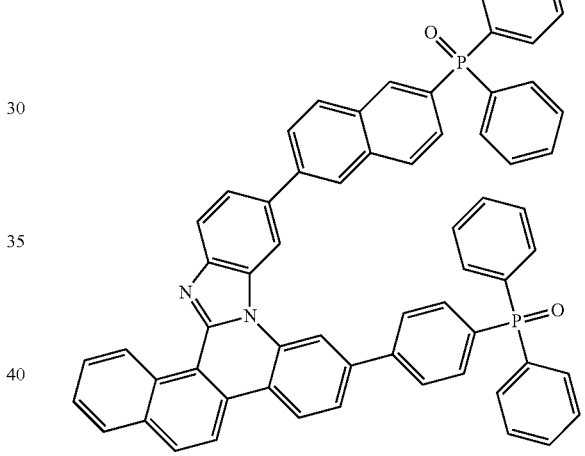
[Compound 2-51]
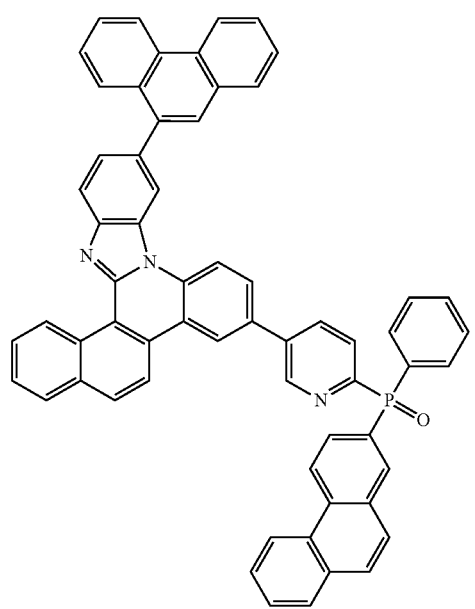
[Compound 3-2]
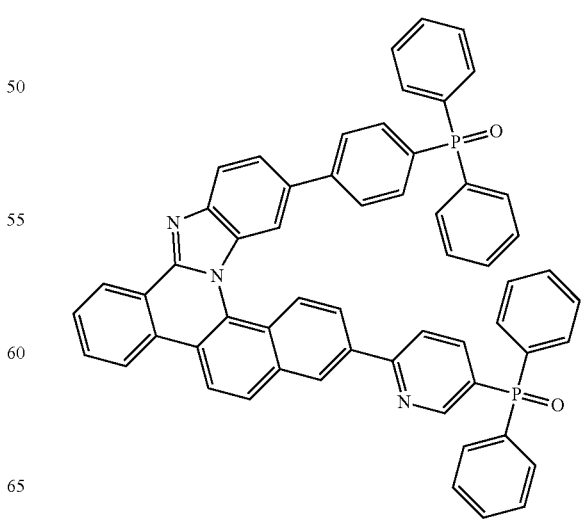

[Compound 3-3]
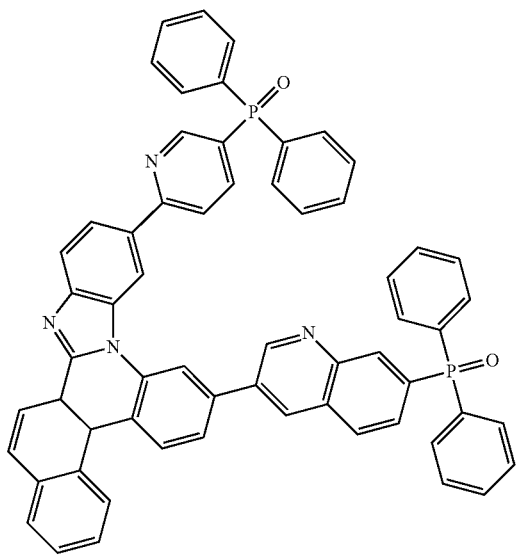
[Compound 3-5]
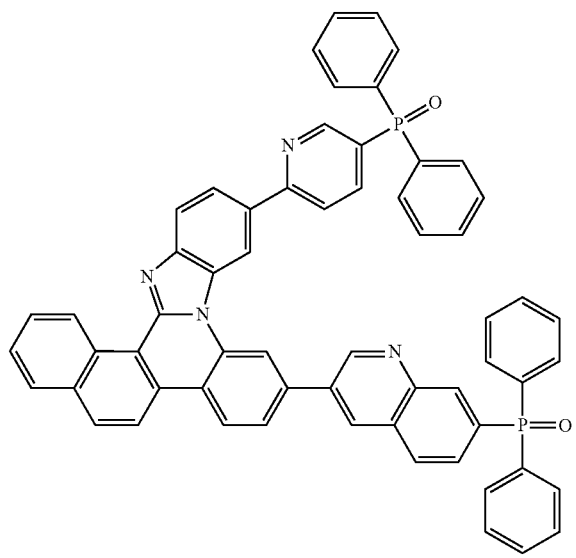
[Compound 3-4]
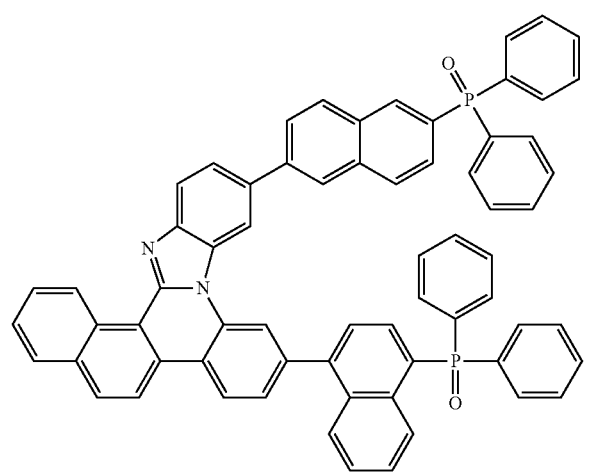
[Compound 3-7]
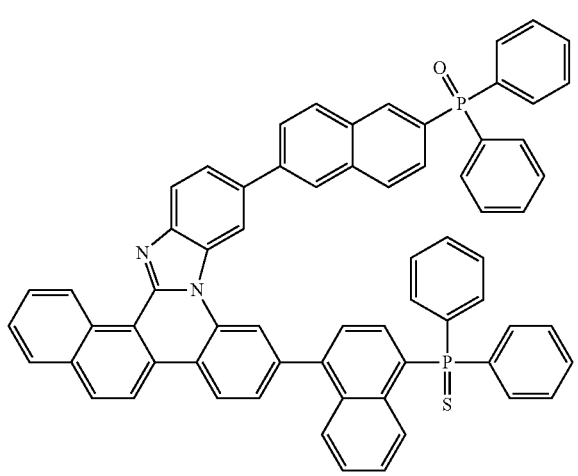
[Compound 3-5]
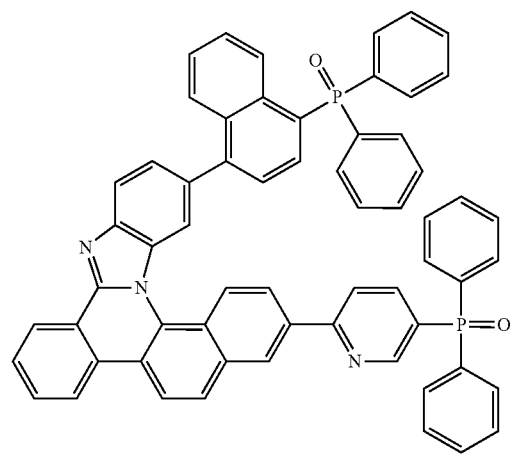
[Compound 3-8]
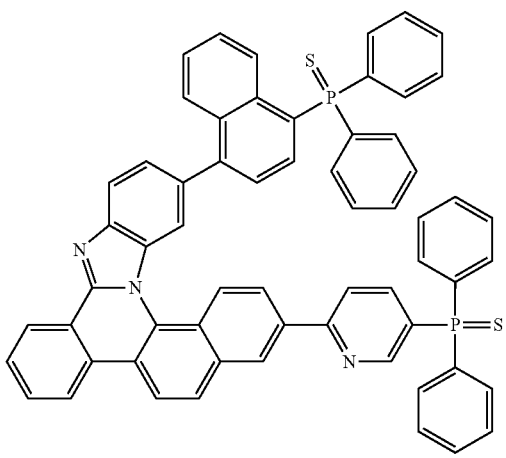

[Compound 3-9]
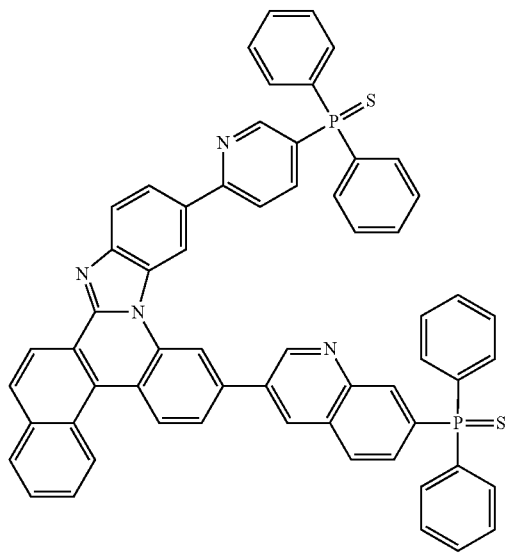
[Compound 3-12]
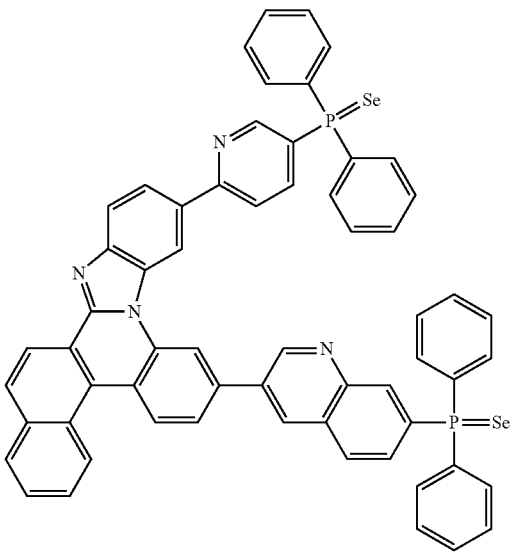
[Compound 3-10]
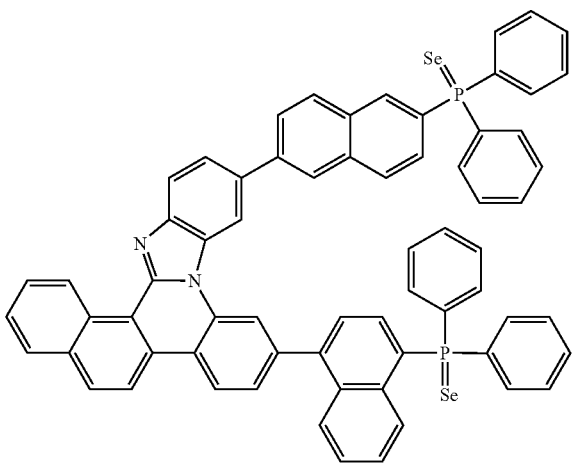
[Compound 3-13]
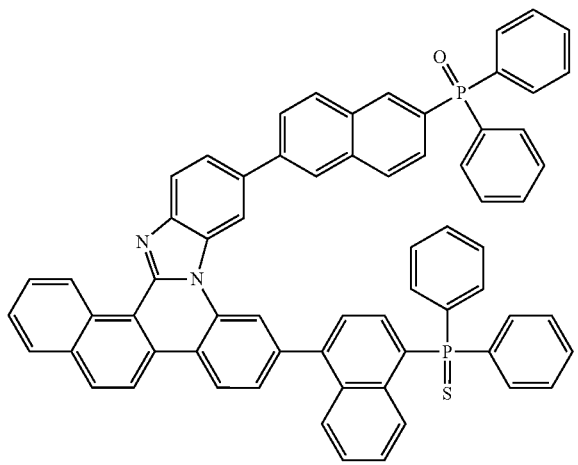
[Compound 3-11]
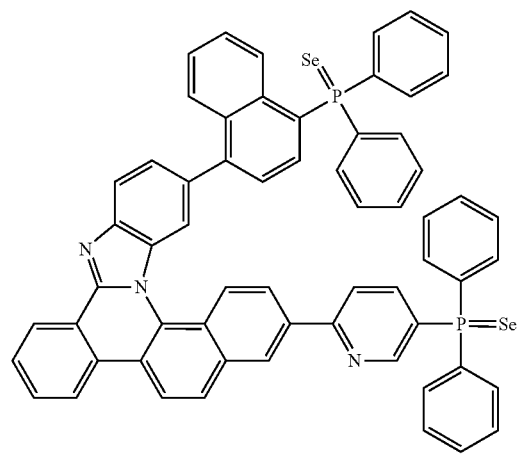
[Compound 3-14]
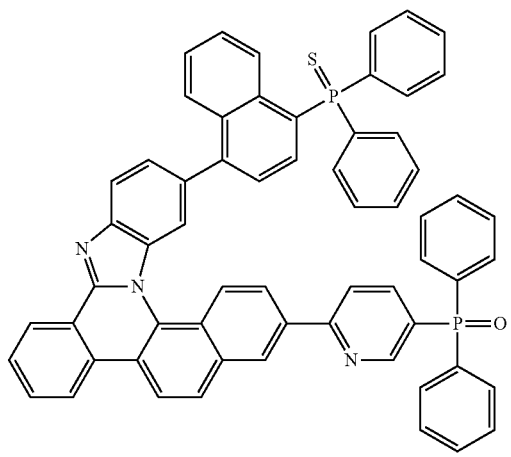

[Compound 3-15]
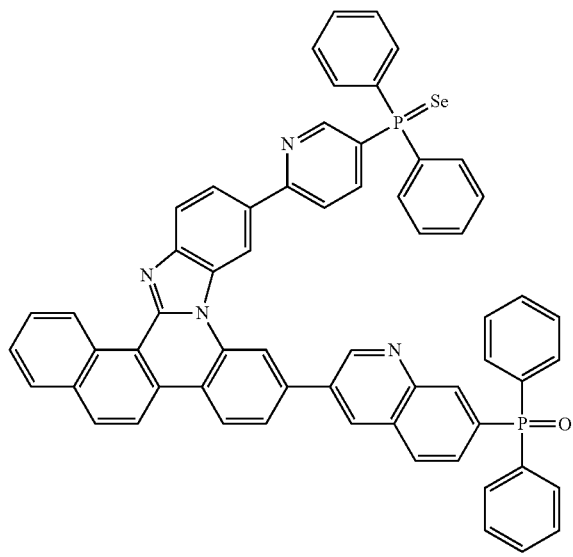
[Compound 3-18]
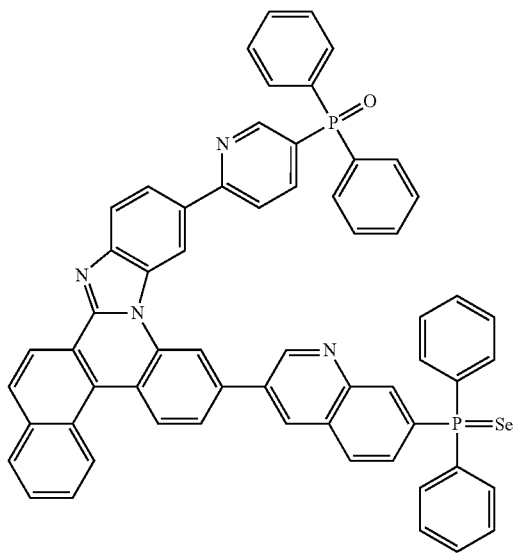
[Compound 3-16]
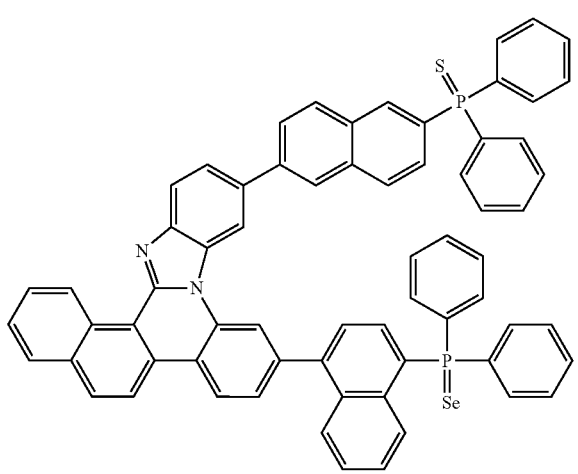
[Compound 3-19]
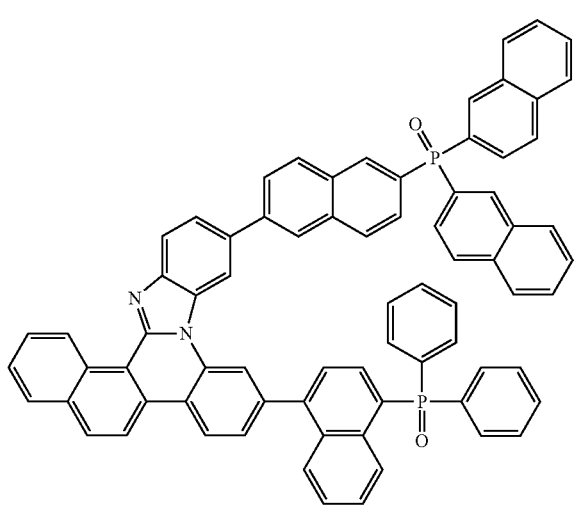
[Compound 3-17]
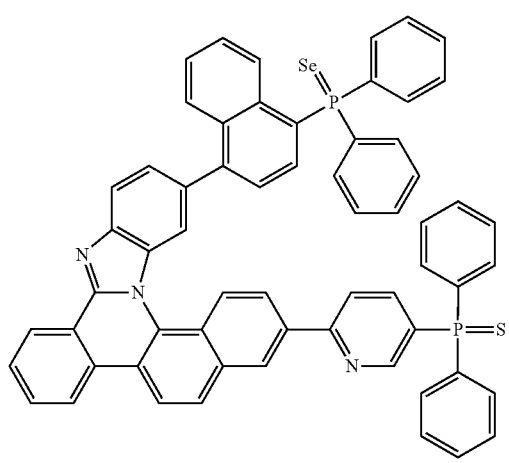
[Compound 3-20]
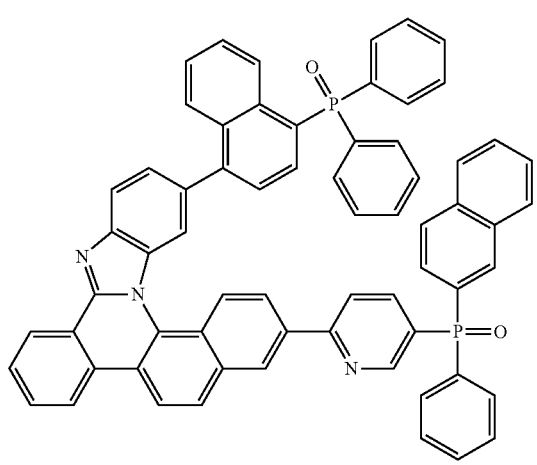

[Compound 3-21]
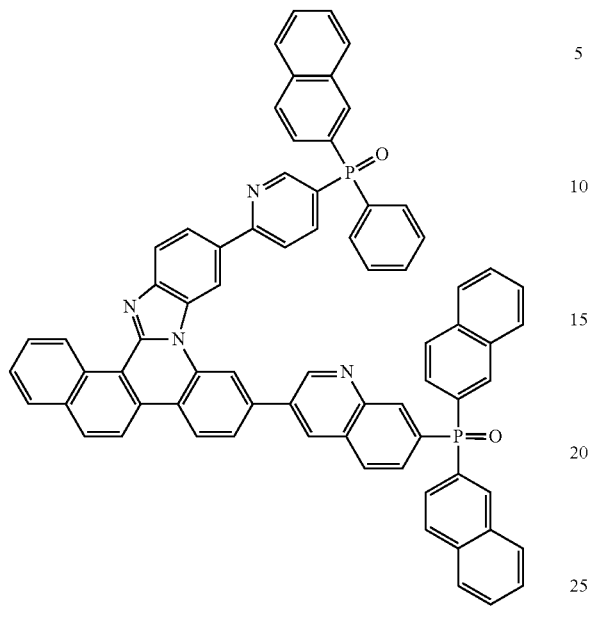
[Compound 3-22]
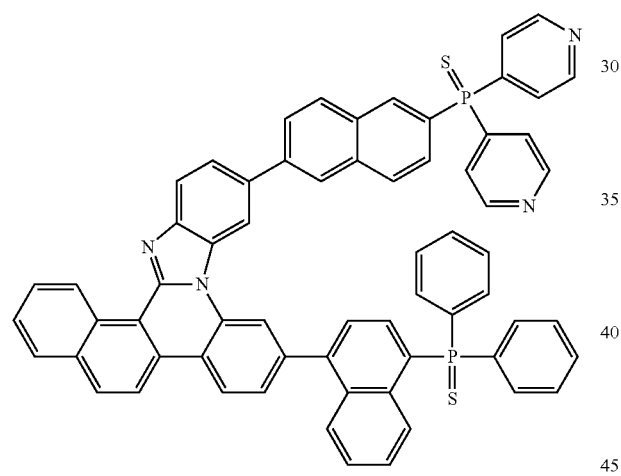
[Compound 3-23]
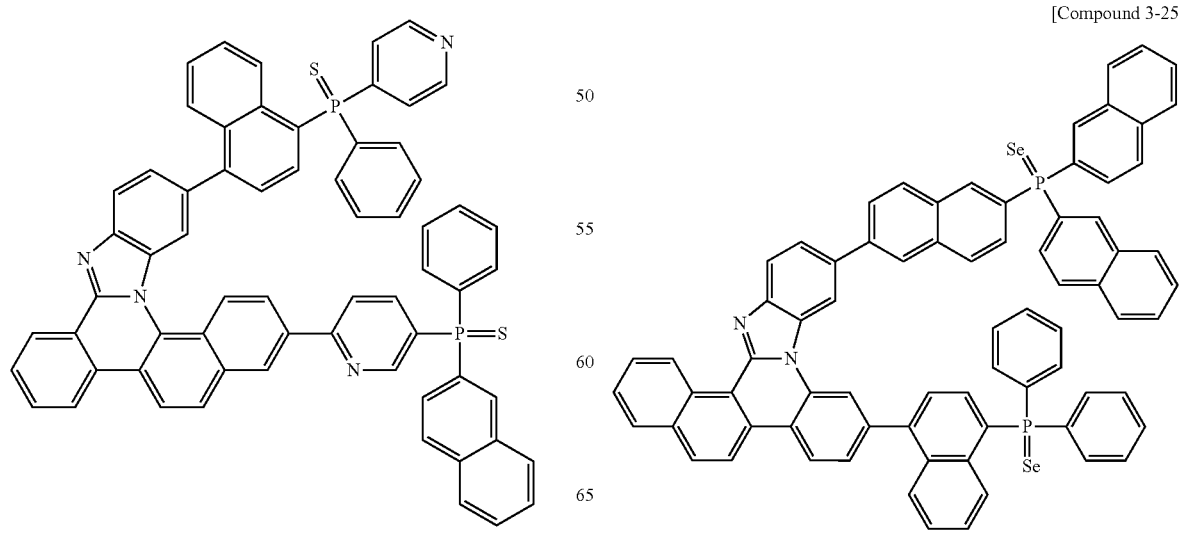
[Compound 3-24]
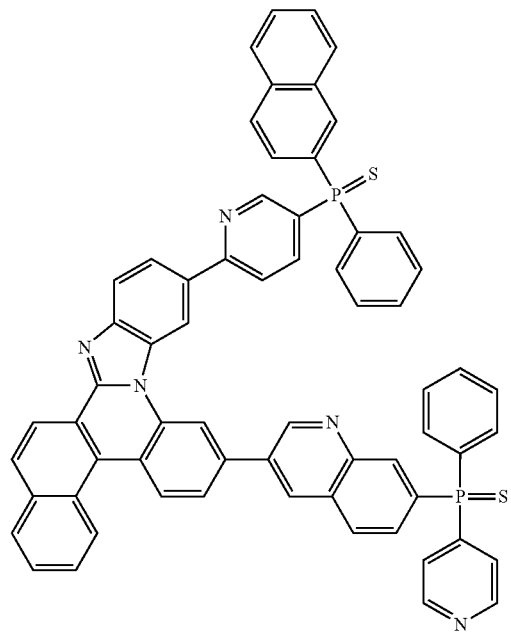
[Compound 3-25]

[Compound 3-26]
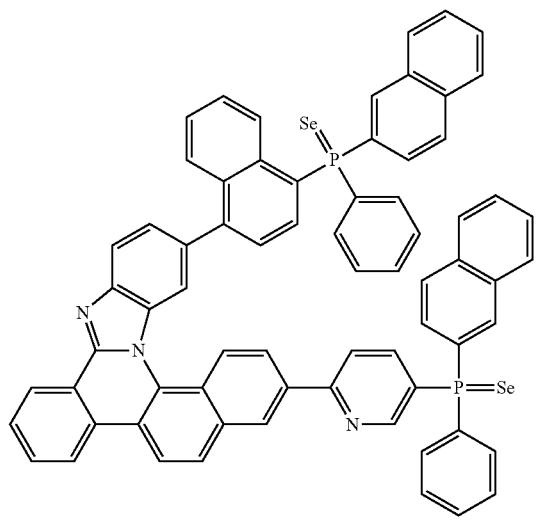
[Compound 3-28]
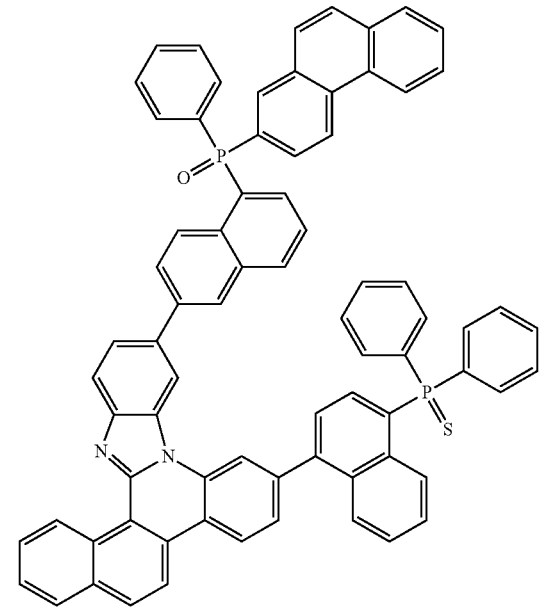
[Compound 3-29]
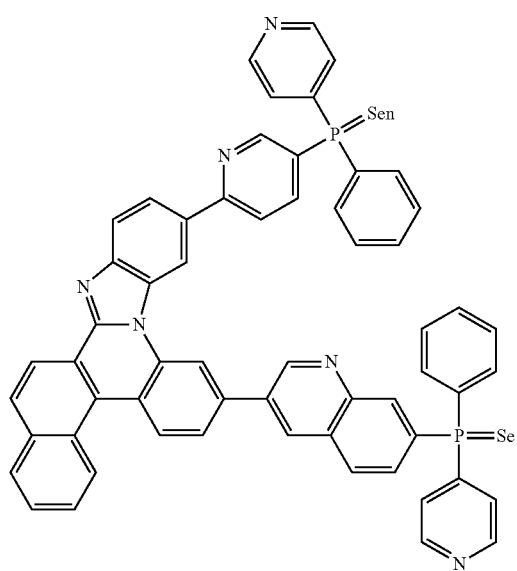
[Compound 3-27]
[Compound 3-30]
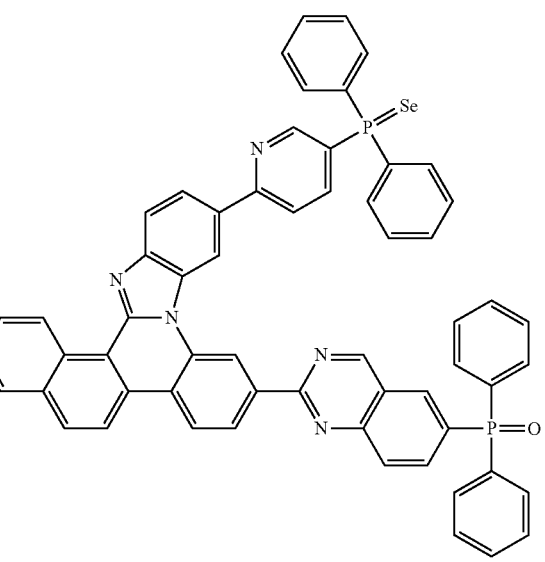

[Compound 3-31]
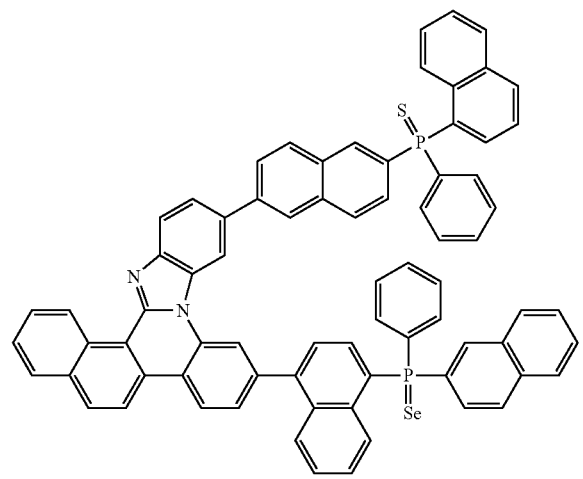
[Compound 3-32]
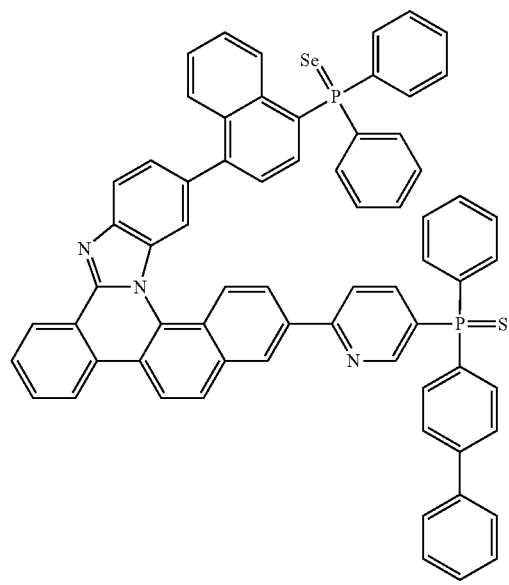
[Compound 3-33]
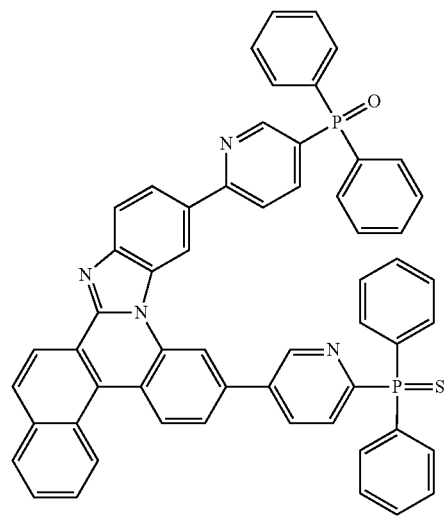
[Compound 4-1]
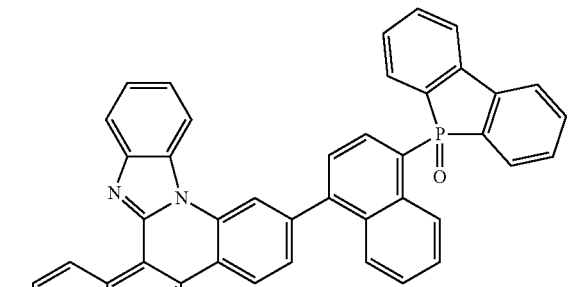
[Compound 4-2]
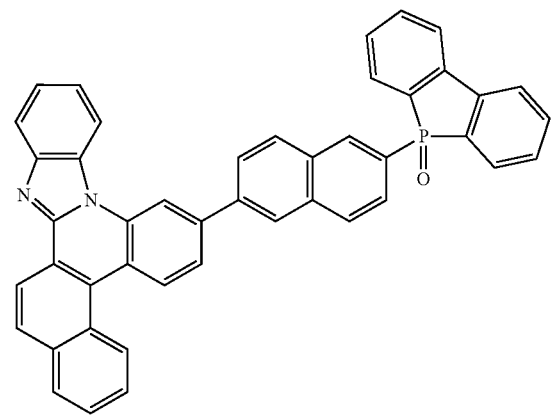
[Compound 4-3]
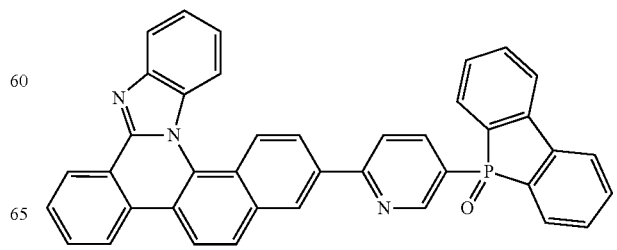

[Compound 4-4]
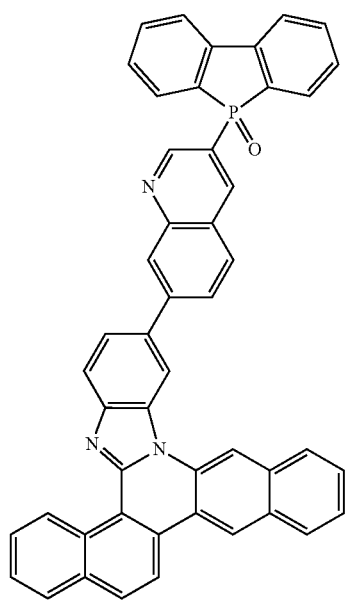
[Compound 4-6]
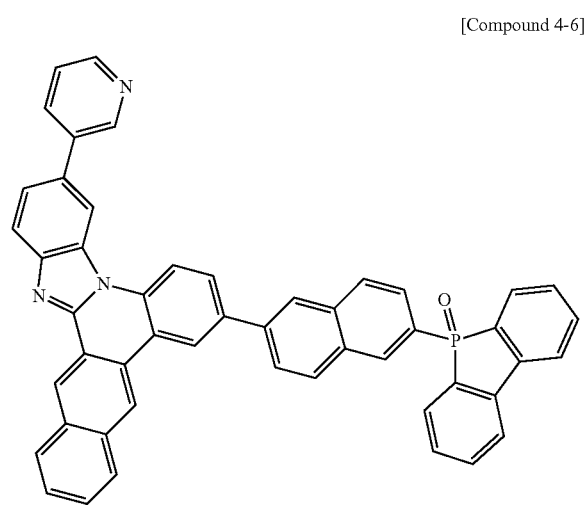
[Compound 4-7]
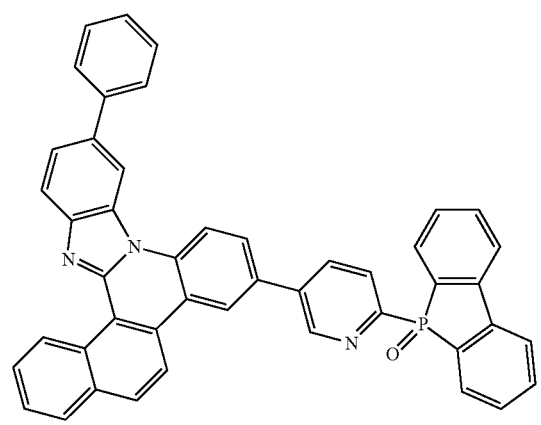
[Compound 4-8]
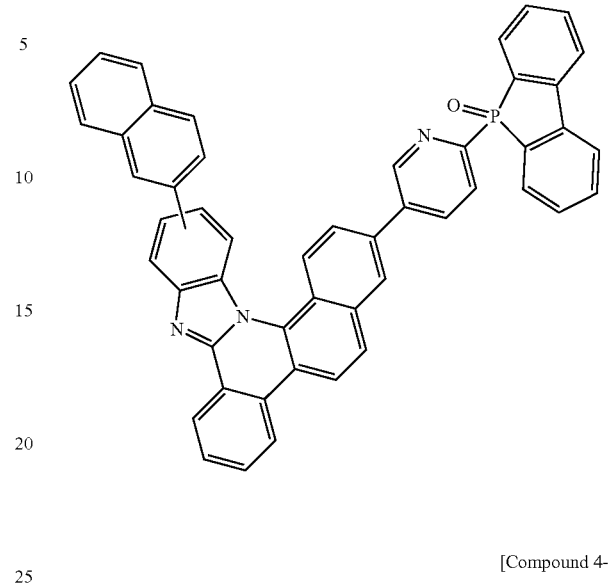
[Compound 4-9]
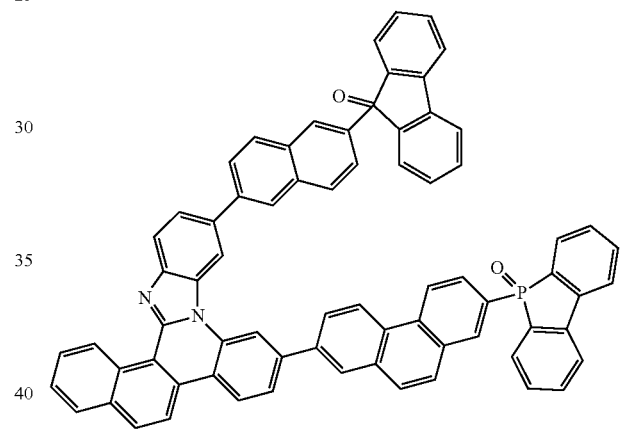
[Compound 4-10]
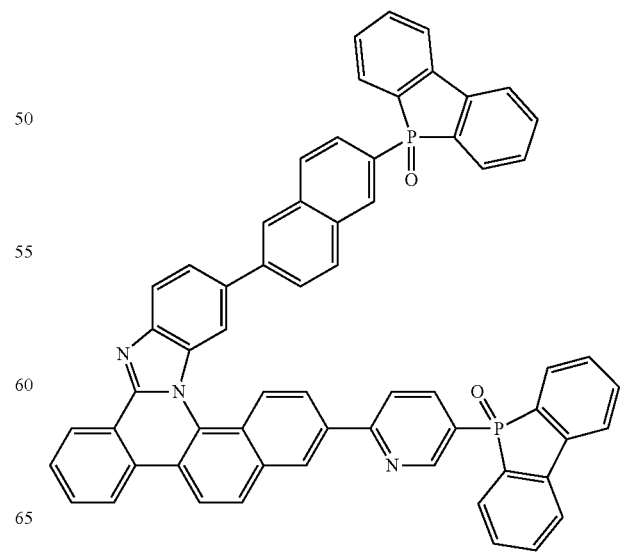

[Compound 4-11]

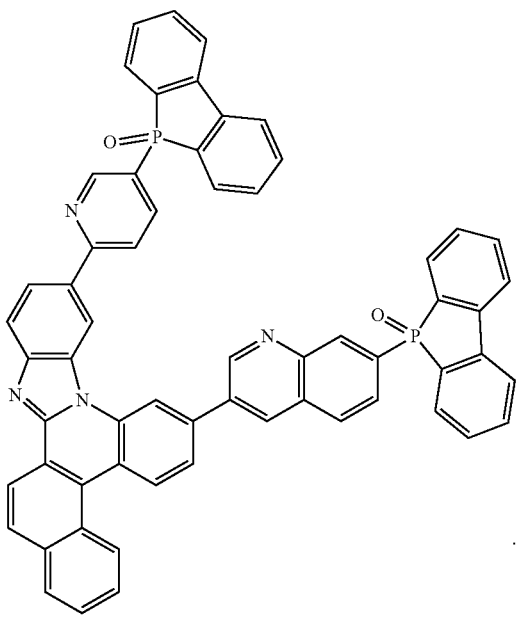

9. An organic light emitting device, comprising:
a first electrode;
a second electrode provided to face the first electrode; and
one or more organic material layers provided between the first electrode and the second electrode,
wherein one or more layers of the organic material layers comprise the compound of claim 1.

10. The organic light emitting device of claim 9, wherein the organic material layer comprising the compound is a hole injection layer, a hole transporting layer, or a layer which simultaneously injects and transports holes.

11. The organic light emitting device of claim 9, wherein the organic material layer comprising the compound is an electron injection layer, an electron transporting layer, or a layer which simultaneously injects and transports electrons.

12. The organic light emitting device of claim 9, wherein the organic material layer comprising the compound is a light emitting layer.

* * * * *